US010030029B2

(12) United States Patent
He et al.

(10) Patent No.: US 10,030,029 B2
(45) Date of Patent: Jul. 24, 2018

(54) IMIDAZOLE DERIVATIVE USED AS ANTIVIRAL AGENT AND USE THEREOF IN PREPARATION OF MEDICAMENT

(71) Applicant: Shandong Danhong Pharmaceutical Co., Ltd., Heze, Shandong Province (CN)

(72) Inventors: Haiying He, Shanghai (CN); Weihua Shi, Shanghai (CN); Zhigan Jiang, Shanghai (CN); Lixia Han, Shanghai (CN); Jikui Sun, Shanghai (CN); Jian Li, Shanghai (CN); Shuhui Chen, Shanghai (CN)

(73) Assignee: Shandong Danhong Pharmaceutical Co., Ltd., Heze (CN)

( * ) Notice: Subject to any disclaimer, the term of this patent is extended or adjusted under 35 U.S.C. 154(b) by 0 days.

(21) Appl. No.: 15/708,906

(22) Filed: Sep. 19, 2017

(65) Prior Publication Data

US 2018/0009820 A1 Jan. 11, 2018

Related U.S. Application Data

(62) Division of application No. 15/103,189, filed as application No. PCT/CN2014/090771 on Nov. 11, 2014, now Pat. No. 9,850,251.

(30) Foreign Application Priority Data

Dec. 10, 2013 (CN) .......................... 2013 1 0661317
Jan. 22, 2014 (CN) .......................... 2014 1 0028072
May 7, 2014 (CN) .......................... 2014 1 0191550

(51) Int. Cl.
| | | |
|---|---|---|
| *A61K 31/437* | (2006.01) |
| *C07D 487/10* | (2006.01) |
| *C07D 471/20* | (2006.01) |
| *A61K 31/4184* | (2006.01) |
| *C07D 403/06* | (2006.01) |
| *C07D 471/10* | (2006.01) |
| *C07D 471/18* | (2006.01) |

(52) U.S. Cl.
CPC ........ *C07D 487/10* (2013.01); *A61K 31/4184* (2013.01); *A61K 31/437* (2013.01); *C07D 403/06* (2013.01); *C07D 471/10* (2013.01); *C07D 471/18* (2013.01); *C07D 471/20* (2013.01)

(58) Field of Classification Search
CPC .. C07D 487/10; C07D 471/20; C07D 471/18; C07D 403/06; C07D 471/10; A61K 31/4184; A61K 31/437

See application file for complete search history.

(56) References Cited

U.S. PATENT DOCUMENTS

| | | | |
|---|---|---|---|
| 4,324,794 A | 4/1982 | Tidwell et al. |
| 4,525,358 A | 6/1985 | Baltes et al. |
| 5,256,668 A | 10/1993 | Hsu et al. |
| 9,617,289 B2 | 4/2017 | Tahri |
| 9,850,251 B2 | 12/2017 | He |
| 2002/0099208 A1 | 7/2002 | Yu et al. |
| 2013/0261151 A1 | 10/2013 | Cooymans et al. |
| 2014/0308282 A1 | 10/2014 | Cockerill |
| 2016/0318943 A1 | 11/2016 | He |
| 2018/0009820 A1 | 1/2018 | He |

FOREIGN PATENT DOCUMENTS

| | | |
|---|---|---|
| AU | 1470497 A | 8/1997 |
| CN | 103347881 A | 10/2013 |
| CN | 201410028072 A | 1/2014 |
| CN | 201410191550 A | 5/2014 |
| CN | 104693211 A | 6/2015 |
| CN | 105793265 A | 7/2016 |
| EP | 0058146 A1 | 8/1982 |
| EP | 3081569 A1 | 10/2016 |
| WO | 9938508 A1 | 8/1999 |
| WO | 0004900 A1 | 2/2000 |
| WO | 2010103306 A1 | 9/2010 |
| WO | 2012080449 A1 | 6/2012 |
| WO | 2013068769 A1 | 5/2013 |
| WO | 2014060411 A1 | 4/2014 |
| WO | 2015085844 A1 | 6/2015 |

OTHER PUBLICATIONS

1st Office Action issued in counterpart European patent application EP14870381.2 dated Jul. 4, 2017.
English translation of 2nd Office Action issued in counterpart Chinese patent application CN201480061605.X dated Jul. 20, 2017.
International Search Report issued in International Patent Application No. PCT/CN2014/090771 dated Feb. 17, 2015.
Written Opinion of the International Searching Authority issued in International Patent Application No. PCT/CN2014/090771 dated Feb. 17, 2015.
National Respiratory and Enteric Virus Surveillance System collaborating laboratories et al., "Update: Respiratory Syncytial Virus Activity—United States, 1996-97 Season", JAMA, 1997, 277, 12-13.
Machine Translation of The State Intellectual Property Office of People's Republic of China, "The First Office Action, (PCT Application Entering the National Phase)", issued in connection with Publication No. 201480061605.X, dated Feb. 28, 2017.
Machine Translation of Japanese Patent Office, "Notification of Reasons for Refusal" issued in connection with Japanese Patent Application No. 2016-539200, drafted on Dec. 19, 2016.
Erik De Clercq, "Perspectives for the chemotherapy of respiratory syncytial virus (RSV) infections", International Journal of Antimicrobial Agents, 1996, 7, 193-202.

(Continued)

*Primary Examiner* — Sudhakar Katakam
(74) *Attorney, Agent, or Firm* — Millen White Zelano and Branigan, PC; John Sopp

(57) ABSTRACT

Disclosed are an antiviral compound and a use thereof in the preparation of a medicament for the treatment of virus infections. Specifically, the present invention relates an imidazole derivative for treating respiratory syncytial virus infection.

18 Claims, No Drawings

(56) References Cited

OTHER PUBLICATIONS

Tidwell et al., "Aromatic Amidines: Comparison of Their Ability to Block Respiratory Syncytial Virus Induced Cell Fusion and to Inhibit Plasmin, Urokinase, Thrombin, and Trypsin", American Chemical Society, 1983, 26, 294-298.
Dubovi et al., "Inhibition of Respiratory Syncytial Virus-Host Cell Interactions by Mono- and Diamidines", Antimicrobial Agents and Chemotherapy, 1981, 19(4), 649-656.
P.R. Wyde et al., "CL387626 exhibits marked and unusual antiviral activity against respiratory syncytial virus in tissue culture and in cotton rats", Antiviral Research, 1998, 38, 31-42.
S. Shigeta et al., "Inhibitory effect of pyridobenzoazoles on orthomyxo and paramyxovirus replication in vitro", Antiviral Chemistry & Chemotherapy, 1992, 3(3), 171-177.
Roderick et al., "Bisbenzimidazoles. Potent Inhibitors of Rhinoviruses", Journal of Medicinal Chemistry, 1972, 16(6), 655-658.
Stephen M. Berge et al., "Pharmaceutical Salts", Journal of Pharmaceutical Sciences, 1997, 66(1), 1-19.
European Search Report issued in counterpart European patent application EP14870381.2 dated Sep. 27, 2016.
Office Action of Japanese Patent Application No. 2016-539200, prepared Oct. 27, 2016, dated Nov. 1, 2016, 2 pages, English translation.
Second Office Action corresponding to European Application No. 14 870 381.2 dated Feb. 2, 2018.

IMIDAZOLE DERIVATIVE USED AS ANTIVIRAL AGENT AND USE THEREOF IN PREPARATION OF MEDICAMENT

FIELD OF INVENTION

The present invention relates to an antiviral compound and a use thereof in the preparation of a medicament for the treatment of virus infections. Specifically, the present invention relates an imidazole derivative for treating respiratory syncytial virus infection.

PRIOR ARTS

Respiratory syncytial virus (RSV) is the main cause for serious lower respiratory infection to infants, children, the elderly and those with impaired immunity. Severe viral infection can cause bronchiolitis or pneumonia which needs hospitalized treatment or lead to death (JAMA, 1997, 277, 12). Recently, Ribavirin has been approved for the treatment of this virus infection, which is a nucleoside analogue administrated in the form of an intranasal aerosol, with considerable toxicity and controversial effects. In addition to Ribavirin, RespiGam and Synagis, respectively, are immunoglobulin and monoclonal antibody which neutralize RSV. They are two biological agents approved currently for the prophylactic treatment for children high-risk infected with RSV. RespiGam and Synagis are very expensive and require parenteral administration.

It has been known that many drugs can be used for the inhibition of respiratory syncytial virus (De Clercq, Int. J. Antiviral Agent, 1996, 7, 193). Y. Tao et al (EP0058146A1, 1998) discloses an antihistamine agent Cetirizine which displays anti-RSV activity. Both J. Med. Chem. 1983, 26, 294 (U.S. Pat. No. 4,324,794, 1982) by Tidwell et al and Antimicrobial Agents and Chemotherapy, 1981, 19, 649 by Dubovi et al report a series of guanyl compounds as RSV inhibitors. Hsu et al also discloses a series of 6-amino pyrimidones with anti RSV antiviral activity in U.S. Pat. No. 5,256,668 (1993). Besides, Y. Gluzman et al (AU Patent, AU-A-14, 704, 1997) and P. R. Wyde et al (Antiviral Res. 1998, 38, 31) disclose a series of triazine-containing compounds for the treatment and/or prevention of RSV infection. S. Shigeta et al discloses pyrido[1, 2-a]benzopyrrole and pyrimido[1, 2-a]benzimidazole in Antiviral Chem.& Chemother. 1992, 3, 171. It has been proved that these compounds inhibit the replication of orthomyxovirus and paramyxovirus in HeLa cells. It has been reported that di-benzimidazoles with glycol linking group are also effective nasal virus inhibitor (Roderick et al, J. Med. Chem. 1972, 15, 655). Other structurally related compounds are di-benzimidazoles with antifungal activity (B. Cakir et al, Eczacilik Fak Derg. 1988, 5, 71). Very recently, Yu et al find a series of benzimidazoles for the treatment and prevention of RSV infection (WO 00/04900). Moreover, Theodore Nitz also finds a series of compounds represented by formula III which inhibit RSV in the determination of tissue culture media of Hep-2 cells (WO 99/38508).

Currently, BMS discloses BMS433771, the general structure of which is represented by formula (B-I):

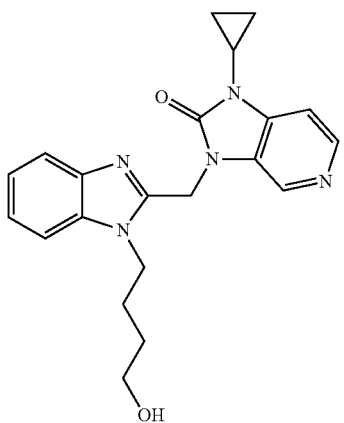

(B-I)

Viral discloses a class of compounds in WO2013068769A1, the general structure of which is represented by formula (B-II):

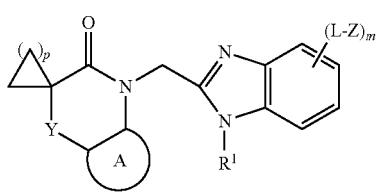

(B-II)

AstraZeneca discloses a class of compounds in WO2010103306A1, the general structure of which is represented by formula (B-III):

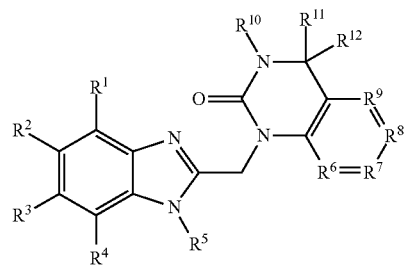

(B-III)

Although the above-mentioned compounds in prior art can be used for the inhibition of respiratory syncytial virus, an improvement in activity and solubility, etc. is still required.

CONTENT OF THE PRESENT INVENTION

An aim of the present invention is to provide a compound represented by formula (I), (II), (III) or (IV) or a pharmaceutically acceptable salt thereof,

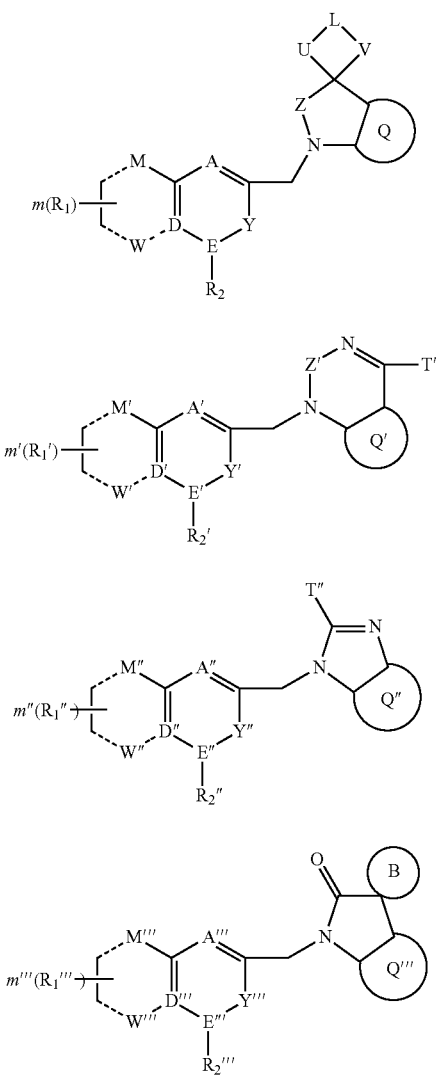

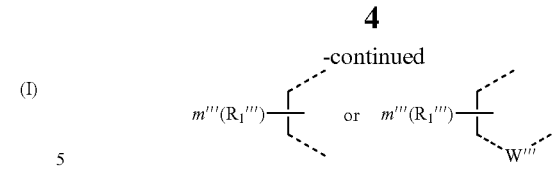

Wherein, each of A, E, A', E', A", E", A''' and E''' independently represents N or optionally substituted CH;

each of Y, Y', Y" and Y''' independently represents optionally substituted $(CH_2)_p$, p is an integer among 0~3, when p is 0, Y, Y', Y", Y''' represent a single bond just for the linkage;

The dotted line represents a single bond, double bond or no bond, when the dotted lines in

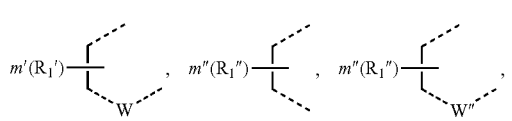

represent no bond, the structural unit does not exist;

each of D, D', D" and D''' independently represents C or N, when D, D', D" or D''' is C, the dotted line it connects represents a single bond, when D, D', D" or D''' is N, the dotted line it connects represents no bond;

each of M, W, M', W', M", W", M''' and W''' independently represents H, a halogen, CN or an optionally substituted substituent selected from the group consisting of OH, SH, $NH_2$, $PH_2$, a hydrocarbon group and a hetero-hydrocarbon group;

each of $R_1$, $R_1'$ and $R_1"$ is independently selected from H, a halogen, CN or an optionally substituted substituent selected from the group consisting of OH, SH, $NH_2$, $PH_2$, a hydrocarbon group and a hetero-hydrocarbon group;

$R_1'''$ represents F, Cl, Br, I, CN, OH, SH, $NH_2$, a substituent selected from the group consisting of a $C_{1-6}$ alkyl, a $C_{2-6}$ alkenyl and a $C_{2-6}$ alkynyl which is unsubstituted or substituted by a halogen or a hydroxyl;

each of m, m' and m" is independently selected from 0, 1, 2, 3 or 4;

m''' is selected from 1, 2, 3 or 4;

each of $R_2$, $R_2'$, $R_2"$ and $R_2'''$ is independently selected from H, a halogen, CN or an optionally substituted substituent selected from the group consisting of OH, SH, $NH_2$, $PH_2$, a hydrocarbon group and a hetero-hydrocarbon group;

each of Z and Z' independently represents optionally substituted NH, $(R_5)_t(CH_2)_q$ or $(CH_2)_q(R_5)_t$, $R_5$ is selected from C=O, C=S, S(=O), S(=O)$_2$, O or S, t is 0 or 1, q is 0, 1, 2 or 3, t and q are not 0 at the same time;

each of U and V independently represents optionally substituted $(NH)_{r1}(R_6)_{r2}(CH_2)_{r3}$, $(R_6)_{r2}(NH)_{r1}(CH_2)_{r3}$, $(CH_2)_{r3}(NH)_{r1}(R_6)_{r2}$, $(NH)_{r1}(CH_2)_{r3}(R_6)_{r2}$, $(R_6)_{r2}(CH_2)_{r3}(NH)_{r1}$ or $(CH_2)_{r3}(R_6)_{r2}(NH)_{r1}$, $R_6$ is selected from C=O, C=S, S(=O), S(=O)$_2$, O or S, each of $r_1$ and $r_3$ is independently selected from 0, 1, 2 or 3, $r_2$ is 0 or 1, that $r_1$, $r_2$ and $r_3$ are 0 at the same time means that U or V represents a single bond just for the linkage, and U and V are not a single bond at the same time;

L represents a heteroatom or a heteroatom group;

each of T' and T" independently represents H, a halogen, CN or an optionally substituted substituent selected from the group consisting of OH, SH, $NH_2$, $PH_2$, a hydrocarbon group and a hetero-hydrocarbon group;

B represents an optionally substituted 3- to 8-membered alicyclic hydrocarbon;

each of Q, Q', Q" and Q''' independently represents an optionally substituted 5- to 12-membered cyclic hydrocarbon or 5- to 12-membered heterocyclic hydrocarbon; optionally, the compound or the pharmaceutically acceptable salt thereof contains one or more chiral centers;

optionally, the structural unit

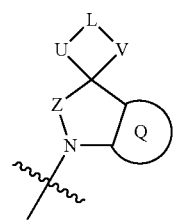

can be replaced with

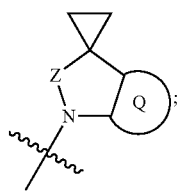

optionally, the structural unit

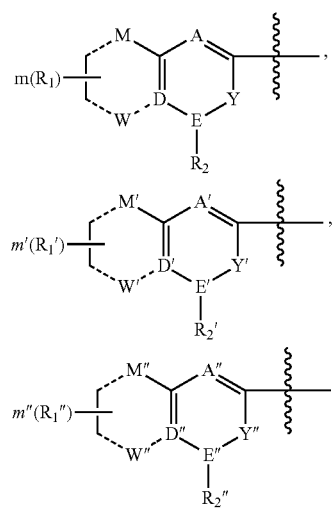

can be replaced with

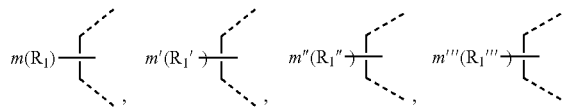

zero, one or two of $T_{1-4}$ is selected from N, the rest is selected from $C(R_t)$;

one of $D_{1-4}$ is selected from a single bond or —$C(R_{d1})(R_{d2})$—, another is selected from —$C(R_{d1})(R_{d2})$—, —$C(=O)N(R_{d3})$—, —$N(R_{d4})$—, —$C(=NR_{d5})$—, —$S(=O)_2N(R_{d6})$—, —$S(=O)$ $N(R_{d7})$—, —O—, —S—, —$C(=O)O$—, —$C(=O)$—, —$C(=S)$—, —$S(=O)$— or —$S(=O)_2$—, the remaining two are selected from —$C(R_{d1})(R_{d2})$—;

each of $R_t$, $R_{d1}$ and $R_{d2}$ is independently selected from H, F, Cl, Br, I, CN, OH, SH, NH$_2$, CHO, COOH, or selected from the group consisting of a $C_{1-10}$ alkyl or a heteroalkyl which is optionally substituted by $R_{01}$, a $C_{3-10}$ cyclic hydrocarbon group or a heterocyclic hydrocarbon group, a $C_{1-10}$ alkyl or a heteroalkyl substituted by a $C_{3-10}$ cyclic hydrocarbon group or a heterocyclic hydrocarbon group;

$R_{01}$ is selected from F, Cl, Br, I, CN, OH, SH, NH$_2$, CHO, COOH, $R_{02}$;

$R_{02}$ is selected from a $C_{1-10}$ alkyl, a $C_{1-10}$ alkyl amino, a N,N-bis($C_{1-10}$ alkyl) amino, a $C_{1-10}$ alkoxyl, a $C_{1-10}$ alkyl acyl, a $C_{1-10}$ alkoxycarbonyl, a $C_{1-10}$ alkyl sulfonyl, a $C_{1-10}$ alkyl sulfinyl, a $C_{3-10}$ cycloalkyl, a $C_{3-10}$ cycloalkyl amino, a $C_{3-10}$ heterocycloalkyl amino, a $C_{3-10}$ cycloalkoxyl, a $C_{3-10}$ cycloalkyl acyl, a $C_{3-10}$ cycloalkoxycarbonyl, a $C_{3-10}$ cycloalkyl sulfonyl, a $C_{3-10}$ cycloalkyl sulfinyl;

each of the heteroatom and heteroatom group is independently selected from —$C(=O)N(R_{d3})$—, —$N(R_{d4})$—, —$C(=NR_{d5})$—, —$S(=O)_2N(R_{d6})$—, —$S(=O)N(R_{d7})$—, —O—, —S—, =O, =S, —$C(=O)O$—, —$C(=O)$—, —$C(=S)$—, —$S(=O)$— and/or —$S(=O)_2$—;

each of $R_{d3-d7}$ is independently selected from H, $R_{03}$;

$R_{03}$ is selected from a $C_{1-10}$ alkyl, a $C_{1-10}$ alkyl acyl, a $C_{1-10}$ alkoxycarbonyl, a $C_{1-10}$ alkyl sulfonyl, a $C_{1-10}$ alkyl sulfinyl, a $C_{3-10}$ cycloalkyl, a $C_{3-10}$ cycloalkyl acyl, a $C_{3-10}$ cycloalkoxycarbonyl, a $C_{3-10}$ cycloalkyl sulfonyl, a $C_{3-10}$ cycloalkyl sulfinyl;

$R_{02}$, $R_{03}$ are optionally substituted by $R_{001}$;

$R_{001}$ is selected from F, Cl, Br, I, CN, OH, N(CH$_3$)$_2$, NH(CH$_3$), NH$_2$, CHO, COOH, trifluoromethyl, aminomethyl, hydroxymethyl, methyl, methoxyl, formyl, methoxycarbonyl, methylsulphonyl, methylsulfinyl;

a number of each of $R_{01}$, $R_{001}$, the heteroatom and the heteroatom group is independently selected from 0, 1, 2 or 3.

In an embodiment of the present invention, the dotted line represents a single bond or a double bond, each of M, W, M', W', M", W", M''' and W''' independently represents optionally substituted CH$_2$CH, NH or N.

In an embodiment of the present invention,

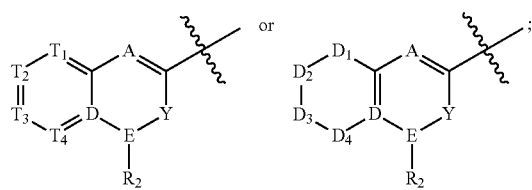

do not exist, each of M, W, M', W', M", W", M''' and W''' independently represents a $C_{1-12}$ hydrocarbon group, a $C_{1-12}$ hetero-hydrocarbon group, a $C_{1-12}$ hydrocarbon-substituting heteroatom group, a $C_{1-12}$ hydrocarbon group substituted by a $C_{1-12}$ hydrocarbon-substituting heteroatom group, —$C_{1-12}$OH, —$C_{0-12}$COOH, —$OC_{1-12}$COOH, —$C_{1-12}$CN, —$C_{0-12}$C(=O)NH$_2$, —$C_{0-12}$OC$_{1-12}$, —$C_{0-12}$C(=O) $C_{1-12}$, —$C_{0-12}$C(=O)OC$_{1-12}$, —$C_{0-12}$O(O=)CC$_{1-12}$, —$C_{0-12}$S(=O) $C_{1-12}$ or —$C_{0-12}$S(=O)$_2$C$_{1-12}$ which is optionally substituted, wherein, the above-mentioned group itself is optionally in the form of an aromatic ring, a hetero-aromatic ring, a cycloaliphatic ring, a hetero-cycloaliphatic ring, an aliphatic chain and/or a hetero-aliphatic chain, and a number of the aromatic ring, hetero-aromatic ring, cycloaliphatic ring, hetero-cycloaliphatic ring, aliphatic chain and/or hetero-aliphatic chain, the ring-forming atom and the number thereof, the linking form between the rings, or the ring and the chain, or the chains can all be arbitrary under the premise of stability available in chemistry, each of the heteroatom and heteroatom group is independently selected from O, S, N, S(=O) and/or S(=O)$_2$, a number of the heteroatom or heteroatom group can be arbitrary under the premise of stability available in chemistry.

In an embodiment of the present invention, each of M, W, M', W', M", W", M''', W''' independently represents a $C_{6-12}$ aryl or a heteroaryl or an aryl heteroatomic group, a $C_{3-8}$ alcyl or a heteroalcyl or an alcyl heteroatomic group, a $C_{1-6}$ alkyl, a $C_{1-6}$ alkyl heteroatomic group, a $C_{1-6}$ heteroalkyl, a $C_{2-6}$ alkenyl or alkynyl, a $C_{2-6}$ heteroalkenyl or heteroalkynyl, a $C_{2-6}$ alkenyl heteroatomic group or alkynyl heteroatomic group which is unsubstituted or substituted by a halogen or a hydroxyl or an amino, each of the heteroatom or heteroatom group is independently selected from O, S, N, S(=O) and/or S(=O)$_2$, a number of the heteroatom or the heteroatom group can be arbitrary under the premise of stability available in chemistry.

In an embodiment of the present invention, each of M, W, M', W', M", W", M'" and W'" independently represents a phenyl,

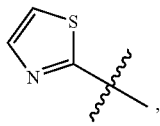 [SMILES: *c1nccs1]

a biphenyl, a naphthyl, a cyclopentyl, a furyl, a 3-pyrrolyl, a pyrrolidinyl, 1,3-dioxlanyl, a pyrazolyl, a 2-pyrazolinyl, a pyrazolidinyl, an imidazolyl, an oxazolyl, a thiazolyl, a 1,2,3-azolyl, a 1,2,3-triazolyl, a 1,2,4-triazolyl, a 1,3,4-thiadiazolyl, a 4H-pyranyl, a pyridyl, a piperidyl, a 1,4-dioxanyl, a morpholinyl, a pyridazinyl, a pyrimidinyl, a pyrazinyl, a piperazinyl, a 1,3,5-trithianyl, a 1,3,5-triazinyl, a benzofuranyl, a benzothiophenyl, an indolyl, a benzimidazolyl, a benzothiazolyl, a purinyl, a quinolinyl, an isoquinolinyl, a cinnolinyl or a quinoxalinyl which is unsubstituted or substituted by a halogen, a hydroxyl or an amino.

In an embodiment of the present invention, each of M and W independently represents a methyl or an ethyl which is unsubstituted or substituted by a halogen, a hydroxyl or an amino.

In an embodiment of the present invention, each of Q, Q', Q" and Q'" independently represents a structural unit represented by formula (a):

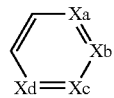

Wherein, each of $X_a$, $X_b$, $X_c$ and $X_d$ independently represents N or an optionally substituted CH.

In an embodiment of the present invention, B represents an optionally substituted cyclopropyl or cyclobutyl or cyclopentyl or cyclohexyl or suberyl or cyclooctyl.

In an embodiment of the present invention, the compound or the pharmaceutically acceptable salt thereof has a structure represented by formula (V), (VI), (VII) or (VIII):

(V)

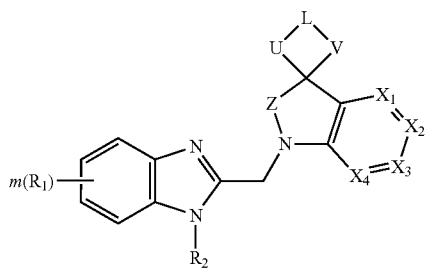

-continued (VI)

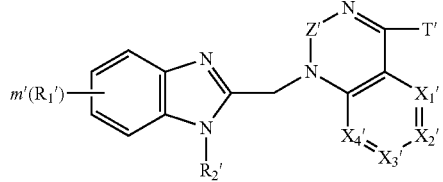

(VII)

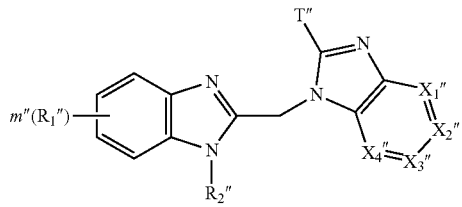

(VIII)

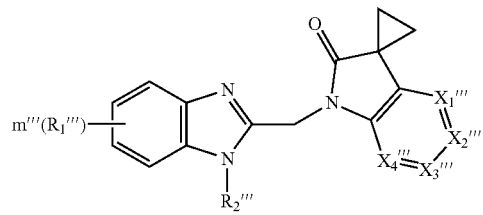

Wherein, each of $X_1$, $X_2$, $X_3$, $X_4$, $X_1'$, $X_2'$, $X_3'$, $X_4'$, $X_1''$, $X_2''$, $X_3''$, $X_4''$, $X_1'''$, $X_2'''$, $X_3'''$ and $X_4'''$ independently represents N or an optionally substituted CH;

Optionally, the structural unit

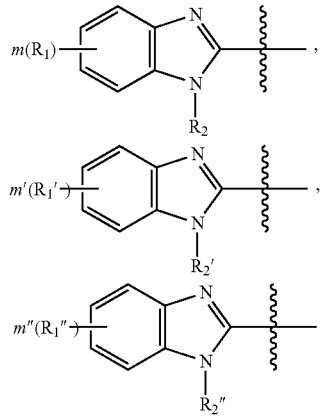

can be replaced with

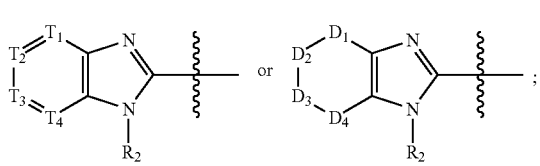

$T_{1-4}$, $D_{1-4}$ are defined as claim 1.

In an embodiment of the present invention, the compound or the pharmaceutically acceptable salt thereof has a structure represented by formula (X):

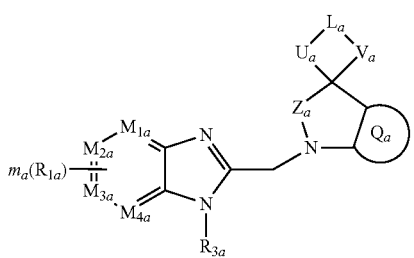

(X)

Wherein, each of $M_{1a}$, $M_{2a}$, $M_{3a}$, $M_{4a}$ independently represents N or an optionally substituted CH, and at least one of which is N;

$R_{1a}$ is selected from H, a halogen, CN or an optionally substituted substituent selected from the group consisting of OH, SH, $NH_2$, $PH_2$, a hydrocarbon group and a heterohydrocarbon group;

$m_a$ is selected from 0, 1, 2, 3 or 4;

$R_{3a}$ is selected from H, a halogen, CN or an optionally substituted substituent selected from the group consisting of OH, SH, $NH_2$, $PH_2$, a hydrocarbon group and a heterohydrocarbon group;

$Z_a$ represents optionally substituted NH, $(R_5)_t(CH_2)_q$ or $(CH_2)_q(R_5)_t$, $R_5$ is selected from C=O, C=S, S(=O), S(=O)$_2$, O or S, t is 0 or 1, q is 0, 1, 2 or 3, t and q are not 0 at the same time;

each of $U_a$ and $V_a$ independently represents optionally substituted $(NH)_{r1}(R_6)_{r2}(CH_2)_{r3}$, $(R_6)_{r2}(NH)_{r1}(CH_2)_{r3}$, $(CH_2)_{r3}(NH)_{r1}(R_6)_{r2}$, $(NH)_{r1}(CH_2)_{r3}(R_6)_{r2}$, $(R_6)_{r2}(CH_2)_{r3}(NH)_{r1}$ or $(CH_2)_{r3}(R_6)_{r2}(NH)_{r1}$, $R_6$ is selected from C=O, C=S, S(=O), S(=O)$_2$, O or S, each of $r_1$ and $r_3$ is independently selected from 0, 1, 2 or 3, $r_2$ is 0 or 1, that $r_1$, $r_2$ and $r_3$ are 0 at the same time means that $U_a$ or $V_a$ represents a single bond just for the linkage, and $U_a$ and $V_a$ are not a single bond at the same time;

$L_a$ represents a heteroatom or a heteroatom group;

$Q_a$ represents an optionally substituted 5- to 12-membered cyclic hydrocarbon or 5- to 12-membered heterocyclic hydrocarbon; and optionally, the compound or the pharmaceutically acceptable salt thereof contains one or more chiral centers.

In an embodiment of the present invention, the compound or the pharmaceutically acceptable salt thereof has a structure represented by formula (XI):

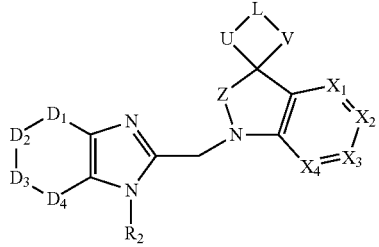

(XI)

Wherein, each parameter is defined as 1, 2, 6 or 8.

In an embodiment of the present invention, each of $R_1$, $R_1'$, $R_1''$, $R_t$, $R_{d1}$, $R_{d2}$ and $R_{1a}$ is independently selected from F, Cl, Br, I, CN, an optionally substituted $NH_2$, a $C_{1-6}$ alkyl which is unsubstituted or substituted by a halogen or a hydroxyl or an amino, a $C_{2-6}$ alkenyl or an alkynyl which is unsubstituted or substituted by a halogen or a hydroxyl or an amino.

In an embodiment of the present invention, each of $R_1$, $R_1'$, $R_1''$, $R_t$, $R_{d1}$, $R_{d2}$ and $R_{1a}$ is independently selected from F, Cl, Br, I, CN, $CF_3$, $NH_2$, $CH_3$, $CH_2NH_2$ or $CH(NH_2)_2$.

In an embodiment of the present invention, $R_1'''$ is selected from F, Cl, Br, I, $CH_3$, $CF_3$, CN, OH, SH or $NH_2$.

In an embodiment of the present invention, each of $R_2$, $R_2'$, $R_2''$, $R_2'''$ and $R_{3a}$ is independently selected from an optionally substituted $—C_{1-10}R_3$, one or more than one heteroatom or heteroatom group is optionally inserted into the carbon chain or carbon cycle, wherein, $R_3$ is selected from $OR_4$, H, a halogen, CN, =O or an optionally substituted substituent selected from the group consisting of $NH_2$, an amide, —COOH and —OS(=O)$_2CH_3$:

$R_4$ is selected from an ester of phosphoric acid, a phosphonate, an ester of sulphonic acid, a sulfonate, an ester of sulfinic acid, a sulfinate or H;

the heteroatom or heteroatom group in the carbon chain or carbon cycle is selected from —C(=O)N($R_{d3}$)—, —N($R_{d4}$)—, —C(=N$R_{d5}$)—, —S(=O)$_2$N($R_{d6}$)—, —S(=O) N($R_{d7}$)—, —O—, —S—, =O, =S, —C(=O) O—, —C(=O)—, —C(=S)—, —S(=O)— and/or —S(=O)$_2$—, $R_{d3-d7}$ are defined as claim 1;

preferably, the heteroatom or heteroatom group is selected from O, NH, —S(=O)$_2$—Si, Si(Me$_2$) and/or Si(OH).

In an embodiment of the present invention, $R_2$, $R_2'$, $R_2''$, $R_2'''$, $R_{3a}$ are selected from

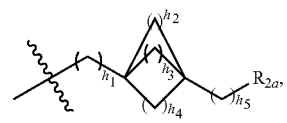

$C_{1-6}R_{2b}$,

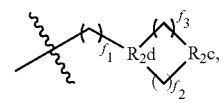

$C_{1-6}$ alkyl or

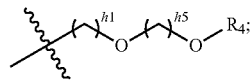

each of $h_{1-5}$ and $f_{1-3}$ is independently selected from 0, 1, 2, 3;

each of $R_{2a}$ and $R_{2b}$ is independently selected from CN, $OR_{2x}$, C(=O)$R_{2y}$;

$R_{2x}$ is selected from H, an ester of phosphoric acid, a phosphonate, an ester of sulfonic acid, a sulfonate, an ester of sulfinic acid or a sulfinate;

$R_{2y}$ is selected from the group consisting of OH, $NH_2$ and —OC$_{1-6}$ which is optionally substituted by a halogen, a methyl, a trifluoromethyl or a methoxy $R_{2c}$ is selected from O, S, C=O, C=S, S(=O), S(=O)$_2$, CR$_{2c1}$R$_{2c2}$, NR$_{2c3}$;

$R_{2d}$ is selected from N, CR$_{2d1}$;

each of $R_{2c1}$, $R_{2c2}$, $R_{2c3}$ and $R_{2d1}$ is independently selected from H, a halogen, CN or an optionally substituted substituent selected from the group consisting of OH, SH, $NH_2$, $PH_2$, a hydrocarbon group and a hetero-hydrocarbon group;

$R_4$ is selected from an ester of phosphonic acid, a phosphonate, an ester of sulfonic acid, a sulfonate, an ester of sulfinic acid, a sulfinate or H.

In an embodiment of the present invention, $R_2$ is selected from a $C_{1-6}$ alkyl or a $C_{2-6}$ alkenyl optionally substituted by 0-3 of halogen, $NH_2$, CN or $OR_4$, one of —C(=O)—, —S(=O)— or —S(=O)$_2$— is optionally inserted into the carbon chain.

In an embodiment of the present invention, $R_2$, $R_2'$, $R_2''$, $R_2'''$, $R_{3a}$ are selected from

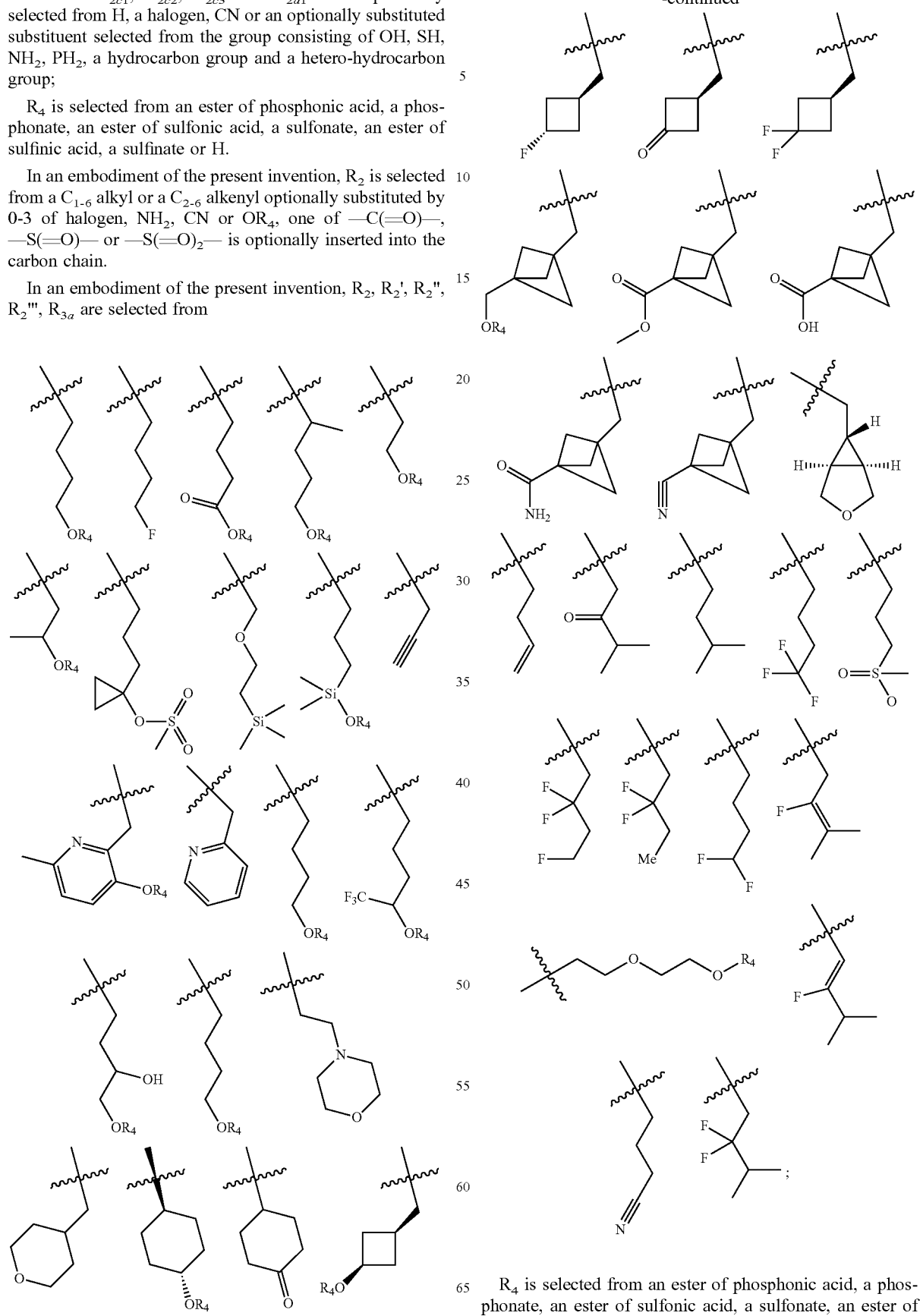

$R_4$ is selected from an ester of phosphonic acid, a phosphonate, an ester of sulfonic acid, a sulfonate, an ester of sulfinic acid, a sulfinate or H.

In an embodiment of the present invention, the ester of phosphonic acid or the phosphonate is selected from —P(=O)(OC$_2$H$_5$)$_2$, —P(=O)(ONa)$_2$ or —P(=O)(OK)$_2$.

In an embodiment of the present invention, Z, Z', Z$_a$ represent C=O, C=S or an optionally substituted CH$_2$.

In an embodiment of the present invention, each of U, V, U$_a$ and V$_a$ independently represents optionally substituted [CH$_2$, (CH$_2$)$_2$, O(CH$_2$)$_2$, (CH$_2$)$_2$O, NH(C=O), (C=O)NH] or C=O.

In an embodiment of the present invention, L, L$_a$ represent O, S, S=O, S(=O)$_2$ or an optionally substituted NH.

In an embodiment of the present invention, each of T' and T'' is independently selected from a C$_{1-6}$ alkyl which is unsubstituted or substituted by a halogen or a hydroxyl or an amino, a C$_{2-6}$ alkenyl or alkynyl which is unsubstituted or substituted by a halogen or a hydroxy or an amino, a C$_{1-6}$ alkoxy which is unsubstituted or substituted by a halogen or a hydroxy or an amino, an optionally substituted NH$_2$, an optionally substituted 5- to 12-membered cyclic group or heterocyclic group or cycloheteroyl group, the optionally substituted NH$_2$ is substituted by a C$_{1-6}$ alkyl, a C$_{5-8}$ heterocyclic group, a C$_{1-6}$ alkyl substituted by a C$_{5-8}$ heterocyclic group or a C$_{1-6}$ alkyl substituted by a C$_{5-8}$ cycloheteroyl group, NH$_2$ is substituted by 1 or 2 substituent, the heteroatom or heteroatom group is selected from O, S, N, S(=O) or S(=O)$_2$.

In an embodiment of the present invention, each of T' and T'' is independently selected from CH$_3$, CH(CH$_3$)$_2$, cyclopropyl, OCH$_3$, OCH(CH$_3$)$_2$, N(CH$_3$)$_2$, N(CH$_2$CH$_3$)$_2$,

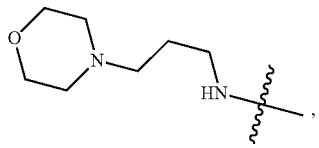 [SMILES: *NCCCN1CCOCC1]

phenyl

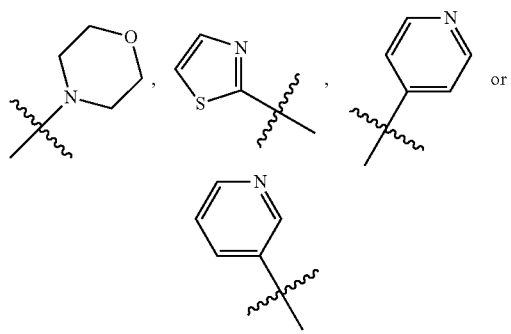

which is unsubstituted or substituted by a halogen or a hydroxyl or an amino.

In an embodiment of the present invention, the substituent of A, A', A'', A''', E, E', E'', E''', Y, Y', Y'', Y''', M, W, M', W', M'', W'', M''', W''', R$_1$, R$_1$', R$_1$'', R$_1$''', R$_2$, R$_2$', R$_2$'', R$_2$''', R$_3$, Z, Z', U, V, L, T', T'', Q, Q', Q'', Q''', X$_1$, X$_2$, X$_3$, X$_4$, X$_1$', X$_2$', X$_3$', X$_4$', X$_1$'', X$_2$'', X$_3$'', X$_4$'', X$_1$''', X$_2$''', X$_3$''', X$_4$''', M$_{1a}$, M$_{2a}$, M$_{3a}$, M$_{4a}$, R$_{1a}$, R$_{3a}$, R$_3$, Z$_a$, U$_a$, V$_a$, L$_a$, Q$_a$, X$_a$, X$_b$, X$_c$, X$_d$ is selected from a halogen, CN, =O, =S or an optionally substituted substituent selected from the group consisting of OH, SH, NH$_2$, PH$_2$, a hydrocarbon group or a heterohydrocarbon group.

In an embodiment of the present invention, the hydrocarbon group, heterohydrocarbon group are optionally substituted and selected from the group consisting of a C$_{1-12}$ hydrocarbon group, a C$_{1-12}$ heterohydrocarbon group, a C$_{1-12}$ cycloheteroyl group, a C$_{1-12}$ hydrocarbon group substituted by a C$_{1-12}$ cycloheteroyl group, —C$_{1-12}$OH, —C$_{0-12}$COOH, —OC$_{1-12}$COOH, —C$_{1-12}$CN, —C$_{0-12}$C(=O)NH$_2$, —C$_{0-12}$OC$_{1-12}$, —C$_{0-12}$C(=O) C$_{1-12}$, —C$_{0-12}$C(=O)OC$_{1-12}$, —C$_{0-12}$O(O=)CC$_{1-12}$, —C$_{0-12}$S(=O) C$_{1-12}$ or —C$_{0-12}$S(=O)$_2$C$_{1-12}$, wherein, the above-mentioned groups themselves are optionally in the form of an aromatic ring, a hetero-aromatic ring, a cycloaliphatic ring, a hetero-cycloaliphatic ring, an aliphatic chain and/or a hetero-aliphatic chain, and a number of the aromatic ring, hetero-aromatic ring, cycloaliphatic ring, hetero-cycloaliphatic ring, aliphatic chain and/or hetero-aliphatic chain, the ring-forming atom and the number thereof, the linking forms between the rings, the ring and the chain, or the chains can be arbitrary under the premise of stability available in chemistry, each of the heteroatom or heteroatom group is independently selected from O, S, N, S(=O) and/or S(=O)$_2$, the number of the heteroatom or heteroatom group is arbitrary under the premise of stability available in chemistry.

In an embodiment of the present invention, the substituent for substitution is selected from F, Cl, Br, I, CN, OH, SH, NH$_2$, CHO, COOH, or selected from a C$_{1-12}$ alkyl or a heteroalkyl optionally substituted by R$_{01}$, a C$_{3-12}$ cyclic hydrocarbon group or a heterocyclic hydrocarbon group, a C$_{1-12}$ alkyl or a heteroalkyl substituted by a C$_{3-12}$ cyclic hydrocarbon group or a heterocyclic hydrocarbon group;

R$_{01}$ is selected from F, Cl, Br, I, CN, OH, SH, NH$_2$, CHO, COOH, R$_{02}$;

R$_{02}$ is selected from a C$_{1-12}$ alkyl, a C$_{1-12}$ alkyl amino, a N,N-bis(C$_{1-12}$ alkyl) amino, a C$_{1-12}$ alkoxy, a C$_{1-12}$ alkyl acyl, a C$_{1-12}$ alkoxycarbonyl, a C$_{1-12}$ alkyl sulfonyl, a C$_{1-12}$ alkyl sulfinyl, a C$_{3-12}$ cycloalkyl, a C$_{3-12}$ cycloalkyl amino, a C$_{3-12}$ heterocycloalkyl amino, a C$_{3-12}$ cycloalkoxy, a C$_{3-12}$ cycloalkyl acyl, a C$_{3-12}$ cycloalkoxycarbonyl, a C$_{3-12}$ cycloalkyl sulfonyl, a C$_{3-12}$ cycloalkyl sulfinyl;

each of the heteroatom or heteroatom group is independently selected from —C(=O)N(R$_{d3}$)—, —N(R$_{d4}$)—, —C(=NR$_{d5}$)—, —S(=O)$_2$N(R$_{d6}$)—, —S(=O)N(R$_{d7}$)—, —O—, —S—, =O, =S, —C(=O)O—, —C(=O)—, —C(=S)—, —S(=O)— and/or —S(=O)$_2$—;

each of R$_{d3-d7}$ is independently selected from H, R$_{03}$;

R$_{03}$ is selected from a C$_{1-12}$ alkyl, a C$_{1-12}$ alkyl acyl, a C$_{1-12}$ alkoxycarbonyl, a C$_{1-12}$ alkyl sulfonyl, a C$_{1-12}$ alkyl sulfinyl, a C$_{3-12}$ cycloalkyl, a C$_{3-12}$ cycloalkyl acyl, a C$_{3-12}$ cycloalkoxycarbonyl, a C$_{3-12}$ cycloalkyl sulfonyl, a C$_{3-12}$ cycloalkyl sulfinyl;

R$_{02}$, R$_{03}$ are optionally substituted by R$_{001}$;

R$_{001}$ is selected from F, Cl, Br, I, CN, OH, N(CH$_3$)$_2$, NH(CH$_3$), NH$_2$, CHO, COOH, trifluoromethyl, aminomethyl, hydroxymethyl, methyl, methoxy, formyl, methoxycarbonyl, methylsulphonyl, methylsulfinyl;

A number of R$_{01}$, R$_{001}$, the heteroatom or the heteroatom group is independently selected from 0, 1, 2 or 3.

In an embodiment of the present invention, the substituent for substitution is selected from a halogen, OH, SH, NH$_2$, PH$_2$, CN, =O, =S, CF$_3$, —OCF$_3$, —OCH$_3$.

In an embodiment of the present invention, the substituent in Z, Z', Z$_a$ is selected from a C$_{1-6}$ alkyl which is unsubstituted or substituted by a halogen or a hydroxyl or an amino, a C$_{2-6}$ alkenyl or alkynyl which is unsubstituted or substituted by a halogen or a hydroxyl or an amino, an optionally substituted NH$_2$, an optionally substituted 5- to 12-membered cyclic group or heterocyclic group, the substituent in NH$_2$ is selected from a C$_{1-6}$ alkyl, a C$_{5-8}$ heterocyclic group, a C$_{1-6}$ alkyl substituted by a C$_{5-8}$ heterocyclic group or a C$_{1-6}$ alkyl substituted by a C$_{5-8}$ cycloheteroyl group, a number of the substituent in NH$_2$ is 1 or 2, the heteroatom or heteroatom group is selected from O, S, N, S(=O) or S(=O)$_2$.

In an embodiment of the present invention, the substituent in Z, Z', Z$_a$ is selected from CF$_3$,

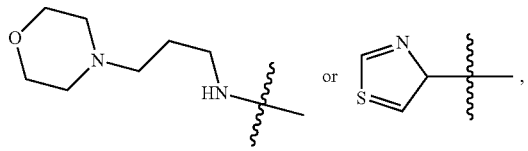

a number of the substituent is 1 or 2.

In an embodiment of the present invention, the substituent in L, L$_a$ is selected from a C$_{1-6}$ alkyl which is unsubstituted or substituted by a halogen or a hydroxyl or an amino, —C(=O)OC$_{1-6}$ alkyl, —C(=O)O alkylenebenzene, —C(=O) C$_{1-6}$ alkyl, —S(=O)$_2$C$_{1-6}$ alkyl, a C$_{1-6}$ cycloalkyl or a C$_{1-6}$ heterocycloalkyl, —S(=O)$_2$C$_{3-5}$ cycloalkyl, —C(=O)C$_{3-5}$ cycloalkyl, —C(=O)OC$_{3-6}$ cycloalkyl, —CHO, the heteroatom is selected from O, S or N, a number of the heteroatom is 1 or 2.

In an embodiment of the present invention, the substituent in L, L$_a$ is selected from a methyl, —C(=O)OC(CH$_3$)$_3$, —C(=O)OCH(CH$_3$)$_2$, a benzyloxycarbonyl, —C(=O)CH(CH$_3$)$_2$, —S(=O)$_2$CH$_3$,

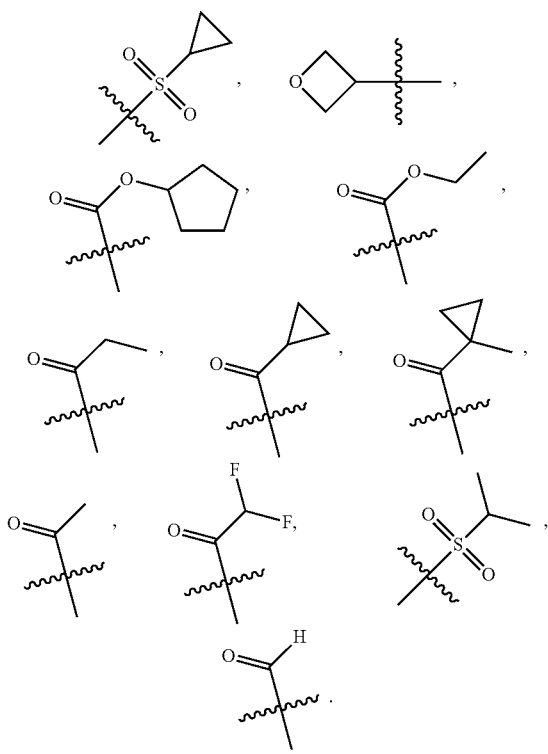

Another aim of the present invention is to provide a compound represented by formula (IX) or a pharmaceutically acceptable salt thereof,

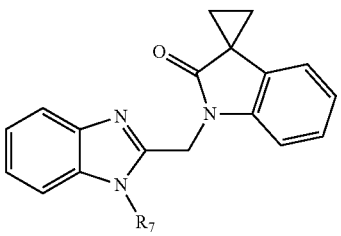

Wherein,
R$_7$ is selected from —R$_{8a}$OR$_{8b}$,

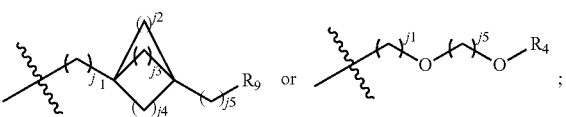

R$_{8a}$ is selected from a —C$_{1-10}$ hydrocarbon group optionally substituted by a halogen, a methyl, a trifluoromethyl or a methoxyl;

R$_{8b}$ is selected from an ester of phosphonic acid, a phosphonate, an ester of sulfonic acid, a sulfonate, an ester of sulfinic acid or a sulfinate;

each of j$_{1-5}$ is independently selected from 0, 1, 2, 3;

R$_9$ is selected from CN, OR$_{9a}$, C(=O)R$_{9b}$;

R$_{9a}$ is selected from H, an ester of phosphonic acid, a phosphonate, an ester of sulfonic acid, a sulfonate, an ester of sulfinic acid or a sulfinate;

R$_{9b}$ is selected from H, a substituent selected from the group consisting of OH, NH$_2$ or —OC$_{1-6}$ which is optionally substituted by a halogen, a methyl, a trifluoromethyl or a methoxyl;

R$_4$ is selected from an ester of phosphonic acid, a phosphonate, an ester of sulfonic acid, a sulfonate, an ester of sulfinic acid, a sulfinate or H.

In an embodiment of the present invention, R$_{8a}$ is selected from

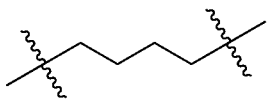

In an embodiment of the present invention, the structural unit

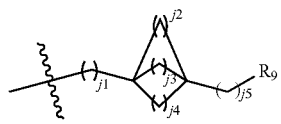

is selected from

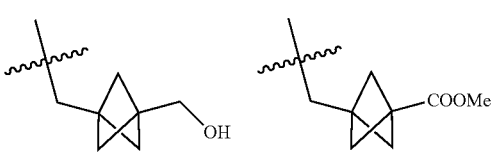

-continued

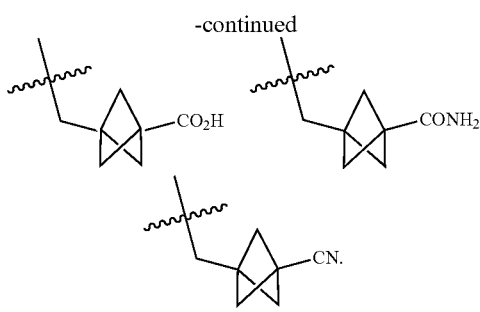

In an embodiment of the present invention, the structural unit

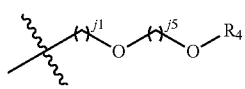

is selected from

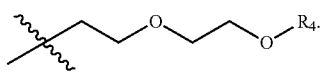

In an embodiment of the present invention, $R_{8b}$ or $R_{9a}$ is selected from $-P(=O)(OC_2H_5)_2$, $-P(=O)(ONa)_2$ or $-P(=O)(OK)_2$.

The following embodiments are preferred in the present invention:

62) Isopropyl 1'-((1-(4-hydroxybutyl)-4,5,6,7-tetrahydro-1H-benzo[d]imidazol-2-yl)methyl)-2'-oxospiro[azetidine-3,3'-indoline]-1-carboxylate;
63) 1'-((1-(4-Hydroxybutyl)-4,5,6,7-tetrahydro-1H-benzo[d]imidazol-2-yl)methyl)spiro[cyclopropane-1,3'-indoline]-2'-one;
64) Isopropyl 1'-((1-(4,4-difluorobutyl)-4,5,6,7-tetrahydro-1H-benzo[d]imidazol-2-yl)methyl)-2'-oxospiro[azetidine-3,3'-indoline]-1-carboxylate;
65) Isopropyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
66) Isopropyl 2'-oxo-1'-((1-(2,2,4-trifluorobutyl)-4,5,6,7-tetrahydro-1H-benzo[d]imidazol-2-yl)methyl)spiro[azetidine-3,3'-indoline]-1-carboxylate;
67) Isopropyl 1'-((1-(2,2-difluorobutyl)-4,5,6,7-tetrahydro-1H-benzo[d]imidazol-2-yl)methyl)-2'-oxospiro[azetidine-3,3'-indoline]-1-carboxylate;
68) Isopropyl 1'-((1-(3-methyl-2-oxobutyl)-4,5,6,7-tetrahydro-1H-benzo[d]imidazol-2-yl)methyl)-2'-oxospiro[azetidine-3,3'-indoline]-1-carboxylate;
69) Isopropyl 1'-((1-(2,2-difluoro-3-methylbutyl)-4,5,6,7-tetrahydro-1H-benzo[d]imidazol-2-yl)methyl)-2'-oxospiro[azetidine-3,3'-indoline]-1-carboxylate;
70) (Z)-isopropyl 1'-((1-(2-fluoro-3-methylbut-1-en-1-yl)-4,5,6,7-tetrahydro-1H-benzo[d]imidazol-2-yl)methyl)-2'-oxospiro[azetidine-3,3'-indoline]-1-carboxylate;
71) Isopropyl 1'-((1-(2-fluoro-3-methylbut-2-en-1-yl)-4,5,6,7-tetrahydro-1H-benzo[d]imidazol-2-yl)methyl)-2'-oxospiro[azetidine-3,3'-indoline]-1-carboxylate;
72) Ethyl 1'-((1-isopentyl-4,5,6,7-tetrahydro-1H-benzo[d]imidazol-2-yl)methyl)-2'-oxospiro[azetidine-3,3'-indoline]-1-carboxylate;
73) Ethyl 1'-((1-(3-fluorobutyl)-4,5,6,7-tetrahydro-1H-benzo[d]imidazol-2-yl)methyl)-2'-oxospiro[azetidine-3,3'-indoline]-1-carboxylate;
74) Ethyl 1'-((1-(3-cyanopropyl)-4,5,6,7-tetrahydro-1H-benzo[d]imidazol-2-yl)methyl)-2'-oxospiro[azetidine-3,3'-indoline]-1-carboxylate;
75) Ethyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
76) Ethyl 1'-((1-(3-(methyl sulfonyl)propyl)-4,5,6,7-tetrahydro-1H-benzo[d]imidazol-2-yl)methyl)-2'-oxospiro[azetidine-3,3'-indoline]-1-carboxylate;
77) Cyclopentyl 1'-((1-(3-hydroxybutyl)-4,5,6,7-tetrahydro-1H-benzo[d]imidazol-2-yl)methyl)-2'-oxospiro[azetidine-3,3'-indoline]-1-carboxylate;
78) Isopropyl 5'-bromo-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate;
79) Isopropyl 5'-bromo-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
80) Isopropyl 5'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
81) Isopropyl 6'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
82) Isopropyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
83) Ethyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
84) 1-(Cyclopropanecarbonyl)-6'-fluoro-1'-((1-(4,4,4-trifluorobutyl)-4,5,6,7-tetrahydro-1H-benzo[d]imidazol-2-yl)methyl)spiro[azetidine-3,3'-indoline]-2'-one;
85) Isopropyl 4'-chloro-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate;
86) Isopropyl 4'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
87) Ethyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate;
88) Isopropyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate;
89) 1-(Cyclopropanecarbonyl)-1'-((1-(4,4,4-trifluorobutyl)-4,5,6,7-tetrahydro-1H-benzo[d]imidazol-2-yl)methyl)spiro[azetidine-3,3'-pyrrolo[2,3-c]pyridine]-2'(1'H)-one;
90) 2'-Oxo-1'-((1-(4,4,4-trifluorobutyl)-4,5,6,7-tetrahydro-1H-benzo[d]imidazol-2-yl)methyl)spiro[azetidine-3,3'-indoline]-1-carbaldehyde;
91) 1-(1-Methylcyclopropanecarbonyl)-1'-((1-(4,4,4-trifluorobutyl)-4,5,6,7-tetrahydro-1H-benzo[d]imidazol-2-yl)methyl)spiro[azetidine-3,3'-pyrrole[2,3-c]pyridine]-2'-one;
92) 1-Acetyl-1'-((1-(4,4,4-trifluorobutyl)-4,5,6,7-tetrahydro-1H-benzo[d]imidazol-2-yl)methyl)spiro[azetidine-3,3'-indoline]-2'-one;
93) 1-(Cyclopropanecarbonyl)-1'-((1-(4,4,4-trifluorobutyl)-4,5,6,7-tetrahydro-1H-benzo[d]imidazol-2-yl)methyl)spiro[azetidine-3,3'-indoline]-2'-one;

94) 1-Propionyl-1'-((1-(4,4,4-trifluorobutyl)-4,5,6,7-tetrahydro-1H-benzo[d]imidazol-2-yl)methyl)spiro[azetidine-3,3'-indoline]-2'-one;
95) 1-Isobutyryl-1'-((1-(4,4,4-trifluorobutyl)-4,5,6,7-tetrahydro-1H-benzo[d]imidazol-2-yl)methyl)spiro[azetidine-3,3'-indoline]-2'-one;
96) 1-(2,2-Difluoroacetyl)-1'-((1-(4,4,4-trifluorobutyl)-4,5,6,7-tetrahydro-1H-benzo[d]imidazol-2-yl)methyl)spiro[azetidine-3,3'-indoline]-2'-one;
97) 1-(Methyl sulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one;
98) 1-(Cyclopropylsulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one;
99) 1-(Isopropylsulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one;
100) 1'-((1-(4-hydroxybutyl)-4,5-dimethyl-1H-imidazol-2-yl)methyl)-2'-oxospiro[azetidine-3,3'-indoline]-1-carboxylate;
101) Ethyl 1'-((4,5-diethyl-1-(4-hydroxybutyl)-1H-imidazol-2-yl)methyl)-2'-oxospiro[azetidine-3,3'-indoline]-1-carboxylate;
102) Isopropyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate;
103) Isopropyl 1'-((1-(4-hydroxybutyl)-1,4,5,6-tetrahydrocyclopenta[d]imidazol-2-yl)methyl)-2'-oxospiro[azetidine-3,3'-indoline]-1-carboxylate;
104) Ethyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate;
105) 1-Isobutyryl-1'-((1-(4,4,4-trifluorobutyl)-1,4,5,6-tetrahydrocyclopenta[d]imidazol-2-yl)methyl)spiro[azetidine-3,3'-indoline]-2'-one;
106) 1-(Methyl sulfonyl)-1'-((1-(4,4,4-trifluorobutyl)-1,4,5,6-tetrahydrocyclopenta[d]imidazol-2-yl)methyl)spiro[azetidine-3,3'-indoline]-2'-one;
107) Isopropyl 1'-((1-(but-3-en-1-yl)-4,5,6,7-tetrahydro-1H-benzo[d]imidazol-2-yl)methyl)-6'-chloro-2'-oxospiro[azetidine-3,3'-indoline]-1-carboxylate;
108) Isopropyl 2'-oxo-1'-((7-oxo-1-(4,4,4-trifluorobutyl)-4,5,6,7-tetrahydro-1H-benzo[d]imidazol-2-yl)methyl)spiro[azetidine-3,3'-indoline]-1-carboxylate;
109) Isopropyl 1'-((7-hydroxy-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate;
110) Ethyl 1'-((4-methyl-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate;

Optionally, the above-mentioned compound or the pharmaceutically acceptable salt thereof contains one or more chiral centers.

Another aim of the present invention is to provide a pharmaceutical composition, which comprises a therapeutically effective amount of the above-mentioned compound or the pharmaceutically acceptable salt thereof, and a pharmaceutically acceptable carrier.

Another aim of the present invention is to provide a use of the above-mentioned compound or the pharmaceutically acceptable salt or the pharmaceutical composition thereof in manufacturing a medicament for treating respiratory syncytial virus infection.

When $R_4$ is selected from an ester of phosphonic acid, a phosphonate, an ester of sulfonic acid, a sulfonate, an ester of sulfinic acid and a sulfinate, the corresponding structure represents a prodrug, the water solubility of which is greatly improved so as to be suitable for intravenous or intramuscular injection.

$C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$.

The $C_{1-12}$ alkyl or heteroalkyl, $C_{3-12}$ cyclic group or heterocyclic hydrocarbon group, a $C_{1-12}$ alkyl or heteroalkyl substituted by a $C_{3-12}$ cyclic hydrocarbon group or heterocyclic hydrocarbon group includes but not limited to:

a $C_{1-12}$ alkyl, a $C_{1-12}$ alkyl amino, a N,N-bis($C_{1-12}$ alkyl) amino, a $C_{1-12}$ alkoxyl, a $C_{1-12}$ alkyl acyl, a $C_{1-12}$ alkoxycarbonyl, a $C_{1-12}$ alkyl sulfonyl, a $C_{1-12}$ alkyl sulfinyl, a $C_{3-12}$ cycloalkyl, a $C_{3-12}$ cycloalkyl amino, a $C_{3-12}$ heterocycloalkyl amino, a $C_{3-12}$ cycloalkoxy, a $C_{3-12}$ cycloalkyl acyl, a $C_{3-12}$ cycloalkoxycarbonyl, a $C_{3-12}$ cycloalkyl sulfonyl, a $C_{3-12}$ cycloalkyl sulfinyl;

a methyl, an ethyl, a n-propyl, an isopropyl, —CH$_2$C(CH$_3$)(CH$_3$)(OH), a cyclopropyl, a cyclobutyl, a propyl methylene, a cyclopropionyl, a benzyloxy, a trifluoromethyl, an aminomethyl, a hydroxymethyl, a methoxy, a formyl, a methoxy carbonyl, a methyl sulfonyl, a methyl sulfinyl, an ethoxy, an acetyl, an ethyl sulfonyl, an ethoxy carbonyl, a dimethylamino, a diethylamino, a dimethyl amino carbonyl, a diethyl amino carbonyl;

N(CH$_3$)$_2$, NH(CH$_3$), —CH$_2$CF$_3$, —CH$_2$CH$_2$CF$_3$, —CH$_2$CH$_2$F, —CH$_2$CH$_2$S(=O)$_2$CH$_3$, —CH$_2$CH$_2$CN,

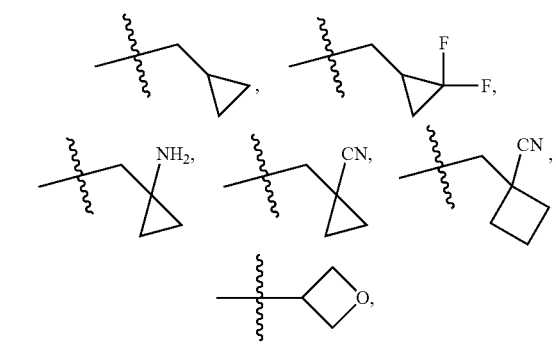

—CH$_2$CH(OH)(CH$_3$)$_2$, —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$OCH$_3$, —CH$_2$CH$_2$CH$_2$OCH$_3$, —CH$_2$CH$_2$N(CH$_3$)$_2$, —S(=O)$_2$CH$_3$, —CH$_2$CH$_2$S(=O)$_2$CH$_3$,

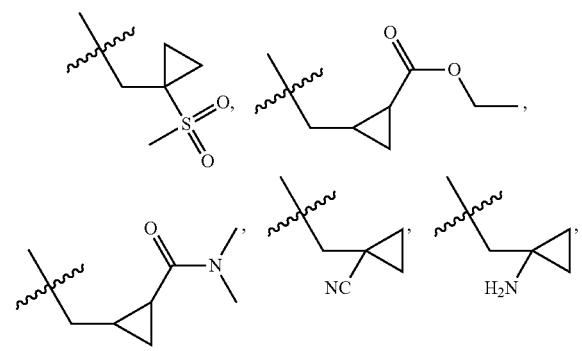

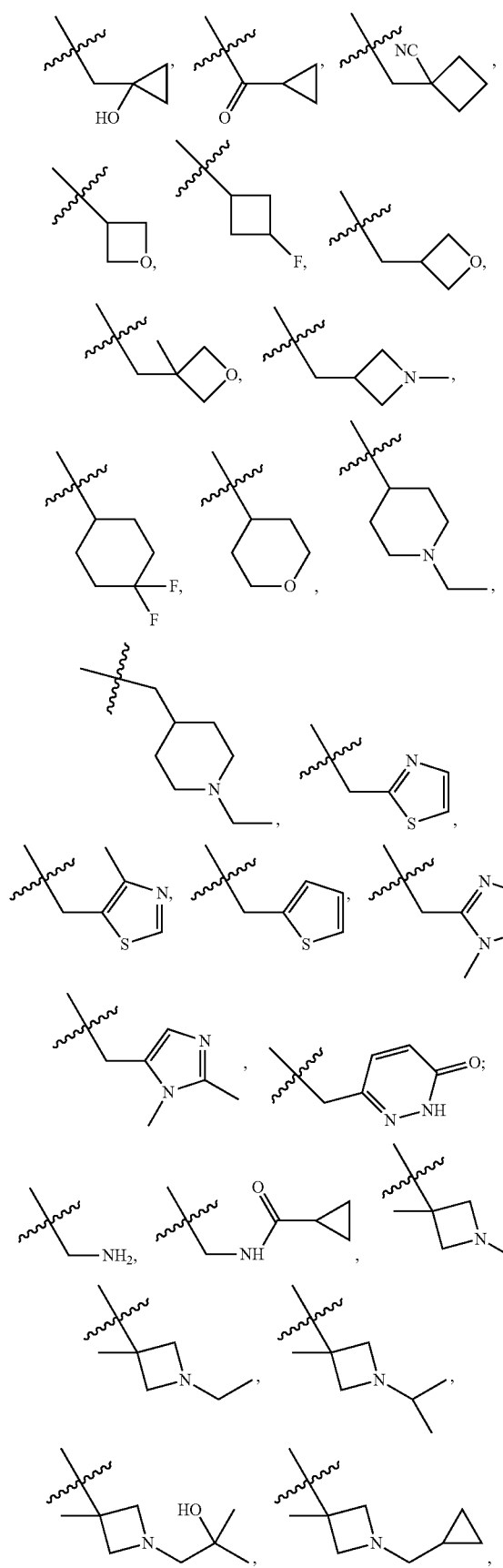
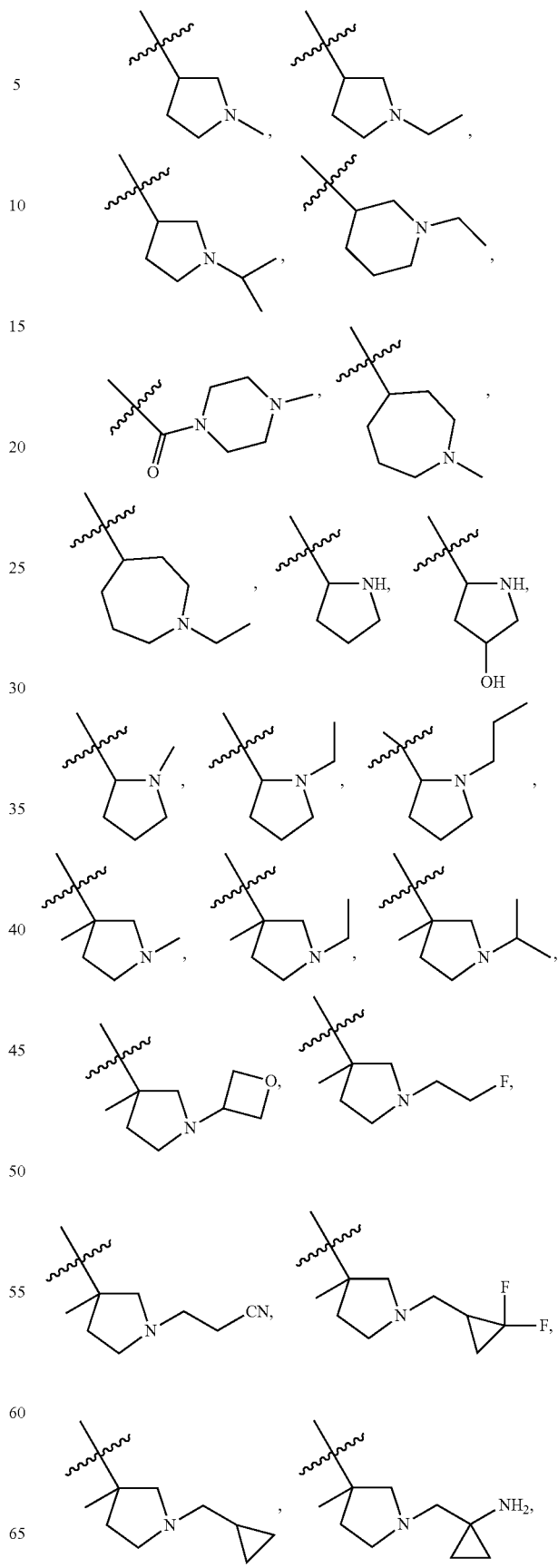

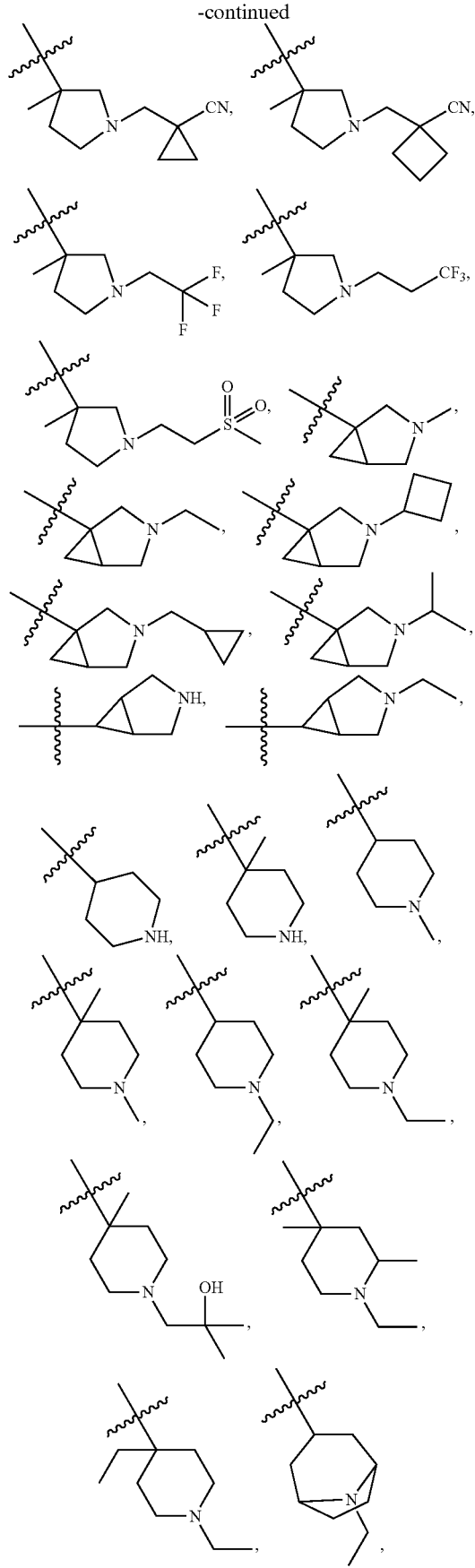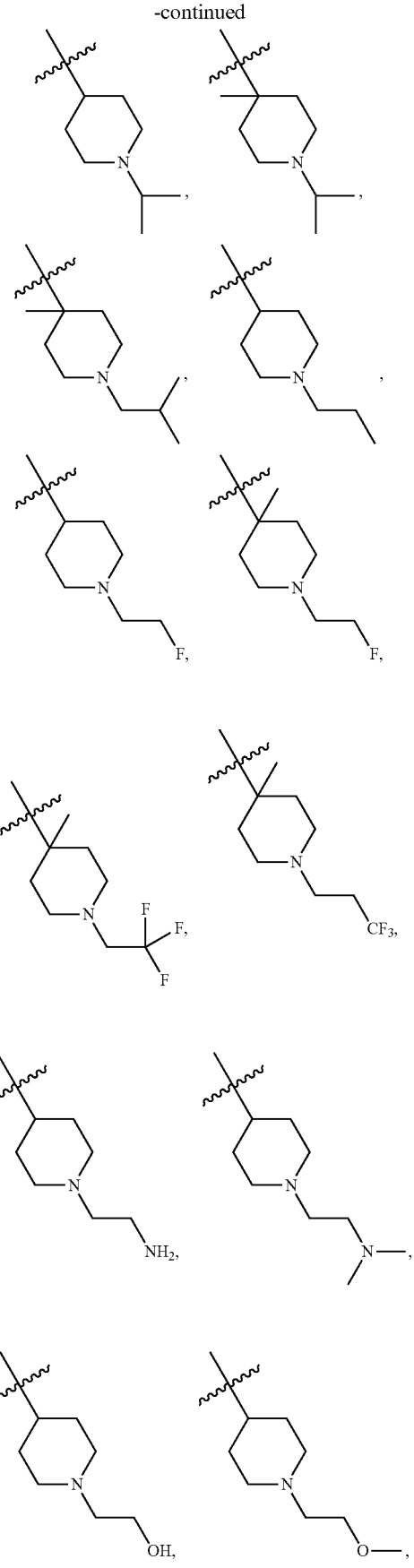

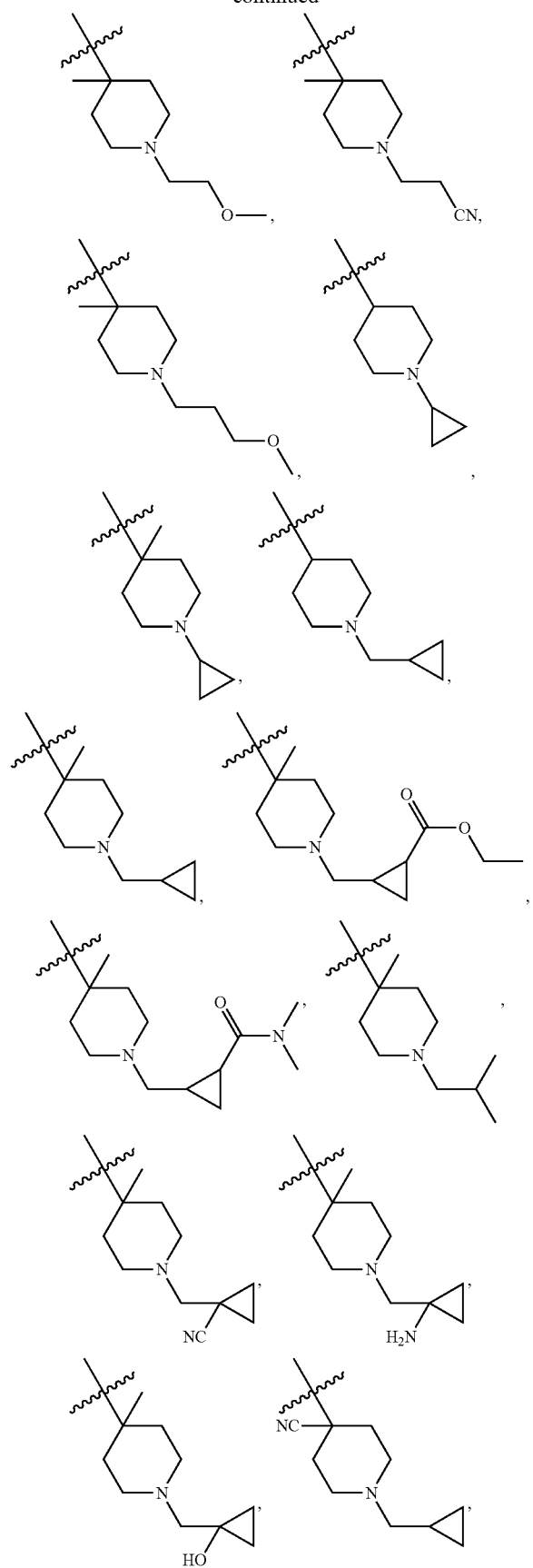
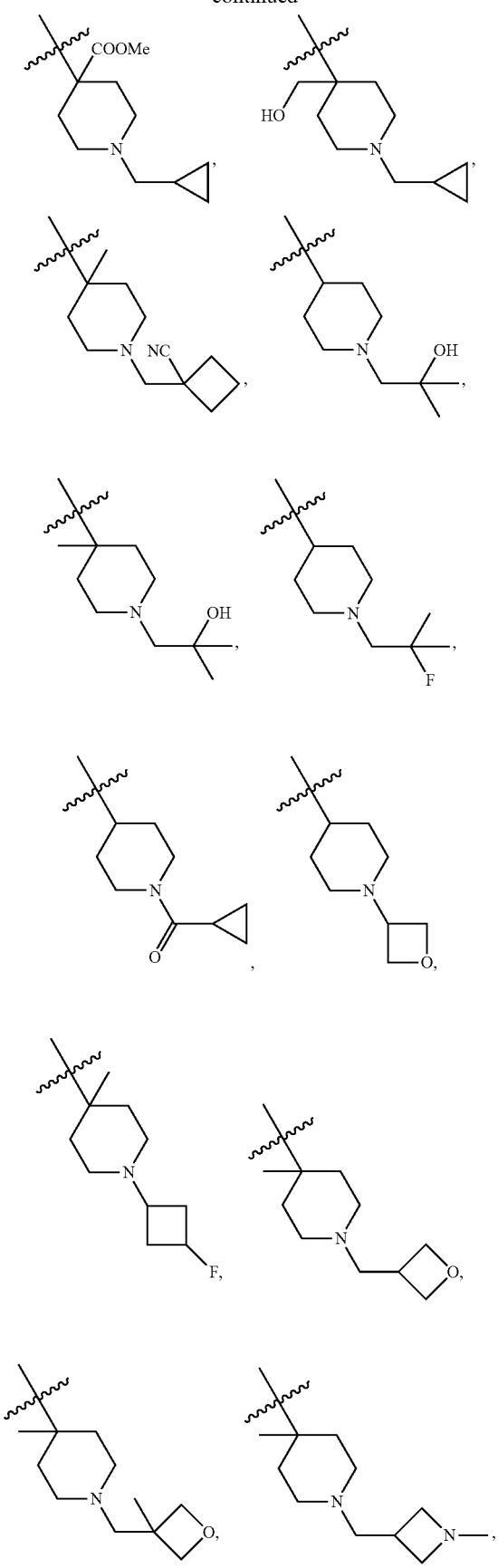

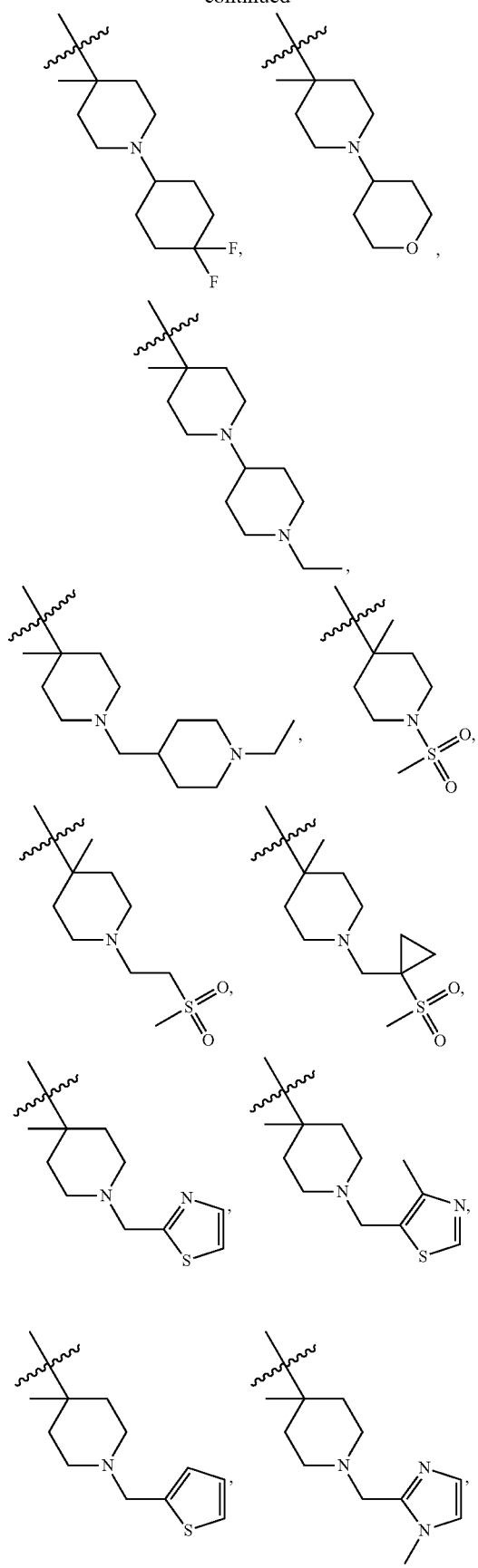
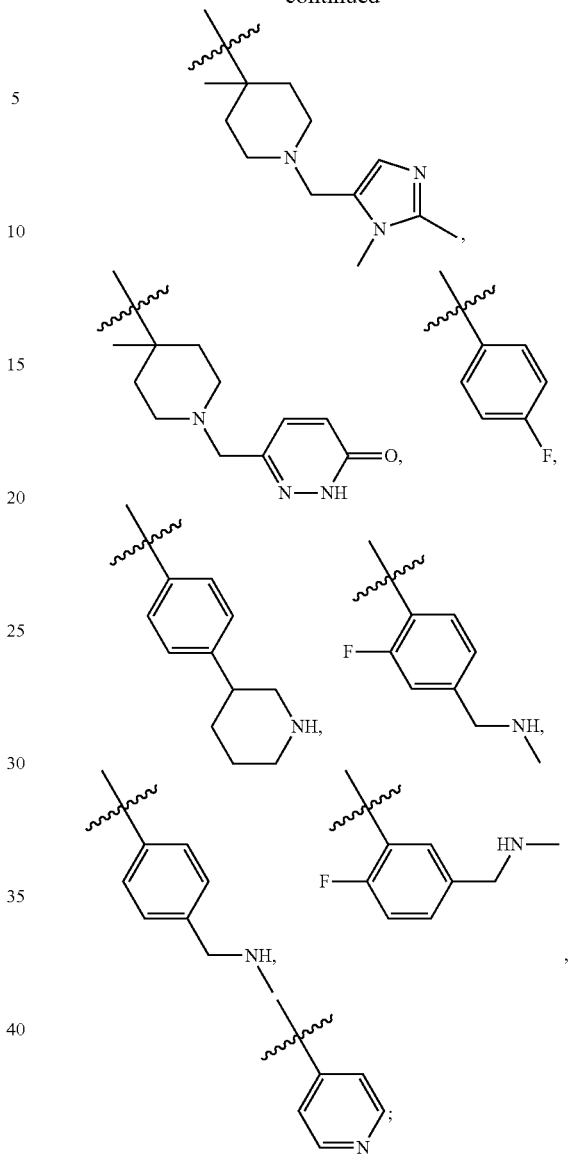

a phenyl, a thiazolyl, a biphenyl, a naphthyl, a cyclopentyl, a furyl, a 3-pyrrolinyl, a pyrrolidinyl, a 1,3-dioxanyl, a pyrazolyl, a 2-pyrazolinyl, a pyrazolidinyl, an imidazolyl, an oxazolyl, a thiazolyl, a 1,2,3-azolyl, a 1,2,3-triazolyl, a 1,2,4-triazolyl, a 1,3,4-thiadiazolyl, a 4H-pyranyl, a pyridyl, a piperidyl, a 1,4-dioxanyl, a morpholinyl, a pyridazinyl, a pyrimidinyl, a pyrazinyl, a piperazinyl, a 1,3,5-trithianyl, a 1,3,5-triazinyl, a benzofuranyl, a benzothiophenyl, an indolyl, a benzimidazolyl, a benzothiazolyl, a purinyl, a quinolinyl, an isoquinolinyl, a cinnolinyl or a quinoxalinyl;

Herein, the term "pharmaceutically acceptable" is aimed at those compounds, materials, compositions and/or dosage forms, which are within the scope of reliable medical judgment and applicable for use in contact with human and animal tissue but without too much toxicity, irritation, allergic reactions or other problems or complications, also meet the reasonable benefit/risk ratio.

The term "pharmaceutically acceptable salt" refers to the salt of the compound of the present invention, which is prepared by the compound with specific substituent discovered by the present invention and relatively non-toxic acid or alkali. When the compound of the present invention contains a relatively acidic functional group, an alkali-addition salt can be obtained by contacting the compound in a neutral form with sufficient amount of alkali in a pure solution or suitable inert solvent. The pharmaceutically acceptable alkali-addition salt includes the salt of sodium, potassium, calcium, ammonium, organic ammonia or magnesium or the like. When the compound of the present invention contains a relatively alkaline functional group, an acid-addition salt can be obtained by contacting the compound in a neutral form with sufficient amount of acid in a pure solution or suitable inert solvent. Examples of the pharmaceutically acceptable acid-addition salt include a salt of inorganic acid, the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid etc; and salt of organic acid, the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes salt of amino acid (e.g. arginine etc.), and salt of organic acid such as glucuronic acid and the like (see Berge et al., "Pharmaceutical Salts", Journal of Pharmaceutical Science 66: 1-19 (1977)). Some specific compound of the present invention contains both alkaline and acidic functional groups so as to be transformed to be any alkali-addition or acid-addition salt.

Preferably, the neutral form of a compound is regenerated by contacting a salt with a base or an acid in a conventional manner and then separating the parent compound. The difference between a parent form of a compound and the various salt forms lies in some physical properties, such as that the solubility in a polar solvent is different.

The "pharmaceutically acceptable salt" in the present invention is the derivatives of the compound of the present invention, wherein, the parent compound is modified by salifying with an acid or an alkali. Examples of the pharmaceutically acceptable salt include but not limited to: an inorganic acid or organic acid salt of an alkali such as amine, an alkali metal or organic salt of acid radical such as carboxylic acid and so on. The pharmaceutically acceptable salt includes conventionally non-toxic salts or quaternary ammonium salts of the parent compound, such as a salt formed by a non-toxic inorganic acid or organic acid. The conventionally non-toxic salt includes but not limited to those salts derived from inorganic acids and organic acids, the inorganic acids or organic acids are selected from 2-acetoxybenzoic acid, 2-isethionic acid, acetic acid, ascorbic acid, phenylsulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthoic, isethionic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonan, propionic acid, salicylic acid, stearic acid, folinate acid, succinic acid, aminosulfonic acid, sulfanilic acid, sulphuric acid, tannic acid, tartaric acid and p-toluene sulfonic acid.

The pharmaceutically acceptable salt of the present invention can be prepared by a conventional method with a parent compound containing an acidic or alkaline group. Generally, the preparation method of the salt comprises that in water or an organic solvent or the mixture of water and organic solvent, reacting these compounds in forms of free acids or alkalis with stoichiometric amount of proper alkalis or acids. In general, preferably choose non-aqueous media such as ether, ethyl acetate, ethanol, isopropanol or acetonitrile and so on.

Except for the form of salt, there is a form of prodrug for the compound in the present invention. The prodrug of the compound described in the present invention is easily transformed to be the compound of the present invention via chemical changes under physiological conditions. Besides, the prodrug can be transformed to be the compound of the present invention via chemical or biochemical method in vivo environment.

Some compounds of the present invention can exist in the form of non-solvate or solvate forms, including hydrate forms. In general, the solvate form is similar to the non-solvate form, both of which are included within the scope of the present invention. Some compounds of the present invention can exist in polycrystalline or amorphous form.

Some compounds of the present invention can contain asymmetric carbon atoms (optical center) or double bonds. The racemic isomers, diastereomers, geometric isomers and single isomers are included within the scope of the present invention.

The diagrammatic representation of the racemic isomer, the ambiscalemic and scalemic or the enantiopure compound of the present invention is from Maehr, J. Chem. Ed. 1985, 62: 114-120. Unless otherwise indicated, the absolute configuration of a stereocenter is represented by the wedge and dashed lines. When the compound of the present invention contains a vinyl double bond or other geometric asymmetric center, unless otherwise specified, E, Z geometric isomers are included. Similarly, all tautomeric forms are included within the scope of the present invention.

The compound of the present invention may exist as a specific geometric or stereoisomeric isomer. The present invention envisages all of this class of compounds, including cis- and trans-isomers, (−)- and (+)-antimers, (R)- and (S)-antimers, diastereomers, (D)-isomer, (L)-isomer, as well as racemic mixtures and other mixtures, such as enantiomers- or diastereoisomers-enriched mixtures, all of these mixtures are within the scope of the present invention. Other asymmetric carbon atoms may exist in substituents such as in an alkyl. All of these isomers and their mixtures are included within the scope of the present invention.

Optically active (R)- and (S)-isomers, (D)- and (L)-isomers can be prepared by asymmetric synthesis or chiral reagents or other conventional techniques. If an enantiomer of a compound of the present invention are wanted, asymmetric synthesis or derivatization action of the chiral auxiliaries can be employed in preparation, in which the resulting diastereomer mixtures are isolated, and the auxiliary groups are cleaved to provide the pure desired enantiomer. Or, when a molecule contains an alkaline functional group (such as amino) or an acidic functional groups (such as carboxyl), a salt of diastereomer is formed with an appropriate optical active acid or alkali, and then the pure enantiomer can be recycled after separated by the fractional crystallization or chromatography method which is known in the art. In addition, the separation of an enantiomer and a diastereomer is usually realized by the chromatographic method, the chromatography method employs a chiral stationary phase, and optionally combined with the chemical derivatization method (e.g. an amine generates a carbamate).

One or more atoms constituting the compound of the present invention may comprise an unnatural proportion of atomic isotopes. For example, the compound can be labeled by a radioactive isotope, such as tritium ($^3H$), iodine-125 ($^{125}I$) or C-14 ($^{14}C$). All the variations in the isotopic composition of the compound disclosed in the present invention, whether radioactive or not, are included within the scope of the present invention.

The term "a pharmaceutically acceptable carrier" refers to any formulation or carrier medium which is capable of delivering effective amount of the active substance disclosed in the present invention, does not interfere with the biological activity of the active substance, and is with no toxic side-effects on host or patient, representative carrier includes water, oil, vegetables and minerals, cream base, lotion matrix, ointment matrix etc. The matrix comprises a suspension, a viscosity increaser, transdermal enhancers etc. Their formulation are well known to the person in cosmetic or topical drug art. Other information about the carrier can refer to Remington: The Science and Practice of Pharmacy, 21st Ed., Lippincott, Williams & Wilkins (2005), the content of which is incorporated into this article as reference.

The term "excipient" usually refers to a carrier, diluent and/or medium required for the preparation of an effective pharmaceutical composition.

In terms of drug or pharmacological active agent, the term "effective amount" or "therapeutically effective amount" refers to enough quantity of the drug or formulation that can achieve desired effects but is with no toxicity. For the oral formulation of the present invention, "an effective amount" of one active substance in the composition is the amount required to achieve desired effects in combination with another active substance in the composition. The determination of the effective amount varies from person to person, which depends on the age and the general situation of the recipient, also on the specific active substance. In one case, an appropriate effective amount can be determined by the person skilled in the art according to conventional tests.

The term "active ingredient", "therapeutic agent", "active substance" or "active agent" refers to a chemical entity, which can effectively treat disorder, illness or disease of a target subject.

The term "substituted" refers to one or more hydrogen atoms in a specific atom optionally substituted by a substituent, including a deuterium and a variant of hydrogen, as long as the valence state of the specific atom is normal and the compound obtained after substitution is stable. When the substituent is a ketone group (i.e. =O), it means that two hydrogen atoms are substituted. A substitution of ketone group does not occur in an aryl. The term "optionally substituted" means that it may be substituted or not be substituted, unless otherwise specified, the type and number of substituents can be arbitrary under the premise of stability available in chemistry.

When any parameter (e.g. R) shows an occurrence for more than one time in the composition or structure of the compound, the definition of each occurrence is independent. Therefore, for example, if a group is substituted by 0-2 of R, the group may optionally be substituted by at most two R, and R has an independent option in each case. In addition, the combination of substituents and/or their variants is allowed only if such a combination will lead to a stable compound.

When bonds of a substituent can be crossly connected to two atoms of a ring, the substituent can be bonded to arbitrary atoms in the ring. When the listed substituent does not specify through which atom it is connected to the general structure formula including the compound that is not specifically mentioned, the substituent can be bonded through any of its atoms. The combination of substituents and/or their variants is allowed only if such a combination will lead to a stable compound. For example, the structural unit

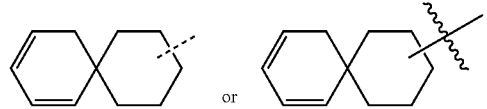

represents that the connection can occur on any atom in the cyclohexyl or cyclic dienyl.

The substituent in alkyl and heteroalkyl group is generally called "alkyl substituent", which can be selected from but not limited to the group consisting of —R', —OR', =O, =NR', =N—OR', —NR'R", —SR', halogen, —SiR'R"R''', OC(O)R', —C(O)R', —CO$_2$R', —C(=O)NR'R", —OC(O)NR'R", —NR"C(O)R', NR'C(O)NR"R''', —NR"C(O)$_2$R', —NR''''-C(NR'R"R''')=NR'''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$ and fluoro($C_1$-$C_4$)alkyl, the number of the substituent is between 0 and (2m'+1), wherein m' is the total number of the carbon atoms in the group. R', R", R''', R'''' and R''''' are independently selected from H, substituted or unsubstituted heteroalkyl, substituted or unsubstituted aryl (e.g. aryl substituted by 1~3 of halogen), substituted or unsubstituted alkyl, alkoxy, thioalkoxy or aralkyl. When the compound of the present invention includes more than one R group, for example, each of the R group is independently selected, as each of R', R", R''', R'''' and R''''' group is when more than one of them are included. When R' and R" are attached to the same nitrogen atom, they can form 5-, 6-, or 7-membered ring together with the nitrogen atom. For example, —NR'R" includes but not limited to 1-pyrrolidinyl and 4-morpholinyl. According to the above discussion on substituent, the person skilled in the art can understand, the term "alkyl" is intended to include a group formed by bonding a carbon atom to a non-hydrogen group, such as a halogenated alkyl (e.g. —CF$_3$, —CH$_2$CF$_3$) and an acyl (e.g. —C(O)CH$_3$, —C(O)CF$_3$, C(O)CH$_2$OCH$_3$, etc.).

Similar to the substituent in the alkyl group, the substituent in aryl and heteroaryl group is generally called "aryl substituent", which can be selected from such as —R', —OR', —NR'R", —SR', -halogen, —SiR'R"R''', OC(O)R', —C(O)R', —CO$_2$R', —C(=O)NR'R", —OC(O)NR'R", —NR"C(O)R', NR' C(O)NR"R''', —NR"C(O)$_2$R', —NR''''—C(NR'R"R''')=NR'''', NR'''' C(NR'R")=NR''', —S(O)R', —S(O)$_2$R', —S(O)$_2$NR'R", NR"SO$_2$R', —CN, —NO$_2$, —N$_3$, —CH(Ph)$_2$, fluoro($C_1$-$C_4$) alkoxy and fluoro ($C_1$-$C_4$)alkyl, etc., a number of the substituent ranges from 0 to the total opening valence of the aromatic ring; wherein R', R", R''', R'''' and R''''' are independently and preferably selected from H, substituted or unsubstituted alkyl, substituted or unsubstituted heteroalkyl, substituted or unsubstituted aryl and substituted or unsubstituted heteroaryl. When the compound of the present invention includes more than one R group, for example, each of the R group is independently selected, as each of R', R", R''', R'''' and R''''' group is when more than one of them are included.

Two substituents attached to adjacent atoms in an aryl or a heteroaryl ring can optionally be substituted by a substituent with a general formula as -T-C(O)—(CRR')q-U—, wherein the T and U are independently selected from —NR—, —O—, CRR'— or a single bond, q is an integer from 0 to 3. As an alternative, two substituents attached to adjacent atoms in an aryl or a heteroaryl ring can optionally be substituted by a substituent with a general formula as -A (CH$_2$)r B—, wherein the A and B are independently selected from —CRR'—, —O—, —NR—, —S—, —S(O)—, S(O)$_2$—, —S(O)$_2$NR'— or a single bond, r is an integer from 1 to 4. Optionally, a single bond in the new ring thereby formed can be replaced by a double bond. As an alternative, two substituents attached to adjacent atoms in an aryl or a heteroaryl ring can optionally be substituted by a substituent with a general formula as -A (CH$_2$)r B—, wherein the s and d are independently selected from an integer from 0 to 3, X is —O—, —NR', —S—, —S(O)—, —S(O)$_2$— or —S(O)$_2$NR'—. The substituent R, R', R'' and R''' are respectively and preferably selected from hydrogen and substituted or unsubstituted (C$_1$-C$_6$) alkyl.

Unless otherwise specified, the term "halogenated" or "halogen" itself or as a part of another substituent refers to fluorine, chlorine, bromine or iodine atom. In addition, the term "halogenated alkyl" is intended to include monohalogenated alkyl and polyhalogenated alkyl. For example, the term "halogenated (C$_1$-C$_4$) alkyl" is intended to include but not limited to trifluoromethyl, 2, 2, 2-trifluoroethyl, 4-chlorobutyl and 3-bromopropyl, etc.

Examples of halogenated alkyl include but not limited to: trifluoromethyl, trichloromethyl, pentafluoroethyl, and pentachloroethyl. The alkoxy represents that the alkyl group with a specific number of carbon atoms is connected by an oxygen bridge. The C$_{1-6}$ alkoxy includes C$_1$, C$_2$, C$_3$, C$_4$, C$_5$ and C$_6$ alkoxy. Examples of alkoxy include but not limited to: methoxy, ethoxy, n-propoxy, iso-propoxy, n-butoxy, sec-butoxy, tert-butoxy, n-pentyloxy and S-pentyloxy. The "cycloalkyl" includes saturated cyclic group, such as cyclopropyl, cyclobutyl or cyclopentyl. The 3- to 7-membered cycloalkyl includes C$_3$, C$_4$, C$_5$, C$_6$ and C$_7$ cycloalkyl. The "alkenyl" includes linear or branched hydrocarbon chain, wherein any stable sites on the chain exist one or more C—C double bonds, such as vinyl and propenyl.

The term "halo" or "halogen" refers to fluorine, chlorine, bromine and iodine.

Unless otherwise specified, the term "hetero" refers to a heteroatom or a heteroatom group (i.e. a group containing a heteroatom), including atoms except carbon (C) and hydrogen (H) and groups containing these heteroatoms, such as including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O) N(H)—.

Unless otherwise specified, the "ring" refers to substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a joint ring, a spiro ring, a fused ring or a bridged ring. A number of the atoms in the ring is usually defined as the member of the ring, for example, "5- to 7-membered ring" is a ring looped with 5 to 7 atoms. Unless otherwise specified, the ring optionally contains 1~3 of heteroatoms. Therefore, "5- to 7-membered ring" includes, for example, phenyl pyridine and piperidinyl; on the other hand, the term "5- to 7-membered heterocycloalkyl" includes pyridyl and piperidinyl, but does not include phenyl. The term "ring" also includes a ring system containing at least one ring, wherein each ring is of the above definition independently.

Unless otherwise specified, the term "heterocycle" or "heterocyclic group" refers to a stable monocyclic, bicyclic or tricyclic ring containing a heteroatom and a heteroatom group, they can be saturated, partially unsaturated or unsaturated (aromatic), they contain carbon atoms and 1, 2, 3 or 4 of heteroatom in the ring which is independently selected from the group consisting of N, O and S, wherein any of the heterocycle can be fused to a benzene ring to form a bicyclic ring. Nitrogen and sulfur atoms can be optionally oxidized (i.e., NO and S(O)$_p$). The Nitrogen atom can be substituted or unsubstituted (i.e. N or NR, wherein R is H or other substituent that has been defined herein). The heterocycle can be attached to the side group of any heteroatom or carbon atom to form a stable structure. If the formed compound is stable, the heterocycle described herein can be substituted on its carbon or nitrogen atom. The nitrogen atom in the heterocycle is optionally quaternized. As a preferred embodiment of the present invention, when the total number of S and O atoms contained in the heterocycle exceeds 1, these heteroatoms are not adjacent to each other. As another preferred embodiment of the present invention, the total number of S and O atoms in the heterocycle is no more than 1. As used herein, the term "aromatic heterocyclic group" or "heteroaryl" refers to a stable 5-, 6-, 7-membered monocycle or bicycle or 7-, 8-, 9- or 10-membered bicyclic heteroaromatic ring, which contains carbon atoms and 1, 2, 3 or 4 of heteroatom in the ring which independently selected from the group consisting of N, O and S. The Nitrogen atom can be substituted or unsubstituted (i.e. N or NR, wherein R is H or other substituent that has been defined herein). Nitrogen and sulfur atoms can be optionally oxidized (i.e., NO and S(O)$_p$). It is worth noting that, the total number of S and O atoms in the heteroaromatic ring is no more than 1. Bridged rings are also included in the definition of the heterocycle. When one or more atoms (i.e. C, O, N, or S) are connected to two nonadjacent carbon atoms or nitrogen atoms, a bridged ring is formed. The preferred bridged ring includes but not limited to: one carbon atom, two carbon atoms, one nitrogen atom, two nitrogen atoms and one carbon-nitrogen group. It is worth noting that, a bridge always converts a monocyclic ring into a tricyclic ring. In the bridged ring, the substituent in the ring can also locate on the bridge.

Examples of heterocyclic compound include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, pyran, isoindolyl, isoindolinyl, isoindolyl, indolyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isooxazolyl, hydroxyl indyl, pyrimidyl, phenanthridinyl, phenanthrolinyl, phenazine, phenothiazine, benzopurinyl, phenoxazinyl, phthalazinyl, piperazinyl, piperidyl, oxopiperidinyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridinoimidazole, pyridinothiazole, pyridyl, pyrimidyl, pyrrolidinyl, pyrrolinyl, 2H-pyrrolyl, pyrrolyl, pyrazolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienyl, thiophenoxazolyl, thiophenothiazolyl, thiophenoimidazolyl, thienyl, triazinyl, 1,2,3-triazolyl, 1,2,4-triazolyl, 1,2,5-triazolyl, 1,3,4-triazolyl and xanthenyl. Fused ring and spiro ring compound are also included.

Unless otherwise specified, the term "hydrocarbon group" or its specific concept (such as alkyl, alkenyl, alkynyl, phenyl, etc.) itself or as a part of another substituent represents a linear, branched or cyclic hydrocarbon group or a combination thereof, which can be fully saturated, monocyclic or polycyclic unsaturated, can be monosubstituted, disubstituted or polysubstituted, can be univalent (such as methyl), bivalent (such as methylene) or multivalent (such as methenyl), can include bivalent or multivalent atomic groups, with a specified number of carbon atoms (such as that $C_1$-$C_{10}$ refers to having 1~10 carbon atoms). The term "alkyl" includes but not limited to an aliphatic hydrocarbon group and aromatic hydrocarbon group, the aliphatic hydrocarbon group includes linear and cyclic structures, specifically includes but not limited to alkyl, alkenyl and alkynyl, the aromatic hydrocarbon group includes but not limited to 6- to 12-membered aromatic hydrocarbon group such as benzene, naphthalene and the like. In some embodiments, the term "alkyl" refers to linear or branched groups or their combination, which can be completely saturated, monocyclic or polycyclic unsaturated, can include divalent and polyvalent groups. Examples of saturated hydrocarbon groups include but not limited to homologues or isomers of methyl, ethyl, n-propyl, iso-propyl, n-butyl, tert-butyl, isobutyl, sec-butyl, iso-butyl, cyclohexyl, (cyclohexyl) methyl, cyclopropyl methyl, and n-amyl, n-hexyl, n-heptyl, n-octyl and the like. Unsaturated alkyl has one or more double or triple bond, examples of which includes but not limited to vinyl, 2-propenyl, butenyl, crotyl, 2-isopentenyl, 2-butadienyl, 2,4-(pentadienyl), 3-(1,4-pentadienyl), acetenyl, 1- and 3-propinyl, 3-butynyl, and more advanced homologues and isomers.

Unless otherwise specified, the term "heterohydrocarbon group" or its specific concepts (such as heteroalkyl, heteroalkenyl, heteroalkynyl, heteroaryl, etc.) itself or the term combining with another term refers to a stable linear, branched or cyclic hydrocarbon group or their combinations, which consists of a certain number of carbon atoms and at least one heteroatom. In some embodiments, the term "heteroalkyl" itself or the term combining with another term refers to a stable linear, branched hydrocarbon group or their combinations, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. Heteroatoms B, O, N and S can be located in any internal position of the heterohydrocarbon group (including the position where hydrocarbon group is attached to the rest part of the molecule). Examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms are adjacent, such as —$CH_2$—NH—$OCH_3$.

The terms "alkoxy", "alkylamino" and alkylthio" (or thioalkoxy) are the idiomatic expressions, which refers to the alkyl group is attached to the rest of molecule through an oxygen, an amino, or a sulfur atom, respectively.

Unless otherwise specified, the term "cyclohydrocarbon group", "heterocyclo hydrocarbon group" or its specific concepts (such as aryl, heteroaryl, cycloalkyl, heterocycloalkyl, cycloalkenyl, heterocyclovinyl, cycloalkynyl, heterocycloalkynyl, etc.) itself or the term combining with other terms respectively refers to a cyclic "hydrocarbon group", "heterohydrocarbon group". In addition, in terms of heterohydrocarbon group or heterocyclohydrocarbon group (such as heteroalkyl, heterocycloalkyl), heteroatoms can occupy the position where the heterocyclic ring is attached to the rest part of the molecule. Examples of the cycloalkyl include but not limited to cyclopentyl, cyclohexyl, 1-cyclohexenyl, 3-cyclohexenyl, cycloheptyl etc. Unrestricted examples of the heterocyclic group include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophene-2-yl, tetrahydrothiophene-3-yl, 1-piperazinyl and 2-piperazinyl.

Unless otherwise specified, the term "aryl" refers to a polyunsaturated aromatic hydrocarbon substituent, which can be monosubstituted, disubstituted or multisubstituted, can be univalent, bivalent or multivalent. It can be monocyclic or polycyclic (preferably 1~3 rings). They fuse together or connect by a covalent linkage. The term "heteroaryl" refers to an aryl (or ring) containing 1~4 heteroatoms. In an exemplary embodiment, the heteroatom is selected from the group consisting of B, N, O, and S, in which the nitrogen and sulfur atoms are optionally oxidized, and the nitrogen atom is optionally quaternized. The heteroaryl group can be connected to the rest part of the molecule via a heteroatom. Unrestricted examples of an aryl or a heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. Any one of the substituents in the aryl and heteroaryl ring system is selected from the acceptable substituents described below.

For the sake of briefness, when used in combination with other terms (e.g. aryloxy, arylthio, aralkyl), the aryl includes the definition of aryl and heteroaryl ring defined above. Therefore, the term "aralkyl" is intended to include the groups that aryl attached to alkyl (e.g. benzyl, phenyl ethyl, pyridyl methyl), including those alkyls wherein carbon atoms (such as methylene) has been replaced by such as oxygen atoms, such as phenoxy methyl, 2-pyridyloxymethyl-3-(1-naphthoxy) propyl, etc.

The term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate, such as mesylate, tosylate, p-bromobenzene sulfonate, p-tosylate etc.; acyloxy, such as acetoxy, trifluoroacetoxy and so on.

The term "protecting group" includes but not limited to "the protecting group of an amino", "the protecting group of a hydroxyl", or "the protecting group of a mercapto". The term "the protecting group of an amino" refers to a protecting group that is suitable for preventing side reactions occur at the nitrogen atom of an amino group. A representative protecting group of an amino includes but not limited to:

formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl) methyl; silyl, such as trimethylsilyl (TMS) and tert-butyldimethylsilyl (TBS) and etc. The term "the protecting group of a hydroxyl" refers to a protecting group that is suitable for preventing side reactions of a hydroxyl group. A representative protecting group of a hydroxyl includes but not limited to: alkyl, such as methyl, ethyl, and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and etc.

The compound of the present invention can be prepared through many synthetic methods which are well-known to the person skilled in the art, including the specific embodiments listed below and its combination with other chemical synthetic methods and the equivalent alternative methods which are known to the person skilled in the art, the preferred embodiments include but not limited to the embodiments of the present invention.

Unless otherwise specified, an eluting system of the column chromatography and a developing system of the thin-layer chromatography used for purifying the compound includes: A: a system of dichloromethane and methanol, B: a system of petroleum ether and ethyl acetate, C: a system of dichloromethane and acetone. A ratio of the solvent volume is regulated according to the polarity of the compound, which also can be regulated by adding a small amount of alkaline or acidic reagent such as triethylamine and acetic acid etc.

The present invention adopts the following abbreviations: aq represents water; HATU represents 2-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents m-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; Cbz represents benzyloxycarbonyl, a protecting group of an amino; Boc represents tert-butoxycarbonyl, a protecting group of an amine; HOAc represents acetic acid; NaCNBH₃ represents sodium cyanoborohydride; r.t. represents room temperature; O/N represents overnight; THF represents tetrahydrofuran; Boc₂O represents di-tert-butyl dicarbonate; TFA represents trifluoroacetic acid; DIPEA represents diisopropylethyl amine; SOCl₂ represents thionyl chloride; CS₂ represents carbon disulfide; TsOH represents p-toluene sulfonic acid; NFSI represents N-fluorobenzenesulfonimide; NCS represents N-chlorosuccinimide; n-Bu4NF represents tetrabutylammonium fluoride; iPrOH represents 2-propanol; mp represents melting point; LDA represents lithium diisopropylamide; PE represents petroleum ether; PMB represents p-methoxybenzyl; AIBN represents 2,2'-azo bisisobutyronitrile; i-Pr-PEPPSI represents [1,3-bis(2,6-diisopropylbenzyl) imidazolyl-2-ene (3-chloropyridinyl)]palladium chloride.

Compounds are named by manual work or software ChemDraw®, commercially available compounds are named in accordance with suppliers' catalogue.

The compound of the present invention is of high efficiency, low toxicity, and is remarkable in activity, solubility and pharmacokinetics etc., the druggability of which is good, and is more suitable for the manufacture of pharmaceuticals.

DETAILED DESCRIPTION OF THE PREFERRED EMBODIMENT

The following examples further illustrate the present invention, but it does not mean any unfavorable limitation to the present invention. The application has already described the present invention in details, in which the embodiments also have been disclosed, therefore, it is obvious for the person skilled in the art to vary and improve the embodiments of the present invention without departing from the spirit and scope of the present invention.

Reference 1 tert-Butyl 2'-oxospiro[azetidine-3,3'-indoline]-1-carboxylate

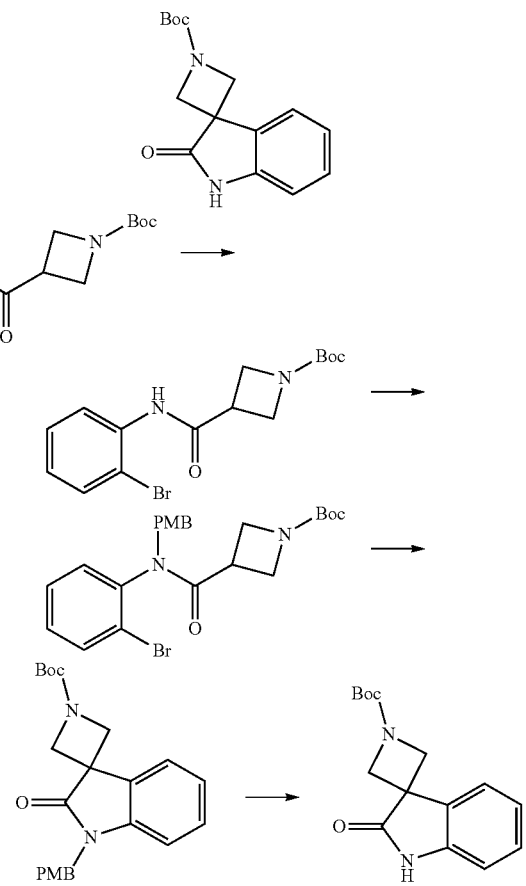

Step 1 tert-Butyl 3-((2-bromophenyl)carbamoyl)azetidine-1-carboxylate 1-(tert-Butoxycarbonyl)azetidine-3-carboxylic acid (5.85 g, 29.07 mmol) was dissolved in 50 mL THF, N,N'-carbonyldiimidazole (4.95 g, 30.52 mmol) was then added at r.t., stirring at reflux for 90 min. 2-Bromoaniline (5.0 g, 29.07 mmol) was then added at r.t., stirring at reflux for 12 h, the reaction mixture was concentrated under reduced pressure to obtain the crude, 300 mL water was added, extracted with EA (200 mL×2), organic phases were combined and washed in sequence with water (200 mL×2), saturated sodium chloride solution (200 mL×2), dried over anhydrous sodium sulfate, filtered, the filtrate was concentrated under reduced pressure, the residue was purified by silica gel column chromatography with eluting system B to obtain tert-butyl 3-((2-bromophenyl)carbamoyl)azetidine-1-carboxylate (5 g, colorless oil), yield: 48.4%.

$^1$H NMR (400 MHz, CDCl$_3$), δ 8.35 (d, J=7.9 Hz, 1H), 7.66 (br. s., 1H), 7.55 (d, J=7.9 Hz, 1H), 7.34 (t, J=7.7 Hz, 1H), 7.02 (t, J=7.5 Hz, 1H), 4.29-4.14 (m, 4H), 3.46-3.34 (m, 1H), 1.46 (s, 9H).

Step 2 tert-Butyl 3-((2-bromophenyl)(4-methoxybenzyl) carbamoyl)azetidine-1-carboxylate tert-Butyl 3-((2-bromophenyl)carbamoyl)azetidine-1-carboxylate (5 g, 14.08 mmol) was dissolved in 50 mL anhydrous DMF, 60% sodium hydride (0.676 g, 16.89 mmol) was added under ice-bath condition, stirring for 0.5 h under nitrogen gas atmosphere, then 4-methoxybenzyl chloride (2.42 g, 15.48 mmol) was added, the reaction mixture was stirred for 2 h at r.t. 300 mL water was added into the reaction mixture, extracted with EA (200 mL×2), organic phases were combined and washed in sequence with water (200 mL×3), saturated sodium chloride solution (200 mL×2), dried over anhydrous sodium sulfate, filtered, the filtrate was concentrated under reduced pressure, the residue was purified by silica gel column chromatography with eluting system B to obtain tert-butyl 3-((2-bromophenyl)(4-methoxybenzyl)carbamoyl)azetidine-1-carboxylate (6.5 g, colorless oil), yield: 97.2%.

$^1$H NMR (400 MHz, CDCl$_3$) δ 7.69 (dd, J=1.9, 7.7 Hz, 1H), 7.25-7.16 (m, 2H), 7.10 (d, J=8.5 Hz, 2H), 6.79 (d, J=8.8 Hz, 2H), 6.65 (dd, J=2.0, 7.3 Hz, 1H), 5.56 (d, J=14.1 Hz, 1H), 4.29 (br. s., 1H), 4.00 (d, J=14.3 Hz, 2H), 3.79 (s, 3H), 3.72 (br. s., 1H), 3.56 (br. s., 1H), 3.10-3.01 (m, 1H), 1.41 (s, 9H).

Step 3 tert-Butyl 1'-(4-methoxybenzyl)-2'-oxospiro[azetidine-3,3'-indoline]-1-carboxylate tert-Butyl 3-((2-bromophenyl)(4-methoxybenzyl)carbamoyl)azetidine-1-carboxylate (1.63 g, 3.42 mmol) was dissolved in 5 mL anhydrous toluene, Pd catalyst i-Pr-PEPPSI9 (163 mg, CAS: 905459-27-0) and sodium tert-butoxide (493 mg, 5.13 mmol) were added, stirring for 0.5 h under 110° C. microwave. 100 mL water was added into the reaction mixture, extracted with EA (100 mL×2), organic phases were combined and washed in sequence with water (100 mL×3), saturated sodium chloride solution (100 mL×2), dried over anhydrous sodium sulfate, filtered, the filtrate was concentrated under reduced pressure, the residue was purified by silica gel column chromatography with eluting system B to obtain tert-butyl 1'-(4-methoxybenzyl)-2'-oxospiro[azetidine-3,3'-indoline]-1-carboxylate (3.7 g, colorless oil), yield: 68.6%.

$^1$H NMR (400 MHz, CDCl$_3$) δ 7.59 (d, J=7.3 Hz, 1H), 7.32-7.26 (m, 3H), 7.15 (t, J=8.0 Hz, 1H), 6.89 (d, J=8.5 Hz, 2H), 6.82 (d, J=7.8 Hz, 1H), 4.89 (s, 2H), 4.47 (d, J=8.3 Hz, 2H), 4.13 (d, J=8.0 Hz, 2H), 3.82 (s, 3H), 1.55 (s, 9H).

Step 4 tert-Butyl 2'-oxospiro[azetidine-3,3'-indoline]-1-carboxylate tert-Butyl 1'-(4-methoxybenzyl)-2'-oxospiro[azetidine-3,3'-indoline]-1-carboxylate (3.68 g, 9.34 mmol) was dissolved in 108 mL acetonitrile and 36 mL water, ammonium ceric nitrate (20.47 g, 37.36 mmol) was added, stirring for 2 h at r.t. 100 mL water was added into the reaction mixture, extracted with EA (100 mL×2), organic phases were combined and washed in sequence with water (100 mL×3), saturated sodium chloride solution (100 mL×2), dried over anhydrous sodium sulfate, filtered, the filtrate was concentrated under reduced pressure, the residue was purified by silica gel column chromatography with eluting system B to obtain tert-butyl 2'-oxospiro[azetidine-3,3'-indoline]-1-carboxylate (500 mg, yellow oil), yield: 19.5%.

$^1$H NMR (400 MHz, CDCl$_3$) δ 7.96 (br. s., 1H), 7.54 (d, J=7.3 Hz, 1H), 7.31-7.27 (t, J=8.0 Hz, 1H), 7.18-7.09 (t, J=8.0 Hz, 1H), 6.90 (d, J=7.8 Hz, 1H), 4.39 (d, J=8.3 Hz, 2H), 4.11-4.06 (m, 2H), 1.50 (s, 9H).

Reference 2 tert-Butyl 1'-(4-methoxybenzyl)-2'-oxo-1',2'-dihydrospiro[azetidine-3,3'-pyrrolo[2,3-c]pyridine]-1-carboxylate

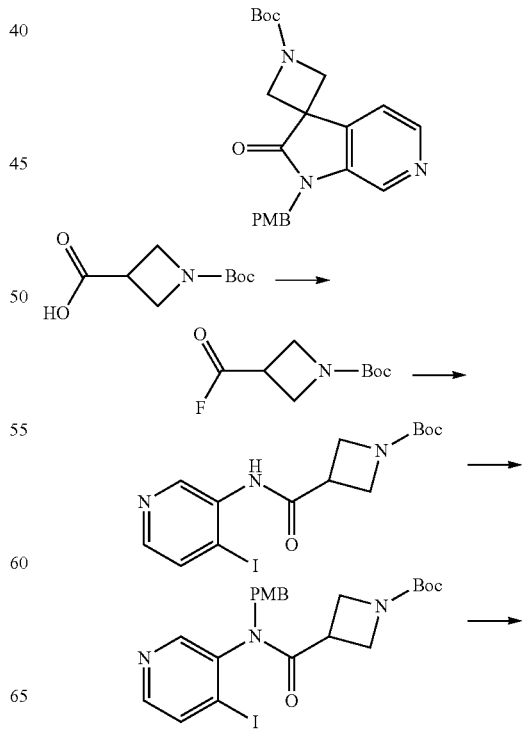

-continued

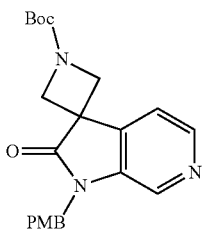

Step 1 tert-Butyl 3-(fluorocarbonyl)azetidine-1-carboxylate 1-(tert-Butoxycarbonyl)azetidine-3-carboxylic acid (9.74 g, 0.048 mol, 1.0 eq.) was dissolved in 100 mL anhydrous DCM, N, N-diethylaminosulfur trifluoride (11.59 g, 0.072 mol) was added under an ice-bath condition, stirring for 10 h at r.t., the reaction mixture was poured into a mixed solution of 100 mL ice-water and 100 mL EA, organic phase was washed in sequence with ice water (100 mL×3), saturated sodium chloride solution (100 mL×2), dried over anhydrous sodium sulfate, filtered, the filtrate was concentrated under reduced pressure to obtain a crude product of tert-butyl tert-butyl 3-(fluorocarbonyl)azetidine-1-carboxylate (10.82 g, colorless oil), which is directly used for the next step.

Step 2 tert-Butyl 3-((4-iodopyridin-3-yl)carbamoyl)azetidine-1-carboxylate

4-Iodo-3-aminopyridine (5.0 g, 215 mmol) was dissolved in 40 mL anhydrous DMF, 60% sodium hydride (1.03 g, 430 mmol) was added under an ice-bath condition, stirring for 0.5 h under nitrogen gas atmosphere. tert-Butyl 3-(fluorocarbonyl)azetidine-1-carboxylate (6.56 g, 330 mmol) was added into the reaction system, stirring for 10 h at r.t., the reaction mixture was poured into a mixed solution of 100 mL NH$_4$Cl aqueous solution and 100 mL EA, organic phase was washed in sequence with ice-water (70 mL×3), saturated sodium chloride solution (70 mL×2), dried over anhydrous sodium sulfate, filtered, the filtrate was concentrated under reduced pressure, the residue was purified by silica gel column chromatography with eluting system B to obtain tert-butyl 3-((4-iodopyridin-3-yl)carbamoyl)azetidine-1-carboxylate (5.64 g, light yellow oil), yield: 64.97%.
$^1$H NMR (400 MHz, CDCl$_3$) δ 9.18 (s, 1H), 7.99 (d, J=5.0 Hz, 1H), 7.74 (d, J=5.3 Hz, 1H), 7.61 (br. s., 1H), 4.25-4.13 (m, 4H), 3.49-3.39 (m, 1H), 1.43 (s, 9H).

Step 3 tert-Butyl 3-((4-iodopyridin-3-yl)(4-methoxybenzyl)carbamoyl)azetidine-1-carboxylate tert-Butyl 3-((4-iodopyridin-3-yl)carbamoyl)azetidine-1-carboxylate (5.64 g, 139.9 mmol) was dissolved in 20 mL anhydrous DMF, 60% sodium hydride (436.2 mg, 181.8 mmol) was added under an ice-bath condition, stirring for 0.5 h under nitrogen gas atmosphere. 4-Methoxybenzyl chloride (3.27 g, 209.9 mmol) was dripped into the reaction system, stirring for 10 h at r.t., the reaction mixture was poured into a mixed solution of 100 mL saturated sodium bicarbonate aqueous solution and 100 mL EA, organic phase was washed in sequence with ice-water (70 mL×3), saturated sodium chloride solution (70 mL×2), dried over anhydrous sodium sulfate, filtered, the filtrate was concentrated under reduced pressure, the residue was purified by silica gel column chromatography with eluting system B to obtain tert-butyl 3-((4-iodopyridin-3-yl)(4-methoxybenzyl)carbamoyl)azetidine-1-carboxylate (4.92 g, yellow oil), yield: 31.86%.
$^1$H NMR (400 MHz, CDCl$_3$) δ 8.14-8.13 (d, J=5.2 Hz, 1H), 7.90 (d, J=5.0 Hz, 1H), 7.69 (s, 1H), 7.06 (d, J=8.5 Hz, 2H), 6.78 (d, J=8.8 Hz, 2H), 5.62-5.54 (m, 1H), 4.30 (t., 1H), 4.00 (t., 1H), 3.94 (d, J=14.3 Hz, 1H), 3.77 (s, 3H), 3.73 (m., 1H), 3.59 (t, J=8.4 Hz, 1H), 2.98-2.89 (m, 1H), 1.41-1.37 (s, 9H).

Step 4 tert-Butyl 1'-(4-methoxybenzyl)-2'-oxo-1',2'-dihydrospiro[azetidine-3,3'-pyrrolo[2,3-c]pyridine]-1-carboxylate tert-Butyl 3-((4-iodopyridin-3-yl)(4-methoxybenzyl)carbamoyl)azetidine-1-carboxylate (4.2 g, 8.03 mmol) was dissolved in 10 mL anhydrous toluene, sodium tert-butoxide (1.16 g, 12.05 mmol) and i-Pr-PEPPSI (210 mg) were added at one time under nitrogen gas atmosphere, the reaction system was reacted for 40 min under 110° C. microwave, the reaction mixture was poured into a mixed solution of 80 mL saturated sodium bicarbonate aqueous solution and 80 mL EA, organic phase was washed in sequence with ice-water (60 mL×3), saturated sodium chloride solution (60 mL×2), dried over anhydrous sodium sulfate, filtered, the filtrate was concentrated under reduced pressure, the residue was purified by silica gel column chromatography with eluting system B to obtain tert-butyl 1'-(4-methoxybenzyl)-2'-oxo-1',2'-dihydrospiro[azetidine-3,3'-pyrrolo[2,3-c]pyridine]-1-carboxylate (2.05 g, yellow oil), yield: 64.8%.
$^1$H NMR (400 MHz, CDCl$_3$) δ=8.43 (d, J=4.5 Hz, 1H), 8.13 (s, 1H), 7.50 (d, J=4.5 Hz, 1H), 7.28-7.22 (m, J=8.8 Hz, 2H), 6.85 (d, J=8.5 Hz, 2H), 4.86 (s, 2H), 4.44 (d, J=8.3 Hz, 2H), 4.09-4.04 (m, 2H), 3.80-3.75 (m, 3H), 1.53-1.46 (m, 9H).

Reference 3

Isopropyl 2'-oxo[azetidine-3,3'-indoline]-1-carboxylate

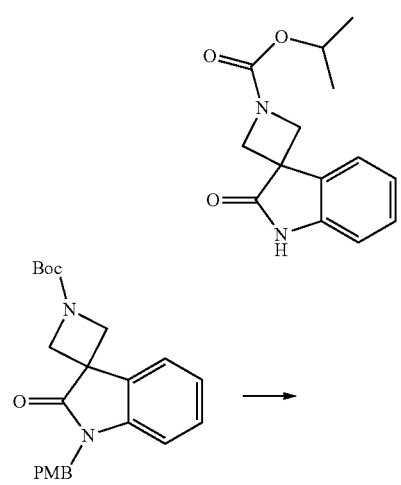

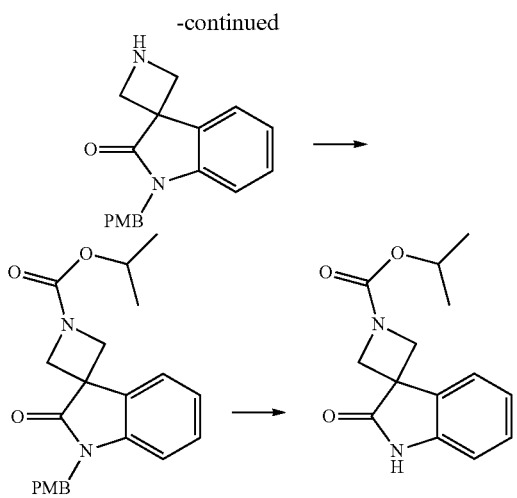

Step 1

1'-(4-Methoxybenzyl)spiro[azetidine-3,3'-indoline]-2'-one tert-Butyl 1'-(4-methoxybenzyl)-2'-oxospiro[azetidine-3,3'-indoline]-1-carboxylate (500 mg, 1.27 mmol) was dissolved in 2 mL MeOH, HCl/MeOH (4 N, 2 mL) was added at r.t., the reaction mixture was stirred for 1 h at r.t. The reaction mixture was added with 100 mL saturated sodium carbonate solution to adjust pH to 9, extracted with EA (100 mL×3), organic phases were combined and washed in sequence with water (50 mL×3), saturated sodium chloride solution (50 mL×2), dried over anhydrous sodium sulfate, filtered, the filtrate was concentrated under reduced pressure to obtain 1'-(4-methoxybenzyl)spiro[azetidine-3,3'-indoline]-2'-one (360 mg, yellow oil), which is directly used for the next step without purification.

$^1$H NMR (400 MHz, DMSO-d6), δ 7.73 (d, J=7.3 Hz, 1H), 7.28-7.17 (m, 3H), 7.09 (t, J=8.0 Hz, 1H), 6.94-6.81 (m, 3H), 4.79 (s, 2H), 4.00 (d, J=7.3 Hz, 2H), 3.69 (s, 3H), 3.55 (d, J=7.3 Hz, 2H).

Step 2

Isopropyl 1'-(4-methoxybenzyl)-2'-oxo[azetidine-3,3'-indoline]-1-carboxylate

1'-(4-Methoxybenzyl)spiro[azetidine-3,3'-indoline]-2'-one (360 mg, 1.22 mmol) was dissolved in 4 mL DCM, TEA (371 mg, 3.67 mL) was added at r.t., isopropoxy formyl chloride (164 mg, 1.34 mmol) was added dropwise under an ice-bath condition, stirring for 1 h at r.t. The reaction mixture was added with 100 mL water, extracted with DCM (100 mL×3), organic phases were combined and washed in sequence with 1N HCl (100 mL×3), saturated sodium carbonate solution (100 mL×2), water (100 mL×2), dried over anhydrous sodium sulfate, filtered, the filtrate was concentrated under reduced pressure to obtain isopropyl 1'-(4-methoxybenzyl)-2'-oxo[azetidine-3,3'-indoline]-1-carboxylate (460 mg, yellow oil), which is directly used for the next step without purification.

$^1$H NMR (400 MHz, CDCl$_3$) δ 7.55 (d, J=7.3 Hz, 1H), 7.26-7.19 (m, 3H), 7.11 (t, J=8.0 Hz, 1H), 6.85 (d, J=8.5 Hz, 2H), 6.78 (d, J=7.8 Hz, 1H), 5.01-4.95 (m, 1H), 4.84 (s, 2H), 4.46 (d, J=8.0 Hz, 2H), 4.13 (d, J=8.0 Hz, 2H), 3.78 (s, 3H), 1.29 (d, J=6.3 Hz, 6H).

Step 3

2,6-Dicarboxylic acid pyridine-1-oxide

Pyridine-2,6-dicarboxylic acid (15 g, 89.7 mmol) was added into 50 mL hydrogen peroxide to form a suspension, catalytic amount of sodium tungstate (975 mg) was added at r.t., the suspension was heated to 100° C. and stirred for 2 h. After cooling to r.t., 103 mL hydrogen peroxide was added again and the suspension was heated to 100° C. and stirred for 18 h. The reaction solution was cooled to 0° C., white crystal was precipitated, filtered and the filtrate-cake was washed with ice-water to obtain 2,6-dicarboxylic acid pyridine-1-oxide (10 g, white solid), yield: 61%.

$^1$H NMR (400 MHz, CDCl$_3$) δ 8.73 (d, J=8.0 Hz, 2H), 7.98 (t, J=8.0 Hz, 1H).

Step 4

Isopropyl 2'-oxo[azetidine-3,3'-indoline]-1-carboxylate

Isopropyl 1'-(4-methoxybenzyl)-2'-oxo[azetidine-3,3'-indoline]-1-carboxylate (350 mg, 0.92 mmol) was dissolved in 10.5 mL acetonitrile and 3.5 mL water, ammonium ceric nitrate (3.03 g, 5.52 mmol) and 2,6-dicarboxylic acid pyridine-1-oxide (1.01 g, 5.52 mmol) were added and stirring for 2 h at r.t. Saturated sodium carbonate solution and 100 mL water were added, the mixture was extracted with EA (100 mL×2), organic phases were combined and washed in sequence with water (100 mL×3), saturated sodium chloride solution (100 mL×2), dried over anhydrous sodium sulfate, filtered, the filtrate was concentrated under reduced pressure, the residue was purified by silica gel column chromatography with eluting system B to obtain isopropyl 2'-oxo[azetidine-3,3'-indoline]-1-carboxylate (70 mg, yellow oil), yield: 29.3%.

$^1$H NMR (400 MHz, CDCl$_3$) δ 7.67 (br. s., 1H), 7.55 (d, J=7.5 Hz, 1H), 7.32-7.27 (m, 1H), 7.18-7.11 (m, 1H), 6.90 (d, J=8.0 Hz, 1H), 5.03-4.94 (m, 1H), 4.43 (d, J=8.0 Hz, 2H), 4.15-4.09 (m, 2H), 1.31-1.26 (d, J=4.0 Hz, 6H).

Reference 4

1-Isobutyrylspiro[azetidine-3,3'-indoline]-2'-one

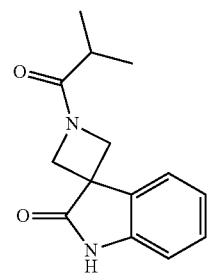

-continued

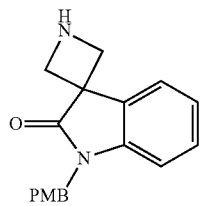

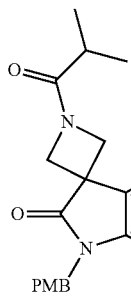 → 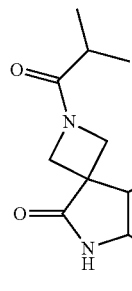

Step 1

1-Isobutyryl-1'-(4-methoxybenzyl)spiro[azetidine-3,3'-indoline]-2'-one

1'-(4-Methoxybenzyl)spiro[azetidine-3,3'-indoline]-2'-one (800 mg, 2.72 mmol) was dissolved in 8 mL DCM, TEA (400 mg, 3.95 mL) was added at r.t., isobutyryl chloride (400 mg, 3.77 mmol) was added dropwise under an ice-bath condition, stirring for 18 h at r.t. The reaction mixture was added with 100 mL water, extracted with DCM (100 mL×2), organic phases were combined and washed in sequence with 1N HCl (100 mL×3), saturated sodium carbonate solution (100 mL×2), water (100 mL×2), dried over anhydrous sodium sulfate, filtered, the filtrate was concentrated under reduced pressure, the residue was purified by silica gel column chromatography with eluting system B to obtain 1-isobutyryl-1'-(4-methoxybenzyl)spiro[azetidine-3,3'-indoline]-2'-one (930 mg, yellow oil), yield: 93.9%.

$^1$H NMR (400 MHz, CDCl$_3$) δ 7.48 (d, J=7.03 Hz, 1H), 7.21-7.26 (m, 3H), 7.08-7.14 (m, 1H), 6.85 (d, J=8.53 Hz, 2H), 6.79 (d, J=7.53 Hz, 1H), 4.84 (d, J=2.01 Hz, 2H), 4.62 (d, J=8.03 Hz, 1H), 4.46 (d, J=9.03 Hz, 1H), 4.29 (d, J=8.03 Hz, 1H), 4.19 (d, J=9.54 Hz, 1H), 3.75-3.79 (m, 3H), 2.53 (td, J=6.96, 13.68 Hz, 1H), 1.19 (d, J=7.03 Hz, 6H).

Step 2

1-Isobutyryl spiro[azetidine-3,3'-indoline]-2'-one

1-Isobutyryl-1'-(4-methoxybenzyl)spiro[azetidine-3,3'-indoline]-2'-one (830 mg, 2.277 mmol) was dissolved in 24 mL acetonitrile and 8 mL water, ammonium ceric nitrate (7.5 g, 13.641 mmol) and 2,6-dicarboxylic acid pyridine-1-oxide (1.6 g, 9.1 mmol) were added and stirring for 2 h at r.t. Saturated sodium carbonate solution and 100 mL water were added, the mixture was extracted with EA (100 mL×2), organic phases were combined and washed in sequence with water (100 mL×3), saturated sodium chloride solution (100 mL×2), dried over anhydrous sodium sulfate, filtered, the filtrate was concentrated under reduced pressure, the residue was purified by silica gel column chromatography with eluting system B to obtain 1-isobutyrylspiro[azetidine-3,3'-indoline]-2'-one (100 mg, yellow oil), yield: 18%.

$^1$H NMR (400 MHz, CDCl$_3$) δ 8.19 (br. s., 1H), 7.48 (d, J=7.03 Hz, 1H), 7.27-7.34 (m, 1H), 7.09-7.18 (m, 1H), 6.93 (d, J=8.03 Hz, 1H), 4.60 (d, J=8.03 Hz, 1H), 4.44 (d, J=9.54 Hz, 1H), 4.29 (d, J=8.03 Hz, 1H), 4.19 (d, J=9.54 Hz, 1H), 2.53 (td, J=6.78, 13.55 Hz, 1H), 1.14-1.22 (m, 6H).

Embodiment 62

Isopropyl 1'-((1-(4-hydroxybutyl)-4,5,6,7-tetrahydro-1H-benzo[d]imidazol-2-yl)methyl)-2'-oxospiro[azetidine-3,3'-indoline]-1-carboxylate

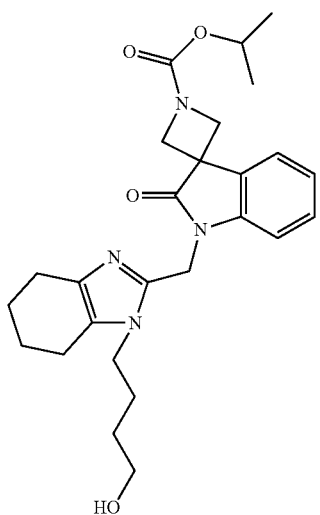

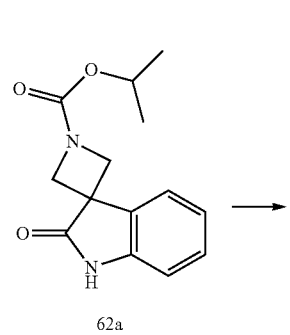

62a

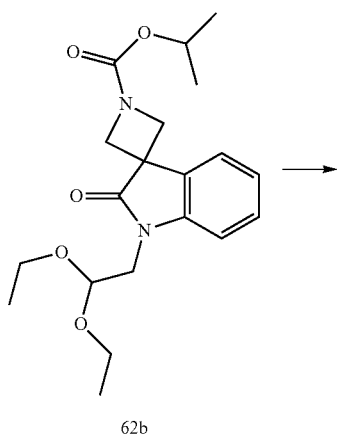

62b

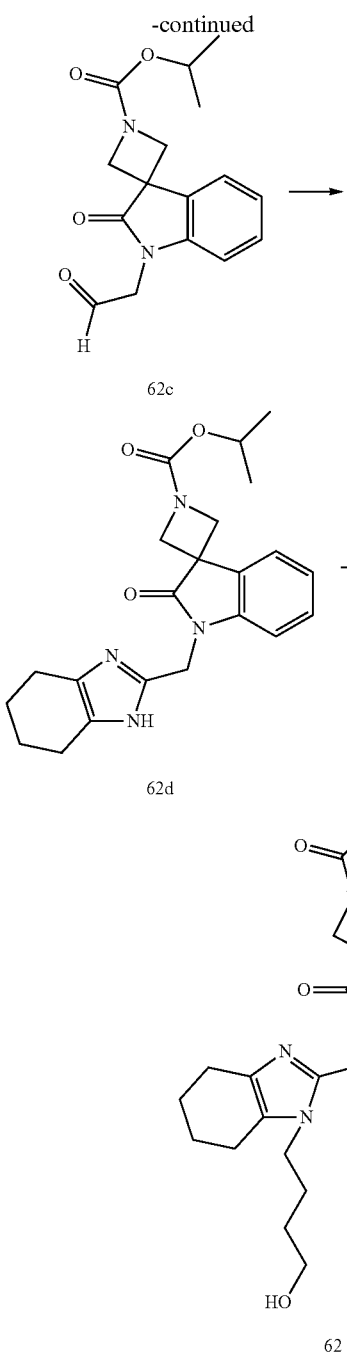

62c

62d

62

Step 1

Isopropyl 1'-(2,2-diethoxyethyl)-2'-oxospiro[azetidine-3,3'-indoline]-1-carboxylate Isopropyl 2'-oxospiro[azetidine-3,3'-indoline]-1-carboxylate 62a (1.5 g, 5.8 mmol) was dissolved in 15 mL DMF, 2-bromo-1,1-diethoxyethane (1.36 g, 7.0 mmol), cesium carbonate (2.5 g, 7.0 mmol), potassium iodide (0.16 g, 1.0 mmol) were added, and the reaction solution was heated to 100° C. and stirred for 18 h. The mixture was cooled to r.t., 50 mL water was added, extracted with EA (50 mL×3), organic phases were combined and washed in sequence with water (30 mL×3), saturated sodium chloride solution (30 mL×2), dried over anhydrous sodium sulfate, filtered, the filtrate was concentrated under reduced pressure, the residue was purified by silica gel column chromatography with eluting system C to obtain isopropyl 1'-(2,2-diethoxyethyl)-2'-oxospiro[azetidine-3,3'-indoline]-1-carboxylate 62b (1.12 g, colorless oil), yield: 51.4%.

$^1$H NMR (400 MHz, CD$_3$OD) δ 7.62 (d, J=7.5 Hz, 1H), 7.38-7.31 (m, 1H), 7.18 (t, J=7.5 Hz, 1H), 7.13 (d, J=8.0 Hz, 1H), 5.00-4.90 (m, 1H), 4.77 (t, J=5.1 Hz, 1H), 4.31 (d, J=8.3 Hz, 2H), 4.15 (d, J=7.5 Hz, 2H), 3.86 (d, J=5.0 Hz, 2H), 3.80-3.70 (m, 2H), 3.59-3.49 (m, 2H), 1.30 (d, J=6.3 Hz, 6H), 1.12 (t, J=7.0 Hz, 6H).

Step 2

Isopropyl 2'-oxo-1'-(2-oxoethyl)spiro[azetidine-3,3'-indoline]-1-carboxylate

Isopropyl 1'-(2,2-diethoxyethyl)-2'-oxospiro[azetidine-3,3'-indoline]-1-carboxylate 62b (0.6 g, 1.6 mmol) was dissolved in 4.5 mL DCM and 1.5 mL water, 4.5 mL trifluoroacetic acid was added, stirring for 1 h at r.t. The reaction mixture was adjusted to neutral with saturated potassium carbonate aqueous solution, extracted with DCM (30 mL×3), organic phases were combined and washed in sequence with water (30 mL×2), saturated sodium chloride solution (30 mL×2), dried over anhydrous sodium sulfate, filtered, the filtrate was concentrated under reduced pressure to obtain the crude product of isopropyl 2'-oxo-1'-(2-oxoethyl)spiro[azetidine-3,3'-indoline]-1-carboxylate 62c (0.32 g, colorless oil), yield: 66.4%.

Step 3

Isopropyl 2'-oxo-1'-((4,5,6,7-tetrahydro-1H-benzo[d]imidazol-2-yl)methyl)spiro[azetidine-3,3'-indoline]-1-carboxylate Isopropyl 2'-oxo-1'-(2-oxoethyl)spiro[azetidine-3,3'-indoline]-1-carboxylate 62c (0.32 g, 1.06 mmol) was dissolved in 5 mL anhydrous ethanol, cyclohexane-1,2-dione (0.135 g, 1.2 mmol), ammonium acetate (0.41 g, 5.3 mmol) were added, and the reaction mixture was heated to reflux and stirred for 6 h. The reaction mixture was cooled to r.t., 50 mL EA was added, then washed with saturated sodium carbonate aqueous solution (30 mL×2), dried over anhydrous sodium sulfate, filtered, the filtrate was concentrated under reduced pressure, the residue was purified by silica gel column chromatography with eluting system C to obtain isopropyl 2'-oxo-1'-((4,5,6,7-tetrahydro-1H-benzo[d]imidazol-2-yl)methyl)spiro[azetidine-3,3'-indoline]-1-carboxylate 62d (0.38 g, white solid), yield: 91.1%.

$^1$H NMR (400 MHz, CDCl$_3$) δ 7.53 (d, J=7.3 Hz, 1H), 7.36-7.30 (m, 1H), 7.21 (d, J=7.8 Hz, 1H), 7.18-7.12 (m, 1H), 4.93 (s, 2H), 4.38 (d, J=8.3 Hz, 2H), 4.16-4.11 (m, 1H), 4.09 (d, J=8.3 Hz, 2H), 2.51 (br. s., 4H), 1.77 (br. s., 4H), 1.28 (d, J=6.3 Hz, 6H).

Step 4

Isopropyl 1'-((1-(4-hydroxybutyl)-4,5,6,7-tetrahydro-1H-benzo[d]imidazol-2-yl)methyl)-2'-oxospiro[azetidine-3,3'-indoline]-1-carboxylate 2'-oxo-1'-((4,5,6,7-tetrahydro-1H-benzo[d]imidazol-2-yl)methyl)spiro[azetidine-3,3'-indoline]-1-carboxylate 62d (0.28 g, 0.71 mmol) was dissolved in 3 mL acetonitrile, 4-bromobutyl acetate (0.166 g, 0.85 mmol), potassium carbonate (0.138 g, 1.0 mmol), potassium iodide (0.017 g, 0.1 mmol) were added, the reaction mixture was heated to reflux and stirred for 18 h. The reaction solution was cooled to r.t., 30 mL water was added, extracted with EA (30 mL×2), organic phases were combined and washed in sequence with water (20 mL×2), saturated sodium chloride solution (20 mL×2), dried over anhydrous sodium sulfate, filtered, the filtrate was concentrated under reduced pressure to obtain yellow solid. 3 mL 1M NaOH aqueous solution was added to dissolve, stirring for 0.5 h at r.t. The reaction solution was added with 30 mL water, extracted with EA (30 mL×2), organic phases were combined and washed with saturated sodium chloride solution (20 mL×2), dried over anhydrous sodium sulfate, filtered, the filtrate was concentrated under reduced pressure, purified with preparative HPLC to obtain the target product isopropyl 1'-((1-(4-hydroxybutyl)-4,5,6,7-tetrahydro-1H-benzo[d]imidazol-2-yl)methyl)-2'-oxospiro[azetidine-3,3'-indoline]-1-carboxylate 62 (0.1 g, white solid), yield: 35.8%.

MS m/z (ESI): 467.3 [M+1]

$^1$H NMR (400 MHz, CD$_3$OD) δ 7.64 (d, J=7.3 Hz, 1H), 7.33-7.25 (m, 1H), 7.21-7.15 (m, 1H), 7.05 (d, J=7.8 Hz, 1H), 5.01 (s, 2H), 4.96 (d, J=6.3 Hz, 1H), 4.37 (d, J=8.5 Hz, 2H), 4.18 (d, J=8.0 Hz, 2H), 3.99 (t, J=7.5 Hz, 2H), 3.57 (t, J=6.1 Hz, 2H), 2.56 (br. s., 2H), 2.49 (br. s., 2H), 1.82 (br. s., 4H), 1.72-1.62 (m, 2H), 1.61-1.51 (m, 2H), 1.31 (d, J=6.0 Hz, 6H).

Embodiment 63

1'-((1-(4-Hydroxybutyl)-4,5,6,7-tetrahydro-1H-benzo[d]imidazol-2-yl)methyl)spiro[cyclopropane-1,3'-indoline]-2'-one

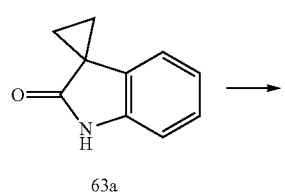

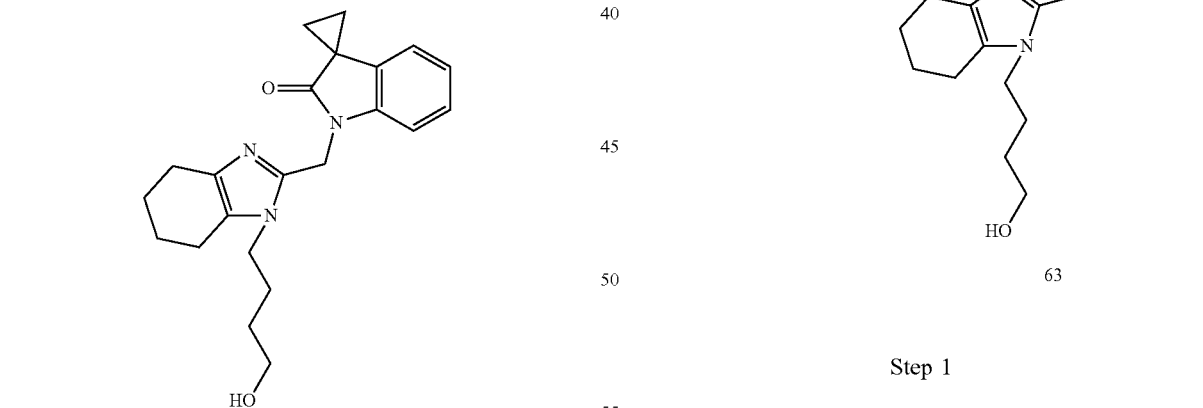

Step 1

1'-(2,2-Dimethoxyethyl)spiro[cyclopropane-1,3'-indoline]-2'-one

Spiro[cyclopropane-1,3'-indoline]-2'-one 63a (3 g, 18.8 mmol) was dissolved in 3 mL acetonitrile, 2-bromo-1,1-dimethoxyethyl (3.34 g, 19.7 mmol), potassium carbonate (12.25 g, 37.6 mmol), potassium iodide (10 mg) were added, and the reaction solution was stirred for 16 h at r.t. The reaction solution was concentrated under reduced pressure, 100 mL water was added, extracted with EA (100 mL×2), organic phases were combined and washed in sequence with water (100 mL×3), saturated sodium chloride solution (100 mL×2), dried over anhydrous sodium sulfate, filtered, the filtrate was concentrated under reduced pressure. Column chromatography (PE:EtOAc=4:1) was used to purify and 1'-(2,2-dimethoxyethyl)spiro[cyclopropane-1,3'-indoline]-2'-one 63b (2 g, yellow solid) was given, yield: 43.0%.

$^1$H NMR (400 MHz, CDCl$_3$) δ 7.25 (d, J=8.0 Hz, 1H), 7.10-7.02 (m, 2H), 6.85 (d, J=4.0 Hz, 1H), 4.66 (t, J=5.2 Hz, 1H), 3.93 (d, J=5.6 Hz, 2H), 3.43 (d, J=2.4 Hz, 6H), 1.79-1.76 (m, 2H), 1.56-1.53 (m, 2H).

Step 2

2-(2'-Oxospiro[cyclopropane-1,3'-indoline]-1'-yl)acetaldehyde

1'-(2,2-Dimethoxyethyl)spiro[cyclopropane-1,3'-indoline]-2'-one 63b (2 g, 8.09 mmol) was dissolved in 3 mL DCM and 1 mL water, 3 mL trifluoroacetic acid was added at r.t., the reaction solution was stirred for 2 h at r.t. The reaction solution was concentrated under reduced pressure, 100 mL saturated sodium bicarbonate was added, extracted with EA (100 mL 2), organic phases were combined and washed in sequence with saturated sodium bicarbonate solution (100 mL×3), saturated sodium chloride solution (100 mL×2), dried over anhydrous sodium sulfate, filtered, the filtrate was concentrated under reduced pressure. Column chromatography (PE:EtOAc=4:1) was used to purify and 2-(2'-oxospiro[cyclopropane-1,3'-indoline]-1'-yl)acetaldehyde 63c (1.5 g, white solid) was given, yield: 92.1%.

$^1$H NMR (400 MHz, CDCl$_3$) δ 9.74 (s, 1H), 7.26 (t, J=7.9 Hz, 1H), 7.09 (t, J=8.0 Hz, 1H), 6.91 (d, J=8.0 Hz, 1H), 6.76 (d, J=8.0 Hz, 1H), 4.62 (s, 2H), 1.86-1.83 (m, 2H), 1.63-1.62 (m, 2H).

Step 3

1'-((4,5,6,7-Tetrahydro-1H-benzo[d]imidazol-2-yl)methyl)spiro[cyclopropane-1,3'-indoline]-2'-one 2-(2'-Oxospiro[cyclopropane-1,3'-indoline]-1'-yl)acetaldehyde 63c (100 mg, 0.5 mmol) was dissolved in 3 mL ethanol, cyclohexane-1,2-dione (56.07 mg, 0.5 mmol), ammonium acetate (231 mg, 3.0 mmol) were added at r.t., and the reaction solution was heated to reflux and stirred for 2 h. 50 mL water was added into the reaction solution, extracted with EA (50 mL×2), organic phases were combined and washed in sequence with water (50 mL×3), saturated sodium chloride solution (50 mL×2), dried over anhydrous sodium sulfate, filtered, the filtrate was concentrated under reduced pressure. Column chromatography (PE:EtOAc=4:1) was used to purify and 1'-((4,5,6,7-tetrahydro-1H-benzo[d]imidazol-2-yl)methyl)spiro[cyclopropane-1,3'-indoline]-2'-one 63d (77 mg, yellow oil) was given, yield: 52.8%.

$^1$H NMR (400 MHz, CDCl$_3$) δ 7.33-7.27 (m, 2H), 7.02 (t, J=7.3 Hz, 1H), 6.82 (d, J=7.5 Hz, 1H), 5.01 (s, 2H), 2.59-2.49 (m, 4H), 1.78 (d, J=3.8 Hz, 6H), 1.59-1.55 (m, 2H).

Step 4

1'-((1-(4-Hydroxybutyl)-4,5,6,7-tetrahydro-1H-benzo[d]imidazol-2-yl)methyl)spiro[cyclopropane-1,3'-indoline]-2'-one 1'-((4,5,6,7-Tetrahydro-1H-benzo[d]imidazol-2-yl)methyl)spiro[cyclopropane-1,3'-indoline]-2'-one 63d (74 mg, 0.25 mmol) was dissolved in 2 mL acetonitrile, 4-bromobutyl acetate (58.53 mg, 0.3 mmol), potassium carbonate (52.52 mg, 0.38 mmol), potassium iodide (4.98 mg, 0.03 mmol) were added at r.t., and the reaction solution was stirred for 12 h at r.t. The reaction solution was added with 50 mL water, extracted with EA (50 mL×2), organic phases were combined and washed in sequence with water (50 mL×3), saturated sodium chloride solution (50 mL×2), dried over anhydrous sodium sulfate, filtered, the filtrate was concentrated under reduced pressure to obtain crude product. The crude product was dissolved in 2 mL methanol, NaOH (80 mg) was added at r.t., the reaction solution was stirred for 2 h at r.t. The reaction solution was added with 50 mL water, extracted with EA (50 mL×2), organic phases were combined and washed in sequence with water (50 mL×3), saturated sodium chloride solution (50 mL×2), dried over anhydrous sodium sulfate, filtered, the filtrate was concentrated under reduced pressure, preparative HPLC was used to purify and the target product 1'-((1-(4-hydroxybutyl)-4,5,6,7-tetrahydro-1H-benzo[d]imidazol-2-yl)methyl)spiro[cyclopropane-1,3'-indoline]-2'-one 63 (12.4 mg, white solid), yield: 13.6%.

MS m/z (ESI): 366.2 [M+1]

$^1$H NMR (400 MHz, METHANOL-d$_4$) δ 7.21-7.14 (m, 2H), 7.06-7.01 (m, 1H), 6.95 (d, J=7.3 Hz, 1H), 5.09 (s, 2H), 3.95-3.88 (m, 2H), 3.48-3.44 (m, 2H), 2.56-2.49 (m, 4H), 1.86-1.77 (m, 4H), 1.72-1.63 (m, 4H), 1.53-1.47 (m, 4H).

Embodiment 64

Isopropyl 1'-((1-(4,4-difluorobutyl)-4,5,6,7-tetrahydro-1H-benzo[d]imidazol-2-yl)methyl)-2'-oxospiro[azetidine-3,3'-indoline]-1-carboxylate

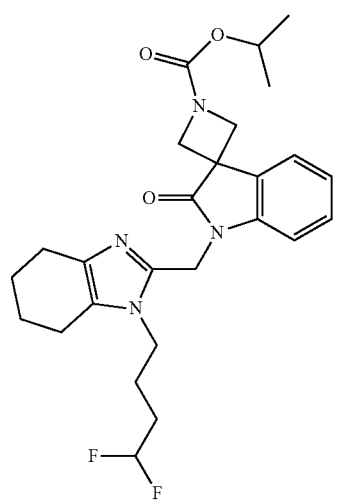

-continued

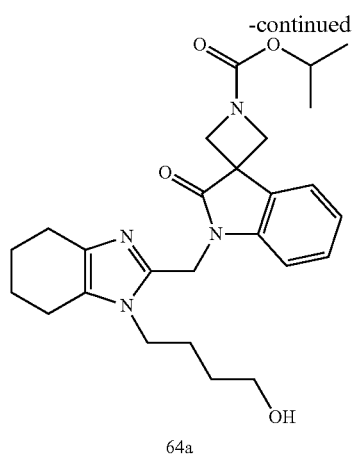

64a

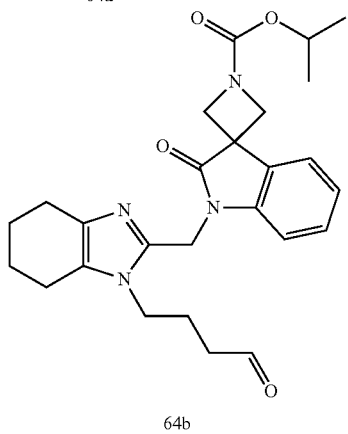

64b

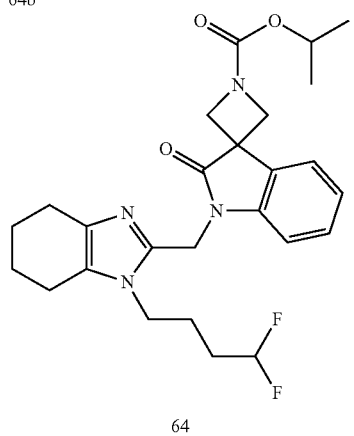

64

Step 1

Isopropyl 2'-oxo-1'-((1-(4-oxobutyl)-4,5,6,7-tetrahydro-1H-benzo[d]imidazol-2-yl)methyl)spiro[azetidine-3,3'-indoline]-1-carboxylate Isopropyl 1'-((1-(4-hydroxybutyl)-4,5,6,7-tetrahydro-1H-benzo[d]imidazol-2-yl)methyl)-2'-oxospiro[azetidine-3,3'-indoline]-1-carboxylate 64a (0.17 g, 0.36 mmol) was dissolved in 5 mL anhydrous DCM, tetrapropylammonium perruthenate (0.17 g, 0.47 mmol), N-methylmorpholine N-oxide (0.06 g, 0.47 mmol), 4 Å molecular sieves (0.17 g, 0.36 mmol) were added, stirring for 2 h at r.t. The reaction solution was filtered, the filtrate was concentrated under reduced pressure to obtain the crude product of isopropyl 2'-oxo-1'-((1-(4-oxobutyl)-4,5,6,7-tetrahydro-1H-benzo[d]imidazol-2-yl)methyl)spiro[azetidine-3,3'-indoline]-1-carboxylate 64b (0.20 g, dark brown oil).

$^1$H NMR (400 MHz, CDCl$_3$) δ 9.78 (s, 1H), 7.56 (m, 2H), 7.32 (t, J=7.60 Hz, 1H), 7.14 (t, J=7.60 Hz, 1H), 4.97 (m, 3H), 4.34 (d, J=8.00 Hz, 2H), 4.08 (d, J=8.00 Hz, 2H), 3.90 (t, J=8.00 Hz, 2H), 2.58 (m, 4H), 2.48 (m, 2H), 1.82-1.60 (m, 6H), 1.27 (d, J=6.00 Hz, 6H).

Step 2

Isopropyl 1'-((1-(4,4-difluorobutyl)-4,5,6,7-tetrahydro-1H-benzo[d]imidazol-2-yl)methyl)-2'-oxospiro[azetidine-3,3'-indoline]-1-carboxylate Isopropyl 2'-oxo-1'-((1-(4-oxobutyl)-4,5,6,7-tetrahydro-1H-benzo[d]imidazol-2-yl)methyl)spiro[azetidine-3,3'-indoline]-1-carboxylate 64b (0.20 g, 0.43 mmol) was dissolved in 2 mL anhydrous DCM, diethylaminosulfur trifluoride (0.22 g, 1.29 mmol) was added at 0° C., and the reaction mixture was stirred for 16 h at r.t. 50 mL water was added, the mixture was extracted with DCM (50 mL×3), organic phases were combined and washed in sequence with water (50 mL×3), saturated sodium chloride solution (50 mL×2), dried over anhydrous sodium sulfate, filtered, the filtrate was concentrated under reduced pressure, preparative HPLC was used to purify and the target product isopropyl 1'-((1-(4,4-difluorobutyl)-4,5,6,7-tetrahydro-1H-benzo[d]imidazol-2-yl)methyl)-2'-oxospiro[azetidine-3,3'-indoline]-1-carboxylate 64 (5 mg, light yellow solid) was given, yield: 2.39%.

MS m/z (ESI): 487.3 [M+1]

$^1$H NMR (400 MHz, CD$_3$OD) δ 7.64 (d, J=7.28 Hz, 1H), 7.34-7.25 (m, 1H), 7.23-7.15 (m, 1H), 7.08 (d, J=7.78 Hz, 1H), 6.14-5.76 (m, 1H), 5.02 (s, 2H), 4.99-4.94 (m, 1H), 4.37 (d, J=8.03 Hz, 2H), 4.17 (d, J=8.03 Hz, 2H), 4.03 (t, J=7.65 Hz, 2H), 2.65-2.38 (m, 4H), 2.01-1.64 (m, 8H), 1.31 (d, J=6.27 Hz, 6H).

Embodiment 65

Isopropyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate

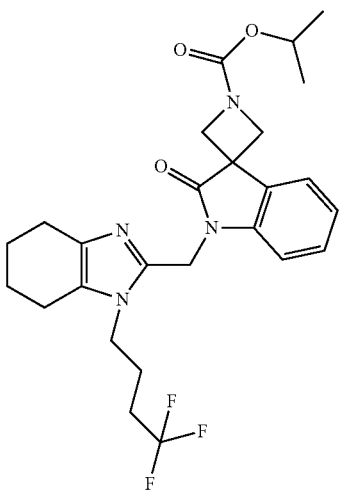

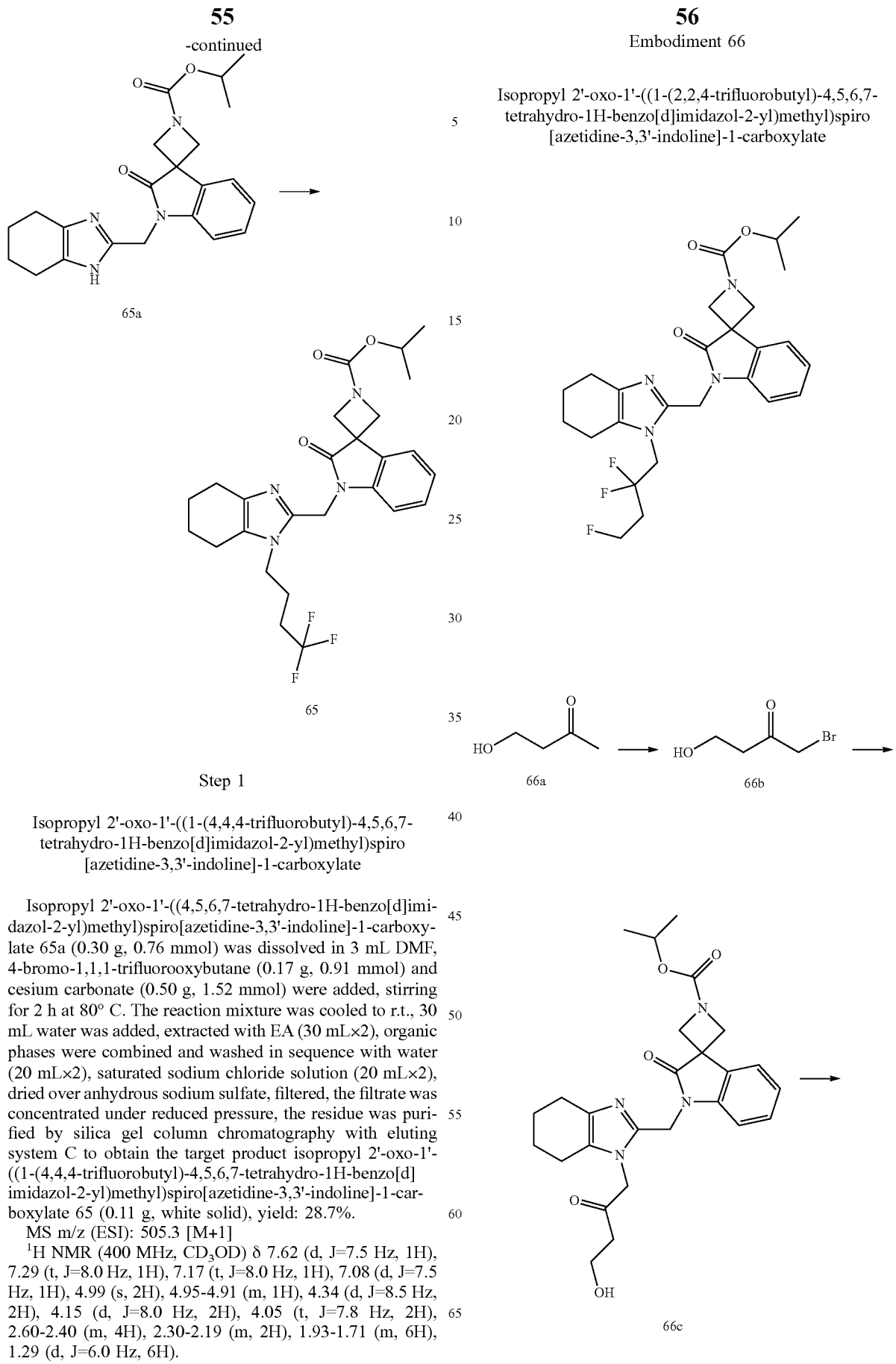

Step 1

Isopropyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate Isopropyl 2'-oxo-1'-((4,5,6,7-tetrahydro-1H-benzo[d]imidazol-2-yl)methyl)spiro[azetidine-3,3'-indoline]-1-carboxylate 65a (0.30 g, 0.76 mmol) was dissolved in 3 mL DMF, 4-bromo-1,1,1-trifluorooxybutane (0.17 g, 0.91 mmol) and cesium carbonate (0.50 g, 1.52 mmol) were added, stirring for 2 h at 80° C. The reaction mixture was cooled to r.t., 30 mL water was added, extracted with EA (30 mL×2), organic phases were combined and washed in sequence with water (20 mL×2), saturated sodium chloride solution (20 mL×2), dried over anhydrous sodium sulfate, filtered, the filtrate was concentrated under reduced pressure, the residue was purified by silica gel column chromatography with eluting system C to obtain the target product isopropyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 65 (0.11 g, white solid), yield: 28.7%.

MS m/z (ESI): 505.3 [M+1]

$^1$H NMR (400 MHz, CD$_3$OD) δ 7.62 (d, J=7.5 Hz, 1H), 7.29 (t, J=8.0 Hz, 1H), 7.17 (t, J=8.0 Hz, 1H), 7.08 (d, J=7.5 Hz, 1H), 4.99 (s, 2H), 4.95-4.91 (m, 1H), 4.34 (d, J=8.5 Hz, 2H), 4.15 (d, J=8.0 Hz, 2H), 4.05 (t, J=7.8 Hz, 2H), 2.60-2.40 (m, 4H), 2.30-2.19 (m, 2H), 1.93-1.71 (m, 6H), 1.29 (d, J=6.0 Hz, 6H).

Embodiment 66

Isopropyl 2'-oxo-1'-((1-(2,2,4-trifluorobutyl)-4,5,6,7-tetrahydro-1H-benzo[d]imidazol-2-yl)methyl)spiro[azetidine-3,3'-indoline]-1-carboxylate -continued

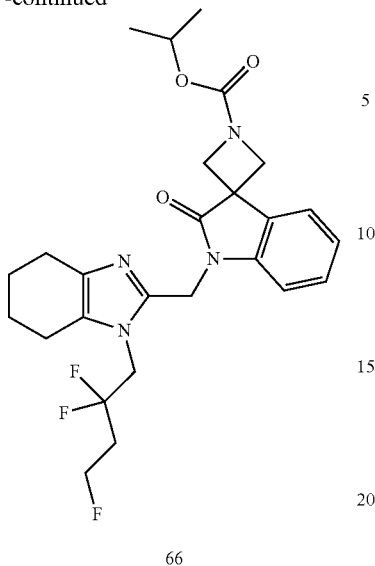

66

Step 1

1-Bromo-4-hydroxybutan-2-one

4-Hydroxybutanyl 66a (6.00 g, 68.10 mmol) was dissolved in 30 mL methanol, bromine (10.34 g, 64.70 mmol) was added dropwise at 0° C., stirring for 2 h at r.t. 30 mL 2N sulphuric acid was added, stirring for 12 h at r.t. The reaction mixture was added with 30 mL water, extracted with DCM/MeOH=10:1 (V/V) (30 mL×3), organic phases were combined and washed in sequence with water (20 mL×2), saturated sodium chloride solution (20 mL×2), dried over anhydrous sodium sulfate, filtered, the filtrate was concentrated under reduced pressure, the residue was purified by silica gel column chromatography with eluting system C to give 1-bromo-4-hydroxybutan-2-one 66b (2.80 g, yellow oil), yield: 24.6%.

$^1$H NMR (400 MHz, CDCl$_3$) δ 3.95 (s, 2H), 3.91 (t, J=5.52 Hz, 2H), 2.92 (t, J=5.40 Hz, 2H), 2.28 (br. s., 1H).

Step 2

Isopropyl 1'-((1-(4-hydroxy-2-oxobutyl)-4,5,6,7-tetrahydro-1H-benzo[d]imidazol-2-yl)methyl)-2'-oxospiro[azetidine-3,3'-indoline]-1-carboxylate Isopropyl 2'-oxo-1'-((4,5,6,7-tetrahydro-1H-benzo[d]imidazol-2-yl)methyl)spiro[azetidine-3,3'-indoline]-1-carboxylate (0.50 g, 1.27 mmol) was dissolved in 10 mL THF, 1-bromo-4-hydroxybutan-2-one 66b (0.42 g, 2.54 mmol) and TEA (0.38 g, 3.80 mmol) were added, stirring for 12 h at 70° C. The reaction solution was cooled to r.t., 50 mL water was added, extracted with EA (30 mL×3), organic phases were combined and washed in sequence with water (20 mL×2), saturated sodium chloride solution (20 mL×2), dried over anhydrous sodium sulfate, filtered, the filtrate was concentrated under reduced pressure, the residue was purified by silica gel column chromatography with eluting system C to give isopropyl 1'-((1-(4-hydroxy-2-oxobutyl)-4,5,6,7-tetrahydro-1H-benzo[d]imidazol-2-yl)methyl)-2'-oxospiro[azetidine-3,3'-indoline]-1-carboxylate 66c (0.49 g, light yellow solid), yield: 68.3%.

$^1$H NMR (400 MHz, CDCl$_3$) δ 7.60 (d, J=7.78 Hz, 1H), 7.50 (d, J=7.03 Hz, 1H), 7.32-7.39 (m, 1H), 7.16 (t, J=7.28 Hz, 1H), 4.81-5.04 (m, 5H), 4.30 (d, J=8.28 Hz, 2H), 4.08 (d, J=8.28 Hz, 2H), 3.94 (t, J=5.40 Hz, 2H), 2.76 (t, J=5.40 Hz, 2H), 2.58 (br. s., 2H), 2.26 (br. s., 2H), 1.85-1.60 (m, 4H), 1.22-1.32 (m, 6H).

Step 3

Isopropyl 2'-oxo-1'-((1-(2,2,4-trifluorobutyl)-4,5,6,7-tetrahydro-1H-benzo[d]imidazol-2-yl)methyl)spiro[azetidine-3,3'-indoline]-1-carboxylate Diethylaminosulfur trifluoride (0.5 mL) was added dropwise into isopropyl 1'-((1-(4-hydroxy-2-oxobutyl)-4,5,6,7-tetrahydro-1H-benzo[d]imidazol-2-yl)methyl)-2'-oxospiro[azetidine-3,3'-indoline]-1-carboxylate 66c (0.10 g, 0.21 mmol) at 0° C., stirring for 5 h at 50° C. The reaction mixture was cooled to 0° C., 30 mL water was added, extracted with DCM (20 mL×3), organic phases were combined and washed in sequence with water (20 mL×2), saturated sodium chloride solution (20 mL×2), dried over anhydrous sodium sulfate, filtered, the filtrate was concentrated under reduced pressure, the residue was purified by preparative HPLC to give the target product isopropyl 2'-oxo-1'-((1-(2,2,4-trifluorobutyl)-4,5,6,7-tetrahydro-1H-benzo[d]imidazol-2-yl)methyl)spiro[azetidine-3,3'-indoline]-1-carboxylate 66 (40 mg, white solid), yield: 36.2%.

MS m/z (ESI): 505.2 [M+1]

$^1$H NMR (400 MHz, CDCl$_3$) δ 7.60 (d, J=7.78 Hz, 1H), 7.51 (d, J=7.03 Hz, 1H), 7.35 (t, J=7.91 Hz, 1H), 7.15 (t, J=7.28 Hz, 1H), 5.04-4.92 (m, 3H), 4.82 (t, J=5.40 Hz, 1H), 4.70 (t, J=5.40 Hz, 1H), 4.49-4.32 (m, 4H), 4.09 (d, J=8.53 Hz, 2H), 2.59 (br. s., 2H), 2.51-2.41 (m, 4H), 1.79 (br. s., 4H), 1.29 (d, J=6.02 Hz, 6H).

Embodiment 67

Isopropyl 1'-((1-(2,2-difluorobutyl)-4,5,6,7-tetrahydro-1H-benzo[d]imidazol-2-yl)methyl)-2'-oxospiro[azetidine-3,3'-indoline]-1-carboxylate

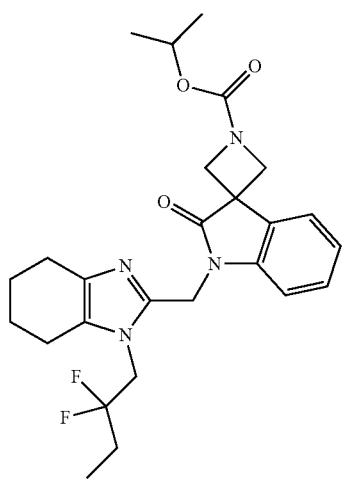

-continued

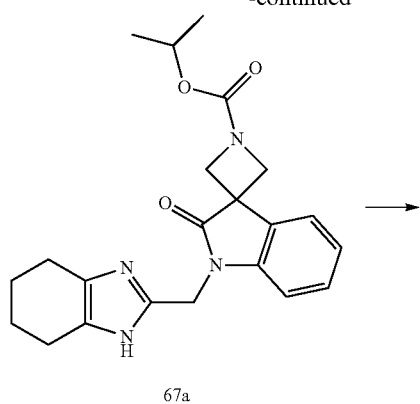

67a

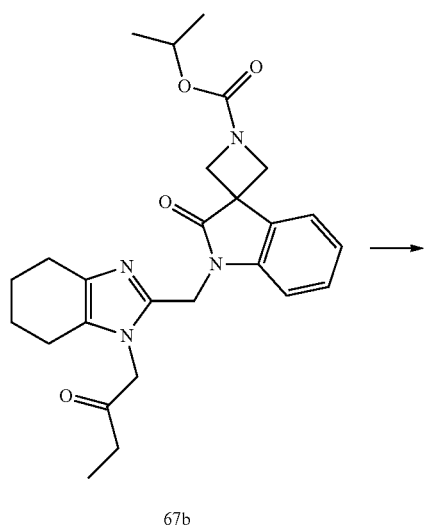

67b

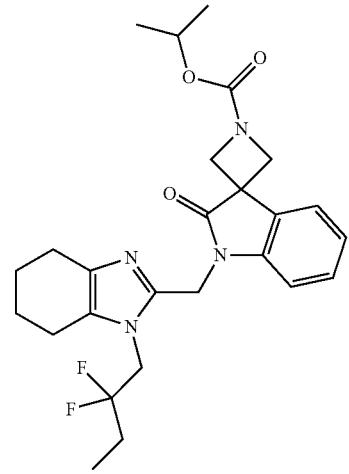

67

Step 1

Isopropyl 2'-oxo-1'-((1-(2-oxobutyl)-4,5,6,7-tetrahydro-1H-benzo[d]imidazol-2-yl)methyl)spiro[azetidine-3,3'-indoline]-1-carboxylate Isopropyl 2'-oxo-1'-((4,5,6,7-tetrahydro-1H-benzo[d]imidazol-2-yl)methyl)spiro[azetidine-3,3'-indoline]-1-carboxylate 67a (0.20 g, 0.51 mmol) was dissolved in 10 mL THF, 1-bromo-2-butanone (0.09 g, 0.61 mmol) and TEA (0.05 g, 0.51 mmol) were added, stirring for 12 h at 70° C. The reaction solution was cooled to r.t., 30 mL water was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, the residue was purified by silica gel column chromatography with elution system C to give isopropyl 2'-oxo-1'-((1-(2-oxobutyl)-4,5,6,7-tetrahydro-1H-benzo[d]imidazol-2-yl)methyl)spiro[azetidine-3,3'-indoline]-1-carboxylate 67b (0.13 g, light yellow solid), yield: 34.2%.

1H NMR (400 MHz, CDCl$_3$) δ 7.60 (d, J=8.03 Hz, 1H), 7.50 (d, J=7.28 Hz, 1H), 7.35 (t, J=7.53 Hz, 1H), 7.18-7.12 (t, J=7.20 Hz, 1H), 5.00-4.90 (m, 5H), 4.29 (d, J=8.28 Hz, 2H), 4.07 (d, J=8.28 Hz, 2H), 2.49-2.66 (m, 4H), 2.25 (br. s., 2H), 1.78 (br. s., 4H), 1.28 (d, J=6.27 Hz, 6H), 1.10 (t, J=7.28 Hz, 3H).

Step 2

Isopropyl 1'-((1-(2,2-difluorobutyl)-4,5,6,7-tetrahydro-1H-benzo[d]imidazol-2-yl)methyl)-2'-oxospiro[azetidine-3,3'-indoline]-1-carboxylate Diethylaminosulfur trifluoride (0.61 g, 3.78 mmol) was added dropwise into isopropyl 2'-oxo-1'-((1-(2-oxobutyl)-4,5,6,7-tetrahydro-1H-benzo[d]imidazol-2-yl)methyl)spiro[azetidine-3,3'-indoline]-1-carboxylate 67b (30 mg, 0.06 mmol) at 0° C., stirring for 5 h at 50° C. The reaction solution was cooled to 0° C., 30 mL water was added, extracted with DCM (20 mL×3), organic phases were combined and washed in sequence with water (20 mL×2), saturated sodium chloride solution (20 mL×2), dried over anhydrous sodium sulfate, filtered, the filtrate was concentrated under reduced pressure, the residue was purified by preparative HPLC to give isopropyl 1'-((1-(2,2-difluorobutyl)-4,5,6,7-tetrahydro-1H-benzo[d]imidazol-2-yl)methyl)-2'-oxospiro[azetidine-3,3'-indoline]-1-carboxylate 67 (15 mg, light white solid), yield: 46.8%.

MS m/z (ESI): 487.3 [M+1]

$^1$H NMR (400 MHz, CDCl$_3$) δ 7.62 (d, J=8.03 Hz, 1H), 7.51 (d, J=7.28 Hz, 1H), 7.35 (t, J=7.53 Hz, 1H), 7.15 (t, J=7.53 Hz, 1H), 5.07-4.91 (m, 3H), 4.45-4.32 (m, 4H), 4.09 (d, J=8.28 Hz, 2H), 2.59 (br. s., 2H), 2.47 (br. s., 2H), 2.11-1.94 (m, 2H), 1.79 (br. s., 4H), 1.28 (d, J=6.27 Hz, 6H), 1.13 (t, J=7.53 Hz, 3H).

Embodiment 68

Isopropyl 1'-((1-(3-methyl-2-oxobutyl)-4,5,6,7-tetrahydro-1H-benzo[d]imidazol-2-yl)methyl)-2'-oxospiro[azetidine-3,3'-indoline]-1-carboxylate

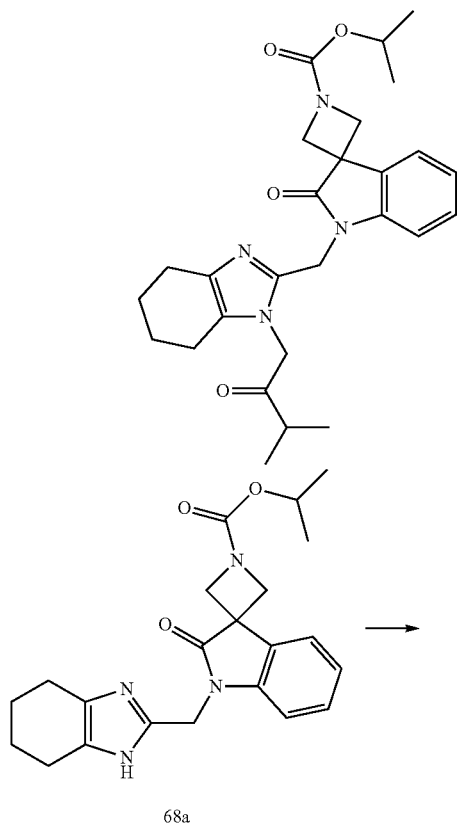

Step 1

Isopropyl 1'-((1-(3-methyl-2-oxobutyl)-4,5,6,7-tetrahydro-1H-benzo[d]imidazol-2-yl)methyl)-2'-oxospiro[azetidine-3,3'-indoline]-1-carboxylate Isopropyl 2'-oxo-1'-((4,5,6,7-tetrahydro-1H-benzo[d]imidazol-2-yl)methyl)spiro[azetidine-3,3'-indoline]-1-carboxylate 68a (0.25 g, 0.63 mmol) was dissolved in 10 mL THF, 1-bromo-3-methyl-2-butanone (0.21 g, 1.27 mmol) and TEA (0.19 g, 1.90 mmol) were added, stirring for 12 h at 70° C. The reaction solution was cooled to r.t., 30 mL water was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, the residue was purified by silica gel column chromatography with eluting system C to give the target product isopropyl 1'-((1-(3-methyl-2-oxobutyl)-4,5,6,7-tetrahydro-1H-benzo[d]imidazol-2-yl)methyl)-2'-oxospiro[azetidine-3,3'-indoline]-1-carboxylate 68 (0.21 g, yellow solid), yield: 69.2%.

MS m/z (ESI): 479.4 [M+1]

$^1$H NMR (400 MHz, CDCl$_3$) δ 7.61 (d, J=8.03 Hz, 1H), 7.49 (d, J=7.03 Hz, 1H), 7.37-7.31 (m, 1H), 7.14 (t, J=7.40 Hz, 1H), 5.01-4.92 (m, 3H), 4.84 (s, 2H), 4.31 (d, J=8.28 Hz, 2H), 4.07 (d, J=8.28 Hz, 2H), 2.85-2.75 (m, 1H), 2.57 (br. s., 2H), 2.22 (br. s., 2H), 1.77 (br. s., 4H), 1.26 (dd, J=12.80, 6.53 Hz, 12H).

Embodiment 69

Isopropyl 1'-((1-(2,2-difluoro-3-methylbutyl)-4,5,6,7-tetrahydro-1H-benzo[d]imidazol-2-yl)methyl)-2'-oxospiro[azetidine-3,3'-indoline]-1-carboxylate

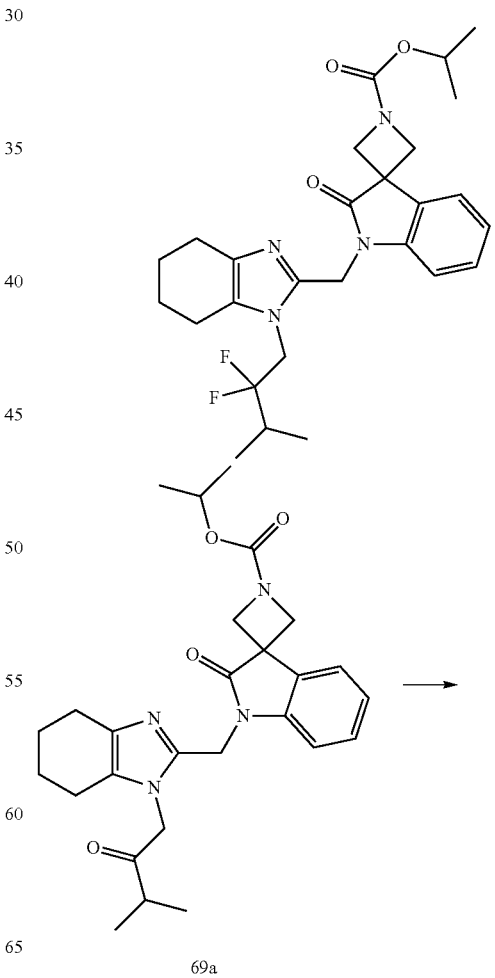

Step 1

Isopropyl 1'-((1-(2,2-difluoro-3-methylbutyl)-4,5,6,7-tetrahydro-1H-benzo[d]imidazol-2-yl)methyl)-2'-oxospiro[azetidine-3,3'-indoline]-1-carboxylate Diethylaminosulfur trifluoride (7.01 g, 43.46 mmol) was added into isopropyl 1'-((1-(3-methyl-2-oxobutyl)-4,5,6,7-tetrahydro-1H-benzo[d]imidazol-2-yl)methyl)-2'-oxospiro[azetidine-3,3'-indoline]-1-carboxylate 69a (0.26 g, 0.54 mmol), stirring for 1 h at 50° C. The reaction solution was cooled to 0° C., 80 mL water was added, extracted with DCM (50 mL×3), organic phases were combined and washed in sequence with water (50 mL×2), saturated sodium chloride solution (50 mL×2), dried over anhydrous sodium sulfate, filtered, the filtrate was concentrated under reduced pressure, the residue was purified by preparative HPLC to give the target product isopropyl 1'-((1-(2,2-difluoro-3-methylbutyl)-4,5,6,7-tetrahydro-1H-benzo[d]imidazol-2-yl)methyl)-2'-oxospiro[azetidine-3,3'-indoline]-1-carboxylate 69 (40 mg, white solid), yield: 15.2%.

MS m/z (ESI): 501.3 [M+1]

<sup>1</sup>H NMR (400 MHz, CD<sub>3</sub>OD) δ 7.61 (d, J=7.5 Hz, 1H), 7.31-7.25 (m, 1H), 7.19-7.13 (m, 1H), 7.07 (d, J=7.8 Hz, 1H), 4.98 (s, 2H), 4.94 (d, J=6.5 Hz, 1H), 4.53 (t, J=16.3 Hz, 2H), 4.34 (d, J=8.3 Hz, 2H), 4.14 (d, J=8.3 Hz, 2H), 2.49 (d, J=19.6 Hz, 4H), 2.31 (td, J=6.9, 14.0 Hz, 1H), 1.79 (br. s., 4H), 1.29 (d, J=6.3 Hz, 6H), 1.17 (d, J=6.8 Hz, 6H).

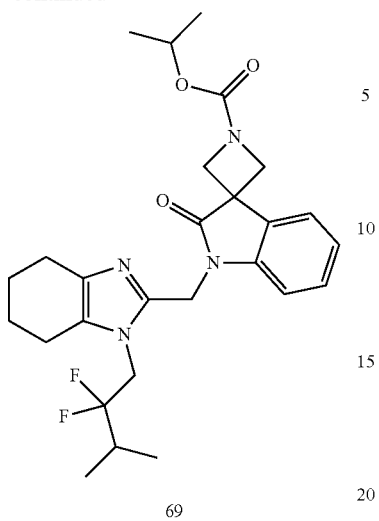

69

Embodiment 70

Isopropyl (Z)-1'-((1-(2-fluoro-3-methylbut-1-en-1-yl)-4,5,6,7-tetrahydro-1H-benzo[d]imidazol-2-yl)methyl)-2'-oxospiro[azetidine-3,3'-indoline]-1-carboxylate

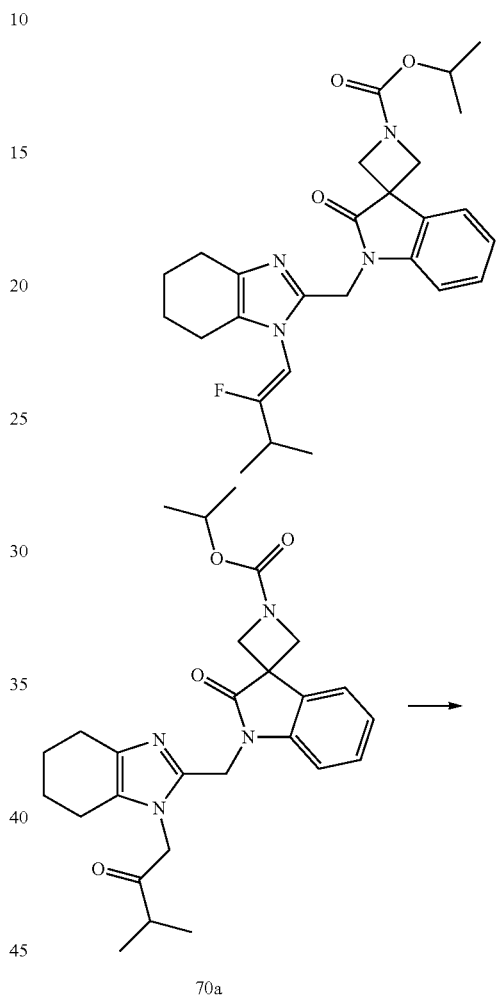

70a

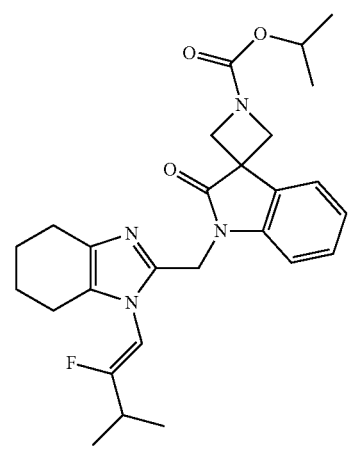

70

Step 1

Isopropyl (Z)-1'-((1-(2-fluoro-3-methylbut-1-en-1-yl)-4,5,6,7-tetrahydro-1H-benzo[d]imidazol-2-yl)methyl)-2'-oxospiro[azetidine-3,3'-indoline]-1-carboxylate Diethylaminosulfur trifluoride (7.01 g, 43.46 mmol) was added into isopropyl 1'-((1-(3-methyl-2-oxobutyl)-4,5,6,7-tetrahydro-1H-benzo[d]imidazol-2-yl)methyl)-2'-oxospiro[azetidine-3,3'-indoline]-1-carboxylate 70a (0.26 g, 0.54 mmol), stirring for 1 h at 50° C. The reaction solution was cooled to 0° C., 80 mL water was added, extracted with DCM (50 mL×3), organic phases were combined and washed in sequence with water (50 mL×2), saturated sodium chloride solution (50 mL×2), dried over anhydrous sodium sulfate, filtered, the filtrate was concentrated under reduced pressure, the residue was purified by preparative HPLC to give the target product isopropyl (Z)-1'-((1-(2-fluoro-3-methylbut-1-en-1-yl)-4,5,6,7-tetrahydro-1H-benzo[d]imidazol-2-yl)methyl)-2'-oxospiro[azetidine-3,3'-indoline]-1-carboxylate 70 (10 mg, white solid), yield: 3.8%.

MS m/z (ESI): 481.3 [M+1]

$^1$H NMR (400 MHz, CD$_3$OD) δ 7.61 (d, J=7.3 Hz, 1H), 7.29-7.23 (m, 1H), 7.19-7.12 (m, 1H), 6.88 (d, J=7.8 Hz, 1H), 6.20-6.12 (m, 1H), 4.94 (d, J=6.5 Hz, 1H), 4.34 (d, J=8.0 Hz, 2H), 4.15 (d, J=8.0 Hz, 2H), 2.71-2.63 (m, 1H), 2.44 (d, J=17.6 Hz, 4H), 1.79 (br. s., 4H), 1.68 (br. s., 1H), 1.29 (d, J=6.3 Hz, 6H), 1.24 (d, J=7.0 Hz, 6H).

Embodiment 71

Isopropyl 1'-((1-(2-fluoro-3-methylbut-2-en-1-yl)-4,5,6,7-tetrahydro-1H-benzo[d]imidazol-2-yl)methyl)-2'-oxospiro[azetidine-3,3'-indoline]-1-carboxylate

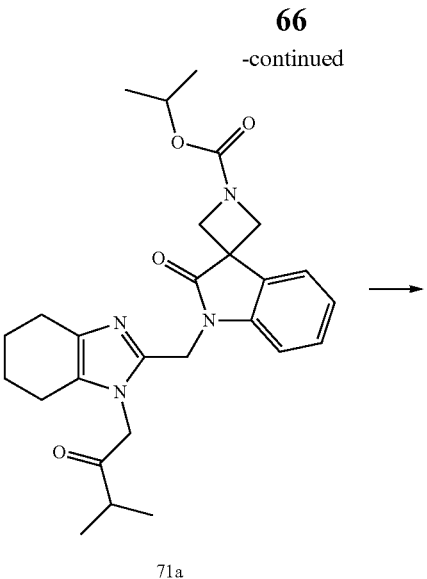

71a

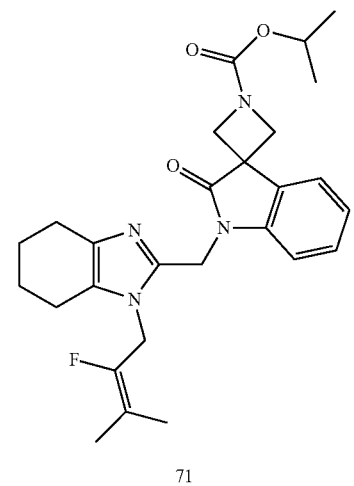

71

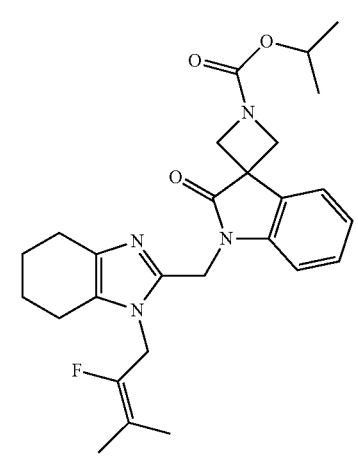

Step 1

Isopropyl 1'-((1-(2-fluoro-3-methylbut-2-en-1-yl)-4,5,6,7-tetrahydro-1H-benzo[d]imidazol-2-yl)methyl)-2'-oxospiro[azetidine-3,3'-indoline]-1-carboxylate Diethylaminosulfur trifluoride (7.01 g, 43.46 mmol) was added into isopropyl 1'-((1-(3-methyl-2-oxobutyl)-4,5,6,7-tetrahydro-1H-benzo[d]imidazol-2-yl)methyl)-2'-oxospiro[azetidine-3,3'-indoline]-1-carboxylate 71a (0.26 g, 0.54 mmol), stirring for 1 h at 50° C. The reaction solution was cooled to 0° C., 80 mL water was added, extracted with DCM (50 mL×3), organic phases were combined and washed in sequence with water (50 mL×2), saturated sodium chloride solution (50 mL×2), dried over anhydrous sodium sulfate, filtered, the filtrate was concentrated under reduced pressure, the residue was purified by preparative HPLC to give the target product isopropyl 1'-((1-(2-fluoro-3-methylbut-2-en-1-yl)-4,5,6,7-tetrahydro-1H-benzo[d]imidazol-2-yl)methyl)-2'-oxospiro[azetidine-3,3'-indoline]-1-carboxylate 71 (10 mg, white solid), yield: 3.8%.

MS m/z (ESI): 481.4 [M+1]

$^1$H NMR (400 MHz, CD$_3$OD) δ 7.61 (d, J=7.5 Hz, 1H), 7.30-7.24 (m, 1H), 7.19-7.12 (m, 1H), 7.05 (d, J=7.8 Hz, 1H), 5.01 (s, 2H), 4.95-4.91 (m, 3H), 4.32 (d, J=8.3 Hz, 2H), 4.14 (d, J=7.8 Hz, 2H), 2.47 (d, J=4.0 Hz, 4H), 1.79 (d, J=2.5 Hz, 7H), 1.64 (d, J=3.0 Hz, 3H), 1.29 (d, J=6.3 Hz, 6H).

Embodiment 72

Ethyl 1'-((1-isopentyl-4,5,6,7-tetrahydro-1H-benzo[d]imidazol-2-yl)methyl)-2'-oxospiro[azetidine-3,3'-indoline]-1-carboxylate

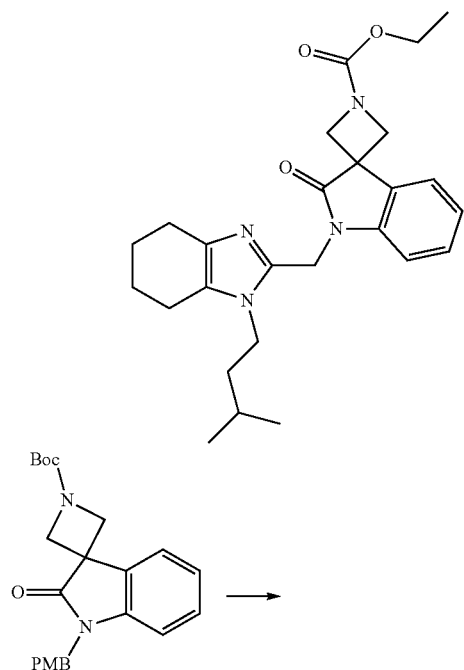

72a

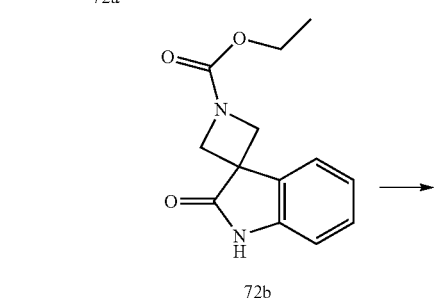

72b

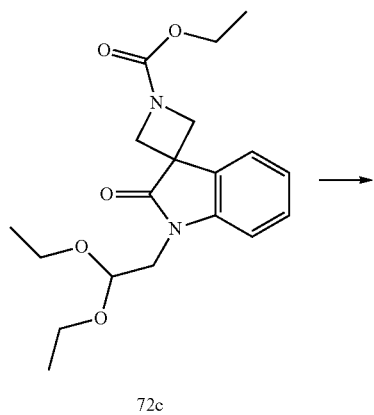

72c

-continued

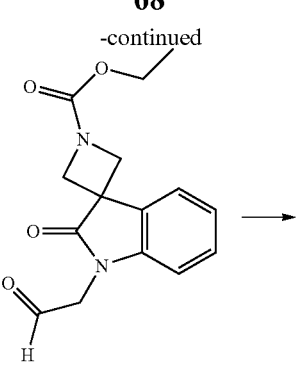

72d

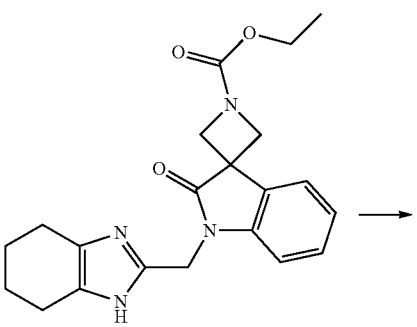

72e

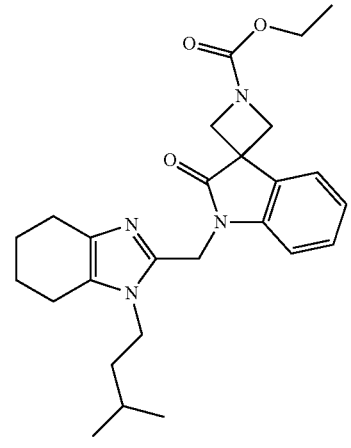

72

Step 1

Ethyl 2'-oxospiro[azetidine-3,3'-indoline]-1-carboxylate tert-Butyl 1'-(4-methoxybenzyl)-2'-oxospiro[azetidine-3,3'-indoline]-1-carboxylate 72a (4 g, 10.5 mmol) was dissolved in 40 mL trifluoroacetic acid, stirring for 10 min at r.t., trifluoromethanesulfonic acid (4.731 g, 31.54 mmol) was added dropwise at 0° C., stirring for 4 h at r.t. The reaction solution was concentrated under reduced pressure, 28 mL THF and 28 mL water were added into the residue, pH was adjusted to 9-10 with sodium carbonate, ethyl chlorocarbonate (1.90 g, 17.51 mmol) was added dropwise at 0° C., stirring for 12 h at r.t. 100 mL water was added, the mixture was extracted with EA (80 mL×3), organic phases were combined and washed in sequence with water (80 mL×2), saturated sodium chloride solution (80 mL×2), dried over anhydrous sodium sulfate, filtered, the filtrate was concentrated under reduced pressure, the residue was purified by silica gel column chromatography with eluting system C to give ethyl 2'-oxospiro[azetidine-3,3'-indoline]-1-carboxylate 72b (2.4 g, yellow solid), yield: 96.0%.

$^1$H NMR (400 MHz, CDCl$_3$) δ 8.68 (br. s., 1H), 7.54 (d, J=7.3 Hz, 1H), 7.32-7.27 (m, 1H), 7.18-7.10 (t, J=8.0 Hz, 1H), 6.95 (d, J=7.5 Hz, 1H), 4.44 (d, J=8.3 Hz, 2H), 4.27-4.09 (m, 4H), 1.30 (t, J=8.0 Hz, 3H).

Step 2

Ethyl 1'-(2,2-diethoxyethyl)-2'-oxospiro[azetidine-3,3'-indoline]-1-carboxylate

Ethyl 2'-oxospiro[azetidine-3,3'-indoline]-1-carboxylate 72b (20.0 g, 81.2 mmol) was dissolved in 100 mL DMF, 2-bromo-1,1-diethoxyethane (32.0 g, 162.4 mmol), cesium carbonate (59.9 g, 183.9 mmol), potassium iodide (1.35 g, 8.13 mmol) were added, stirring for 4 h at 90° C. The reaction mixture was added with 300 mL H$_2$O, extracted with EA (300 mL×3), organic phases were combined and washed in sequence with water (200 mL×2), saturated sodium chloride solution (200 mL×2), dried over anhydrous sodium sulfate, filtered, the filtrate was concentrated under reduced pressure, the residue was purified by silica gel column chromatography with elution system C to give ethyl 1'-(2,2-diethoxyethyl)-2'-oxospiro[azetidine-3,3'-indoline]-1-carboxylate 72c (24.5 g, yellow solid), yield: 74.9%.

$^1$H NMR (400 MHz, CDCl$_3$) δ 7.51 (d, J=7.04 Hz, 1H), 7.27-7.33 (m, 1H), 7.12 (t, J=7.52 Hz, 1H), 7.04 (d, J=7.52 Hz, 1H), 4.69 (t, J=5.28 Hz, 1H), 4.40 (d, J=8.04 Hz, 2H), 4.17 (q, J=7.04 Hz, 2H), 4.07-4.14 (m, 2H), 3.82 (d, J=5.52 Hz, 2H), 3.69-3.78 (m, 2H), 3.44-3.55 (m, 2H), 1.28 (t, J=7.04 Hz, 3H), 1.13 (t, J=7.03 Hz, 6H).

Step 3

Ethyl 2'-oxo-1'-(2-oxoethyl)spiro[azetidine-3,3'-indoline]-1-carboxylate

Ethyl 1'-(2,2-diethoxyethyl)-2'-oxospiro[azetidine-3,3'-indoline]-1-carboxylate 72c (10.0 g, 27.59 mmol) was dissolved in 45 mL DCM and 15 mL H$_2$O, trifluoroacetic acid (68.00 g, 596.39 mmol) was added, stirring for 2 h at r.t., sodium carbonate was used to neutralize, 150 mL H$_2$O was added into the reaction mixture. The mixture was extracted with DCM (150 mL×3), organic phases were combined and washed in sequence with water (80 mL×2), saturated sodium chloride solution (80 mL×2), dried over anhydrous sodium sulfate, filtered, the filtrate was concentrated under reduced pressure to give the crude product ethyl 2'-oxo-1'-(2-oxoethyl)spiro[azetidine-3,3'-indoline]-1-carboxylate 72d (7.5 g, yellow oil), yield: 94.3%.

Step 4

Ethyl 2'-oxo-1'-((4,5,6,7-tetrahydro-1H-benzo[d]imidazol-2-yl)methyl)spiro[azetidine-3,3'-indoline]-1-carboxylate Ethyl 2'-oxo-1'-(2-oxoethyl)spiro[azetidine-3,3'-indoline]-1-carboxylate 72d (5.50 g, 19.08 mmol) was dissolved in 50 mL ethanol, ammonium acetate (7.35 g, 95.40 mmol), 1,2-cyclohexanedione (2.57 g, 22.9 mmol) were added, refluxing for 4 h. The reaction solution was cooled to r.t., 150 mL water was added, extracted with EA (150 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with elution system C to give ethyl 2'-oxo-1'-((4,5,6,7-tetrahydro-1H-benzo[d]imidazol-2-yl)methyl)spiro[azetidine-3,3'-indoline]-1-carboxylate 72e (4.3 g, yellow oil), yield: 59.2%.

MS m/z (ESI): 381.0 [M+1]

Step 5

Ethyl 1'-((1-isopentyl-4,5,6,7-tetrahydro-1H-benzo[d]imidazol-2-yl)methyl)-2'-oxospiro[azetidine-3,3'-indoline]-1-carboxylate Ethyl 2'-oxo-1'-((4,5,6,7-tetrahydro-1H-benzo[d]imidazol-2-yl)methyl)spiro[azetidine-3,3'-indoline]-1-carboxylate 72e (0.3 g, 0.79 mmol) was dissolved in 10 mL DMSO, 1-bromo-3-methylbutane (0.14 g, 0.95 mmol), potassium carbonate (0.33 g, 2.37 mmol), potassium iodide (13.09 mg, 0.08 mmol) were added, refluxing for 5 h. The reaction mixture was cooled to r.t., 30 mL H$_2$O was added, extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and ethyl 1'-((1-isopentyl-4,5,6,7-tetrahydro-1H-benzo[d]imidazol-2-yl)methyl)-2'-oxospiro[azetidine-3,3'-indoline]-1-carboxylate 72 (43 mg, white solid) was given, yield: 12.0%.

MS m/z (ESI): 451.3 [M+1]

$^1$H NMR (400 MHz, CD$_3$OD) δ 7.64 (d, J=7.2 Hz, 1H), 7.22 (d, J=7.2 Hz, 1H), 7.19 (d, J=7.6 Hz, 1H), 7.04 (d, J=8.0 Hz, 1H), 5.00 (s, 2H), 4.30 (t, J=8.8 Hz, 2H), 4.21 (d, J=7.2 Hz, 4H), 3.96 (t, J=7.2 Hz, 2H), 2.47-2.54 (m, 4H), 1.686 (s, 4H), 1.47-1.45 (m, 3H), 1.31 (s, 3H), 0.98 (d, J=7.2 Hz, 6H).

Embodiment 73

Ethyl 1'-((1-(3-fluorobutyl)-4,5,6,7-tetrahydro-1H-benzo[d]imidazol-2-yl)methyl)-2'-oxospiro[azetidine-3,3'-indoline]-1-carboxylate

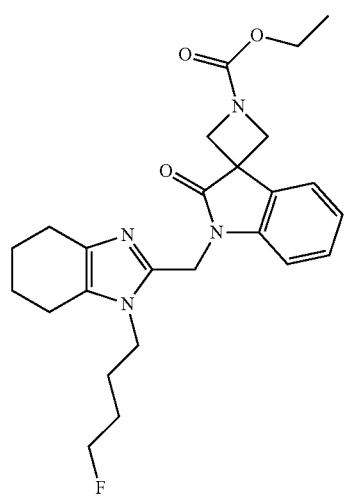

-continued

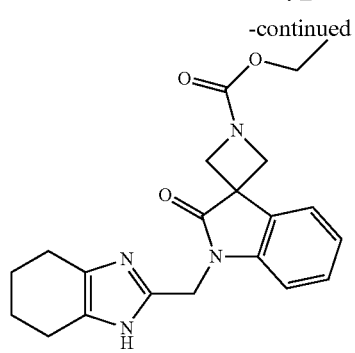

73a

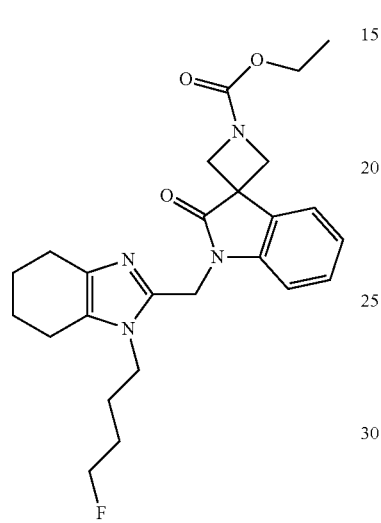

73

Step 1

Ethyl 1'-((1-(3-fluorobutyl)-4,5,6,7-tetrahydro-1H-benzo[d]imidazol-2-yl)methyl)-2'-oxospiro[azetidine-3,3'-indoline]-1-carboxylate Ethyl 2'-oxo-1'-((4,5,6,7-tetrahydro-1H-benzo[d]imidazol-2-yl)methyl)spiro[azetidine-3,3'-indoline]-1-carboxylate 73a (0.30 g, 0.79 mmol) was dissolved in 5 mL DMSO, 1-bromo-4-fluorobutane (0.15 g, 0.95 mmol), cesium carbonate (0.51 g, 1.58 mmol), potassium iodide (0.01 g, 0.08 mmol) were added, stirring for 5 h at 80° C. The reaction solution was cooled to r.t., 30 mL H₂O was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and ethyl 1'-((1-(3-fluorobutyl)-4,5,6,7-tetrahydro-1H-benzo[d]imidazol-2-yl)methyl)-2'-oxospiro[azetidine-3,3'-indoline]-1-carboxylate 73 (77 mg, white solid) was given, yield: 21.5%.

MS m/z (ESI): 455.3 [M+1]

$^1$H NMR (400 MHz, CD$_3$OD) δ 7.64 (d, J=6.8 Hz, 1H), 7.20 (s, 1H), 7.17 (d, J=6.8 Hz, 1H), 7.06 (d, J=8.0 Hz, 1H), 5.00 (s, 2H), 4.52-4.35 (m, 4H), 4.20 (d, J=6.8 Hz, 4H), 4.00 (s, 2H), 2.55-2.49 (m, 4H), 1.81-1.61 (m, 8H), 1.31 (t, J=7.2 Hz, 3H).

Embodiment 74

Ethyl 1'-((1-(3-cyanopropyl)-4,5,6,7-tetrahydro-1H-benzo[d]imidazol-2-yl)methyl)-2'-oxospiro[azetidine-3,3'-indoline]-1-carboxylate

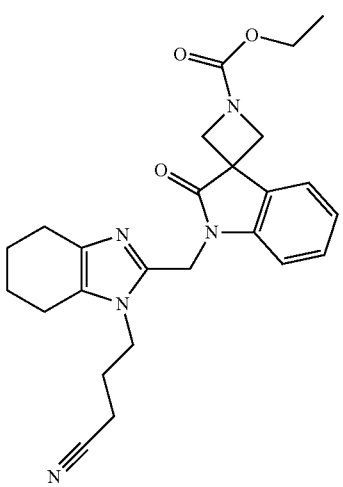

74a

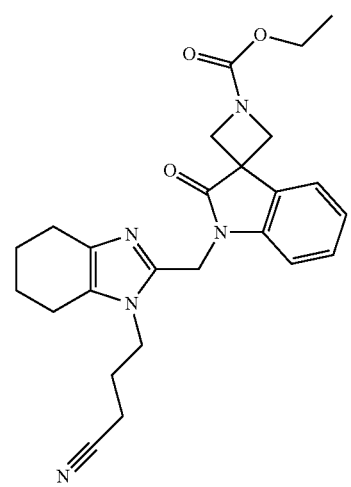

74

Step 1

Ethyl 1'-((1-(3-cyanopropyl)-4,5,6,7-tetrahydro-1H-benzo[d]imidazol-2-yl)methyl)-2'-oxospiro[azetidine-3,3'-indoline]-1-carboxylate Ethyl 2'-oxo-1'-((4,5,6,7-tetrahydro-1H-benzo[d]imidazol-2-yl)methyl)spiro[azetidine-3,3'-indoline]-1-carboxylate 74a (0.30 g, 0.79 mmol) was dissolved in 5 mL DMSO, 4-bromobutyronitrile (0.14 g, 0.95 mmol), cesium carbonate (0.51 g, 1.58 mmol), potassium iodide (0.01 g, 0.08 mmol) were added, stirring for 5 h at 80° C. The reaction solution was cooled to r.t., 30 mL H₂O was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and ethyl 1'-((1-(3-cyanopropyl)-4,5,6,7-tetrahydro-1H-benzo[d]imidazol-2-yl)methyl)-2'-oxospiro[azetidine-3,3'-indoline]-1-carboxylate 74 (77 mg, white solid) was given, yield: 21.8%.

MS m/z (ESI): 448.3 [M+1]

$^1$H NMR (400 MHz, CD$_3$OD) δ 7.64 (d, J=7.8 Hz, 1H), 7.30 (t, J=7.2 Hz, 1H), 7.20 (t, J=7.2 Hz, 1H), 7.07 (d, J=7.2 Hz, 1H), 5.02 (s, 2H), 4.30 (s, 2H), 4.20 (d, J=7.2 Hz, 4H), 4.09 (t, J=7.6 Hz, 2H), 2.58-2.41 (m, 6H), 2.01 (d, J=8 Hz, 2H), 1.82 (t, J=6 Hz, 4H), 1.31 (t, J=7.2 Hz, 3H).

Embodiment 75

Ethyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate

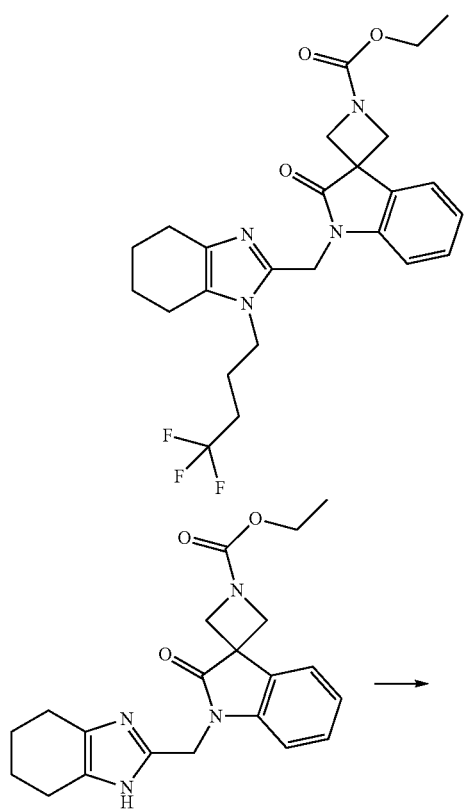

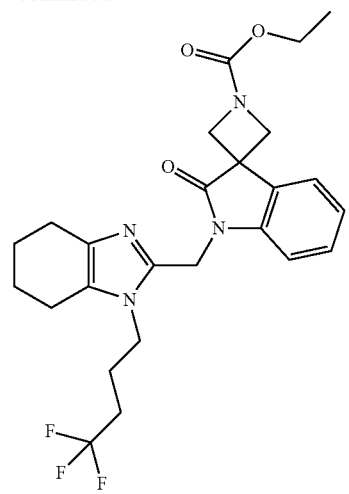

Step 1

Ethyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate Ethyl 2'-oxo-1'-((4,5,6,7-tetrahydro-1H-benzo[d]imidazol-2-yl)methyl)spiro[azetidine-3,3'-indoline]-1-carboxylate 75a (0.30 g, 0.79 mmol) was dissolved in 5 mL DMSO, 4-bromo-1,1,1-trifluorobutytane (0.15 g, 0.95 mmol), cesium carbonate (0.51 g, 1.58 mmol), potassium iodide (0.01 g, 0.08 mmol) were added, stirring for 5 h at 80° C. The reaction solution was cooled to r.t., 30 mL H₂O was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and ethyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 75 (57 mg, white solid) was given, yield: 14.6%.

MS m/z (ESI): 491.3 [M+1]

$^1$H NMR (400 MHz, CD$_3$OD) δ 7.64 (d, J=7.6 Hz, 1H), 7.20 (d, J=7.2 Hz, 1H), 7.17 (s, 1H), 7.09 (d, J=7.6 Hz, 1H), 5.01 (s, 2H), 4.36-4.06 (m, 8H), 2.55-2.35 (m, 6H), 1.84 (d, J=7.6 Hz, 6H), 1.31 (s, 3H).

Embodiment 76

Ethyl 1'-((1-(3-(methylsulfonyl)propyl)-4,5,6,7-tetrahydro-1H-benzo[d]imidazol-2-yl)methyl)-2'-oxospiro[azetidine-3,3'-indoline]-1-carboxylate

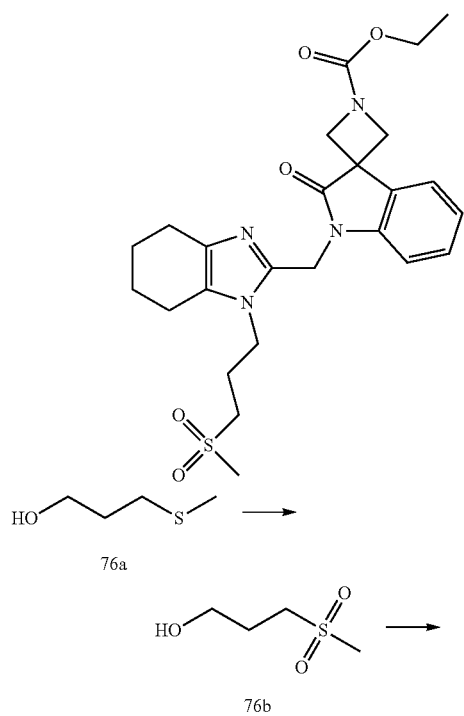

Step 1

3-(Methyl sulfonyl)propan-1-ol 3-(Methylthio)propan-1-ol 76a (6.50 g, 61.21 mmol) was dissolved in 100 mL DCM, benzoyl hydroperoxide (10.56 g, 61.21 mmol) was added at 0° C., stirring for 5.5 h at r.t. The reaction solution was filtered, the filtrate was concentrated under reduced pressure to obtain the crude product of 3-(methylsulfonyl)propan-1-ol 76b (8.8 g, light yellow oil).

Step 2

1-Bromo-3-(methylsulfonyl)propane 3-(Methylsulfonyl)propan-1-ol 76b (1.50 g, 10.85 mmol) was dissolved in 20 mL DCM, phosphorus tribromide (4.41 g, 16.28 mmol) was added at 0° C., stirring for 16 h at r.t. 100 mL saturated sodium carbonate aqueous solution was added at 0° C., the mixture was extracted with DCM (100 mL×3), organic phases were combined and washed in sequence with water (100 mL×2), saturated sodium chloride solution (100 mL×2), dried over anhydrous sodium sulfate, filtered, the filtrate was concentrated under reduced pressure to obtain 1-bromo-3-(methylsulfonyl)propane 76c (1.2 g, yellow oil).

1H NMR (400 MHz, CDCl$_3$) δ 3.57 (t, J=6.3 Hz, 2H), 3.29-3.18 (m, J=7.8 Hz, 2H), 2.97 (s, 3H), 2.52-2.34 (m, J=6.8 Hz, 2H).

Step 3

Ethyl 1'-((1-(3-(methylsulfonyl)propyl)-4,5,6,7-tetrahydro-1H-benzo[d]imidazol-2-yl)methyl)-2'-oxospiro[azetidine-3,3'-indoline]-1-carboxylate Ethyl 2'-oxo-1'-((4,5,6,7-tetrahydro-1H-benzo[d]imidazol-2-yl)methyl)spiro[azetidine-3,3'-indoline]-1-carboxylate (0.30 g, 0.79 mmol) was dissolved in 10 mL DMSO, the crude product of 1-bromo-3-(methylsulphonyl)-propane 76c (0.19 g, 0.95 mmol), cesium carbonate (0.25 g, 0.79 mmol) were added, stirring for 1 h at r.t. The reaction solution was cooled to r.t., 30 mL H$_2$O was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product ethyl 1'-((1-(3-(methyl sulfonyl)propyl)-4,5,6,7-tetrahydro-1H-benzo[d]imidazol-2-yl)methyl)-2'-oxospiro[azetidine-3,3'-indoline]-1-carboxylate 76 (0.19 g, white solid) was given, yield: 48.6%.

MS m/z (ESI): 501.0 [M+1]

$^1$H NMR (400 MHz, CDCl$_3$) δ 7.58-7.45 (m, 1H), 7.37-7.29 (m, 1H), 7.19-7.11 (m, J=7.5 Hz, 1H), 4.95 (br. s., 2H), 4.37 (d, J=8.2 Hz, 2H), 4.26-4.04 (m, J=7.1 Hz, 7H), 3.09 (t, J=7.3 Hz, 2H), 2.94 (s, 3H), 2.60-2.42 (m, 4H), 2.11 (br. s., 2H), 1.78 (br. s., 4H), 1.34-1.25 (m, 3H).

77
Embodiment 77
Cyclopentyl 1'-((1-(3-hydroxybutyl)-4,5,6,7-tetra-hydro-1H-benzo[d]imidazol-2-yl)methyl)-2'-oxospiro[azetidine-3,3'-indoline]-1-carboxylate
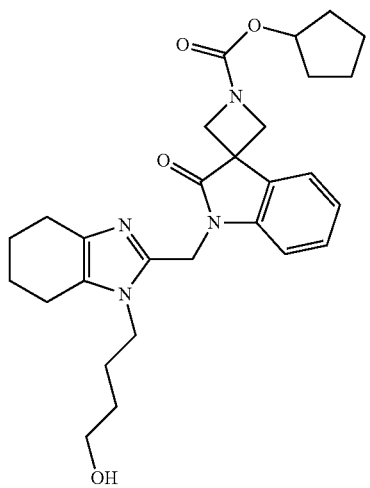
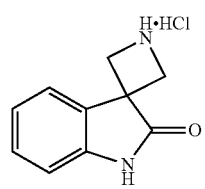
77a
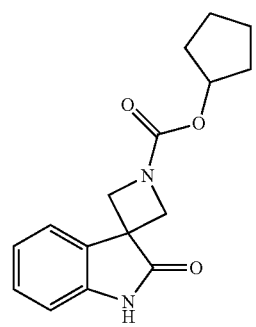
77b
78
-continued
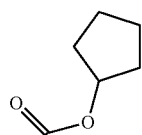
77c
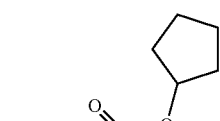
77d
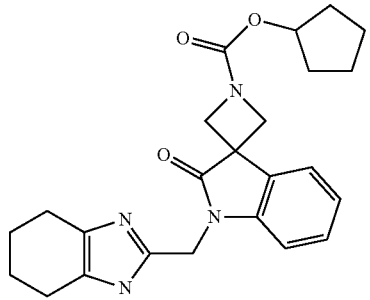
77e -continued

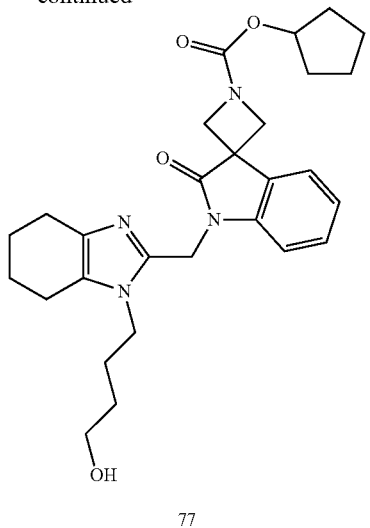

77

Step 1

Cyclopentyl 2'-oxospiro[azetidine-3,3'-indoline]-1-carboxylate

Spiro[azetidine-3,3'-indoline]-2'-one hydrochloride 77a (9.82 g, 46.59 mmol) was dissolved in 50 mL THF, NaOH (1.86 g, 46.59 mmol) aqueous solution, sodium carbonate (4.94 g, 46.59 mmol) aqueous solution were added at 0° C., stirring for 10 min at 0° C., cyclopentyl chlorocarbonate (9.00 g, 60.57 mmol) was added, stirring for 2 h at r.t. 150 mL H$_2$O was added, extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with eluting system C to obtain cyclopentyl 2'-oxospiro[azetidine-3,3'-indoline]-1-carboxylate 77b (1.54 g, yellow solid), yield: 11.1%.

$^1$H NMR (400 MHz, CDCl$_3$) δ 9.17-9.10 (m, 1H), 7.52 (d, J=7.53 Hz, 1H), 7.27 (s, 1H), 7.15-7.09 (m, 1H), 6.95 (d, J=7.53 Hz, 1H), 5.18-5.12 (m, 1H), 4.40 (d, J=8.53 Hz, 2H), 1.86 (m, 2H), 1.72 (m, 4H), 1.64-1.52 (m, 2H).

Step 2

Cyclopentyl 1'-(2,2-diethoxyethyl)-2'-oxospiro[azetidine-3,3'-indoline]-1-carboxylate Cyclopentyl 2'-oxospiro[azetidine-3,3'-indoline]-1-carboxylate 77b (1.54 g, 5.38 mmol) was dissolved in 15 mL DMF, cesium carbonate (3.50 g, 10.76 mmol), potassium carbonate (44.64 mg, 0.27 mmol) were added, stirring for 3 h at 90° C. 50 mL H$_2$O was added, the mixture was extracted with EA (50 mL×3), organic phases were combined and washed in sequence with water (50 mL×2), saturated sodium chloride solution (50 mL×2), dried over anhydrous sodium sulfate, filtered, the filtrate was concentrated under reduced pressure, the residue was purified by silica gel column chromatography with eluting system C to give cyclopentyl 1'-(2,2-diethoxyethyl)-2'-oxospiro[azetidine-3,3'-indoline]-1-carboxylate 77c (1.60 g, light yellow oil), yield: 68.0%.

$^1$H NMR (400 MHz, CDCl$_3$) δ 7.53 (d, J=7.53 Hz, 1H), 7.35-7.26 (m, 1H), 7.14 (t, J=7.53 Hz, 1H), 7.05 (d, J=7.78 Hz, 1H), 5.16 (t, J=5.77 Hz, 1H), 4.71 (t, J=5.27 Hz, 1H), 4.40 (d, J=8.28 Hz, 2H), 4.18-4.06 (m, 2H), 3.84 (d, J=5.27 Hz, 2H), 3.75 (dd, J=7.15, 9.16 Hz, 2H), 3.57-3.46 (m, 2H), 1.95-1.82 (m, 2H), 1.80-1.69 (m, 4H), 1.60 (d, J=1.76 Hz, 2H), 1.15 (t, J=6.90 Hz, 6H).

Step 3

Cyclopentyl 2'-oxo-1'-(2-oxoethyl)spiro[azetidine-3,3'-indoline]-1-carboxylate

Cyclopentyl 1'-(2,2-diethoxy)-2'-oxospiro[azetidine-3,3'-indoline]-1-carboxylate 77c (1.60 g, 3.98 mmol) was dissolved in 28 mL DCM and 5 mL H$_2$O, 28 mL trifluoroacetic acid was added dropwise at 0° C., stirring for 2 h at r.t. 50 mL H$_2$O was added, the mixture was extracted with DCM (50 mL×3), organic phases were combined and washed in sequence with saturated sodium bicarbonate aqueous solution (50 mL×2), saturated sodium chloride solution (50 mL×2), dried over anhydrous sodium sulfate, filtered, the filtrate was concentrated under reduced pressure to obtain the crude product of cyclopentyl 2'-oxo-1'-(2-oxoethyl)spiro[azetidine-3,3'-indoline]-1-carboxylate 77d (1.2 g, light yellow oil).

Step 4

Cyclopentyl 2'-oxo-1'-((4,5,6,7-tetrahydro-1H-benzo[d]imidazol-2-yl)methyl)spiro[azetidine-3,3'-indoline]-1-carboxylate Cyclopentyl 2'-oxo-1'-(2-oxoethyl)spiro[azetidine-3,3'-indoline]-1-carboxylate 77d (0.79 g, 2.41 mmol) was dissolved in 8 mL ethanol, 1,2-cyclohexanedione (0.32 g, 2.89 mmol), ammonium acetate (0.93 g, 12.05 mmol) were added, stirring at reflux for 6 h. The reaction solution was concentrated under reduced pressure, 30 mL H$_2$O was added, extracted with DCM (30 mL×3), organic phases were combined and washed in sequence with saturated sodium bicarbonate aqueous solution (30 mL×2), saturated sodium chloride solution (30 mL×2), dried over anhydrous sodium sulfate, filtered, the filtrate was concentrated under reduced pressure, the residue was purified by silica gel column chromatography with eluting system C to obtain cyclopentyl 2'-oxo-1'-((4,5,6,7-tetrahydro-1H-benzo[d]imidazol-2-yl)methyl)spiro[azetidine-3,3'-indoline]-1-carboxylate 77e (0.78 g, yellow solid), yield: 70.8%.

$^1$H NMR (400 MHz, CDCl$_3$) δ 7.52 (d, J=7.53 Hz, 1H), 7.32 (s, 1H), 7.25-7.19 (m, 1H), 7.14 (s, 1H), 5.16 (br. s., 1H), 4.89 (s, 2H), 4.37 (d, J=8.03 Hz, 2H), 4.08 (d, J=9.03 Hz, 2H), 2.50 (br. s., 4H), 2.05 (s, 2H), 1.94-1.82 (m, 2H), 1.80-1.67 (m, 6H), 1.65-1.55 (m, 2H).

Step 5

Cyclopentyl 1'-((1-(3-hydroxybutyl)-4,5,6,7-tetrahydro-1H-benzo[d]imidazol-2-yl)methyl)-2'-oxospiro[azetidine-3,3'-indoline]-1-carboxylate Cyclopentyl 2'-oxo-1'-((4,5,6,7-tetrahydro-1H-benzo[d]imidazol-2-yl)methyl)spiro[azetidine-3,3'-indoline]-1-carboxylate 77e (0.17 g, 0.40 mmol) was dissolved in 5 mL DMSO, 4-bromobutyl acetate (0.09 g, 0.49 mmol), potassium carbonate (0.17 g, 1.21 mmol), potassium iodide (6.71 mg, 0.04 mmol) were added, stirring for 5 h at 90° C. The reaction solution was cooled to r.t., 30 mL H₂O was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure to obtain white solid. 3 mL 1M NaOH aqueous solution was added to dissolve, stirring for 1 h at r.t. 30 mL water was added into the reaction solution, the mixture was extracted with EA (30 mL×2), organic phase was combined and washed with saturated sodium chloride solution (20 mL×2), dried over anhydrous sodium sulfate, filtered, the filtrate was concentrated under reduced pressure, preparative HPLC was used to purify and the target product cyclopentyl 1'-((1-(3-hydroxybutyl)-4,5,6,7-tetrahydro-1H-benzo[d]imidazol-2-yl)methyl)-2'-oxospiro[azetidine-3,3'-indoline]-1-carboxylate 77 (11 mg, white solid) was given, yield: 16.9%.

MS m/z (ESI): 493.4 [M+1]

¹H NMR (400 MHz, CD₃OD) δ 1.65-1.80 (m, 15H) 2.47-2.54 (m, 4H) 3.57 (t, J=7.2 Hz, 2H) 3.96 (t, J=6.8 Hz, 2H) 4.21 (d, J=6.8 Hz, 4H) 4.30 (t, J=7.6 Hz, 2H) 5.01 (s, 2H) 7.06 (t, J=8.0 Hz, 1H) 7.19 (d, J=7.2 Hz, 1H) 7.28 (t, J=7.6 Hz, 1H) 7.63 (d, J=7.2 Hz, 1H).

Embodiment 78

Isopropyl 5'-bromo-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate

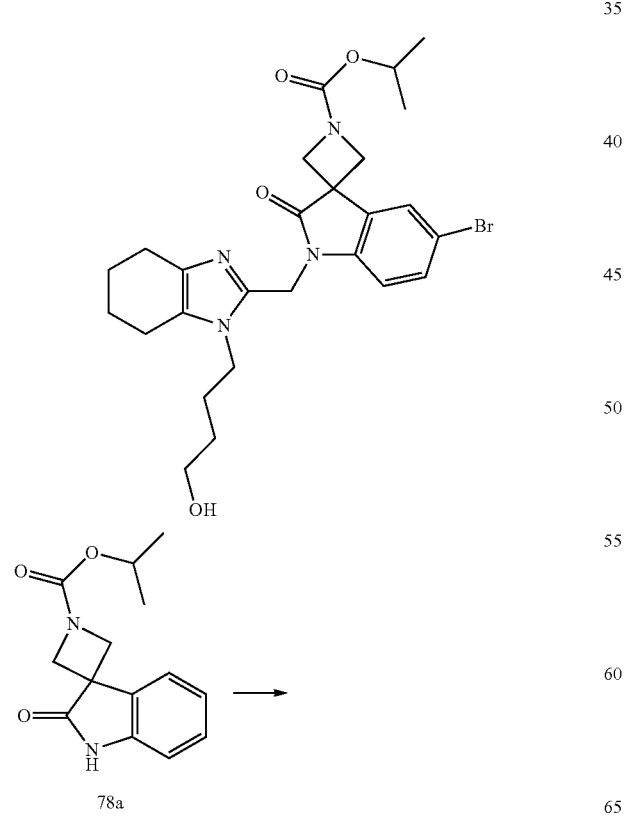

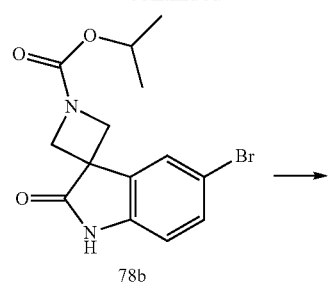

78b

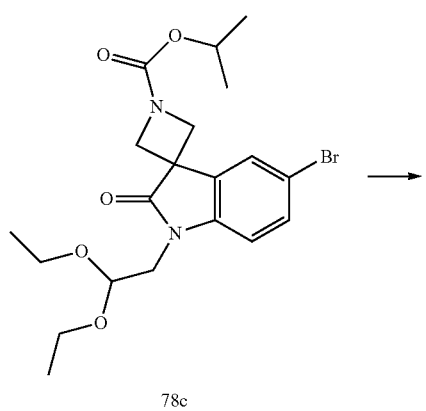

78c

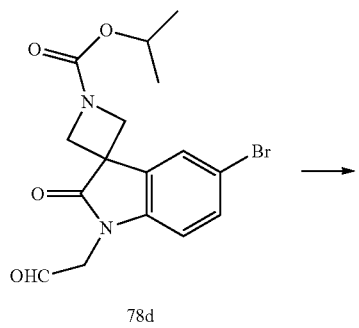

78d

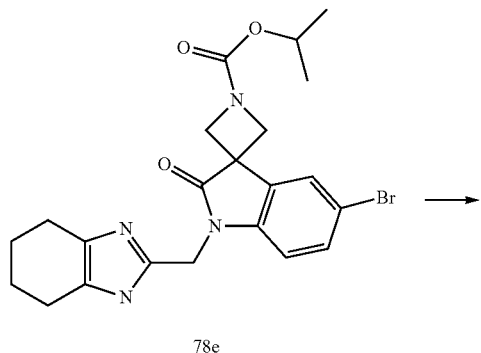

78e

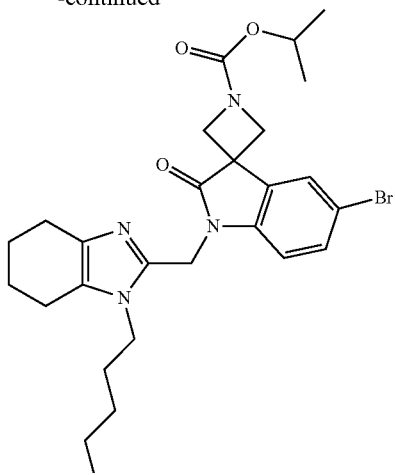

78

Step 1

Isopropyl 5'-bromo-2'-oxospiro[azetidine-3,3'-indoline]-1-carboxylate

Isopropyl 2'-oxospiro[azetidine-3,3'-indoline]-1-carboxylate 78a (1.00 g, 3.84 mmol) was dissolved in 10 mL ethanol, N-bromosuccinimide (0.62 g, 4.61 mmol), 2,2'-azobis(2-methylpropionitrile) (0.06 g, 0.38 mmol) were added, stirring for 2 h at 80° C. The reaction solution was concentrated under reduced pressure, 50 mL H$_2$O was added, extracted with EA (50 mL×3), organic phases were combined and washed in sequence with water (50 mL×2), saturated sodium chloride solution (50 mL×2), dried over anhydrous sodium sulfate, filtered, the filtrate was concentrated under reduced pressure, the residue was purified by silica gel column chromatography with eluting system C to obtain isopropyl 5'-bromo-2'-oxospiro[azetidine-3,3'-indoline]-1-carboxylate 78b (0.90 g, yellow solid), yield: 95.0%.

$^1$H NMR (400 MHz, CD$_3$OD) δ 7.86-7.69 (m, 1H), 7.53-7.35 (m, 1H), 7.02-6.72 (m, 1H), 5.10-4.89 (m, 1H), 4.38-4.24 (m, 2H), 4.20-4.00 (m, 2H), 1.30 (d, J=6.27 Hz, 6H).

Step 2

Isopropyl 5'-bromo-1'-(2,2-diethoxy)-2'-oxospiro[azetidine-3,3'-indoline]-1-carboxylate Isopropyl 5'-bromo-2'-oxospiro[azetidine-3,3'-indoline]-1-carboxylate 78b (0.8 g, 2.46 mmol) was dissolved in 10 mL DMF, 2-bromo-1,1-diethoxyethane (0.53 g, 2.71 mmol), cesium carbonate (1.6 g, 4.92 mmol) were added, stirring for 5 h at 90° C. The reaction solution was cooled to r.t., 100 mL H$_2$O was added, extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure to obtain isopropyl 5'-bromo-1'-(2,2-diethoxy)-2'-oxospiro[azetidine-3,3'-indoline]-1-carboxylate 78c (0.70 g, yellow oil), yield: 64.0%.

$^1$H NMR (400 MHz, CD$_3$OD) δ 7.86-7.69 (m, 1H), 7.53-7.35 (m, 1H), 7.02-6.72 (m, 1H), 5.10-4.89 (m, 2H), 4.38-4.24 (m, 2H), 4.20-4.00 (m, 2H), 3.80-3.50 (m, 6H), 1.30 (d, J=6.27 Hz, 6H), 1.20-1.10 (m, 6H).

Step 3

Isopropyl 5'-bromo-2'-oxo-1'-(2-oxoethyl)spiro[azetidine-3,3'-indoline]-1-carboxylate Isopropyl 5'-bromo-1'-(2,2-diethoxy)-2'-oxospiro[azetidine-3,3'-indoline]-1-carboxylate 78c (0.5 g, 1.13 mmol) was dissolved in 45 mL DCM and 10 mL H$_2$O, 45 mL trifluoroacetic acid was added, stirring for 2 h at r.t. Sodium carbonate was added to adjust pH to 9, 100 mL H$_2$O was added, the mixture was extracted with DCM (100 mL 3), organic phases were combined and washed in sequence with water (100 mL×2), saturated sodium chloride solution (100 mL×2), dried over anhydrous sodium sulfate, filtered, the filtrate was concentrated under reduced pressure to obtain the crude product of isopropyl 5'-bromo-2'-oxo-1'-(2-oxoethyl)spiro[azetidine-3,3'-indoline]-1-carboxylate 78d (0.40 g, yellow oil), yield: 94.0%.

Step 4

Isopropyl 5'-bromo-2'-oxo-1'-((4,5,6,7-tetrahydro-1H-benzo[d]imidazol-2-yl)methyl)spiro[azetidine-3,3'-indoline]-1-carboxylate Isopropyl 5'-bromo-2'-oxo-1'-(2-oxoethyl)spiro[azetidine-3,3'-indoline]-1-carboxylate 78d (0.4 g, 1.05 mmol) was dissolved in 5 mL ethanol, 1,2-cyclohexanedione (0.14 g, 1.26 mmol), ammonium acetate (0.40 g, 5.25 mmol) were added, refluxing for 4 h. The reaction solution was cooled to r.t., 100 mL H$_2$O was added, extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with eluting system C to obtain isopropyl 5'-bromo-2'-oxo-1'-((4,5,6,7-tetrahydro-1H-benzo[d]imidazol-2-yl)methyl)spiro[azetidine-3,3'-indoline]-1-carboxylate 78e (0.30 g, yellow solid), yield: 60.0%.

$^1$H NMR (400 MHz, CDCl$_3$) δ 7.86-7.69 (m, 1H), 7.53-7.35 (m, 1H), 7.02-6.72 (m, 1H), 5.30 (s, 1H), 5.10-4.89 (m, 3H), 4.38-4.24 (m, 2H), 4.20-4.00 (m, 2H), 2.60-2.50 (m, 4H), 1.70-1.60 (m, 4H), 1.30 (d, J=6.27 Hz, 6H).

Step 5

Isopropyl 5'-bromo-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate Isopropyl 5'-bromo-2'-oxo-1'-((4,5,6,7-tetrahydro-1H-benzo[d]imidazol-2-yl)methyl)spiro[azetidine-3,3'-indoline]-1-carboxylate 78e (0.14 g, 0.30 mmol) was dissolved in 5 mL DMSO, 4-bromobutyl acetate (0.07 g, 0.38 mmol), potassium carbonate (0.12 g, 0.89 mmol), potassium iodide (4.9 mg, 0.03 mmol) were added, stirring for 16 h at 90° C. The reaction solution was cooled to r.t., 30 mL H$_2$O was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure to obtain yellow solid. 3 mL 1M NaOH aqueous solution was added to dissolve, stirring for 1 h at r.t. 30 mL water was added into the reaction solution, the mixture was extracted with EA (30 mL×2), organic phases were combined and washed with saturated sodium chloride solution (20 mL×2), dried over anhydrous sodium sulfate, filtered, the filtrate was concentrated under reduced pressure, preparative HPLC was used to purify and the target product isopropyl 5'-bromo-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate 78 (9 mg, white solid), yield: 5.7%.

MS m/z (ESI): 546.3 [M+1]

$^1$H NMR (400 MHz, CD$_3$OD) δ 7.88-7.79 (m, 1H), 7.54-7.38 (m, 1H), 6.98-6.91 (m, 1H), 5.00 (s, 2H), 4.80-4.70 (m, 1H), 4.47-4.29 (m, 2H), 4.28-4.09 (m, 2H), 4.07-3.87 (m, 2H), 3.59 (s, 2H), 2.70-2.38 (m, 4H), 1.93-1.47 (m, 8H), 1.31 (d, J=6.27 Hz, 6H).

Embodiment 79

Isopropyl 5'-bromo-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate

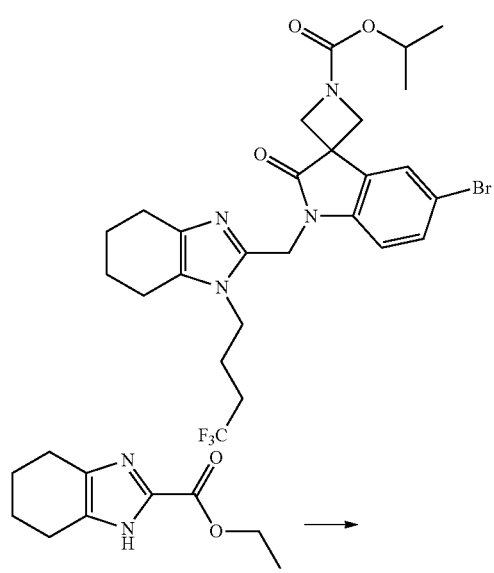

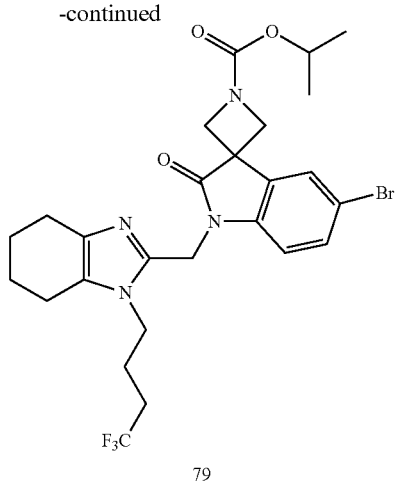

79

Step 1

Ethyl 1-(4,4,4-trifluorobutyl)-4,5,6,7-tetrahydro-1H-benzo[d]imidazole-2-carboxylate Ethyl 4,5,6,7-tetrahydro-1H-benzo[d]imidazole-2-carboxylate 79a (2.0 g, 10.3 mmol) was dissolved in 35 mL DMF, 4-bromo-1,1,1-trifluorobutane (2.16 g, 11.33 mmol), cesium carbonate (6.7 g, 20.6 mmol) were added, stirring for 18 h at 90° C., the reaction mixture was cooled to r.t., 150 mL H$_2$O was added, extracted with EA (100 mL 3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with eluting system C to obtain ethyl 1-(4,4,4-trifluorobutyl)-4,5,6,7-tetrahydro-1H-benzo[d]imidazole-2-carboxylate 79b (3.1 g, yellow oil), yield: 91.0%.

$^1$H NMR (400 MHz, CDCl$_3$) δ 4.43-4.27 (m, 4H), 2.64 (t, J=5.8 Hz, 2H), 2.54 (t, J=6.0 Hz, 2H), 2.22-2.07 (m, 2H), 2.03-1.94 (m, 2H), 1.88-1.79 (m, 4H), 1.40 (t, J=7.3 Hz, 3H).

Step 2

(1-(4,4,4-Trifluorobutyl)-4,5,6,7-tetrahydro-1H-benzo[d]imidazol-2-yl)methanol

Ethyl 1-(4,4,4-trifluorobutyl)-4,5,6,7-tetrahydro-1H-benzo[d]imidazole-2-carboxylate 79c (3.2 g, 10.52 mmol) was dissolved in 3 mL ethanol, cerous chloride (2.59 g, 10.52 mmol), sodium borohydride (0.40 g, 10.52 mmol) were added, stirring for 8 h at r.t. 200 mL H$_2$O was added at 0° C., the mixture was extracted with EA (150 mL×3), organic phases were combined and washed in sequence with water (150 mL×2), saturated sodium chloride solution (150 mL×2), dried over anhydrous sodium sulfate, filtered, the filtrate was concentrated under reduced pressure, the residue was purified by silica gel column chromatography with eluting system A to obtain (1-(4,4,4-trifluorobutyl)-4,5,6,7-tetrahydro-1H-benzo[d]imidazol-2-yl)methanol 79c (2.2 g, white solid), yield: 78.1%.

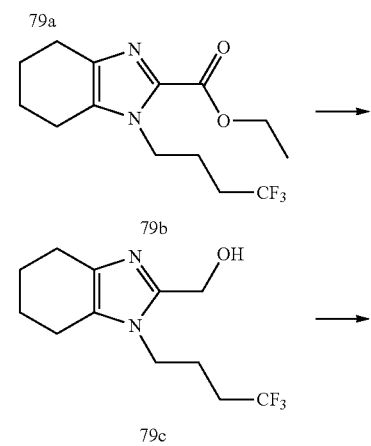

$^1$H NMR (400 MHz, CDCl$_3$) δ 4.61 (s, 2H), 3.98 (t, J=7.4 Hz, 2H), 2.51 (td, J=5.9, 11.1 Hz, 4H), 2.25-2.09 (m, J=9.0 Hz, 2H), 2.09-1.96 (m, J=7.3 Hz, 2H), 1.90-1.74 (m, J=5.3 Hz, 4H).

Step 3

Isopropyl 5'-bromo-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate Isopropyl 5'-bromo-2'-oxospiro[azetidine-3,3'-indoline]-1-carboxylate (70.00 mg, 0.27 mmol) was dissolved in 3 mL THF, (1-(4,4,4-trifluorobutyl)-4,5,6,7-tetrahydro-1H-benzo[d]imidazol-2-yl)methanol 79c (0.11 g, 0.32 mmol), triphenylphosphine (0.08 g, 0.32 mmol) were added, diisopropyl azodicarboxylate (64.7 mg, 0.32 mmol) was added dropwise at 0° C., stirring for 16 h at r.t. 30 mL H$_2$O was added, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product isopropyl 5'-bromo-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 79 (11 mg, white solid), yield: 11.5%.

MS m/z (ESI): 583.1 [M+1]

$^1$H NMR (400 MHz, CD$_3$OD) δ 7.84-7.80 (m, 1H), 7.48-7.43 (m, 1H), 7.03-6.99 (m, 1H), 4.99 (s, 2H), 4.39-4.30 (m, 2H), 4.23-4.14 (m, 2H), 4.11-4.02 (m, 2H), 2.60-2.44 (m, 5H), 2.34-2.23 (m, 2H), 1.95-1.75 (m, 6H), 1.31 (d, J=6.02 Hz, 6H).

Embodiment 80

Isopropyl 5'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate

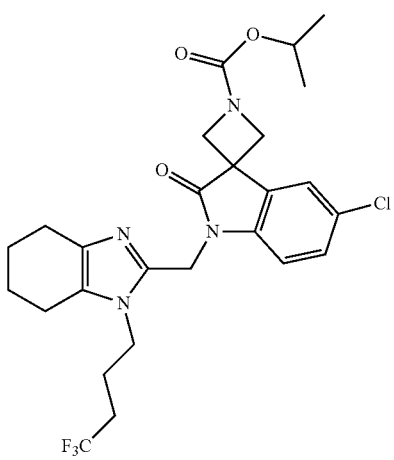

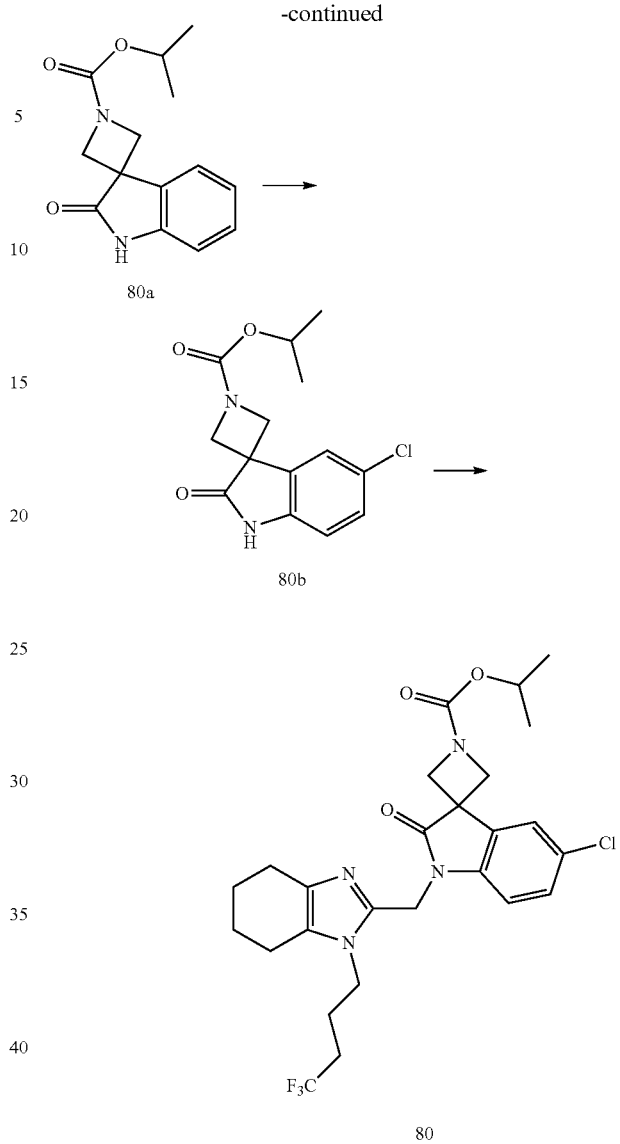

Step 1

Isopropyl 5'-chloro-2'-oxospiro[azetidine-3,3'-indoline]-1-carboxylate

Isopropyl 2'-oxospiro[azetidine-3,3'-indoline]-1-carboxylate 80a (2.00 g, 7.68 mmol) was dissolved in 15 mL ethanol, N-chlorosuccinimide (1.23 g, 9.22 mmol), AIBN (0.13 g, 0.77 mmol) were added, stirring for 3 h at 80° C. The reaction solution was concentrated under reduced pressure, 50 mL H$_2$O was added, extracted with EA (100 mL×3), organic phases were combined and washed in sequence with water (50 mL×2), saturated sodium chloride solution (50 mL×2), dried over anhydrous sodium sulfate, filtered, the filtrate was concentrated under reduced pressure, the residue was purified by silica gel column chromatography with eluting system C to obtain isopropyl 5'-chloro-2'-oxospiro[azetidine-3,3'-indoline]-1-carboxylate 80b (2.01 g, yellow solid), yield: 62.2%.

89

Step 2

Isopropyl 5'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate

Isopropyl 5'-bromo-2'-oxospiro[azetidine-3,3'-indoline]-1-carboxylate 80b (67.0 mg, 0.23 mmol) was dissolved in 2 mL THF, (1-(4,4,4-trifluorobutyl)-4,5,6,7-tetrahydro-1H-benzo[d]imidazol-2-yl)methanol (50 mg, 0.19 mmol), triphenylphosphine (60 mg, 0.23 mmol) were added, diisopropyl azodicarboxylate (46.26 mg, 0.23 mmol) was added dropwise at 0° C., stirring for 4 h at r.t. 30 mL H$_2$O was added, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product isopropyl 5'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 80 (10 mg, white solid) was given, yield: 18.2%.

MS m/z (ESI): 539.2 [M+1]

$^1$H NMR (400 MHz, CD$_3$OD) δ 7.70 (d, J=1.5 Hz, 1H), 7.31 (dd, J=1.8, 8.3 Hz, 1H), 7.06 (d, J=8.5 Hz, 1H), 5.00 (s, 2H), 4.34 (d, J=8.5 Hz, 2H), 4.18 (d, J=8.5 Hz, 2H), 4.08 (d, J=7.5 Hz, 1H), 2.63-2.42 (m, 4H), 2.29 (dd, J=10.8, 16.3 Hz, 2H), 2.18 (s, 1H), 2.02-1.67 (m, 6H), 1.31 (d, J=6.5 Hz, 6H).

Embodiment 81

Isopropyl 6'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate

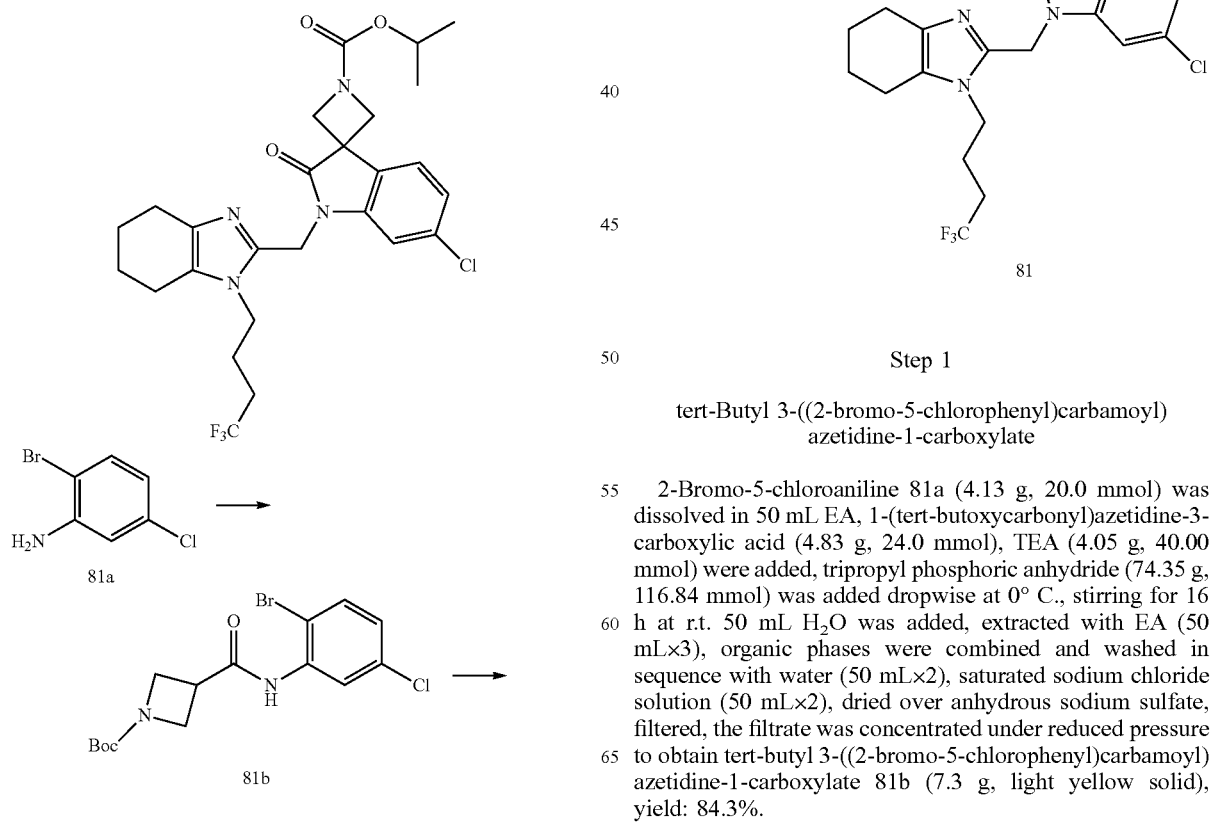

Step 1 tert-Butyl 3-((2-bromo-5-chlorophenyl)carbamoyl)azetidine-1-carboxylate

2-Bromo-5-chloroaniline 81a (4.13 g, 20.0 mmol) was dissolved in 50 mL EA, 1-(tert-butoxycarbonyl)azetidine-3-carboxylic acid (4.83 g, 24.0 mmol), TEA (4.05 g, 40.00 mmol) were added, tripropyl phosphoric anhydride (74.35 g, 116.84 mmol) was added dropwise at 0° C., stirring for 16 h at r.t. 50 mL H$_2$O was added, extracted with EA (50 mL×3), organic phases were combined and washed in sequence with water (50 mL×2), saturated sodium chloride solution (50 mL×2), dried over anhydrous sodium sulfate, filtered, the filtrate was concentrated under reduced pressure to obtain tert-butyl 3-((2-bromo-5-chlorophenyl)carbamoyl)azetidine-1-carboxylate 81b (7.3 g, light yellow solid), yield: 84.3%.

¹H NMR (400 MHz, CDCl₃) δ 8.50 (br. s., 1H), 7.66 (br. s., 1H), 7.49 (d, J=8.53 Hz, 1H), 7.03 (dd, J=2.26, 8.53 Hz, 1H), 4.26-4.16 (m, 4H), 3.42 (s, 1H), 1.48 (s, 9H).

Step 2 tert-Butyl 3-((2-bromo-5-chlorophenyl)(4-methoxybenzyl)carbamoyl)azetidine-1-carboxylate tert-Butyl 3-((2-bromo-5-chlorophenyl)carbamoyl)azetidine-1-carboxylate 81b (7.30 g, 18.7 mmol) was dissolved in 100 mL DMF, cesium carbonate (9.16 g, 28.1 mmol) was added, 4-methoxybenzyl chloride (3.52 g, 22.48 mmol) was added dropwise, stirring for 16 h at 90° C. The reaction solution was cooled to r.t., 200 mL H₂O was added, extracted with EA (200 mL×3), organic phases were combined and washed in sequence with water (200 mL×2), saturated sodium chloride solution (200 mL×2), dried over anhydrous sodium sulfate, filtered, the filtrate was concentrated under reduced pressure to obtain tert-butyl 3-((2-bromo-5-chlorophenyl)(4-methoxybenzyl)carbamoyl)azetidine-1-carboxylate 81c (7.3 g, light yellow oil), yield: 72.9%.

¹H NMR (400 MHz, CDCl₃) δ 7.60 (d, J=8.53 Hz, 1H), 7.21 (dd, J=2.51, 8.53 Hz, 1H), 7.09 (d, J=8.53 Hz, 2H), 6.81 (d, J=8.53 Hz, 2H), 6.67 (d, J=2.26 Hz, 1H), 5.47 (d, J=14.31 Hz, 1H), 4.31-4.20 (m, 1H), 4.04 (d, J=14.30 Hz, 2H), 3.79 (s, 3H), 3.76-3.69 (m, 1H), 3.68-3.59 (m, 1H), 3.04 (s, 1H), 1.41 (s, 9H).

Step 3 tert-Butyl 6'-chloro-1'-(4-methoxybenzyl)-2'-oxospiro[azetidine-3,3'-indoline]-1-carboxylate tert-Butyl 3-((2-bromo-5-chlorophenyl)(4-methoxybenzyl)carbamoyl)azetidine-1-carboxylate 81c (7.30 g, 14.4 mmol) was dissolved in 100 mL 1,4-dioxane, palladium diacetate (0.16 g, 0.72 mmol), sodium tert-butoxide (2.07 g, 21.57 mmol) and tricyclohexylphosphine (2.02 g, 1.44 mmol) were added, stirring for 16 h at 120° C. The reaction solution was concentrated under reduced pressure, cooled to r.t., 200 mL H₂O was added, extracted with EA (200 mL×3), organic phases were combined and washed in sequence with water (200 mL×2), saturated sodium chloride solution (200 mL×2), dried over anhydrous sodium sulfate, filtered, the filtrate was concentrated under reduced pressure, the residue was purified by silica gel column chromatography with eluting system C to obtain tert-butyl 6'-chloro-1'-(4-methoxybenzyl)-2'-oxospiro[azetidine-3,3'-indoline]-1-carboxylate 81d (3.6 g, light yellow oil), yield: 52.5%.

¹H NMR (400 MHz, CDCl₃) δ 7.45 (d, J=8.03 Hz, 1H), 7.22 (d, J=8.53 Hz, 2H), 7.08 (dd, J=1.76, 7.78 Hz, 1H), 6.86 (d, J=8.53 Hz, 2H), 6.75 (d, J=1.51 Hz, 1H), 4.80 (s, 2H), 4.41 (d, J=8.53 Hz, 2H), 4.05 (d, J=8.53 Hz, 2H), 3.81-3.77 (m, 3H), 1.49 (s, 9H).

Step 4

Isopropyl 6'-chloro-2'-oxospiro[azetidine-3,3'-indoline]-1-carboxylate tert-Butyl 6'-chloro-1'-(4-methoxybenzyl)-2'-oxospiro[azetidine-3,3'-indoline]-1-carboxylate 81d (0.80 g, 1.49 mmol) was dissolved in 10 mL trifluoroacetic acid, trifluoromethanesulfonic acid (0.67 g, 4.48 mmol) was added dropwise at 0° C., stirring for 16 h at r.t. The reaction solution was concentrated under reduced pressure, 20 mL THF, 10 mL H₂O were added into the residue, sodium carbonate was added to adjust pH to 9~10, isopropyl chloroformate (0.22 g, 1.79 mmol) was added dropwise at 0° C., stirring for 2 h at r.t. 100 mL H₂O was added, the mixture was extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with eluting system C to obtain isopropyl 6'-chloro-2'-oxospiro[azetidine-3,3'-indoline]-1-carboxylate 81e (0.23 g, black oil), yield: 52.4%.

¹H NMR (400 MHz, CDCl₃) δ 8.85 (br. s., 1H), 7.45 (d, J=8.03 Hz, 1H), 7.11 (dd, J=2.01, 8.03 Hz, 1H), 6.96 (d, J=1.51 Hz, 1H), 4.97 (td, J=6.09, 12.42 Hz, 1H), 4.41 (d, J=8.53 Hz, 2H), 4.09 (d, J=8.03 Hz, 2H), 1.28 (d, J=6.53 Hz, 6H).

Step 5

Isopropyl 6'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate Isopropyl 6'-chloro-2'-oxospiro[azetidine-3,3'-indoline]-1-carboxylate 81e (70.8 mg, 0.24 mmol) was dissolved in 2 mL THF, (1-(4,4,4-trifluorobutyl)-4,5,6,7-tetrahydro-1H-benzo[d]imidazol-2-yl)methanol (70 mg, 0.27 mmol), triphenylphosphine (84 mg, 0.32 mmol) were added, diisopropyl azodicarboxylate (64.7 mg, 0.32 mmol) was added dropwise at 0° C., stirring for 6 h at r.t. 30 mL H₂O was added, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product isopropyl 6'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 81 (17.5 mg, white solid) was given, yield: 12.0%.

MS m/z (ESI): 339.3 [M+1]

¹H NMR (400 MHz, CD₃OD) δ 7.62 (d, J=7.8 Hz, 1H), 7.23-7.12 (m, J=1.8 Hz, 2H), 4.99 (s, 3H), 4.34 (d, J=8.5 Hz, 2H), 4.16 (d, J=8.5 Hz, 2H), 4.07 (t, J=7.9 Hz, 2H), 2.64-2.44 (m, 4H), 2.37-2.19 (m, J=5.5 Hz, 2H), 1.96-1.75 (m, 6H), 1.30 (d, J=6.0 Hz, 6H).

Embodiment 82

Isopropyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate

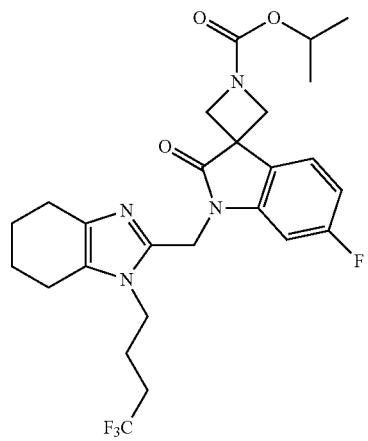

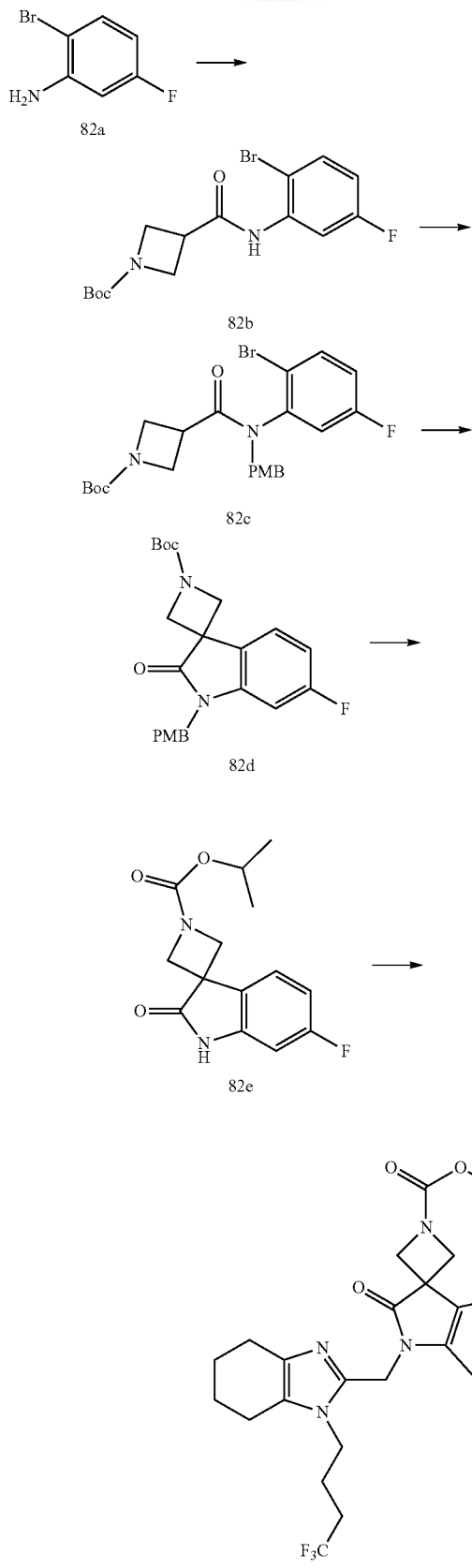

Step 1 tert-Butyl 3-((2-bromo-5-fluorophenyl)carbamoyl)azetidine-1-carboxylate

2-Bromo-5-fluoroaniline 82a (18.50 g, 97.36 mmol) was dissolved in 200 mL EA, 1-(tert-butoxycarbonyl)azetidine-3-carboxylic acid (23.51 g, 0.12 mmol), TEA (19.70 g, 194.73 mmol) were added, tripropyl phosphoric anhydride (74.35 g, 116.84 mmol) was added portionwise at 0° C., stirring for 16 h at r.t. 500 mL H$_2$O was added, the mixture was extracted with EA (500 mL×3), organic phases were combined and washed in sequence with water (500 mL×2), saturated sodium chloride solution (500 mL×2), dried over anhydrous sodium sulfate, filtered, the filtrate was concentrated under reduced pressure, the residue was purified by silica gel column chromatography with eluting system C to obtain tert-butyl 3-((2-bromo-5-fluorophenyl)carbamoyl)azetidine-1-carboxylate 82b (26.5 g, white solid), yield: 65.6%.

$^1$H NMR (400 MHz, CDCl$_3$) δ 8.32-8.21 (m, 1H), 7.75-7.66 (m, 1H), 7.55-7.45 (m, 1H), 6.80-6.71 (m, 1H), 4.28-4.08 (m, 4H), 3.40 (s, 1H), 1.46 (s, 9H).

Step 2 tert-Butyl 3-((2-bromo-5-fluorophenyl)(4-methoxybenzyl)carbamoyl)azetidine-1-carboxylate tert-Butyl 3-((2-bromo-5-fluorophenyl)carbamoyl)azetidine-1-carboxylate 82b (26.0 g, 69.66 mmol) was dissolved in 200 mL DMF, cesium carbonate (45.39 g, 0.14 mmol), 1-chloromethyl-4-methoxybenzene (16.36 g, 0.10 mmol) were added, stirring for 16 h at 90° C. 200 mL H$_2$O was added, the mixture was extracted with EA (300 mL×3), organic phases were combined and washed in sequence with water (300 mL×2), saturated sodium chloride solution (300 mL×2), dried over anhydrous sodium sulfate, filtered, the filtrate was concentrated under reduced pressure, the residue was purified by silica gel column chromatography with eluting system C to obtain tert-butyl 3-((2-bromo-5-fluorophenyl)(4-methoxybenzyl)carbamoyl)azetidine-1-carboxylate 82c (25.0 g, white solid), yield: 61.8%.

$^1$H NMR (400 MHz, CDCl$_3$) δ 7.72-7.62 (m, 1H), 7.11 (d, J=8.28 Hz, 2H), 7.05-6.94 (m, 1H), 6.82 (d, J=8.28 Hz, 2H), 6.50-6.38 (m, 1H), 5.60-5.48 (m, 1H), 4.36-4.24 (m, 1H), 4.03 (d, J=14.05 Hz, 2H), 3.81 (s, 3H), 3.78-3.60 (m, 2H), 3.14-3.02 (m, 1H), 1.49-1.37 (m, 10H).

Step 3 tert-Butyl 6'-fluoro-1'-(4-methoxybenzyl)-2'-oxospiro[azetidine-3,3'-indoline]-1-carboxylate tert-Butyl 3-((2-bromo-5-fluorophenyl)(4-methoxybenzyl)carbamoyl)azetidine-1-carboxylate 82c (18.5 g, 37.5 mmol) was dissolved in 200 mL 1,4-dioxane, palladium acetate (0.42 g, 1.88 mmol), sodium tert-butoxide (5.41 g, 56.25 mmol) and tricyclohexylphosphine (5.26 g, 3.75 mmol) were added, stirring for 16 h at 120° C. The reaction solution was cooled to r.t., 200 mL H$_2$O was added, extracted with EA (200 mL×3), organic phases were combined and washed in sequence with water (200 mL×2), saturated sodium chloride solution (200 mL×2), dried over anhydrous sodium sulfate, filtered, the filtrate was concentrated under reduced pressure, the residue was purified by silica gel column chromatography with eluting system C to obtain tert-butyl 6'-fluoro-1'-(4-methoxybenzyl)-2'-oxospiro[azetidine-3,3'-indoline]-1-carboxylate 82d (7.1 g, yellow oil), yield: 39.0%.

$^1$H NMR (400 MHz, CDCl$_3$) δ 7.72 7.62 (m, 1H), 7.11 (d, J=8.28 Hz, 2H), 7.05-6.94 (m, 1H), 6.82 (d, J=8.28 Hz, 2H), 6.50-6.38 (m, 1H), 5.60-5.48 (m, 1H), 4.36-4.24 (m, 1H), 4.03 (d, J=14.05 Hz, 2H), 3.81 (s, 3H), 3.78-3.60 (m, 2H), 1.49-1.37 (m, 9H).

Step 4

Isopropyl 6'-fluoro-2'-oxospiro[azetidine-3,3'-indoline]-1-carboxylate tert-Butyl 6'-fluoro-1'-(4-methoxybenzyl)-2'-oxospiro[azetidine-3,3'-indoline]-1-carboxylate 82d (2.0 g, 4.85 mmol) was dissolved in 10 mL trifluoroacetic acid, trifluoromethanesulfonic acid (2.18 g, 14.55 mmol) was added dropwise at 0° C., stirring for 16 h at r.t. The reaction solution was concentrated under reduced pressure, 20 mL THF, 10 mL H$_2$O were added into the residue, sodium carbonate was added to adjust pH to 9~10, isopropyl chloroformate (1.04 g, 8.49 mmol) was added dropwise at 0° C., stirring for 4 h at r.t. 100 mL H$_2$O was added, the mixture was extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with eluting system C to obtain isopropyl 6'-fluoro-2'-oxospiro[azetidine-3,3'-indoline]-1-carboxylate 82e (0.97 g, yellow solid), yield: 48.1%.

MS m/z (ESI): 278.9 [M+1]

Step 5

Isopropyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate Isopropyl 6'-fluoro-2'-oxospiro[azetidine-3,3'-indoline]-1-carboxylate 82e (0.1 g, 0.38 mmol) was dissolved in 5 mL THF, (1-(4,4,4-trifluorobutyl)-4,5,6,7-tetrahydro-1H-benzo[d]imidazol-2-yl)methanol (0.1 g, 0.38 mmol), triphenylphosphine (0.1 g, 0.38 mmol) were added, diisopropyl azodicarboxylate (92.5 mg, 0.46 mmol) was added dropwise at 0° C., stirring for 16 h at r.t. 30 mL H$_2$O was added, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product isopropyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 82 (40 mg, white solid) was given, yield: 20.1%.

MS m/z (ESI): 523.4 [M+1]

$^1$H NMR (400 MHz, CD$_3$OD) δ 7.67-7.60 (m, 1H), 7.05-6.81 (m, 2H), 4.99 (s, 2H), 4.61 (s, 1H), 4.43-4.28 (m, 2H), 4.21-4.09 (m, 2H), 4.11-3.95 (m, 2H), 2.64-2.43 (m, 3H), 2.40-2.13 (m, 3H), 1.85 (br. s., 6H), 1.30 (d, J=6.27 Hz, 6H).

Embodiment 83

Ethyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate

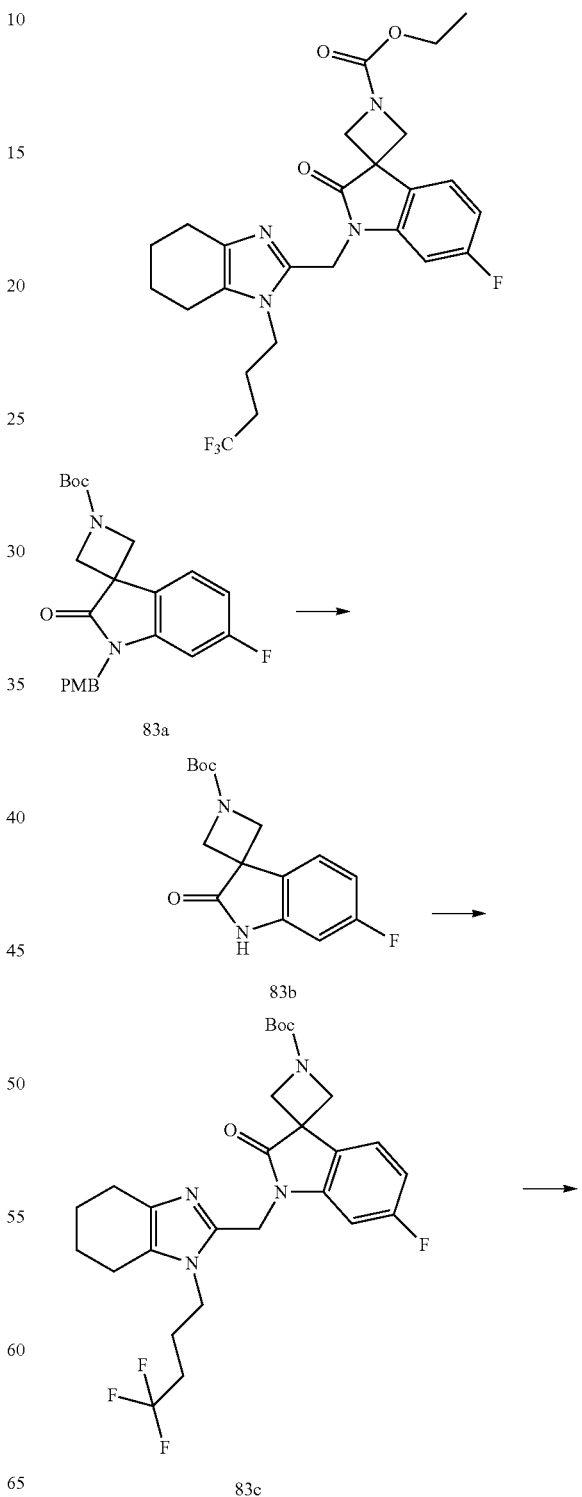

-continued

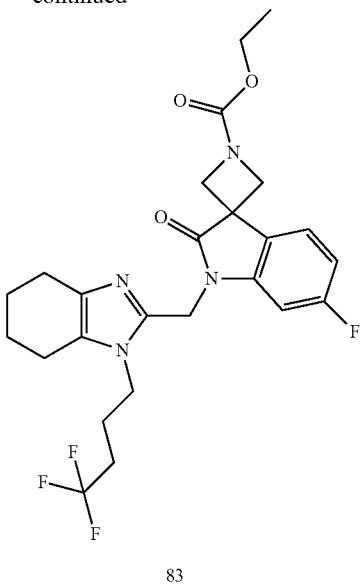

83

Step 1 tert-Butyl 6'-fluoro-2'-oxospiro[azetidine-3,3'-indoline]-1-carboxylate tert-Butyl 6'-fluoro-1'-(4-methoxybenzyl)-2'-oxospiro[azetidine-3,3'-indoline]-1-carboxylate 83a (2.0 g, 4.85 mmol) was dissolved in 10 mL trifluoroacetic acid, trifluoromethanesulfonic acid (2.2 g, 14.55 mmol) was added dropwise at 0° C., stirring for 16 h at r.t. The reaction solution was concentrated under reduced pressure to give red oil. 20 mL THF, 20 mL $H_2O$ were added into the residue, sodium carbonate was added to adjust pH to 9~10, di-tert-butyl dicarbonate (1.38 g, 6.30 mmol) was added, stirring for 4 h at r.t. 100 mL $H_2O$ was added, the mixture was extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with eluting system C to obtain tert-butyl 6'-fluoro-2'-oxospiro[azetidine-3,3'-indoline]-1-carboxylate 83b (1.1 g, white solid), yield: 27.0%.

Step 2 tert-Butyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate tert-Butyl 6'-fluoro-2'-oxospiro[azetidine-3,3'-indoline]-1-carboxylate 83b (1.0 g, 3.42 mmol) was dissolved in 10 mL THF, (1-(4,4,4-trifluorobutyl)-4,5,6,7-tetrahydro-1H-benzo[d]imidazol-2-yl)methanol (1.1 g, 4.12 mmol), diisopropyl azodicarboxylate (0.83 g, 4.10 mmol) were added, triphenylphosphine (1.1 g, 4.10 mmol) was added at 0° C., stirring for 16 h at r.t. 30 mL $H_2O$ was added, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, the residue was purified by silica gel column chromatography with eluting system C to obtain tert-butyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 83c (1.1 g, white solid), yield: 27.0%.

$^1$H NMR (400 MHz, $CD_3Cl_3$) δ 7.57 (d, J=1.00 Hz, 1H), 7.39-7.34 (m, 1H), 6.85-6.78 (m, 1H), 4.95 (s, 2H), 4.31 (s, 2H), 4.17-4.09 (m, 1H), 4.03 (s, 2H), 4.00-3.93 (m, 2H), 2.57 (br. s., 2H), 2.45 (br. s., 3H), 2.24-2.08 (m, 6H), 1.49 (s, 9H).

Step 3

Ethyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate tert-Butyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 83c (0.6 g, 0.52 mmol) was dissolved in 10 mL DCM, trifluoroacetic acid (4.0 g, 35.1 mmol) was added, stirring for 1 h at r.t. The reaction solution was concentrated under reduced pressure, the residue was dissolved in 5 mL DCM, TEA (0.3 g, 2.56 mmol), ethyl chloroformate (55 mg, 0.51 mmol) were added in sequence at 0° C., stirring for 1 h at r.t. 50 mL $H_2O$ was added, the mixture was extracted with DCM (80 mL×3), organic phases were combined and washed in sequence with water (50 mL), saturated sodium chloride solution (50 mL), dried over anhydrous sodium sulfate, filtered, the filtrate was concentrated under reduced pressure, preparative HPLC was used to purify and the target product ethyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 83 (47 mg, white solid) was given, yield: 18.0%.

MS m/z (ESI): 509.3 [M+1]

$^1$H NMR (400 MHz, MeOD) δ 7.67-7.62 (m, 1H), 6.97-6.83 (m, 2H), 4.99 (s, 2H), 4.64-4.40 (m, 2H), 4.39-4.30 (m, 2H), 4.24-4.14 (m, 3H), 4.12-4.03 (m, 2H), 2.60-2.47 (m, 4H), 2.34-2.22 (m, 2H), 1.92-1.78 (m, 5H), 1.31 (s, 3H).

Embodiment 84

1-(Cyclopropanecarbonyl)-6'-fluoro-1'-((1-(4,4,4-trifluorobutyl)-4,5,6,7-tetrahydro-1H-benzo[d]imidazol-2-yl)methyl)spiro[azetidine-3,3'-indoline]-2'-one

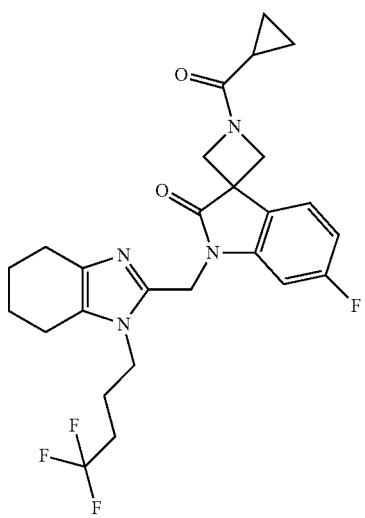

4.54 (m, 1H), 4.38-4.32 (m, 1H), 4.22-4.16 (m, 1H), 4.12-4.05 (m, 2H), 2.61-2.48 (m, 4H), 2.35-2.23 (m, 2H), 1.94-1.77 (m, 6H), 1.71-1.54 (m, 1H), 1.01-0.88 (m, 4H).

Embodiment 85

Isopropyl 4'-chloro-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate

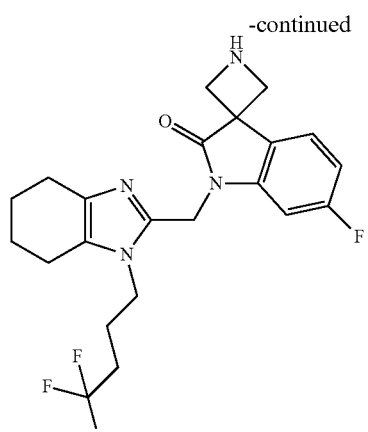

84a

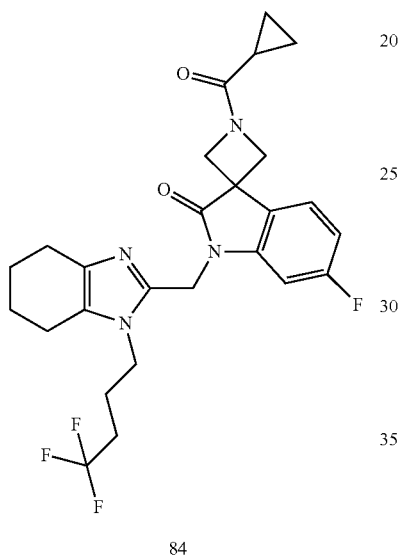

84

Step 1

1-(Cyclopropanecarbonyl)-6'-fluoro-1'-((1-(4,4,4-trifluorobutyl)-4,5,6,7-tetrahydro-1H-benzo[d]imidazol-2-yl)methyl)spiro[azetidine-3,3'-indoline]-2'-one 6'-Fluoro-1'-((1-(4,4,4-trifluorobutyl)-4,5,6,7-tetrahydro-1H-benzo[d]imidazol-2-yl)methyl)spiro[azetidine-3,3'-indoline]-2'-one 84a (0.3 g, 0.69 mmol) was dissolved in 5 mL DCM, cyclopropanecarboxylic acid (77 mg, 0.89 mmol), 2-(7-aza-1H-benzotriazole-1-yl)-N,N,N',N'-tetramethyluronium hexafluorophosphate (0.52 g, 1.37 mmol) and N,N-diisopropylethylamine (0.18 g, 1.37 mmol) were added, stirring for 2 h at r.t. 50 mL H₂O was added, the reaction solution was extracted with DCM (80 mL×3), organic phases were combined and washed in sequence with water (50 mL), saturated sodium chloride solution (50 mL), dried over anhydrous sodium sulfate, filtered, the filtrate was concentrated under reduced pressure, preparative HPLC was used to purify and the target product 1-(cyclopropanecarbonyl)-6'-fluoro-1'-((1-(4,4,4-trifluorobutyl)-4,5,6,7-tetrahydro-1H-benzo[d]imidazol-2-yl)methyl)spiro[azetidine-3,3'-indoline]-2'-one 84 (42 mg, white solid), yield: 12.1%.

MS m/z (ESI): 527.4 [M+23]

¹H NMR (400 MHz, CD₃OD) δ 7.69-7.64 (m, 1H), 6.97-6.87 (m, 2H), 5.01 (s, 2H), 4.70-4.66 (m, 1H), 4.59-

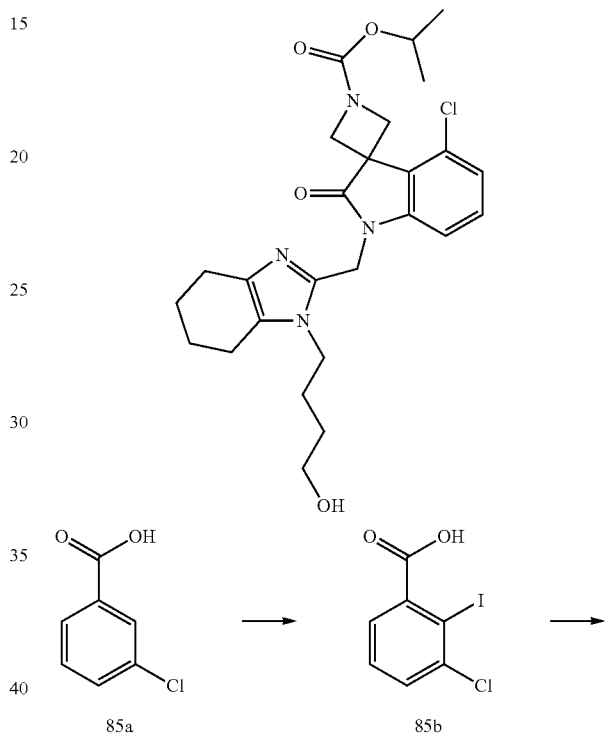

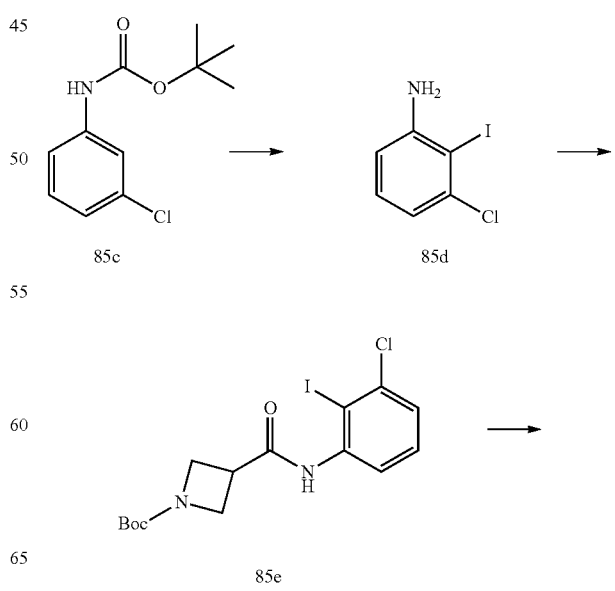

101
-continued
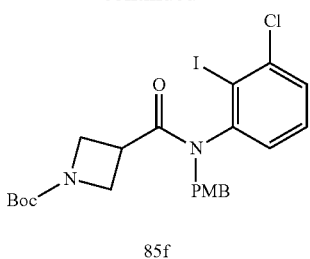
85f
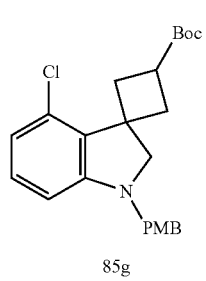
85g
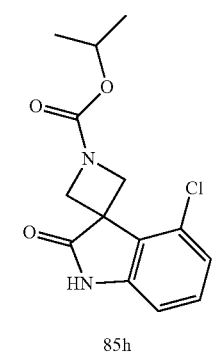
85h
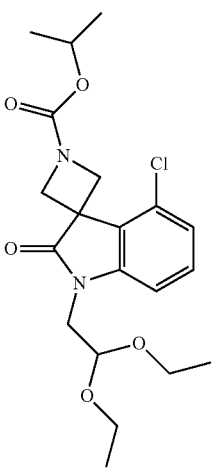
85i
102
-continued
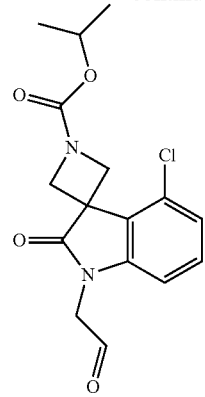
85j
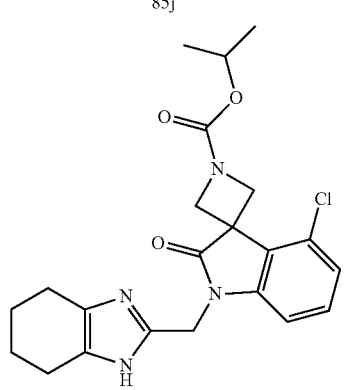
85k
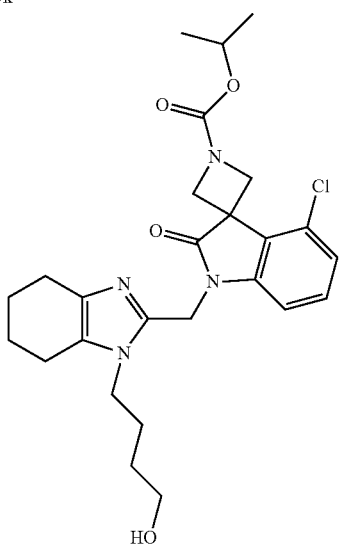
85
Step 1
3-Chloro-2-iodobenzoic acid
2,2,6,6-Tetramethylpiperidine (39.7 g, 281.03 mmol) was dissolved in 100 mL anhydrous THF, under nitrogen gas atmosphere n-BuLi (18.0 g, 281.03 mmol) was slowly added dropwise at −78° C., stirring for 1 h at −78° C. 3-Chlorobenzoic acid 85a (20.0 g, 127.7 mmol) in 150 mL THF was slowly added dropwise into the reaction solution, stirring for 4 h at −78° C. Iodine (129.7 g, 510.96 mmol) in 250 mL THF was slowly added dropwise into the reaction solution, stirring for 3 h at −78° C. The reaction was quenched by H₂O, acidified with 4M HCl aqueous solution, extracted with EA, washed with sodium thiosulfate, organic phases were combined and dried over anhydrous sodium sulfate, filtered, the filtrate was concentrated under reduced pressure to obtain the crude product of 3-chloro-2-iodobenzoic acid 85b (30 g, white solid).

¹H NMR (400 MHz, CD₃Cl₃) δ 7.72 (d, J=7.5 Hz, 1H) 7.65 (d, J=7.8 Hz, 1H) 7.39 (t, J=7.9 Hz, 1H).

Step 2 tert-Butyl (3-chloro-2-iodophenyl)carbamate

3-Chloro-2-iodobenzoic acid 85b (30.0 g, 106.21 mmol) and diphenyl azidophosphate (58.5 g, 212.42 mmol) were dissolved in 10 mL tert-butanol, TEA (21.5 g, 212.42 mmol) was added at r.t., stirring for 12 h at 120° C. The reaction was quenched by H₂O, extracted with EA, washed with water and saturated sodium chloride aqueous solution, organic phases were combined and dried over anhydrous sodium sulfate, filtered, the filtrate was concentrated under reduced pressure, the residue was purified by silica gel column chromatography with eluting system C to obtain tert-butyl (3-chloro-2-iodophenyl)carbamate 85c (34.0 g, yellow oil), yield: 90.5%.

¹H NMR (400 MHz, CD₃Cl₃) δ 8.03-7.94 (m, 1H) 7.26 (t, J=8.2 Hz, 1H) 7.20-7.14 (m, 1H) 7.08 (br. s., 1H) 1.56 (s, 9H).

Step 3

3-Chloro-2-iodoaniline hydrochloride tert-Butyl (3-chloro-2-iodophenyl)carbamate 85c (30.0 g, 84.85 mmol) was slowly added into 10 mL HCl/EA solution, stirring for 12 h at r.t. The reaction solution was concentrated under reduced pressure to obtain the crude product of 3-chloro-2-iodoaniline hydrochloride 85d (30.0 g, yellow solid).

¹H NMR (400 MHz, DMSO) δ 7.08 (t, J=8.0 Hz, 1H) 6.79 (d, J=7.5 Hz, 1H) 6.73 d, J=8.0 Hz, 1H) 6.27 (br. s., 3H).

Step 4 tert-Butyl 3-((3-chloro-2-iodophenyl)carbamoyl)azetidine-1-carboxylate

3-Chloro-2-iodoaniline hydrochloride 85c (28.0 g, 96.58 mmol) was dissolved in 400 mL EA, 1-(tert-butoxycarbonyl)azetidine-3-carboxylic acid (23.3 g, 115.90 mmol), TEA (58.6 g, 579.48 mmol) and tripropyl phosphoric anhydride (61.5 g, 193.16 mmol) were added at r.t., stirring for 3 h at r.t. 500 mL H₂O was added, extracted with EA (500 mL×3), organic phases were combined and washed in sequence with water (500 mL×2), saturated sodium chloride solution (500 mL×2), dried over anhydrous sodium sulfate, filtered, the filtrate was concentrated under reduced pressure to obtain the crude product of tert-butyl 3-((3-chloro-2-iodophenyl)carbamoyl)azetidine-1-carboxylate 85e (26.5 g, white solid), yield: 71.1%.

¹H NMR (400 MHz, CDCl₃) δ 8.95 (d, J=7.4 Hz, 1H), 7.15 (t, J=7.6 Hz, 2H), 4.11 (d, J=14.06 Hz, 4H), 3.17-3.02 (m, 1H), 1.38 (s, 9H).

Step 5 tert-Butyl 3-((3-chloro-2-iodophenyl)(4-methoxybenzyl)carbamoyl)azetidine-1-carboxylate tert-Butyl 3-((3-chloro-2-iodophenyl)carbamoyl)azetidine-1-carboxylate 85e (30.0 g, 68.70 mmol) was dissolved in 200 mL DMF, cesium carbonate (26.9 g, 82.44 mmol), 1-chloromethyl-4-methoxybenzene (12.9 g, 82.44 mmol) were added, stirring for 12 h at 90° C. 200 mL H₂O was added, the mixture was extracted with EA (300 mL×3), organic phases were combined and washed in sequence with water (300 mL×2), saturated sodium chloride solution (300 mL×2), dried over anhydrous sodium sulfate, filtered, the filtrate was concentrated under reduced pressure, the residue was purified by silica gel column chromatography with eluting system C to obtain tert-butyl 3-((3-chloro-2-iodophenyl)(4-methoxybenzyl)carbamoyl)azetidine-1-carboxylate 85f (30.0 g, white solid), yield: 70.6%.

¹H NMR (400 MHz, CDCl₃) δ 7.72-7.62 (m, 1H), 7.11 (d, J=8.28 Hz, 2H), 7.05-6.94 (m, 1H), 6.82 (d, J=8.28 Hz, 2H), 6.50-6.38 (m, 1H), 5.60-5.48 (m, 1H), 4.36-4.24 (m, 1H), 4.03 (d, J=14.05 Hz, 2H), 3.81 (s, 3H), 3.78-3.60 (m, 2H), 3.14-3.02 (m, 1H), 1.49-1.37 (m, 9H).

Step 6 tert-Butyl 4'-chloro-1'-(4-methoxybenzyl)-2'-oxospiro[azetidine-3,3'-indoline]-1-carboxylate tert-Butyl 3-((3-chloro-2-iodophenyl)(4-methoxybenzyl)carbamoyl)azetidine-1-carboxylate 85f (15.0 g, 26.94 mmol) was dissolved in 200 mL 1,4-dioxane, palladium acetate (0.30 g, 1.35 mmol), sodium tert-butoxide (3.9 g, 40.41 mmol) were added at 21° C., the flask was swept with nitrogen gas, tricyclohexylphosphine (7.6 g, 26.94 mmol) was added dropwise at r.t., stirring for 12 h at 110° C. The reaction solution was cooled to r.t., filtered, the filter cake was washed with EA, the filtrate was combined and concentrated under reduced pressure to obtain tert-butyl 4'-chloro-1'-(4-methoxybenzyl)-2'-oxospiro[azetidine-3,3'-indoline]-1-carboxylate 85g (6.0 g, yellow oil), yield: 46.7%.

¹H NMR (400 MHz, CDCl₃) δ 7.23 (d, J=8.8 Hz, 2H), 7.19-7.13 (m, 1H), 7.04 (d, J=8.3 Hz, 1H), 6.90-6.83 (m, 2H), 6.69 (d, J=7.8 Hz, 1H), 4.90-4.80 (m, 2H), 4.58 (br. s, 2H), 4.32 (d, J=8.3 Hz, 2H), 3.82-3.77 (m, 3H), 1.51 (s, 9H).

Step 7

Isopropyl 4'-chloro-2'-oxospiro[azetidine-3,3'-indoline]-1-carboxylate tert-Butyl 4'-fluoro-1'-(4-methoxybenzyl)-2'-oxospiro[azetidine-3,3'-indoline]-1-carboxylate 85g (6.0 g, 13.99 mmol) was dissolved in 120 mL trifluoroacetic acid, trifluoromethanesulfonic acid (6.3 g, 41.97 mmol) was added dropwise at 0° C., stirring for 12 h at r.t. The reaction solution was concentrated under reduced pressure, 60 mL THF and 60 mL H₂O were added into the residue, sodium carbonate was added to adjust pH to 9~10, isopropyl chloroformate (12.3 g, 2.69 mmol) was added dropwise at 0° C., stirring for 16 h at r.t. 100 mL H₂O was added, the mixture was extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with elution system C to obtain isopropyl 4'-chloro-2'-oxospiro[azetidine-3,3'-indoline]-1-carboxylate 85h (3.20 g, white solid), yield: 67.9%.

¹H NMR (400 MHz, CDCl₃) δ 9.05 (br. s., 1H), 7.25-7.16 (m, 1H), 7.06 (d, J=8.03 Hz, 1H), 6.87 (d, J=8.03 Hz, 1H), 4.98 (spt, J=6.19 Hz, 1H), 4.59 (d, J=8.53 Hz, 2H), 4.30 (d, J=8.03 Hz, 2H), 1.27 (d, J=6.02 Hz, 6H).

Step 8

Isopropyl 4'-chloro-1'-(2,2-diethoxyethyl)-2'-oxospiro[azetidine-3,3'-indoline]-1-carboxylate Isopropyl 4'-chloro-2'-oxospiro[azetidine-3,3'-indoline]-1-carboxylate 85h (2.0 g, 6.79 mmol), 2-bromo-1,1-diethoxyethane (1.6 g, 8.15 mmol), cesium carbonate (4.4 g, 13.6 mmol), potassium iodide (56.4 g, 0.34 mmol) were dissolved in 25 mL DMF, stirring for 12 h at 90° C. 30 mL H₂O was added into the reaction solution, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, the residue was purified by silica gel column chromatography with elution system C to obtain isopropyl 4'-chloro-1'-(2,2-diethoxyethyl)-2'-oxospiro[azetidine-3,3'-indoline]-1-carboxylate 85i (2.2 g, yellow oil), yield: 97.0%.

¹H NMR (400 MHz, CDCl₃) δ 7.25-7.18 (m, 1H), 7.04 (d, J=8.0 Hz, 1H), 6.97 (d, J=7.5 Hz, 1H), 4.97 (spt, J=6.2 Hz, 1H), 4.73-4.63 (m, 1H), 4.56 (d, J=8.5 Hz, 2H), 4.27 (d, J=8.5 Hz, 2H), 3.81 (d, J=4.5 Hz, 2H), 3.78-3.68 (m, 2H), 3.55-3.44 (m, 2H), 1.26 (d, J=6.5 Hz, 6H), 1.13 (t, J=7.0 Hz, 6H).

Step 9

Isopropyl 4'-chloro-2'-oxo-1'-(2-oxoethyl)spiro[azetidine-3,3'-indoline]-1-carboxylate Isopropyl 4'-chloro-1'-(2,2-diethoxyethyl)-2'-oxospiro[azetidine-3,3'-indoline]-1-carboxylate 85i (1.2 g, 2.92 mmol) was dissolved in 6 mL DCM and 2 mL H₂O, trifluoroacetic acid (0.33 g, 2.92 mmol) was added at 0° C., stirring for 2 h at r.t., saturated sodium carbonate aqueous solution was added to adjust pH to 9, the mixture was extracted with EA (150 mL×3), organic phases were combined and washed in sequence with water (80 mL×2), saturated sodium chloride solution (80 mL×2), dried over anhydrous sodium sulfate, filtered, the filtrate was concentrated under reduced pressure to obtain the crude product of isopropyl 4'-chloro-2'-oxo-1'-(2-oxoethyl)spiro[azetidine-3,3'-indoline]-1-carboxylate 85j (0.9 g, yellow oil), yield: 91.5%.

¹H NMR (400 MHz, CDCl₃) δ 9.72 (t, J=8.0 Hz, 1H), 7.67 (d, J=8.0 Hz, 1H), 7.25 (t, J=8.0 Hz, 1H) 6.97 (d, J=7.6 Hz, 1H), 4.73-4.63 (m, 1H), 4.49 (d, 7.4 Hz, 2H) 4.25 (d, J=14.06 Hz, 4H), 1.32 (d, J=7.0 Hz, 6H).

Step 10

Isopropyl 4'-chloro-2'-oxo-1'-((4,5,6,7-tetrahydro-1H-benzo[d]imidazol-2-yl)methyl)spiro[azetidine-3,3'-indoline]-1-carboxylate Isopropyl 4'-chloro-2'-oxo-1'-(2-oxoethyl)spiro[azetidine-3,3'-indoline]-1-carboxylate 85j (0.90 g, 2.67 mmol) was dissolved in 20 mL ethanol, 1,2-cyclohexanedione (0.36 g, 3.21 mmol), ammonium acetate (1.03 g, 13.36 mmol) were added, refluxing and stirring for 3 h. The reaction solution was adjusted to pH 8-9 with saturated sodium carbonate aqueous solution, extracted with EA (20 mL×3), organic phases were combined and washed in sequence with saturated sodium bicarbonate aqueous solution (20 mL×2), saturated sodium chloride solution (30 mL×2), dried over anhydrous sodium sulfate, filtered, the filtrate was concentrated under reduced pressure, the residue was purified by silica gel column chromatography with eluting system C to obtain isopropyl 4'-chloro-2'-oxo-1'-(2-oxoethyl)spiro[azetidine-3,3'-indoline]-1-carboxylate 85k (0.60 g, yellow oil), yield: 47.2%.

¹H NMR (400 MHz, CDCl₃) δ 7.29 (s, 1H), 7.22-7.17 (m, 1H), 7.07 (d, J=8.0 Hz, 1H), 4.98 (td, J=6.3 Hz, 12.6 Hz, 1H), 4.88 (d, J=2.5 Hz, 2H), 4.56 (d, J=8.5 Hz, 2H), 4.27 (d, J=8.0 Hz, 2H), 2.51 (br. s, 4H), 1.77 (br. s, 4H), 1.28 (t, J=6.0 Hz, 6H).

Step 11

Isopropyl 4'-chloro-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate Isopropyl 4'-chloro-2'-oxo-1'-(2-oxoethyl)spiro[azetidine-3,3'-indoline]-1-carboxylate 85k (0.10 g, 0.48 mmol), 4-bromobutyl acetate (0.11 g, 0.58 mmol), cesium carbonate (0.31 g, 0.96 mmol) were dissolved in 10 mL DMF, stirring for 4 h at 80° C. The reaction solution was filtered and washed with water, extracted with EA (20 mL×3), organic phases were combined, dried over anhydrous sodium sulfate, filtered, the filtrate was concentrated under reduced pressure, the residue was purified with silica gel column chromatography with elution system C to obtain white solid. 10 mL 1M NaOH aqueous solution was added to dissolve, stirring for 2 h at r.t. 30 mL water was added, the reaction solution was extracted with EA (30 mL×2), washed in sequence with water (20 mL×2), saturated sodium chloride solution (20 mL×2), organic phases were combined, dried over anhydrous sodium sulfate, filtered, the filtrate was concentrated under reduced pressure, preparative HPLC was used to purify and the target product isopropyl 4'-chloro-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate 85 (13 mg, white solid), yield: 14.1%.

MS m/z (ESI): 501.3 [M+1]

¹H NMR (400 MHz, CDCl₃) δ 8.24 (br. s., 1H), 7.40 (d, J=8.03 Hz, 1H), 7.26 (t, 0.1=8.00 Hz, 2H), 7.08 (d, J=8.03 Hz, 1H), 5.23-5.04 (m, 2H), 4.97 (td, 0.1=6.27, 12.55 Hz, 1H), 4.57 (d, J=8.03 Hz, 2H), 4.27 (d, J=8.53 Hz, 2H), 3.95 (d, J=7.03 Hz, 2H), 3.73-3.64 (m, 2H), 2.97 (br. s., 4H), 2.63-2.43 (m, 4H), 1.79 (d, J=5.02 Hz, 4H), 1.28 (d, J=6.53 Hz, 6H).

Embodiment 86

Isopropyl 4'-chloro-2'-oxo-1'-((1-(4,4-trifluorobutyl)-4,5,6,7-tetrahydro-1H-benzo[d]imidazol-2-yl)methyl)spiro[azetidine-3,3'-indoline]-1-carboxylate

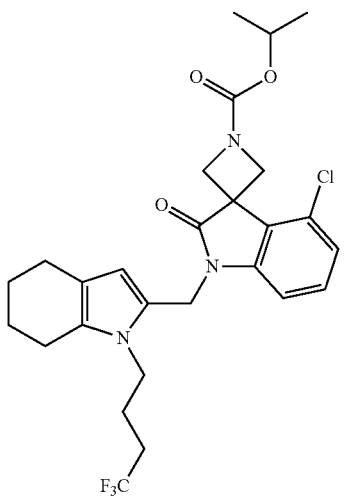

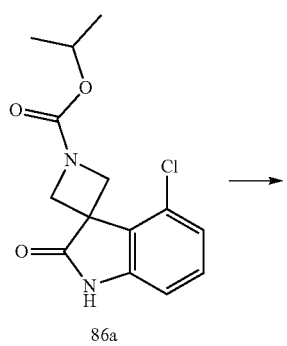

86a

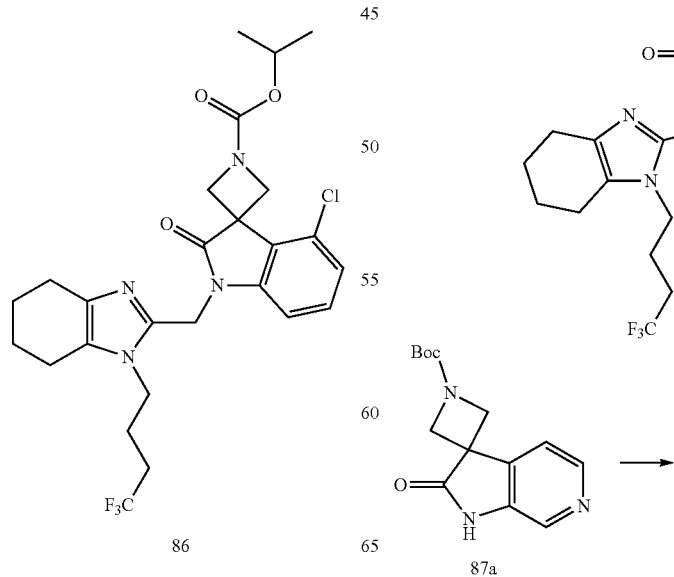

86

Step 1

Isopropyl 4'-chloro-2'-oxo-1'-((1-(4,4-trifluorobutyl)-4,5,6,7-tetrahydro-1H-benzo[d]imidazol-2-yl)methyl)spiro[azetidine-3,3'-indoline]-1-carboxylate Isopropyl 4'-chloro-2'-oxospiro[azetidine-3,3'-indoline]-1-carboxylate 86a (0.11 g, 0.38 mmol) was dissolved in 1 mL THF, (1-(4,4-trifluorobutyl)-4,5,6,7-86a 86 tetrahydro-1H-benzo[d]imidazol-2-yl)methanol (0.10 g, 0.38 mmol), triphenylphosphine (0.12 g, 0.46 mmol) were added, diisopropyl azodicarboxylate (92 mg, 0.46 mmol) in 1 mL THF was added dropwise at 0° C., stirring for 16 h at r.t. 30 mL H$_2$O was added, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product isopropyl 4'-chloro-2'-oxo-1'-((1-(4,4-trifluorobutyl)-4,5,6,7-tetrahydro-1H-benzo[d]imidazol-2-yl)methyl)spiro[azetidine-3,3'-indoline]-1-carboxylate 86 (60 mg, white solid) was given, yield: 29.2%.

MS m/z (ESI): 539.1 [M+1]

$^1$H NMR (400 MHz, CD$_3$OD) δ 7.28 (t, J=8.0 Hz, 1H), 7.12 (d, J=8.0 Hz, 1H), 7.02 (d, J=7.5 Hz, 1H), 4.99 (s, 2H), 4.96-4.91 (m, 1H), 4.55 (m, 2H), 4.26 (m, 2H), 4.05 (t, J=7.8 Hz, 2H), 2.53 (t, J=5.5 Hz, 2H), 2.46 (t, J=5.8 Hz, 2H), 2.32-2.21 (m, 2H), 1.92-1.76 (m, 6H), 1.28 (d, J=6.0 Hz, 6H).

Embodiment 87

Ethyl 2'-oxo-1'-((1-(4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate

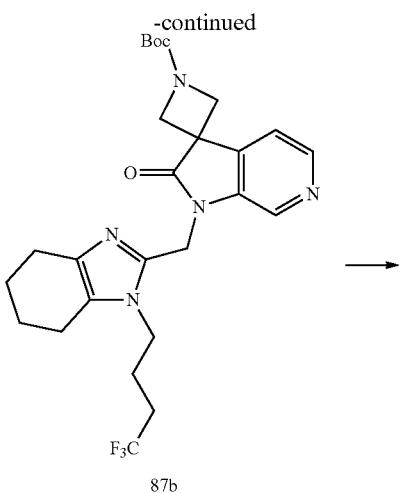

87b

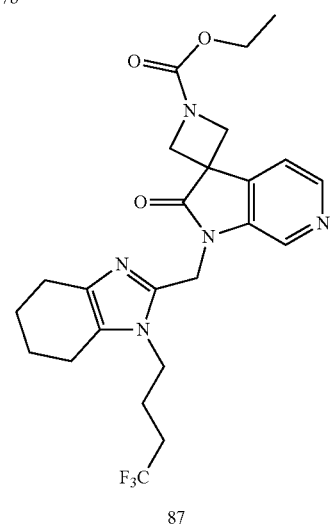

87

Step 1 tert-Butyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate tert-Butyl 2'-oxo-1',2'-dihydrospiro[azetidine-3,3'-pyrrolo[2,3-c]pyridine]-1-carboxylate 87a (0.94 g, 3.43 mmol) was dissolved in 10 mL THF, (1-(4,4,4-trifluorobutyl)-4,5,6,7-tetrahydro-1H-benzo[d]imidazol-2-yl)methanol (0.9 g, 3.43 mmol), triphenylphosphine (1.08 g, 4.12 mmol) were added, diisopropyl azodicarboxylate (0.83 g, 4.12 mmol) was added dropwise at 0° C., stirring for 16 h at r.t. 50 mL H$_2$O was added, the mixture was extracted with EA (50 mL×3), organic phases were combined and washed in sequence with water (50 mL×2), saturated sodium chloride solution (50 mL×2), dried over anhydrous sodium sulfate, filtered, the filtrate was concentrated under reduced pressure, the residue was purified by silica gel column chromatography with eluting system C to obtain tert-butyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate 87b (1.5 g, yellow oil), yield: 46.8%.

$^1$H NMR (400 MHz, CDCl$_3$) δ 8.80 (s, 1H), 8.50 (d, J=4.8 Hz, 1H), 7.50 (d, J=4.8 Hz, 1H), 5.04 (s, 2H), 4.36 (d, J=8.3 Hz, 2H), 4.05 (d, J=8.3 Hz, 2H), 3.99-3.94 (m, J=7.8 Hz, 2H), 2.62-2.43 (m, 4H), 2.21-2.12 (m, 2H), 1.85-1.74 (m, J=6.3 Hz, 6H), 1.50 (s, 9H).

Step 2

Ethyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate tert-Butyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate 87b (0.5 g, 0.962 mmol) was dissolved in 1 mL DCM, 3 mL trifluoroacetic acid was added, stirring for 2 h at r.t. The reaction solution was concentrated under reduced pressure, 3 mL THF and 1.5 mL H$_2$O were added into the residue, sodium carbonate was added to adjust pH to 9~10, ethyl chloroformate (0.16 g, 1.44 mmol) was added dropwise at 0° C., stirring for 2 h at r.t. 100 mL water was added, the mixture was extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, preparative HPLC was used to purify and the target product ethyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate 87 (125 mg, white solid) was given, yield: 26.4%.

MS m/z (ESI): 492.4 [M+1]

$^1$H NMR (400 MHz, CDCl$_3$) δ 8.42 (d, J=5.0 Hz, 1H), 8.27 (s, 1H), 7.77 (d, J=4.8 Hz, 1H), 5.06 (s, 2H), 4.37 (br. s., 2H), 4.21 (q, J=7.0 Hz, 4H), 4.08 (t, J=7.9 Hz, 2H), 2.61-2.41 (m, 4H), 2.39-2.22 (m, J=8.5 Hz, 2H), 1.93 (br. s., 2H), 1.89-1.75 (m, 4H), 1.31 (t, J=7.2 Hz, 3H).

Embodiment 88

Isopropyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate

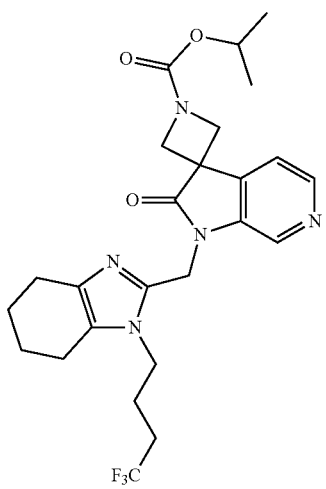

-continued

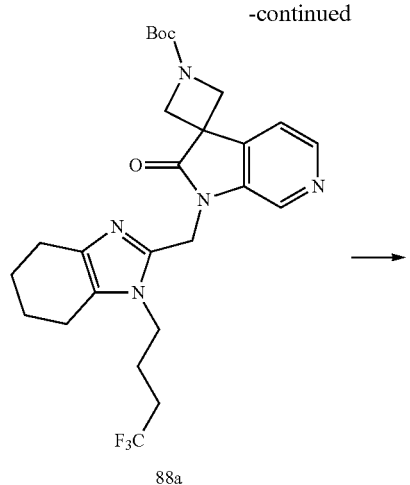

88a

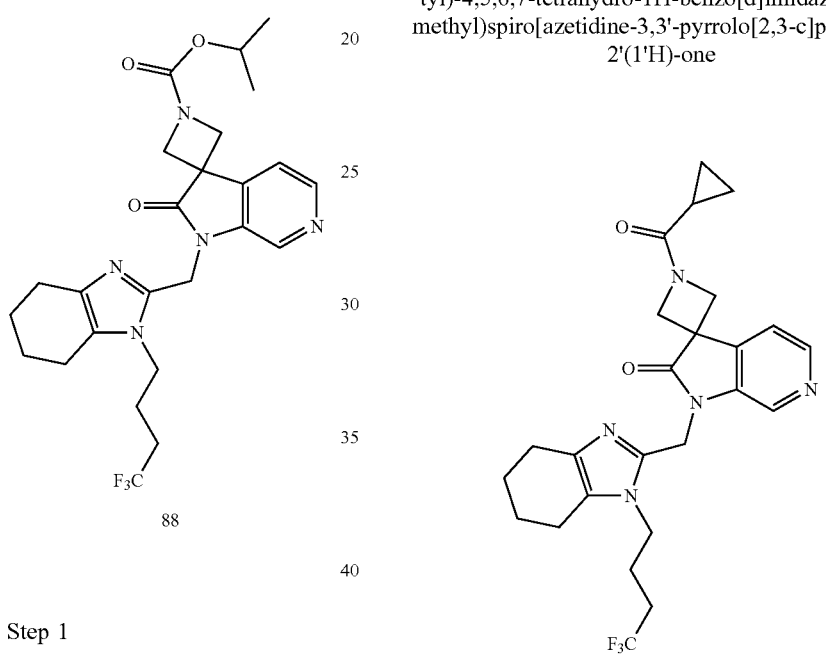

Step 1

Isopropyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate tert-Butyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate 88a (0.1 g, 0.19 mmol) was dissolved in 1 mL DCM, 3 mL trifluoroacetic acid was added, stirring for 2 h at r.t. The reaction solution was concentrated under reduced pressure, 3 mL THF and 1.5 mL H₂O were added into the residue, sodium carbonate was added to adjust pH to 9~10, isopropyl chloroformate (0.31 g, 1.44 mmol) was added dropwise at 0° C., stirring for 2 h at r.t. 100 mL water was added, the mixture was extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and the target product isopropyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate 88 (36 mg, white solid) was given, yield: 29.2%.

MS m/z (ESI): 506.3 [M+1]

¹H NMR (400 MHz, CDCl₃) δ 8.40 (d, J=4.8 Hz, 1H), 8.25 (s, 1H), 7.75 (d, J=4.8 Hz, 1H), 5.04 (s, 2H), 4.97-4.92 (m, 1H), 4.35 (d, J=8.8 Hz, 2H), 4.19 (d, J=8.5 Hz, 2H), 4.06 (t, 0.1=7.8 Hz, 2H), 2.55 (t, 0.1=8.0 Hz, 2H), 2.46 (t, 0.1=5.5 Hz, 2H), 2.34-2.23 (m, 2H), 1.95-1.87 (m, 2H), 1.87-1.76 (m, 4H), 1.29 (d, J=6.0 Hz, 6H).

Embodiment 89

1-(Cyclopropanecarbonyl)-1'-((1-(4,4,4-trifluorobutyl)-4,5,6,7-tetrahydro-1H-benzo[d]imidazol-2-yl)methyl)spiro[azetidine-3,3'-pyrrolo[2,3-c]pyridine]-2'(1'H)-one

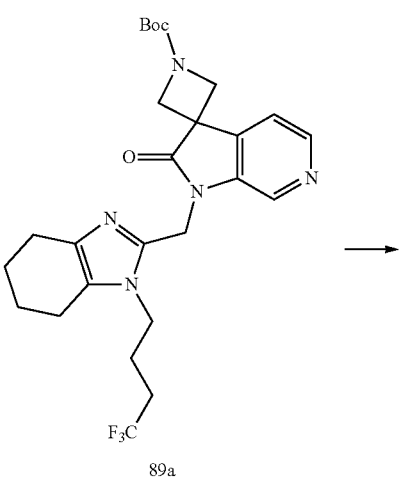

89a

113

-continued

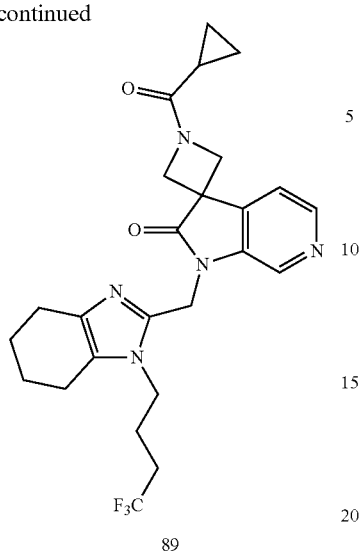

89

Step 1

1-(Cyclopropanecarbonyl)-1'-((1-(4,4,4-trifluorobutyl)-4,5,6,7-tetrahydro-1H-benzo[d]imidazol-2-yl)methyl)spiro[azetidine-3,3'-pyrrolo[2,3-c]pyridine]-2'(1'H)-one tert-Butyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate 89a (0.1 g, 0.19 mmol) was dissolved in 0.5 mL DCM, 1.5 mL trifluoroacetic acid was added, stirring for 2 h at r.t. The reaction solution was concentrated under reduced pressure, 2 mL DCM was added into the residue, TEA was added to adjust pH to 9~10, cyclopropyl chloroformate (0.16 g, 1.44 mmol) was added dropwise at 0° C., stirring for 2 h at r.t. 30 mL water was added, the mixture was extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and the target product 1-(cyclopropanecarbonyl)-1'-((1-(4,4,4-trifluorobutyl)-4,5,6,7-tetrahydro-1H-benzo[d]imidazol-2-yl)methyl)spiro[azetidine-3,3'-pyrrolo[2,3-c]pyridine]-2'(1'H)-one 89 (22.5 mg, white solid), yield: 24.0%.

MS m/z (ESI): 488.2 [M+1]

$^1$H NMR (400 MHz, CD$_3$OD) δ 8.43 (d, J=5.0 Hz, 1H), 8.28 (s, 1H), 7.79 (d, J=4.8 Hz, 1H), 5.08 (s, 2H), 4.74-4.67 (m, 1H), 4.64-4.61 (m, 1H), 4.37 (d, J=9.8 Hz, 1H), 4.24 (d, J=9.8 Hz, 1H), 4.09 (t, J=7.8 Hz, 2H), 2.64-2.44 (m, 4H), 2.38-2.26 (m, 2H), 1.94 (t, J=7.8 Hz, 2H), 1.87-1.80 (m, 4H), 1.73-1.64 (m, J=4.8 Hz, 1H), 0.97-0.92 (m, 4H).

114

Embodiment 90

2'-Oxo-1'-((1-(4,4,4-trifluorobutyl)-4,5,6,7-tetrahydro-H-benzo[d]imidazol-2-yl)methyl)spiro[azetidine-3,3'-indoline]-1-carboxylate

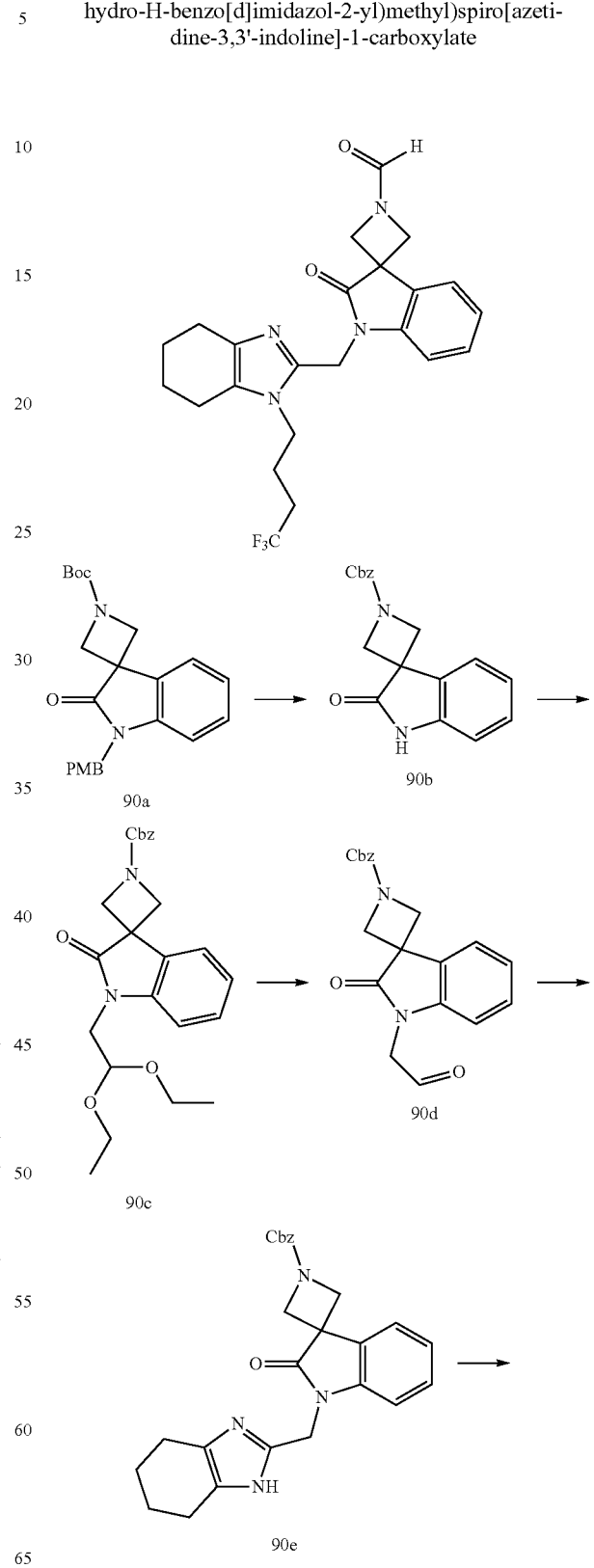

115

-continued

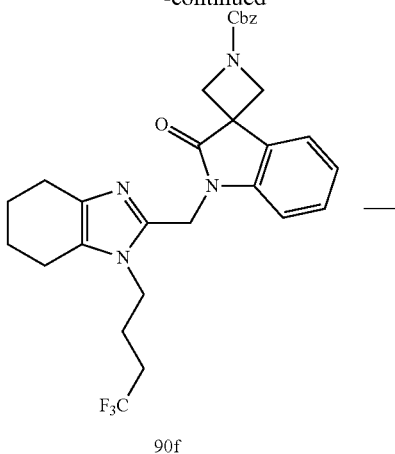

90f

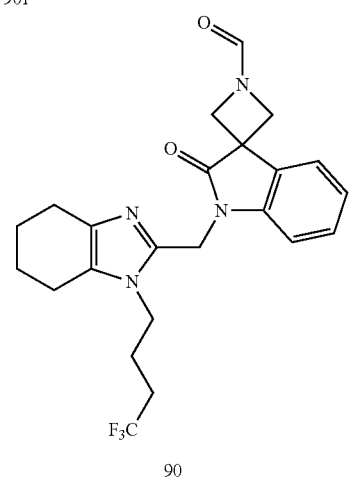

90

Step 1

Benzyl 2'-oxospiro[azetidine-3,3'-indoline]-1-carboxylate tert-Butyl 1'-(4-methoxybenzyl)-2'-oxospiro[azetidine-3,3'-indoline]-1-carboxylate 90a (50.0 g, 126.8 mmol) was dissolved in 250 mL trifluoroacetic acid, stirring for 0.5 h at 0° C., trifluoromethanesulfonic acid (57.1 g, 380.3 mmol) was added dropwise at 0° C., stirring for 16 h at 0° C. The reaction solution was concentrated under reduced pressure to give red oil, 100 mL THF and 100 mL H$_2$O were added into the residue, sodium carbonate was added to adjust pH to 9, phenol chloroformate (23.79 g, 139.44 mmol) was added dropwise, stirring for 4 h at r.t. 1000 mL H$_2$O was added, the mixture was extracted with EA (1000 mL×3), organic phases were combined and washed in sequence with water (1000 mL×2), saturated sodium chloride solution (1000 mL×2), dried over anhydrous sodium sulfate, filtered, the filtrate was concentrated under reduced pressure, the residue was purified by silica gel column chromatography with elution system C to obtain benzyl 2'-oxospiro[azetidine-3,3'-indoline]-1-carboxylate 90b (22.0 g, yellow solid), yield: 50.7%.

$^1$H NMR (400 MHz, CDCl$_3$) δ 8.69 (br. s., 1H), 7.51 (d, J=7.5 Hz, 1H), 7.40-7.31 (m, 5H), 7.26 (t, J=7.3 Hz, 1H), 7.13 (t, J=7.3 Hz, 1H), 6.93 (d, J=8.0 Hz, 1H), 5.18 (s, 2H), 4.47 (d, J=8.5 Hz, 2H), 4.18 (d, J=8.0 Hz, 2H).

116

Step 2

Benzyl 1'-(2,2-diethoxy)-2'-oxospiro[azetidine-3,3'-indoline]-1-carboxylate

Benzyl 2'-oxospiro[azetidine-3,3'-indoline]-1-carboxylate 90b (15.0 g, 48.65 mmol) was dissolved in 100 mL DMF, cesium carbonate (31.7 g, 97.3 mmol), 2-bromo-1,1-diethoxyethane (11.0 g, 55.95 mmol) were added, stirring for 3 h at 100° C. 300 mL saturated sodium carbonate aqueous solution was added, the mixture was extracted with EA (300 mL×3), organic phases were combined and washed in sequence with water (300 mL×2), saturated sodium chloride solution (300 mL×2), dried over anhydrous sodium sulfate, filtered, the filtrate was concentrated under reduced pressure, the residue was purified by silica gel column chromatography with elution system C to obtain benzyl 1'-(2,2-diethoxy)-2'-oxospiro[azetidine-3,3'-indoline]-1-carboxylate 90c (9.5 g, yellow oil), yield: 46.0%.

$^1$H NMR (400 MHz, CDCl$_3$) δ 7.52 (d, J=7.3 Hz, 1H), 7.43-7.29 (m, 6H), 7.13 (t, J=8.0 Hz, 1H), 7.06 (d, J=7.8 Hz, 1H), 5.19 (s, 2H), 4.72 (t, J=5.4 Hz, 1H), 4.47 (d, J=8.3 Hz, 2H), 4.16 (d, J=8.3 Hz, 2H), 3.84 (d, J=5.3 Hz, 2H), 3.76 (qd, J=7.0, 9.2 Hz, 2H), 3.52 (qd, J=7.0, 9.3 Hz, 2H), 1.15 (t, J=7.0 Hz, 6H).

Step 3

Benzyl 2'-oxo-1'-(2-oxoethyl)spiro[azetidine-3,3'-indoline]-1-carboxylate

Benzyl 1'-(2,2-diethoxy)-2'-oxospiro[azetidine-3,3'-indoline]-1-carboxylate 90c (9.5 g, 22.38 mmol) was dissolved in 100 mL DCM and 30 mL H$_2$O, 100 mL trifluoroacetic acid was added dropwise, stirring for 2 h at r.t. 150 mL saturated sodium carbonate aqueous solution was added, the mixture was extracted with DCM (150 mL×3), organic phases were combined and washed in sequence with water (150 mL×2), saturated sodium chloride solution (150 mL×2), dried over anhydrous sodium sulfate, filtered, the filtrate was concentrated under reduced pressure to obtain benzyl 2'-oxo-1'-(2-oxoethyl)spiro[azetidine-3,3'-indoline]-1-carboxylate 90d (7.0 g, yellow oil), yield: 89.3%.

$^1$H NMR (400 MHz, CDCl$_3$) δ 9.68 (s, 1H), 7.57 (d, J=7.0 Hz, 1H), 7.45-7.27 (m, 6H), 7.13 (t, J=8.0 Hz, 1H), 6.65 (d, J=8.0 Hz, 1H), 5.18 (s, 2H), 4.68-4.39 (m, 4H), 4.20 (d, J=8.5 Hz, 2H).

Step 4

Benzyl 2'-oxo-1'-((4,5,6,7-tetrahydro-1H-benzo[d]imidazol-2-yl)methyl)spiro[azetidine-3,3'-indoline]-1-carboxylate Benzyl 2'-oxo-1'-(2-oxoethyl)spiro[azetidine-3,3'-indoline]-1-carboxylate 90d (7.0 g, 19.98 mmol) was dissolved in 50 mL ethanol, 1,2-cyclohexanedione (2.69 g, 23.97 mmol), ammonium acetate (7.7 g, 99.9 mmol) were added, refluxing and stirring for 4 h. 150 mL saturated sodium carbonate aqueous solution was added, the mixture was extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure to obtain the crude product of benzyl 2'-oxo-1'-((4,5,6,7-tetrahydro-1H-benzo[d]imidazol-2-yl)methyl)spiro[azetidine-3,3'-indoline]-1-carboxylate 90e (7.0 g, yellow solid).

¹H NMR (400 MHz, CDCl₃) δ 7.51 (d, J=7.5 Hz, 1H), 7.44-7.30 (m, 6H), 7.21 (d, J=7.8 Hz, 1H), 7.14 (t, J=7.5 Hz, 1H), 5.18 (s, 2H), 4.87 (s, 2H), 4.49-4.38 (m, 2H), 4.14 (d, J=7.8 Hz, 2H), 2.60-2.38 (br, 4H), 1.76 (br. s., 4H).

Step 5

Benzyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate Benzyl 2'-oxo-1'-((4,5,6,7-tetrahydro-1H-benzo[d]imidazol-2-yl)methyl)spiro[azetidine-3,3'-indoline]-1-carboxylate 90e (7.0 g, 15.82 mmol) was dissolved in 50 mL DMF, 4-bromo-1,1,1-trifluorobutane (3.32 g, 17.4 mmol), cesium carbonate (7.73 g, 23.73 mmol), potassium iodide (0.131 g, 0.791 mmol) were added, stirring for 3 h at 90° C. 100 mL H₂O was added, the mixture was extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with elution system C to obtain benzyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 90f (4.8 g, yellow solid), yield: 52.2%.

¹H NMR (400 MHz, CDCl₃) δ 7.57 (d, J=7.8 Hz, 1H), 7.50 (d, J=7.3 Hz, 1H), 7.40-7.30 (m, 6H), 7.16 (t, J=8.0 Hz, 1H), 5.17 (s, 2H), 4.96 (s, 2H), 4.42 (d, J=8.4 Hz, 2H), 4.13 (d, J=8.4 Hz, 2H), 3.97 (t, J=7.8 Hz, 2H), 2.61-2.51 (br, 2H), 2.49-2.38 (br, 2H), 2.24-2.09 (m, 2H), 1.83-1.75 (m, 6H).

Step 6

2'-Oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate Benzyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 90f (0.2 g, 0.36 mmol) was dissolved in 2 mL ethanol, ammonium formate (22.8 mg, 0.36 mmol), Pd/C (20 mg) were added, stirring for 16 h at r.t. 30 mL H₂O was added, the mixture was extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and the target product 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 90 (34.5 mg, white solid) was given, yield: 77.3%.

MS m/z (ESI): 447.2 [M+1]

¹H NMR (400 MHz, CD₃OD) δ 8.14 (s, 1H), 7.66 (d, J=7.28 Hz, 1H), 7.28-7.35 (m, 1H), 7.16-7.23 (m, 1H), 7.08 (d, J=7.78 Hz, 1H), 5.02 (s, 2H), 4.61 (d, J=8.78 Hz, 1H), 4.48 (d, J=8.78 Hz, 1H), 4.39 (d, J=10.04 Hz, 1H), 4.23 (d, J=10.04 Hz, 1H), 4.07 (t, 0.1=7.91 Hz, 2H), 2.45-2.59 (m, 4H), 2.20-2.35 (m, 2H), 1.76-1.94 (m, 6H).

Embodiment 91

1-(1-Methylcyclopropane-1-carbonyl)-1'-((1-(4,4,4-trifluorobutyl)-4,5,6,7-tetrahydro-1H-benzo[d]imidazol-2-yl)methyl)spiro[azetidine-3,3'-pyrrole[2,3-c]pyridine]-2'-one

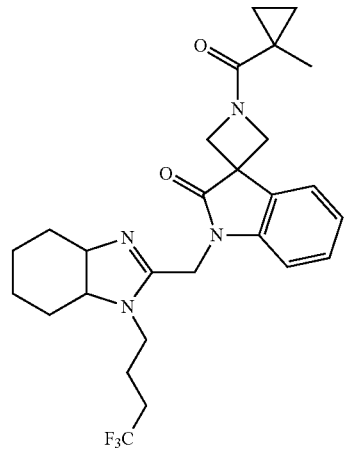

-continued

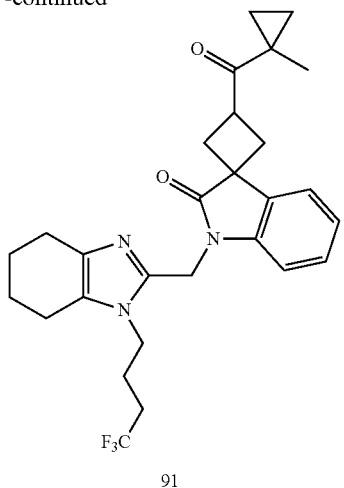

91

Step 1

1'-((1-(4,4,4-Trifluorobutyl)-4,5,6,7-tetrahydro-1H-benzo[d]imidazol-2-yl)methyl)spiro[azetidine-3,3'-indoline]-2'-one tert-Butyl 1'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate 91a (0.1 g, 0.19 mmol) was dissolved in 1 mL DCM, 0.5 mL trifluoroacetic acid was added, stirring for 0.5 h at r.t. 30 mL 1N NaOH aqueous solution was added, the mixture was extracted with DCM (30 mL×3), organic phases were combined and washed in sequence with water (30 mL×2), saturated sodium chloride solution (30 mL×2), dried over anhydrous sodium sulfate, filtered, the filtrate was concentrated under reduced pressure to obtain the crude product 1'-((1-(4,4,4-trifluorobutyl)-4,5,6,7-tetrahydro-1H-benzo[d]imidazol-2-yl)methyl)spiro[azetidine-3,3'-indoline]-2'-one 91b (110, yellow solid).

$^1$H NMR (400 MHz, CDCl$_3$) δ 7.77 (d, J=7.28 Hz, 1H), 7.53 (d, J=7.78 Hz, 1H), 7.36-7.29 (m, 1H), 7.18 (t, J=7.40 Hz, 1H), 4.98 (s, 2H), 4.23 (d, J=7.78 Hz, 2H), 4.00 (t, J=6.78 Hz, 2H), 3.74 (d, J=8.00 Hz, 2H), 2.59 (br. s., 2H), 2.46 (br. s., 2H), 2.24-2.09 (m, 2H), 1.81 (d, J=4.77 Hz, 2H), 1.69-1.51 (m, 2H), 1.49-1.36 (m, 2H).

Step 2

1-(1-Methylcyclopropane-1-carbonyl)-1'-((1-(4,4,4-trifluorobutyl)-4,5,6,7-tetrahydro-1H-benzo[d]imidazol-2-yl)methyl)spiro[azetidine-3,3'-pyrrole[2,3-c]pyridine]-2'-one 1'-((1-(4,4,4-Trifluorobutyl)-4,5,6,7-tetrahydro-1H-benzo[d]imidazol-2-yl)methyl)spiro[azetidine-3,3'-indoline]-2'-one 91b (110 mg, 0.26 mmol) was dissolved in 1 mL EA, 1-methylcyclopropanecarboxylic acid (32 mg, 0.32 mmol), TEA (53 mg, 0.53 mmol) were added, tripropyl phosphorous acid anhydride (251 mg, 0.39 mmol) was added dropwise, stirring for 16 h at r.t. 30 mL 1N NaOH aqueous solution was added, the mixture was extracted with EA (30 mL×3), organic phases were combined and washed in sequence with 1N NaOH aqueous solution (30 mL×2), 0.1N HCl aqueous solution (30 mL×2), saturated sodium chloride solution (30 mL×2), dried over anhydrous sodium sulfate, filtered, the filtrate was concentrated under reduced pressure, preparative HPLC was used to purify and 1-(1-methylcyclopropane-1-carbonyl)-1'-((1-(4,4,4-trifluorobutyl)-4,5,6,7-tetrahydro-1H-benzo[d]imidazol-2-yl)methyl)spiro[azetidine-3,3'-pyrrole[2,3-c]pyridine]-2'-one 91c (60 mg, white solid), yield: 45.6%.

MS m/z (ESI): 501.4 [M+1]

$^1$H NMR (400 MHz, CD$_3$OD) δ 7.66 (d, J=7.53 Hz, 1H), 7.35-7.29 (m, 1H), 7.24-7.17 (m, 1H), 7.10 (d, J=7.78 Hz, 1H), 5.05 (s, 2H), 4.84-4.64 (m, 2H), 4.38 (br. s., 1H), 4.18 (br. s., 1H), 4.09 (t, J=7.78 Hz, 2H), 2.59-2.48 (m, 4H), 2.29 (dd, J=10.54, 16.31 Hz, 2H), 1.91-1.78 (m, 6H), 1.40 (s, 3H), 1.14 (br. s., 2H), 0.65 (d, J=2.26 Hz, 2H).

Embodiment 92

1-Acetyl-1'-((1-(4,4,4-trifluorobutyl)-4,5,6,7-tetrahydro-1H-benzo[d]imidazol-2-yl)methyl)spiro[azetidine-3,3'-indoline]-2'-one

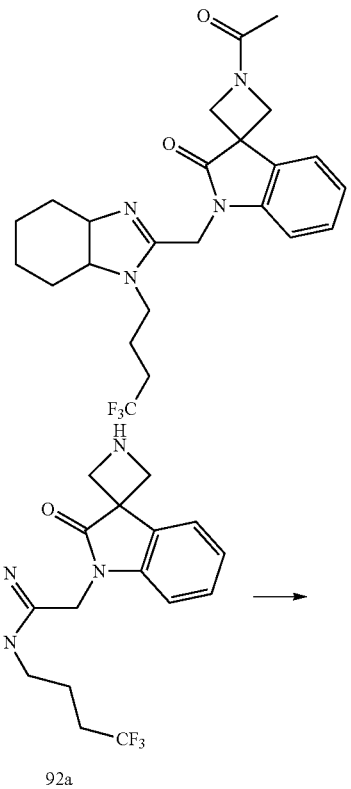

92a

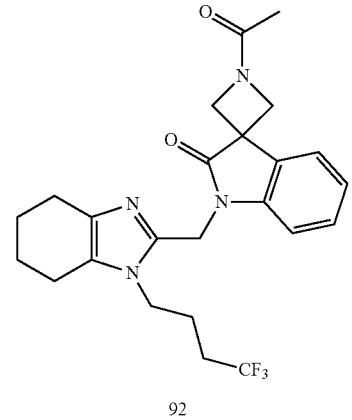

92

Step 1

1-Acetyl-1'-((1-(4,4,4-trifluorobutyl)-4,5,6,7-tetrahydro-1H-benzo[d]imidazol-2-yl)methyl)spiro[azetidine-3,3'-indoline]-2'-one 1'-((1-(4,4,4-Trifluorobutyl)-4,5,6,7-tetrahydro-1H-benzo[d]imidazol-2-yl)methyl)spiro[azetidine-3,3'-indoline]-2'-one 92a (150 mg, 0.36 mmol) was dissolved in 5 mL DCM, TEA (70 mg, 0.69 mmol) was added, acetyl chloride (40 mg, 0.51 mmol) was added dropwise, stirring for 1 h at r.t. 30 mL water was added, the mixture was extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and the target product 1-acetyl-1'-((1-(4,4,4-trifluorobutyl)-4,5,6,7-tetrahydro-1H-benzo[d]imidazol-2-yl)methyl)spiro[azetidine-3,3'-indoline]-2'-one 92 (4 mg, white solid) was given, yield: 2.4%.

MS m/z (ESI): 461.2 [M+1]

$^1$H NMR (400 MHz, CD$_3$OD) δ 7.73 (br. s., 1H), 7.39 (br. s., 1H), 7.27 (br. s., 1H), 7.06 (br. s., 1H), 5.26 (br. s., 2H), 4.46-4.62 (m, 2H), 4.37 (d, J=9.54 Hz, 1H), 4.24 (br. s., 3H), 2.52-2.72 (m, 4H), 2.38 (d, J=4.77 Hz, 2H), 2.02 (br. s., 5H), 1.90 (d, J=5.52 Hz, 4H).

Embodiment 93

1-(Cyclopropanecarbonyl)-1'-((1-(4,4,4-trifluorobutyl)-4,5,6,7-tetrahydro-1H-benzo[d]imidazol-2-yl)methyl)spiro[azetidine-3,3'-indoline]-2'-one

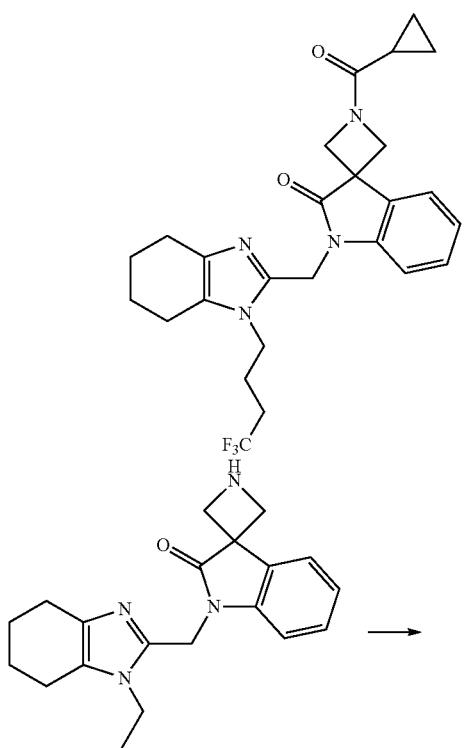

93a

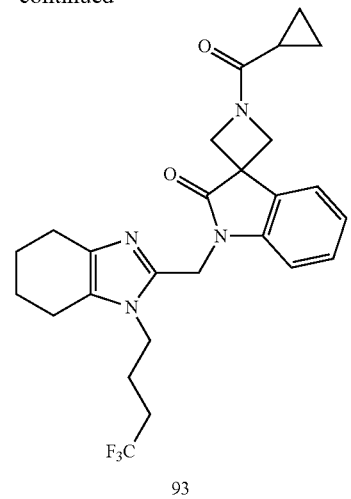

93

Step 1

1-(Cyclopropanecarbonyl)-1'-((1-(4,4,4-trifluorobutyl)-4,5,6,7-tetrahydro-1H-benzo[d]imidazol-2-yl)methyl)spiro[azetidine-3,3'-indoline]-2'-one 1'-((1-(4,4,4-Trifluorobutyl)-4,5,6,7-tetrahydro-1H-benzo[d]imidazol-2-yl)methyl)spiro[azetidine-3,3'-indoline]-2'-one 93a (125 mg, 0.30 mmol) was dissolved in 5 mL DCM, TEA (45 mg, 0.45 mmol) was added, cyclopropionyl chloride (37 mg, 0.36 mmol) was added dropwise, stirring for 4 h at r.t. 30 mL water was added, the mixture was extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and the target product 1-(cyclopropanecarbonyl)-1'-((1-(4,4,4-trifluorobutyl)-4,5,6,7-tetrahydro-1H-benzo[d]imidazol-2-yl)methyl)spiro[azetidine-3,3'-indoline]-2'-one 93 (35 mg, white solid), yield: 24.1%.

MS m/z (ESI): 487.4 [M+1]

$^1$H NMR (400 MHz, CD$_3$OD) δ 7.66 (d, J=7.28 Hz, 1H), 7.35-7.28 (m, 1H), 7.24-7.17 (m, 1H), 7.10 (d, J=7.78 Hz, 1H), 5.03 (s, 2H), 4.70 (d, J=8.78 Hz, 1H), 4.57 (d, J=8.53 Hz, 1H), 4.37 (d, J=9.54 Hz, 1H), 4.19 (d, J=9.54 Hz, 1H), 4.08 (t, J=7.78 Hz, 2H), 2.58-2.46 (m, 4H), 2.35-2.21 (m, 2H), 1.93-1.77 (m, 6H), 1.73-1.65 (m, 1H), 1.03-0.87 (m, 4H).

Embodiment 94

1-Propionyl-1'-((1-(4,4-trifluorobutyl)-4,5,6,7-tetrahydro-1H-benzo[d]imidazol-2-yl)methyl)spiro[azetidine-3,3'-indoline]-2'-one

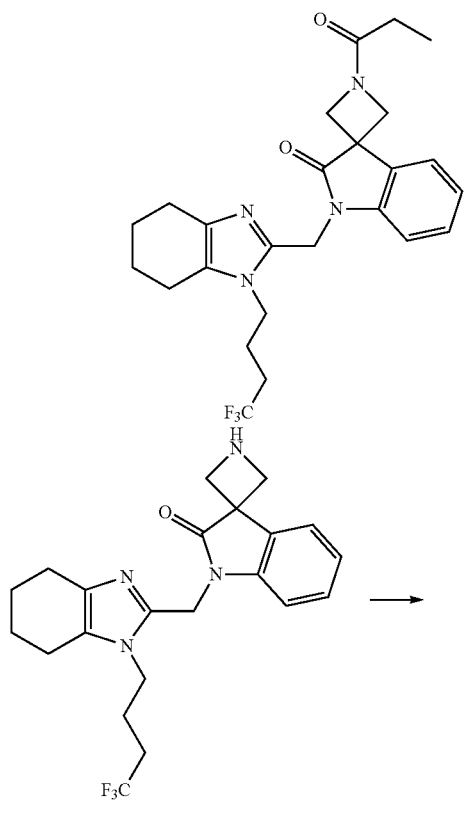

94a

Step 1

1-Propionyl-1'-((1-(4,4-trifluorobutyl)-4,5,6,7-tetrahydro-1H-benzo[d]imidazol-2-yl)methyl)spiro[azetidine-3,3'-indoline]-2'-one 1'-((1-(4,4-Trifluorobutyl)-4,5,6,7-tetrahydro-1H-benzo[d]imidazol-2-yl)methyl)spiro[azetidine-3,3'-indoline]-2'-one 94a (0.6 g, 0.72 mmol) was dissolved in 10 mL DCM, TEA (0.21 g, 2.15 mmol) was added, propionyl chloride (0.13 g, 1.43 mmol) was added dropwise, stirring for 1 h at r.t. 100 mL water was added, the mixture was extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, preparative HPLC was used to purify and the target product 1-propionyl-1'-((1-(4,4-trifluorobutyl)-4,5,6,7-tetrahydro-1H-benzo[d]imidazol-2-yl)methyl)spiro[azetidine-3,3'-indoline]-2'-one 94 (60 mg, white solid) was given, yield: 17.6%.

MS m/z (ESI): 475.2 [M+1]

$^1$H NMR (400 MHz, CD$_3$OD) δ 7.63 (d, J=7.3 Hz, 1H), 7.33-7.26 (m, 1H), 7.21-7.14 (m, 1H), 7.07 (d, J=7.8 Hz, 1H), 5.00 (s, 2H), 4.54 (d, J=8.8 Hz, 1H), 4.43 (d, J=8.5 Hz, 1H), 4.34 (d, J=9.5 Hz, 1H), 4.17 (d, J=9.8 Hz, 1H), 4.05 (t, J=7.8 Hz, 2H), 2.57-2.50 (m, 2H), 2.48 (t, J=5.4 Hz, 2H), 2.34-2.19 (m, 4H), 1.91-1.73 (m, 6H), 1.16 (t, J=7.5 Hz, 3H).

Embodiment 95

1-Isobutyryl-1'-((1-(4,4-trifluorobutyl)-4,5,6,7-tetrahydro-1H-benzo[d]imidazol-2-yl)methyl)spiro[azetidine-3,3'-indoline]-2'-one

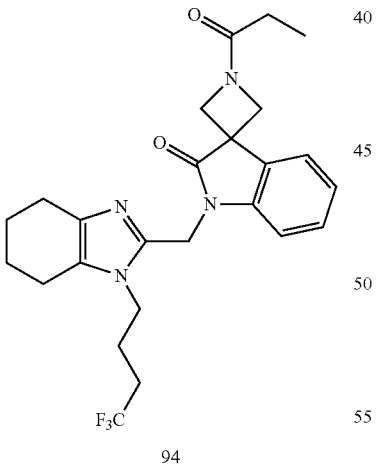

94

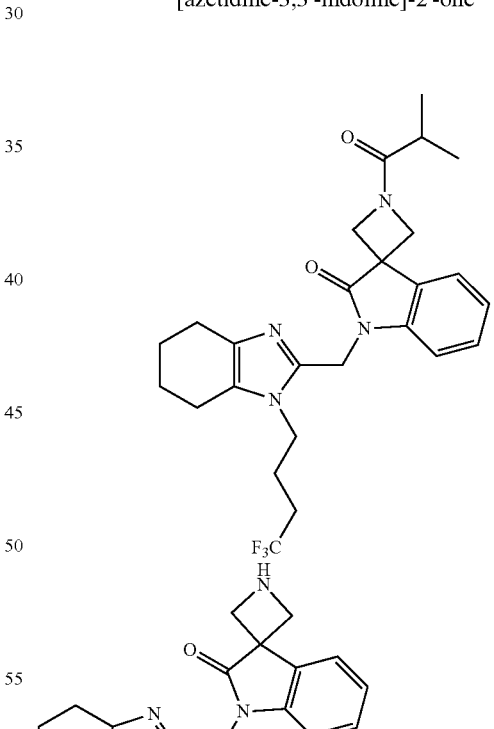

95a

125
-continued

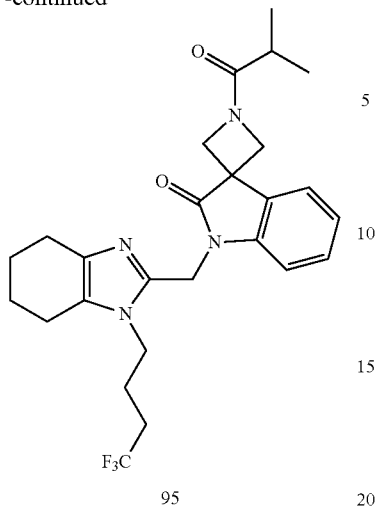

95

Step 1

1-Isobutyryl-1'-((1-(4,4,4-trifluorobutyl)-4,5,6,7-tetrahydro-1H-benzo[d]imidazol-2-yl)methyl)spiro[azetidine-3,3'-indoline]-2'-one 1'-((1-(4,4,4-Trifluorobutyl)-4,5,6,7-tetrahydro-1H-benzo[d]imidazol-2-yl)methyl)spiro[azetidine-3,3'-indoline]-2'-one 95a (0.1 g, 0.24 mmol) was dissolved in 10 mL DCM, TEA (73 mg, 0.72 mmol) was added, 2-methyl propionylchloride (38 mg, 0.36 mmol) was added dropwise, stirring for 1 h at r.t. 30 mL water was added, the mixture was extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and the target product 1-isobutyryl-1'-((1-(4,4,4-trifluorobutyl)-4,5,6,7-tetrahydro-1H-benzo[d]imidazol-2-yl)methyl)spiro[azetidine-3,3'-indoline]-2'-one 95 (30 mg, white solid), yield: 24.9%.

MS m/z (ESI): 489.3 [M+1]

¹H NMR (400 MHz, CD₃OD) δ 7.61 (d, J=8.03 Hz, 1H), 7.49 (d, J=7.28 Hz, 1H), 7.37 (t, J=7.78 Hz, 1H), 7.21-7.15 (m, 1H), 5.05-4.92 (m, 2H), 4.56 (d, J=8.03 Hz, 1H), 4.41 (d, J=9.29 Hz, 1H), 4.28 (d, J=7.78 Hz, 1H), 4.18 (d, J=9.54 Hz, 1H), 4.10-3.91 (m, 2H), 2.63-2.44 (m, 5H), 2.31-2.05 (m, 2H), 1.81 (br. s., 6H), 1.20 (d, J=6.78 Hz, 6H).

126

Embodiment 96

1-(2,2-Difluoroacetyl)-1'-((1-(4,4,4-trifluorobutyl)-4,5,6,7-tetrahydro-1H-benzo[d]imidazol-2-yl)methyl)spiro[azetidine-3,3'-indoline]-2'-one

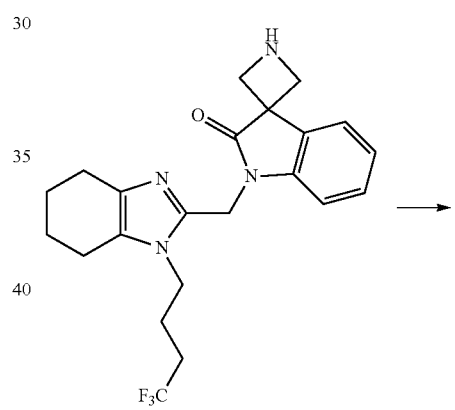

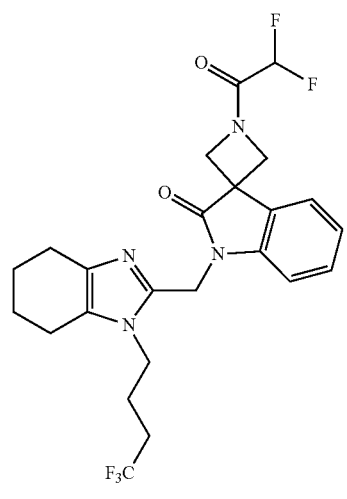

96a

96

Step 1

1-(2,2-Difluoroacetyl)-1'-((1-(4,4,4-trifluorobutyl)-4,5,6,7-tetrahydro-1H-benzo[d]imidazol-2-yl)methyl)spiro[azetidine-3,3'-indoline]-2'-one 1'-((1-(4,4,4-Trifluorobutyl)-4,5,6,7-tetrahydro-1H-benzo[d]imidazol-2-yl)methyl)spiro[azetidine-3,3'-indoline]-2'-one 96a (0.1 g, 0.24 mmol) was dissolved in 2 mL EA, TEA (48 mg, 0.478 mmol), difluoroacetic acid (23 mg, 0.24 mmol), tripropyl phosphorous acid anhydride (0.23 g, 0.36 mmol) were added, stirring for 1.5 h at r.t. 30 mL water was added, the mixture was extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and the target product 1-(2,2-difluoroacetyl)-1'-((1-(4,4,4-trifluorobutyl)-4,5,6,7-tetrahydro-1H-benzo[d]imidazol-2-yl)methyl)spiro[azetidine-3,3'-indoline]-2'-one 96 (22 mg, white solid), yield: 18.2%.

MS m/z (ESI): 519.3 [M+1]

$^1$H NMR (400 MHz, CD$_3$OD) δ 7.68 (d, J=7.0 Hz, 1H), 7.30 (t, J=8.0 Hz, 1H), 7.18 (t, J=8.0 Hz, 1H), 7.05 (d, J=7.5 Hz, 1H), 6.26 (t, J=52.0 Hz, 1H), 5.00 (s, 2H), 4.77 (d, J=9.5 Hz, 1H), 4.64 (d, J=9.5 Hz, 1H), 4.45 (d, J=10.5 Hz, 1H), 4.31 (d, J=10.5 Hz, 1H), 4.06 (t, J=8.0 Hz, 2H), 2.54 (t, J=8.0 Hz, 2H), 2.47 (t, J=8.0 Hz, 2H), 2.27 (m, 2H), 1.92-1.75 (m, 6H).

Embodiment 97

1-(Methylsulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one

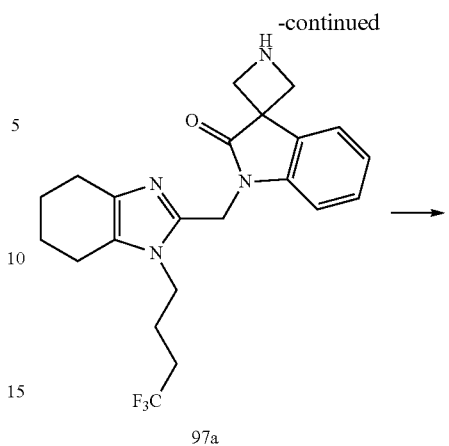

97a

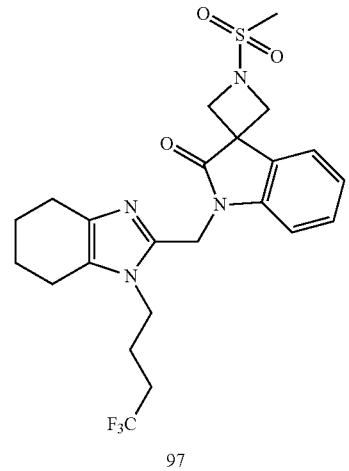

97

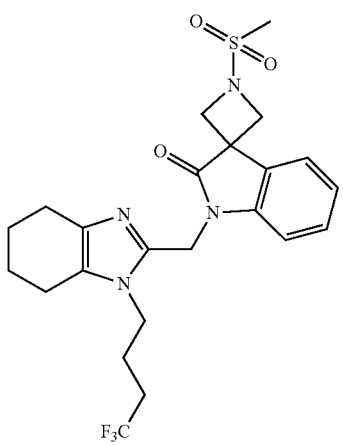

Step 1

1-(Methylsulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one 1'-((1-(4,4,4-Trifluorobutyl)-4,5,6,7-tetrahydro-1H-benzo[d]imidazol-2-yl)methyl)spiro[azetidine-3,3'-indoline]-2'-one 97a (0.1 g, 0.24 mmol) was dissolved in 2 mL DCM, TEA (24 mg, 0.24 mmol) was added, methanesulfonyl chloride (50 mg, 0.44 mmol) was added dropwise, stirring for 2 h at r.t. 30 mL Saturated sodium carbonate aqueous solution was added, the mixture was extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and the target product 1-(methylsulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one 97 (25 mg, white solid) was given, yield: 21.1%.

MS m/z (ESI): 497.3 [M+1]

$^1$H NMR (400 MHz, CD$_3$OD) δ 7.72 (d, J=7.28 Hz, 1H), 7.29-7.35 (m, 1H), 7.18-7.25 (m, 1H), 7.07 (d, J=7.78 Hz, 1H), 5.01 (s, 2H), 4.38 (d, J=8.53 Hz, 2H), 4.14 (d, J=8.28 Hz, 2H), 4.03-4.11 (m, 2H), 3.15 (s, 3H), 2.45-2.59 (m, 4H), 2.24-2.35 (m, 2H), 1.77-1.94 (m, 6H).

Embodiment 98

1-(Cyclopropyl sulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one

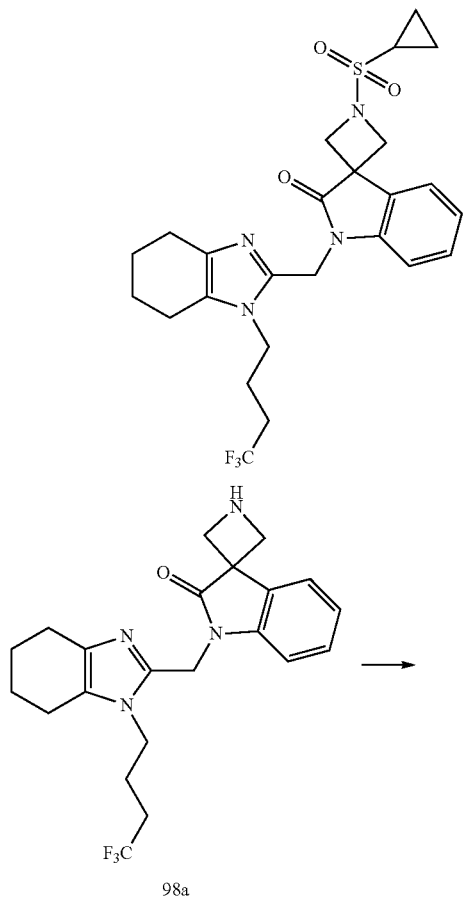

Step 1

1-(Cyclopropyl sulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one 1'-((1-(4,4,4-Trifluorobutyl)-4,5,6,7-tetrahydro-1H-benzo[d]imidazol-2-yl)methyl)spiro[azetidine-3,3'-indoline]-2'-one 98a (0.12 g, 0.29 mmol) was dissolved in 2 mL DCM, TEA (87 mg, 0.86 mmol) was added, cyclopropanesulfonyl chloride (48 mg, 0.34 mmol) was added dropwise, stirring for 2 h at r.t. 30 mL water was added, the mixture was extracted with EA (30 mL×3), organic phases were combined and washed in sequence with water (30 mL×2), saturated sodium chloride solution (30 mL×2), dried over anhydrous sodium sulfate, filtered, the filtrate was concentrated under reduced pressure, preparative HPLC was used to purify and the target product 1-(cyclopropyl sulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one 98 (35.6 mg, white solid) was given, yield: 22.6%.

MS m/z (ESI): 523.4 [M+1]

$^1$H NMR (400 MHz, CD$_3$OD) δ 7.73 (d, J=7.0 Hz, 1H), 7.36-7.27 (m, 1H), 7.25-7.15 (m, 1H), 7.12-6.99 (m, 1H), 5.01 (s, 2H), 4.47 (d, J=8.0 Hz, 2H), 4.14 (d, J=8.0 Hz, 2H), 4.07 (t, J=7.8 Hz, 2H), 2.80 (t, J=5.0 Hz, 1H), 2.62-2.43 (m, 4H), 2.37-2.21 (m, J=5.5 Hz, 2H), 2.02-1.63 (m, J=8.0 Hz, 6H), 1.23-1.10 (m, 4H).

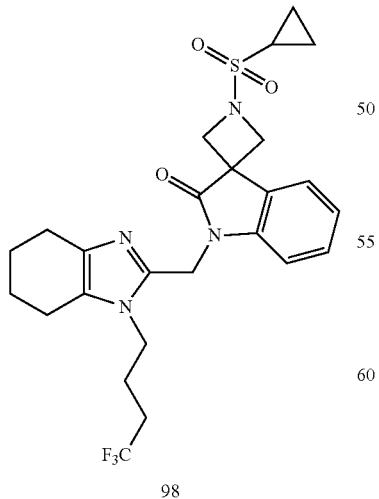

98

Embodiment 99

1-(Isopropylsulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one

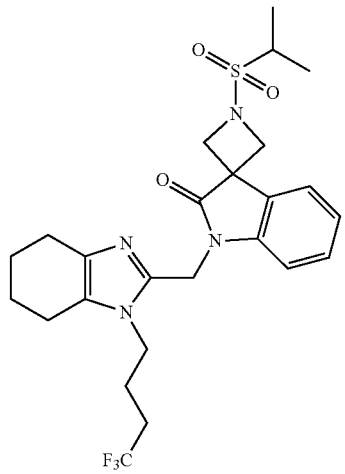

-continued

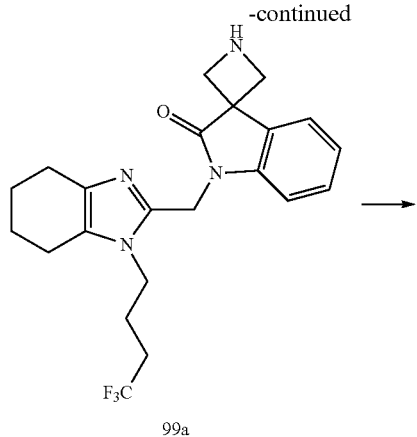

99a

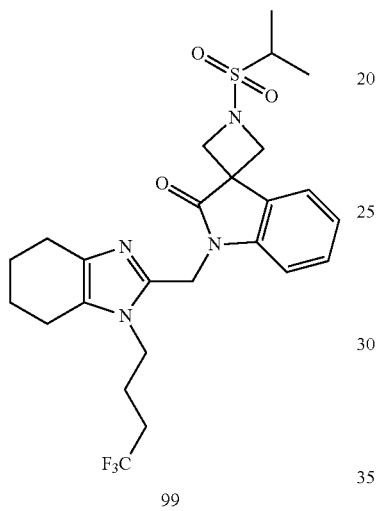

99

Step 1

1-(Isopropylsulfonyl)-1'-((1-(4,4,4-trifluorobutyl)-4,
5,6,7-tetrahydro-1H-benzo[d]imidazol-2-yl)methyl)
spiro[azetidine-3,3'-indoline]-2'-one 1'-((1-(4,4,4-Trifluorobutyl)-4,5,6,7-tetrahydro-1H-benzo
[d]imidazol-2-yl)methyl)spiro[azetidine-3,3'-indoline]-2'-
one 99a (0.38 g, 0.91 mmol) was dissolved in 4 mL DCM,
TEA (0.46 g, 4.54 mmol) was added, isopropanesulfonyl
chloride (0.39 g, 2.72 mmol) was added dropwise at 0° C.,
stirring for 3 h at r.t. 50 mL water was added, the mixture
was extracted with EA (50 mL×3), organic phases were
combined and washed in sequence with water (50 mL×2),
saturated sodium chloride solution (50 mL×2), dried over
anhydrous sodium sulfate, filtered, the filtrate was concentrated under reduced pressure, preparative HPLC was used
to purify and the target product 1-(isopropylsulfonyl)-1'-((1-
(4,4,4-trifluorobutyl)-4,5,6,7-tetrahydro-1H-benzo[d]imidazol-2-yl)methyl)spiro[azetidine-3,3'-indoline]-2'-one 99 (5
mg, white solid), yield: 1.05%.

MS m/z (ESI): 525.3 [M+1]

$^1$H NMR (400 MHz, CD$_3$OD) δ 7.68 (d, J=7.3 Hz, 1H),
7.30 (t, J=8.0 Hz, 1H), 7.19 (t, J=8.0 Hz, 1H), 7.07 (d, J=8.0
Hz, 1H), 4.99 (s, 2H), 4.94 (m., 1H), 4.38 (d, J=7.8 Hz, 2H),
4.11 (d, J=8.0 Hz, 2H), 4.05 (t, J=8.0 Hz, 2H), 2.53 (t, J=8.0
Hz, 2H), 2.47 (t, J=5.5 Hz, 2H), 2.33-2.19 (m, 2H), 1.89-
1.74 (m, 6H), 1.41 (d, J=6.8 Hz, 6H).

Embodiment 100

Isopropyl 1'-((1-(4-hydroxybutyl)-4,5-dimethyl-1H-
imidazol-2-yl)methyl)-2'-oxospiro[azetidine-3,3'-
indoline]-1-carboxylate

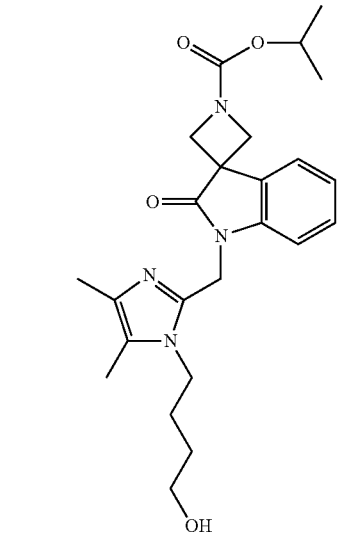

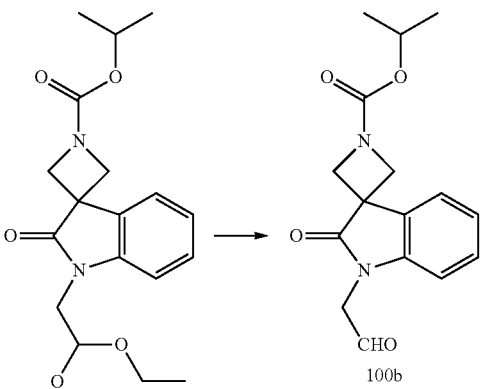

100a     100b

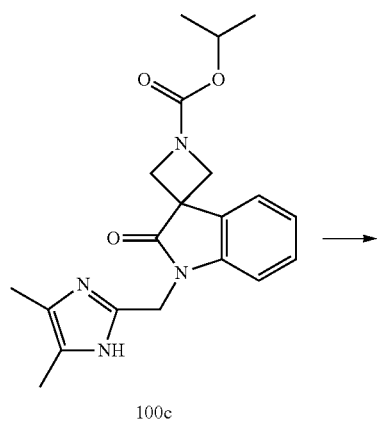

100c

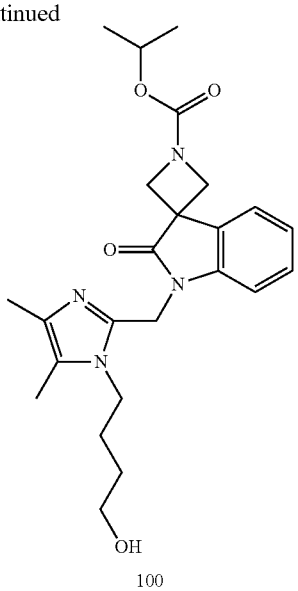

100

Step 1

Isopropyl 2'-oxo-1'-(2-oxoethyl)spiro[azetidine-3,3'-indoline]-1-carboxylate Isopropyl 1'-(2,2-diethoxyethyl)-2'-oxospiro[azetidine-3,3'-indoline]-1-carboxylate 100a (0.60 g, 1.59 mmol) was dissolved in 4.5 mL DCM and 1.5 mL H$_2$O, 4.5 mL trifluoroacetic acid was added at 0° C., stirring for 1 h at r.t. under nitrogen gas atmosphere. Potassium carbonate was added to neutralize the reaction solution, the mixture was extracted with DCM (15 mL×3), organic phases were combined and washed in sequence with water (15 mL×2), saturated sodium chloride solution (15 mL×2), dried over anhydrous sodium sulfate, filtered, the filtrate was concentrated under reduced pressure to obtain the crude product isopropyl 2'-oxo-1'-(2-oxoethyl)spiro[azetidine-3,3'-indoline]-1-carboxylate 100b (0.41 g, yellow oil), yield: 75.9%.

Step 2

Isopropyl 1'-((4,5-dimethyl-1H-imidazol-2-yl)methyl)-2'-oxospiro[azetidine-3,3'-indoline]-1-carboxylate Isopropyl 2'-oxo-1'-(2-oxoethyl)spiro[azetidine-3,3'-indoline]-1-carboxylate 100b (0.90 g, 2.67 mmol) was dissolved in 5 mL ethanol, 2,2-butanedione (0.14 g, 1.58 mmol), ammonium acetate (0.51 g, 6.6 mmol) were added, stirring at reflux for 4 h under nitrogen gas atmosphere. The reaction solution was cooled to r.t., extracted with EA (20 mL×3), organic phases were combined and washed in sequence with water (15 mL×2), saturated sodium chloride solution (15 mL×2), dried over anhydrous sodium sulfate, filtered, the filtrate was concentrated under reduced pressure, the residue was purified by silica gel column chromatography with eluting system C to obtain isopropyl 1'-((4,5-dimethyl-1H-imidazol-2-yl)methyl)-2'-oxospiro[azetidine-3,3'-indoline]-1-carboxylate 100c (0.60 g, white solid), yield: 74.0%.

MS m/z (ESI): 369.1 [M+1]

Step 3

Isopropyl 1'-((1-(4-hydroxybutyl)-4,5-dim ethyl-1H-imidazol-2-yl)methyl)-2'-oxospiro[azetidine-3,3'-indoline]-1-carboxylate Isopropyl 1'-((4,5-dimethyl-1H-imidazol-2-yl)methyl)-2'-oxospiro[azetidine-3,3'-indoline]-1-carboxylate 100c (0.36 g, 0.98 mmol) was dissolved in 5 mL acetonitrile, 4-bromobutyl acetate (0.23 g, 1.17 mmol), potassium carbonate (0.14 g, 0.98 mmol) and potassium iodide (0.16 g, 0.98 mmol) were added, the reaction mixture was heated to reflux and stirred for 18 h under nitrogen gas atmosphere. The reaction solution was filtered, washed with water, extracted with EA (20 mL×3), organic phases were combined and washed in sequence with water (15 mL×2), saturated sodium chloride solution (15 mL×2), dried over anhydrous sodium sulfate, filtered, the filtrate was concentrated under reduced pressure to obtain yellow solid. 3 mL 1M NaOH aqueous solution was added to dissolve, stirring for 1 h at r.t. 30 mL water was added into the reaction solution, the mixture was extracted with EA (30 mL×2), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product isopropyl 1'-((1-(4-hydroxybutyl)-4,5-dimethyl-1H-imidazol-2-yl)methyl)-2'-oxospiro[azetidine-3,3'-indoline]-1-carboxylate 100 (0.14 g, white solid) was given, yield: 47.5%.

MS m/z (ESI): 441.1 [M+1]

$^1$H NMR (400 MHz, CD$_3$OD) δ 7.63 (d, J=7.6 Hz, 1H), 7.41-6.95 (m, 3H), 4.99 (s, 2H), 4.70 (s, 1H), 4.36 (s, 2H), 4.18 (s, 2H), 3.99 (t, J=6.8 Hz, 2H), 3.58 (t, J=6 Hz, 2H), 2.15 (s, 3H), 2.07 (s, 3H), 1.64-1.57 (m, 4H), 1.31 (t, J=6 Hz, 6H).

Embodiment 101

Ethyl 1'-((4,5-diethyl-1-(4-hydroxybutyl)-1H-imidazol-2-yl)methyl)-2'-oxospiro[azetidine-3,3'-indoline]-1-carboxylate

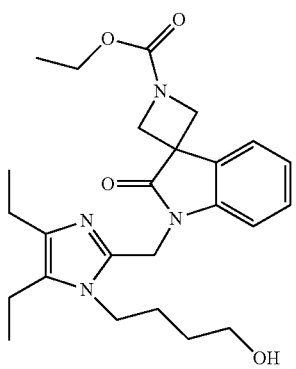

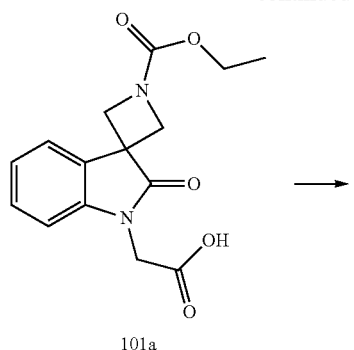

101a

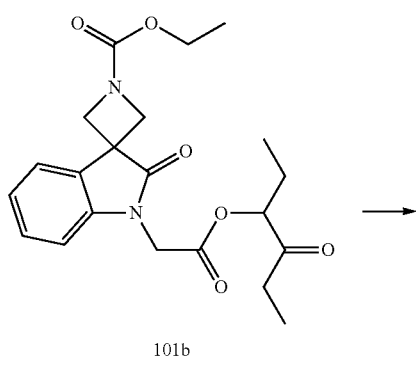

101b

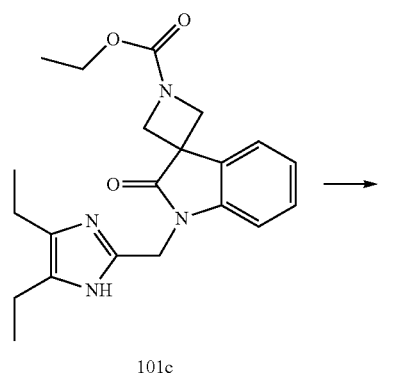

101c

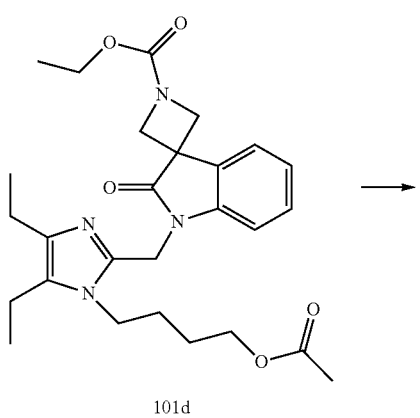

101d

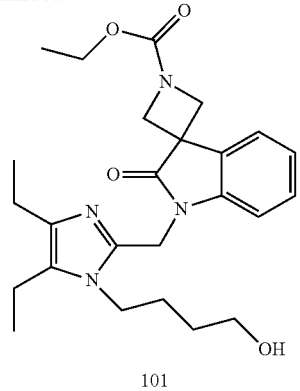

101

Step 1

Ethyl 2'-oxo-1'-(2-oxo-2-((4-oxobutyl-3-yl)oxy)ethyl)spiro[azetidine-3,3'-indoline]-1-carboxylate 2-(1-(Ethoxycarbonyl)-2'-oxospiro[azetidine-3,3'-indoline]-1-carboxylate 101a (1.00 g, 3.29 mmol) was dissolved in 5 mL DCM, oxalyl chloride (1.67 g, 13.16 mmol) was added, stirring for 1 h at r.t., 4-hydroxy hexane-3-one (0.46 g, 3.94 mmol) in 5 mL DCM was added, stirring for 3 h at r.t. 50 mL water was added into the reaction solution, the mixture was extracted with EA (50 mL×3), organic phases were combined and washed in sequence with water (50 mL×2), saturated sodium chloride solution (50 mL×2), dried over anhydrous sodium sulfate, filtered, the filtrate was concentrated under reduced pressure, the residue was purified by silica gel column chromatography with eluting system C to obtain ethyl 2'-oxo-1'-(2-oxo-2-((4-oxobutyl-3-yl)oxy)ethyl)spiro[azetidine-3,3'-indoline]-1-carboxylate 101b (0.09 g, yellow oil), yield: 61.2%.

$^1$H NMR (400 MHz, CDCl$_3$) δ 7.56 (d, J=7.5 Hz, 1H), 7.35 (t, N=7.8 Hz, 1H), 7.17 (t, J=7.5 Hz, 1H), 6.84 (d, J=7.5 Hz, 1H), 5.05 (dd, J=4.3, 7.8 Hz, 1H), 4.71 (d, J=17.6 Hz, 1H), 4.53-4.40 (m, 3H), 4.24-4.12 (m, 4H), 2.43 (dq, J=1.5, 7.2 Hz, 2H), 1.94-1.71 (m, 2H), 1.29 (t, J=7.3 Hz, 3H), 1.05 (t, J=7.0 Hz, 6H), 0.92 (t, J=7.3 Hz, 3H).

Step 2 ethyl 1'-((4,5-diethyl-1H-imidazol-2-yl)methyl)-2'-oxospiro[azetidine-3,3'-indoline]-1-carboxylate Ethyl 2'-oxo-1'-(2-oxo-2-((4-oxobutyl-3-yl)oxy)ethyl)spiro[azetidine-3,3'-indoline]-1-carboxylate 101b (0.80 g, 1.99 mmol) was dissolved in 4 m xylene, ammonium acetate (1.53 g, 19.88 mmol) was added, reacting for 40 min under 16° C. microwave. 10 mL water was added into the reaction mixture, the mixture was extracted with EA (10 mL×3), organic phases were combined and washed in sequence with water (10 mL×2), saturated sodium chloride solution (10 mL×2), dried over anhydrous sodium sulfate, filtered, the filtrate was concentrated under reduced pressure, the residue was purified by thin layer chromatography with eluting system C to obtain isopropyl 1'-((4,5-dimethyl-1H-imidazol-2-yl)methyl)-2'-oxospiro[azetidine-3,3'-indoline]-1-carboxylate 101c (60 mg, yellow oil), yield: 7.1%.

$^1$H NMR (400 MHz, CDCl$_3$) δ 7.53 (d, J=7.0 Hz, 1H), 7.36-7.30 (m, 2H), 7.15 (t, J=7.3 Hz, 1H), 4.90 (s, 1H), 4.40

(d, J=8.0 Hz, 2H), 4.23-4.17 (q, J=7.2 Hz, 2H), 4.12 (d, J=8.0 Hz, 2H), 2.53-2.47 (q, J=7.6 Hz, 4H), 1.30 (t, J=7.6 Hz, 3H), 1.17 (t, J=7.6 Hz, 6H).

Step 3

Ethyl 1'-((1-(4-hydroxybutyl)-4,5-diethyl-1H-imidazol-2-yl)methyl)-2'-oxospiro[azetidine-3,3'-indoline]-1-carboxylate Isopropyl 1'-((4,5-diethyl-1H-imidazol-2-yl)methyl)-2'-oxospiro[azetidine-3,3'-indoline]-1-carboxylate 101c (70 mg, 0.18 mmol) was dissolved in 5 mL DMF, 4-bromobutyl acetate (107 mg, 0.55 mmol), cesium carbonate (179 mg, 0.55 mmol) and potassium iodide (3.0 mg, 0.01 mmol) were added at 90° C., and the reaction mixture was stirred for 20 h at 90° C. The reaction solution was filtered, washed with water, extracted with EA (20 mL×3), organic phases were combined and washed in sequence with water (15 mL×2), saturated sodium chloride solution (15 mL×2), dried over anhydrous sodium sulfate, filtered, the filtrate was concentrated under reduced pressure, the residue was purified by thin layer chromatography with eluting system C to obtain yellow oil. 3 mL 1M NaOH aqueous solution was added to dissolve, stirring for 0.5 h at r.t. 30 mL water was added into the reaction solution, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product ethyl 1'-((1-(4-hydroxybutyl)-4,5-diethyl-1H-imidazol-2-yl)methyl)-2'-oxospiro[azetidine-3,3'-indoline]-1-carboxylate 101 (7 mg, white solid) was given, yield: 38.2%.

MS m/z (ESI): 455.3 [M+1]

$^1$H NMR (400 MHz, CD$_3$OD) δ 7.60 (d, J=7.3 Hz, 1H), 7.28-7.21 (t, J=7.92 Hz, 1H), 7.17-7.11 (t, J=7.92 Hz, 1H), 7.00 (d, J=7.8 Hz, 1H), 4.97 (s, 2H), 4.35 (d, J=8.1 Hz, 2H), 4.16 (q, J=7.1 Hz, 4H), 3.97 (d, J=8.1 Hz, 2H), 3.55 (t, J=6.0 Hz, 2H), 2.57 (q, J=7.6 Hz, 2H), 2.44 (q, J=7.6 Hz, 2H), 1.67-1.45 (m, 4H), 1.28 (t, J=7.1 Hz, 4H), 1.11 (dt, J=4.2, 7.6 Hz, 6H).

Embodiment 102

Isopropyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate

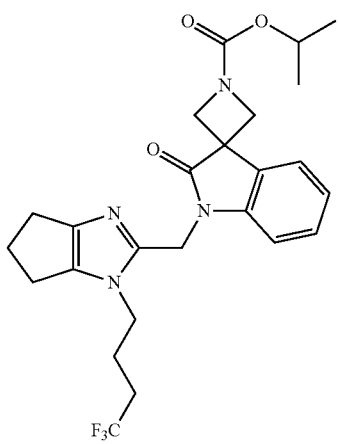

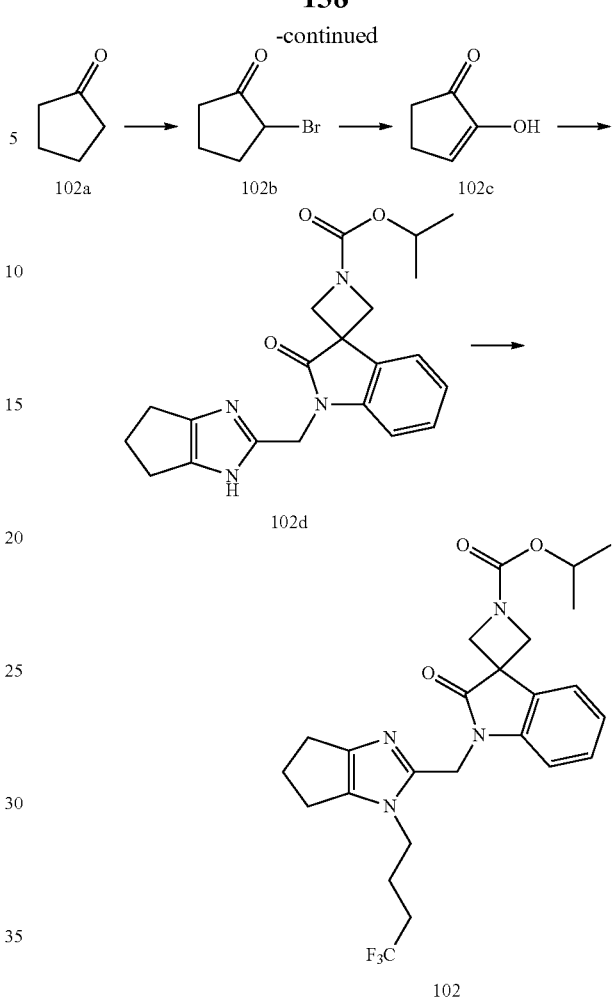

Step 1

2-Bromocyclopentan-1-one

Cyclopentanone 102a (5.04 g, 59.9 mmol) and p-toluene sulfonic acid (1.14 g, 5.99 mmol) were added into the flask with three necks, N-bromosuccinimide (10.66 g, 59.9 mmol) was added in portions at 0° C., stirring for 2 h at r.t. 200 mL water was added, the mixture was extracted with EA (200 mL×3), organic phases were combined and washed in sequence with water (200 mL×2), saturated sodium chloride solution (200 mL×2), dried over anhydrous sodium sulfate, filtered, the filtrate was concentrated under reduced pressure, the residue was purified by silica gel column chromatography with eluting system C to obtain 2-bromocyclopentan-1-one 102b (7.6 g, light yellow liquid), yield: 62.3%.

$^1$H NMR (400 MHz, CDCl$_3$) δ 4.26-4.18 (m, 1H), 2.45-2.35 (m, 2H), 2.28-2.16 (m, 3H), 2.07-1.98 (m, 1H).

Step 2

2-hydroxycyclopenta-2-en-1-one

2-Bromocyclopentan-1-one 102b (0.84 g, 5.14 mmol) was dissolved into 10 mL H$_2$O (preheated to 98° C.), 10 mL FeCl$_3$ (1.65 g, 10.17 mmol) in H$_2$O (preheated to 80° C.) was added, stirring for 10 min at 98° C. The reaction solution was cooled to 40° C., 10 mL saturated ammonium sulfate aqueous solution was added, the mixture was extracted with EA (200 mL×3), organic phases were combined and washed in sequence with water (200 mL×2), saturated sodium chloride solution (200 mL×2), dried over anhydrous sodium sulfate, filtered, the filtrate was concentrated under reduced pressure to obtain the crude product 2-hydroxycyclopenta-2-en-1-one 102c (0.24 g, yellow oil).

$^1$H NMR (400 MHz, CDCl$_3$) δ 6.57 (t, J=3.0 Hz, 1H), 5.65 (br. s., 1H), 2.54-2.50 (m, 2H), 2.47-2.43 (m, 2H).

Step 3

Isopropyl 2'-oxo-1'-((1,4,5,6-tetrahydrocyclopenta[d]imidazol-2-yl)methyl)spiro[azetidine-3,3'-indoline]-1-carboxylate 2-Hydroxycyclopenta-2-en-1-one 102c (85 mg, 0.87 mmol) was dissolved in 4 mL ethanol, isopropyl 2'-oxo-1'-(2-ethoxy)-spiro[azetidine-3,3'-indoline]-1-carboxylate (0.26 g, 0.87 mmol), ammonium carbonate (0.33 g, 4.33 mmol) were added, stirring for 2 h at 80° C. The reaction solution was concentrated under reduced pressure, 20 mL saturated sodium carbonate aqueous solution was added, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, the residue was purified by silica gel column chromatography with eluting system C to obtain isopropyl 2'-oxo-1'-((1,4,5,6-tetrahydrocyclopenta[d]imidazol-2-yl)methyl)spiro[azetidine-3,3'-indoline]-1-carboxylate 102d (50 mg, yellow solid).

$^1$H NMR (400 MHz, CD$_3$OD) δ 7.53 (d, J=7.0 Hz, 1H), 7.36-7.32 (m, 2H), 7.15 (d, J=8.0 Hz, 1H), 4.97 (m, 1H), 4.90 (s, 2H), 4.39 (d, J=8.0 Hz, 2H), 4.12 (d, J=8.0 Hz, 2H), 2.69-2.58 (m, 4H), 2.47-2.41 (m, 2H), 1.29 (d, J=4.0 Hz, 6H).

Step 4

Isopropyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate Isopropyl 2'-oxo-1'-((1,4,5,6-tetrahydrocyclopenta[d]imidazol-2-yl)methyl)-2',3'-dihydrospiro[azetidine-3,1'-indene]-1-carboxylate 102d (50 mg, 0.13 mmol) was dissolved in 1 mL DMF, 4-bromo-1,1,1-trifluorobutane (30 mg, 0.16 mmol), cenium carbonate (85 mg, 0.26 mmol) were added, stirring for 2 h at 80° C. The reaction solution was cooled to r.t., 30 mL water was added, extracted with EA (30 mL×2), organic phases were combined and washed with saturated sodium chloride solution (20 mL×2), dried over anhydrous sodium sulfate, filtered, the filtrate was concentrated under reduced pressure, preparative HPLC was used to purify and the target product isopropyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate 102 (7.5 mg, white solid) was given, yield: 11.6%.

MS m/z (ESI): 491.3 [M+1]

$^1$H NMR (400 MHz, CD$_3$OD) δ 7.62 (d, J=7.5 Hz, 1H), 7.29 (t, J=8.0 Hz, 1H), 7.17 (t, J=8.0 Hz, 1H), 7.12 (d, J=7.5 Hz, 1H), 4.99 (s, 2H), 4.94-4.93 (m, 1H), 4.33 (d, J=8.0 Hz, 2H), 4.15 (d, J=8.0 Hz, 2H), 4.09 (t, J=7.5 Hz, 2H), 2.70 (t, J=6.8 Hz, 2H), 2.59-2.56 (m, 2H), 2.52-2.45 (m, 2H), 2.24-2.17 (m, 2H), 1.94-1.86 (m, 2H), 1.29 (d, J=6.5 Hz, 6H).

Embodiment 103

Isopropyl 1'-((1-(4-hydroxybutyl)-1,4,5,6-tetrahydrocyclopenta[d]imidazol-2-yl)methyl)-2'-oxospiro[azetidine-3,3'-indoline]-1-carboxylate

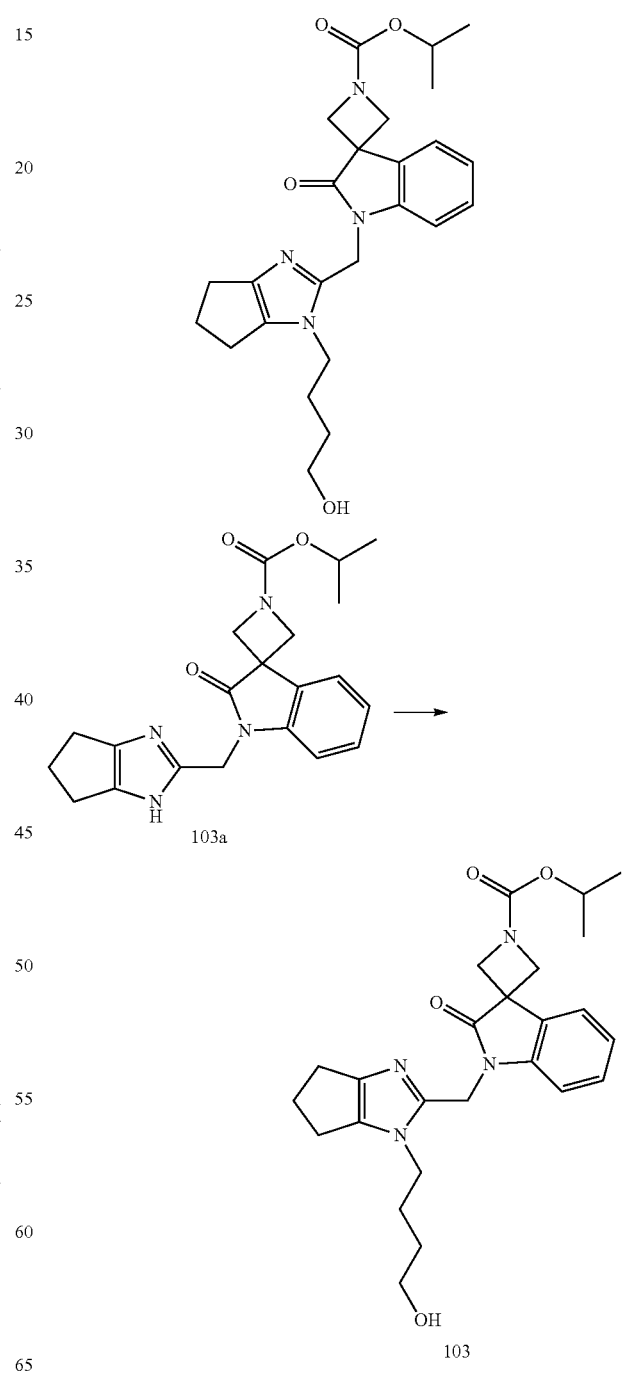

Step 1

Isopropyl 1'-((1-(4-hydroxybutyl)-1,4,5,6-tetrahydrocyclopenta[d]imidazol-2-yl)methyl)-2'-oxospiro[azetidine-3,3'-indoline]-1-carboxylate Isopropyl 2'-oxo-3'-((1,4,5,6-tetrahydrocyclopenta[d]imidazol-2-yl)methyl)-2',3'-dihydrospiro[azetidine-3,1'-indene]-1-carboxylate 103a (0.1 g, 0.26 mmol) was dissolved in 2 mL DMSO, 4-bromobutyl acetate (62 mg, 0.32 mmol), cesium carbonate (0.17 g, 0.53 mmol) were added, the reaction mixture was stirred for 3 h at 80° C. The reaction solution was cooled to r.t., 30 mL water was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure to obtain yellow oil. 2 mL 1M NaOH aqueous solution was added to dissolve, stirring for 1 h at r.t. 30 mL water was added into the reaction solution, the mixture was extracted with EA (30 mL×2), organic phases were combined and washed with saturated sodium chloride solution (20 mL×2), dried over anhydrous sodium sulfate, filtered, the filtrate was concentrated under reduced pressure, preparative HPLC was used to purify and the target product isopropyl 1'-((1-(4-hydroxybutyl)-1,4,5,6-tetrahydrocyclopenta[d]imidazol-2-yl)methyl)-2'-oxospiro[azetidine-3,3'-indoline]-1-carboxylate 103 (21 mg, white solid) was given, yield: 14.99%.

MS m/z (ESI): 453.3 [M+1]

$^1$H NMR (400 MHz, CD$_3$OD) δ 7.62 (d, J=7.5 Hz, 1H), 7.28 (t, J=8.0 Hz, 1H), 7.16 (t, J=8.0 Hz, 1H), 7.08 (d, J=8.0 Hz, 1H), 4.99 (s, 2H), 4.96-4.91 (m, 1H), 4.34 (d, J=8.5 Hz, 2H), 4.16 (d, J=7.5 Hz, 2H), 4.01 (t, J=7.3 Hz, 2H), 3.53 (t, J=6.3 Hz, 2H), 2.70 (t, J=6.5 Hz, 2H), 2.60-2.52 (m, 2H), 2.51-2.42 (m, 2H), 1.74-1.66 (m, 2H), 1.54-1.44 (m, 2H), 1.29 (d, J=6.0 Hz, 6H).

Embodiment 104

Ethyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate

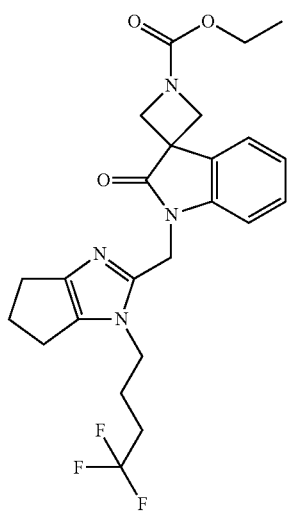

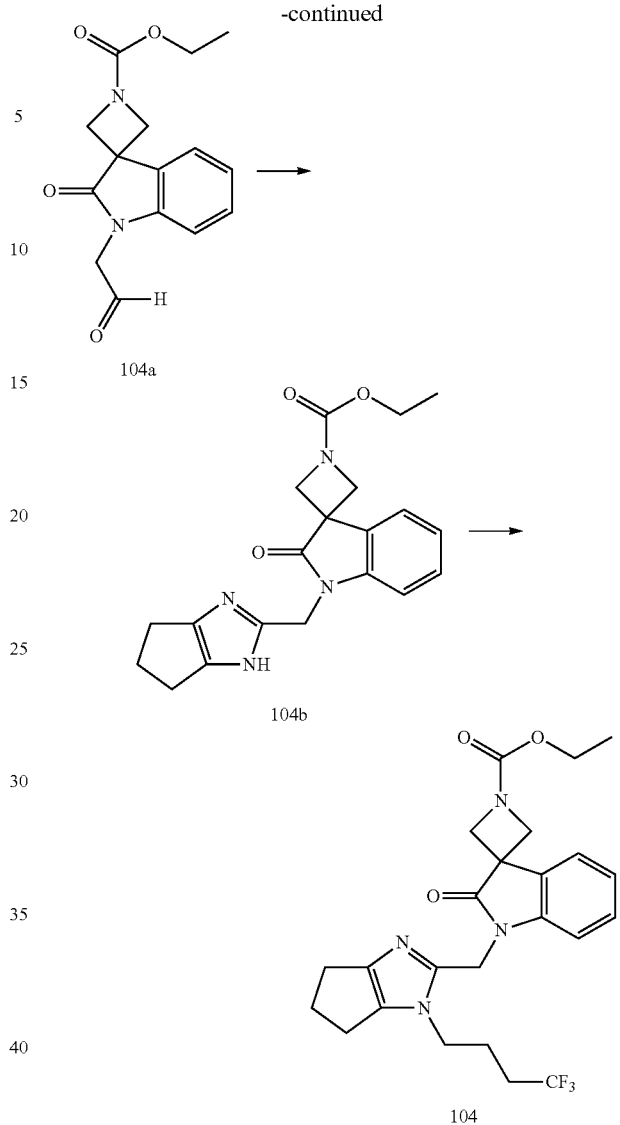

Step 1

Ethyl 2'-oxo-1'-((1,4,5,6-tetrahydrocyclopenta[d]imidazol-2-yl)methyl)spiro[azetidine-3,3'-indoline]-1-carboxylate Ethyl 2'-oxo-1'-(2-ethoxy)spiro[azetidine-3,3'-indoline]-1-carboxylate 104a (1 g, 3.47 mmol) was dissolved in 10 mL ethanol, 2-hydroxycyclopentane-2-enone (0.34 g, 3.47 mmol), ammonium acetate (1.34 g, 17.34 mmol) were added, and the reaction mixture was stirred for 7 h at 80° C. The reaction solution was concentrated under reduced pressure, 100 mL saturated sodium carbonate aqueous solution was added, extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with eluting system C to obtain ethyl 2'-oxo-1'-((1,4,5,6-tetrahydrocyclopenta[d]imidazol-2-yl)methyl)spiro[azetidine-3,3'-indoline]-1-carboxylate 104b (200 mg, yellow solid), yield: 15.74%.

$^1$H NMR (400 MHz, CD$_3$OD) δ 7.62 (d, J=7.3 Hz, 1H), 7.29-7.23 (m, 1H), 7.19-7.12 (m, 1H), 6.83 (d, J=7.8 Hz, 1H), 4.93 (s, 2H), 4.39 (d, J=8.3 Hz, 2H), 4.18 (q, J=7.0 Hz, 4H), 2.70-2.50 (m, 4H), 2.50-2.39 (m, 2H), 1.29 (t, J=7.2 Hz, 3H).

Step 2

Ethyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate Ethyl 2'-oxo-1'-((1,4,5,6-tetrahydrocyclopenta[d]imidazol-2-yl)methyl)spiro[azetidine-3,3'-indoline]-1-carboxylate 104b (0.2 g, 0.55 mmol) was dissolved in 10 mL DMF, 4-bromo-1,1,1-trifluorobutane (0.10 g, 0.55 mmol), cenium carbonate (0.36 g, 1.09 mmol) were added, stirring for 1 h at 80° C. The reaction solution was cooled to r.t., 30 mL water was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product ethyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate 104 (90 mg, white solid) was given, yield: 34.6%.

MS m/z (ESI): 477.3 [M+1]

$^1$H NMR (400 MHz, CD$_3$OD) δ 7.65 (d, J=7.28 Hz, 1H), 7.30 (d, J=7.78 Hz, 1H), 7.22-7.16 (m, 1H), 7.13 (d, J=7.78 Hz, 1H), 5.03 (s, 2H), 4.37 (d, J=8.28 Hz, 2H), 4.24-4.15 (m, 4H), 4.11 (t, J=7.40 Hz, 2H), 2.72 (t, J=6.78 Hz, 2H), 2.60 (d, J=6.27 Hz, 2H), 2.54-2.44 (m, 2H), 2.29-2.13 (m, 2H), 1.91 (br. s., 2H), 1.31 (t, J=7.03 Hz, 3H).

Embodiment 105

1-Isobutyryl-1'-((1-(4,4,4-trifluorobutyl)-1,4,5,6-tetrahydrocyclopenta[d]imidazol-2-yl)methyl)spiro[azetidine-3,3'-indoline]-2'-one

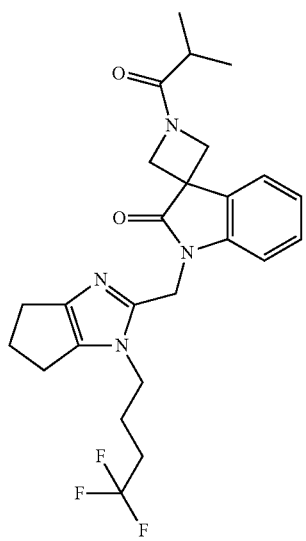

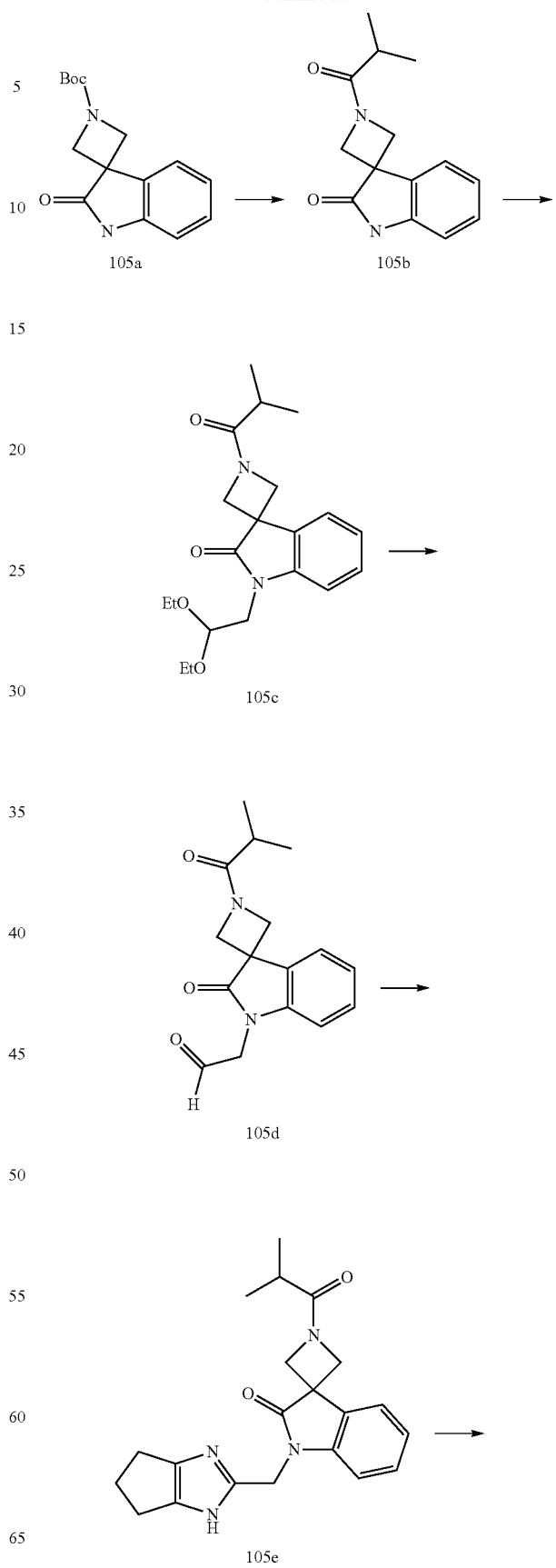

-continued

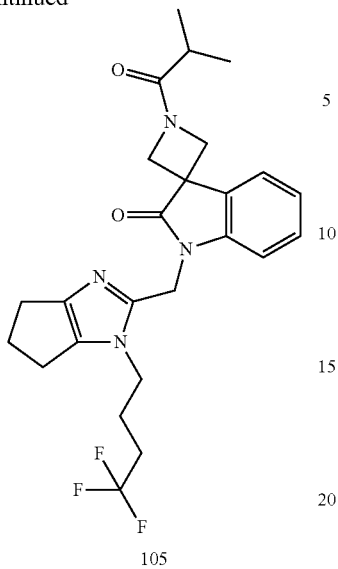

105

Step 1

1-Isobutyrylspiro[azetidine-3,3'-indoline]-2'-one tert-Butyl 2'-oxospiro[azetidine-3,3'-indoline]-1-carboxylate 105a (6.0 g, 21.87 mmol) was dissolved in 50 mL DCM, trifluoroacetic acid (22.5 g, 197.3 mmol) was added, stirring for 16 h at r.t. The reaction solution was concentrated under reduced pressure to obtain black oil. 25 mL DCM, TEA (7.86 g, 77.72 mmol) were added, isobutyryl chloride (2.8 g, 26.25 mmol) was added at 0° C., stirring for 4 h at r.t. 100 mL water was added, the mixture was extracted with DCM (80 mL×3), organic phases were combined and washed in sequence with water (80 mL×2), saturated sodium chloride solution (80 mL×2), dried over anhydrous sodium sulfate, filtered, the filtrate was concentrated under reduced pressure, the residue was purified with silica gel column chromatography with eluting system C to obtain 1-isobutyrylspiro[azetidine-3,3'-indoline]-2'-one 105b (4.2 g, yellow solid), yield: 78.1%.
$^1$H NMR (400 MHz, CDCl$_3$) δ 7.68-7.62 (m, 1H), 7.41-7.32 (m, 1H), 7.30-7.27 (m, 1H), 7.21-7.15 (m, 1H), 4.33 (d, J=8.03 Hz, 1H), 4.30 (d, J=8.03 Hz, 1H), 4.18 (d, J=8.03 Hz, 1H), 4.10 (d, J=8.03 Hz, 1H), 2.50-2.40 (m, 1H), 1.70 (d, J=8.03 Hz, 6H).

Step 2

1'-(2,2-Diethoxy)-1-isobutyrylspiro[azetidine-3,3'-indoline]-2'-one

1-Isobutyrylspiro[azetidine-3,3'-indoline]-2'-one 105b (4.2 g, 17.1 mmol) was dissolved in 20 mL DMF, 2-bromo-1,1-diethoxyl-ethane (3.37 g, 17.1 mmol), cesium carbonate (9.30 g, 28.54 mmol), potassium iodide (0.24 g, 1.43 mmol) were added, stirring for 16 h at 90° C. The reaction solution was cooled to r.t., 100 mL water was added, extracted with DCM (80 mL×3), organic phases were combined and washed in sequence with water (80 mL×2), saturated sodium chloride solution (80 mL×2), dried over anhydrous sodium sulfate, filtered, the filtrate was concentrated under reduced pressure, the residue was purified with silica gel column chromatography with eluting system C to obtain 1'-(2,2-diethoxy)-1-isobutyrylspiro[azetidine-3,3'-indoline]-2'-one 105c (4.2 g, yellow oil), yield: 67.0%.
$^1$H NMR (400 MHz, CDCl$_3$) δ 7.68-7.62 (m, 1H) 7.41-7.32 (m, 1H) 7.30-7.27 (m, 1H) 7.21-7.15 (m, 1H) 4.70 (d, J=8.03 Hz, 1H) 4.60 (d, J=8.03 Hz, 1H) 4.50 (d, J=8.03 Hz, 1H) 4.45 (d, J=8.03 Hz, 1H) 4.40 (d, J=8.03 Hz, 3H) 3.80-3.60 (m, 2H) 3.50-3.40 (m, 2H) 2.50-2.40 (m, 1H) 1.17 (t, J=7.2 Hz, 6H) 1.16 (t, J=7.2 Hz, 6H).

Step 3

2-(1-Isobutyryl-2'-oxospiro[azetidine-3,3'-indoline]-1'-yl)acetaldehyde

1'-(2,2-Diethoxy)-1-isobutyrylspiro[azetidine-3,3'-indoline]-2'-one 105c (3.50 g, 9.71 mmol) was dissolved in 30 mL DCM, 10 mL trifluoroacetic acid was added at 0° C., stirring for 2 h at r.t. 30 mL saturated sodium carbonate aqueous solution was added, the mixture was extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure to obtain the crude product 1'-(2,2-diethoxy)-1-isobutyrylspiro[azetidine-3,3'-indoline]-2'-one 105d (3.0 g, dark brown oil).

Step 4

1-Isobutyryl-1'-((1,4,5,6-tetrahydrocyclopenta[d]imidazol-2-yl)methyl)spiro[azetidine-3,3'-indoline]-2'-one 1'-(2,2-diethoxy)-1-isobutyrylspiro[azetidine-3,3'-indoline]-2'-one 105d (3.21 g, 11.21 mmol) was dissolved in 50 mL ethanol, 2-hydroxylcyclopentane-2-enone (1 g, 10.19 mmol), ammonium acetate (3.93 g, 50.95 mmol) were added, the reaction mixture was stirred for 7 h at 80° C. The reaction solution was concentrated under reduced pressure, 100 mL saturated sodium carbonate aqueous solution was added, extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified with silica gel column chromatography with eluting system C to obtain 1-isobutyryl-1'-((1,4,5,6-tetrahydrocyclopenta[d]imidazol-2-yl)methyl)spiro[azetidine-3,3'-indoline]-2'-one 105e (500 mg, yellow solid), yield: 11.44%.
$^1$H NMR (400 MHz, CDCl$_3$) δ 7.48 (d, J=7.28 Hz, 1H), 7.34 (d, J=7.28 Hz, 1H), 7.31-7.26 (m, 1H), 7.19-7.12 (m, 1H), 4.91 (d, J=11.04 Hz, 2H), 4.57 (d, J=8.03 Hz, 1H), 4.41 (d, J=9.29 Hz, 1H), 4.29 (d, J=8.03 Hz, 1H), 4.16 (d, J=9.54 Hz, 1H), 2.66-2.59 (m, 4H), 2.53 (td, J=6.78, 13.55 Hz, 1H), 2.47-2.39 (m, 2H), 1.19 (d, J=6.78 Hz, 6H).

Step 5

1-Isobutyryl-1'-((1-(4,4,4-trifluorobutyl)-1,4,5,6-tetrahydrocyclopenta[d]imidazol-2-yl)methyl)spiro[azetidine-3,3'-indoline]-2'-one 1-Isobutyryl-1'-((1,4,5,6-tetrahydrocyclopenta[d]imidazol-2-yl)methyl)spiro[azetidine-3,3'-indoline]-2'-one 105e (0.2 g, 0.55 mmol) was dissolved in 10 mL DMF, 4-bromo-1,1,1-trifluorobutane (0.12 g, 0.60 mmol), cesium carbonate (0.36 g, 1.10 mmol) were added, stirring for 1 h at 80° C. The reaction solution was cooled to r.t., 30 mL water was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product 1-isobutyryl-1'-((1-(4,4,4-trifluorobutyl)-1,4,5,6-tetrahydrocyclopenta[d]imidazol-2-yl)methyl)spiro[azetidine-3,3'-indoline]-2'-one 105 (100 mg, yellow solid) was given, yield: 38.0%.

MS m/z (ESI): 475.2 [M+1]

$^{1}$H NMR (400 MHz, CD$_{3}$OD) δ 7.64 (d, J=7.28 Hz, 1H), 7.35-7.28 (m, 1H), 7.23-7.17 (m, 1H), 7.14 (d, J=8.03 Hz, 1H), 5.03 (s, 2H), 4.59 (d, J=8.78 Hz, 1H), 4.48 (d, J=8.78 Hz, 1H), 4.35 (d, J=9.79 Hz, 1H), 4.18 (d, J=9.79 Hz, 1H), 4.12 (t, J=7.53 Hz, 2H), 2.72 (t, J=6.78 Hz, 2H), 2.69-2.56 (m, 3H), 2.50 (d, J=6.27 Hz, 2H), 2.31-2.13 (m, 2H), 1.99-1.85 (m, 2H), 1.18 (d, J=7.03 Hz, 6H).

Embodiment 106

1-(Methylsulfonyl)-1'-((1-(4,4,4-trifluorobutyl)-1,4,5,6-tetrahydrocyclopenta[d]imidazol-2-yl)methyl)spiro[azetidine-3,3'-indoline]-2'-one

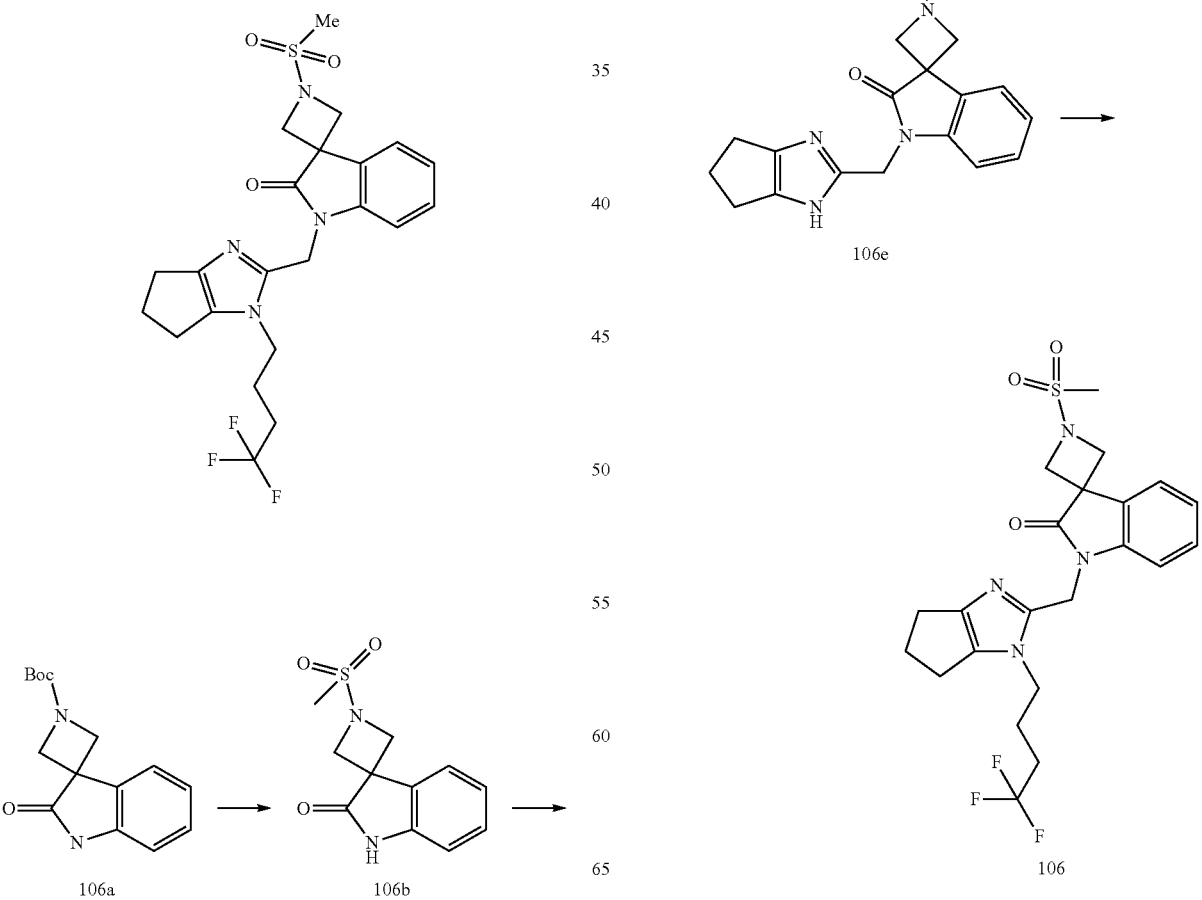

Step 1

1-(Methylsulfonyl)spiro[azetidine-3,3'-indoline]-2'-one tert-Butyl 2'-oxospiro[azetidine-3,3'-indoline]-1-carboxylate 106a (12.0 g, 43.75 mmol) was dissolved in 50 mL DCM, trifluoroacetic acid (22.5 g, 197.3 mmol) was added, stirring for 16 h at r.t. The reaction solution was concentrated under reduced pressure to obtain black oil. 25 mL DCM, TEA (7.86 g, 77.72 mmol) were added, methanesulfonyl chloride (2.67 g, 23.32 mmol) was added at 0° C., 50 mL water was added, the mixture was extracted with DCM (80 mL×3), organic phases were combined and washed in sequence with water (80 mL×2), saturated sodium chloride solution (80 mL×2), dried over anhydrous sodium sulfate, filtered, the filtrate was concentrated under reduced pressure, the residue was purified by silica gel column chromatography with eluting system C to obtain 1-(methylsulfonyl)spiro[azetidine-3,3'-indoline]-2'-one 106b (4.2 g, yellow solid), yield: 77.1%.

$^1$H NMR (400 MHz, CD$_3$OD) δ7.68-7.62 (m, 1H), 7.41-7.32 (m, 1H), 7.30-7.27 (m, 1H), 7.21-7.15 (m, 1H), 4.33 (d, J=8.03 Hz, 2H), 4.18 (d, J=8.03 Hz, 2H), 3.13 (s, 3H).

Step 2

1'-(2,2-Diethoxy)-1-(methylsulfonyl)spiro[azetidine-3,3'-indoline]-2'-one 1-(Methylsulfonyl)spiro[azetidine-3,3'-indoline]-2'-one 106b (3.6 g, 14.27 mmol) was dissolved in 20 mL DMF, 2-bromo-1,1-diethoxyl-ethane (3.37 g, 17.12 mmol), cesium carbonate (9.30 g, 28.54 mmol), potassium iodide (0.24 g, 1.43 mmol) were added, stirring for 16 h at 90° C. The reaction solution was cooled to r.t., 100 mL water was added, extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue by purified with silica gel column chromatography with elution system C to obtain 1'-(2,2-diethoxy)-1-(methylsulfonyl)spiro[azetidine-3,3'-indoline]-2'-one 106c (4.2 g, yellow oil), yield: 75.89%.

$^1$H NMR (400 MHz, CDCl$_3$) δ7.68-7.62 (m, 1H), 7.41-7.32 (m, 1H), 7.30-7.27 (m, 1H), 7.21-7.15 (m, 1H), 4.70 (s, 1H), 4.31 (d, J=8.03 Hz, 2H), 4.33 (d, J=8.03 Hz, 2H), 4.18 (d, J=8.03 Hz, 2H), 3.80-3.60 (m, 2H), 3.50-3.30 (m, 2H), 3.13 (s, 3H), 1.16 (t, J=8.03 Hz, 6H).

Step 3

2-(1-(Methylsulfonyl)-2'-oxospiro[azetidine-3,3'-indoline]-1'-yl)acetaldehyde 1'-(2,2-Diethoxy)-1-(methylsulfonyl)spiro[azetidine-3,3'-indoline]-2'-one 106c (4.2 g, 11.4 mmol) was dissolved in 20 mL DCM and 8 mL H$_2$O, trifluoroacetic acid (31.0 g, 271.9 mmol) was added dropwise at 0° C., stirring for 2 h at r.t. Sodium carbonate was added to adjust pH to 9, the mixture was extracted with DCM (80 mL×3), organic phases were combined and washed in sequence with water (80 mL×2), saturated sodium chloride solution (80 mL×2), dried over anhydrous sodium sulfate, filtered, the filtrate was concentrated under reduced pressure to obtain the crude product 2-(1-(methylsulfonyl)-2'-oxospiro[azetidine-3,3'-indoline]-1'-yl)acetaldehyde 106d (3.2 g, yellow solid).

Step 4

1-(Methylsulfonyl)-1'-((1,4,5,6-tetrahydrocyclopenta[d]imidazol-2-yl)methyl)spiro[azetidine-3,3'-indoline]-2'-one 2-(1-(Methylsulfonyl)-2'-oxospiro[azetidine-3,3'-indoline]-1'-yl)acetaldehyde 106d (3.1 g, 10.53 mmol) was dissolved in 25 mL ethanol, 2-hydroxylcyclopentane-2-enone (1.24 g, 12.64 mmol), ammonium acetate (4.06 g, 52.65 mmol) were added, and the reaction mixture was stirred for 8 h at 80° C. The reaction solution was concentrated under reduced pressure, 100 mL saturated sodium carbonate aqueous solution was added, extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with elution system C to obtain 1-(methylsulfonyl)-1'-((1,4,5,6-tetrahydrocyclopenta[d]imidazol-2-yl)methyl)spiro[azetidine-3,3'-indoline]-2'-one 106e (420 mg, yellow solid), yield: 8.57%.

$^1$H NMR (400 MHz, CDCl$_3$) δ7.68-7.62 (m, 1H), 7.41-7.32 (m, 1H), 7.30-7.27 (m, 1H), 7.21-7.15 (m, 1H), 4.90 (s, 2H), 4.33 (d, J=8.03 Hz, 2H), 4.18 (d, J=8.03 Hz, 2H), 4.15-4.05 (m, 1H), 3.08 (s, 3H), 2.68-2.58 (m, 3H), 2.48-2.39 (m, 2H).

Step 5

1-(Methylsulfonyl)-1'-((1-(4,4,4-trifluorobutyl)-1,4,5,6-tetrahydrocyclopenta[d]imidazol-2-yl)methyl)spiro[azetidine-3,3'-indoline]-2'-one 1-(Methyl sulfonyl)-1'-((1,4,5,6-tetrahydrocyclopenta[d]imidazol-2-yl)methyl)spiro[azetidine-3,3'-indoline]-2'-one 106e (0.2 g, 0.54 mmol) was dissolved in 5 mL DMF, 4-bromo-1,1,1-trifluorobutane (0.12 g, 0.64 mmol), cesium carbonate (0.35 g, 1.07 mmol) and potassium iodide (8.9 mg, 0.05 mmol) were added, stirring for 8 h at 90° C. The reaction solution was cooled to r.t., 30 mL water was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, preparative HPLC was used to purify and the target product 1-(methylsulfonyl)-1'-((1-(4,4,4-trifluorobutyl)-1,4,5,6-tetrahydrocyclopenta[d]imidazol-2-yl)methyl)spiro[azetidine-3,3'-indoline]-2'-one 106 (42 mg, white solid) was given, yield: 15.56%.

MS m/z (ESI): 483.2 [M+1]

$^1$H NMR (400 MHz, CD$_3$OD) δ7.75-7.69 (m, 1H), 7.36-7.28 (m, 1H), 7.25-7.18 (m, 1H), 7.14-7.07 (m, 1H), 5.00 (br. s., 2H), 4.84-4.78 (m, 1H), 4.43-4.34 (m, 2H), 4.18-4.08 (m, 3H), 3.15 (s, 3H), 2.76-2.68 (m, 2H), 2.64-2.55 (m, 2H), 2.54-2.44 (m, 2H), 2.30-2.17 (m, 2H), 1.99-1.89 (m, 2H).

Embodiment 107

Isopropyl 1'-((1-(but-3-en-1-yl)-4,5,6,7-tetrahydro-1H-benzo[d]imidazol-2-yl)methyl)-6'-chloro-2'-oxospiro[azetidine-3,3'-indoline]-1-carboxylate

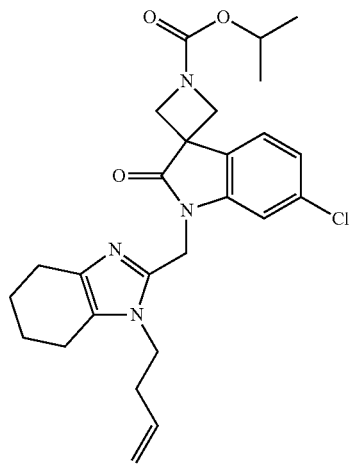

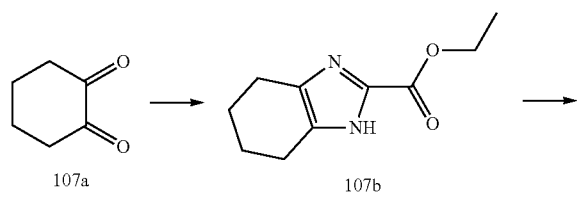
107a → 107b

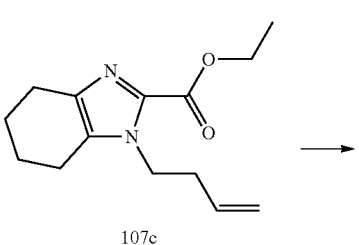
107c

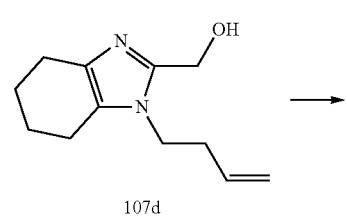
107d

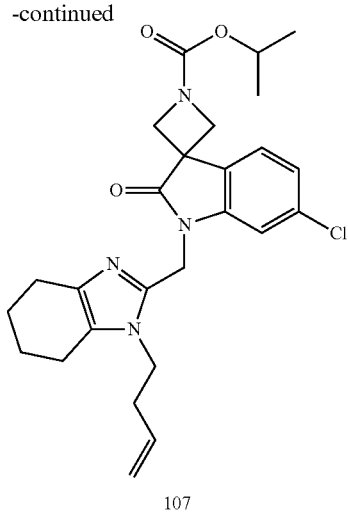
107

Step 1

Ethyl 4,5,6,7-tetrahydro-1H-benzo[d]imidazole-2-carboxylate

Cyclohexane-1,2-dione 107a (200.00 g, 1.78 mol) and formyl methyl formate were dissolved in 2.00 L ethanol, ammonium acetate (687.5 g, 3.57 mol) was added, stirring for 12 h at 90° C. The reaction solution was filtered and concentrated under reduced pressure, the residue was purified with silica gel column chromatography with eluting system C to obtain ethyl 2'-oxo-1'-((4,5,6,7-tetrahydrocyclopenta[d]imidazol-2-yl)methyl)spiro[azetidine-3,3'-indoline]-1-carboxylate 107b (48.00 g, white solid), yield: 13.61%.

$^1$H NMR (400 MHz, METHANOL-d4) δ 4.35 (q, J=7.1 Hz, 2H), 2.65-2.55 (m., 4H), 1.84-1.73 (m, 4H), 1.37 (t, J=7.2 Hz, 3H).

Step 2

Ethyl 1-(but-3-en-1-yl)-4,5,6,7-tetrahydro-1H-benzo[d]imidazole-2-carboxylate

Ethyl 4,5,6,7-tetrahydro-1H-benzo[d]imidazole-2-carboxylate 107b (1.00 g, 5.15 mmol) was dissolved in 8 mL anhydrous DMF, 4-bromobutyl-1-ene (1.06 g, 7.85 mmol), cesium carbonate (3.36 g, 10.30 mmol), potassium iodide (85.49 mg, 515.00 μmol) were added in sequence, stirring for 2 h at 90° C. The reaction solution was cooled to r.t., 100 mL EA was added, washed in sequence with water (100 mL×2) and saturated sodium chloride aqueous solution (100 mL), dried over anhydrous sodium sulfate, filtered, the filtrate was concentrated under reduced pressure to obtain the crude product ethyl 1-(but-3-en-1-yl)-4,5,6,7-tetrahydro-1H-benzo[d]imidazole-2-carboxylate 107c (1.2 g, yellow oil).

Step 3

(1-(But-3-en-1-yl)-4,5,6,7-tetrahydro-1H-benzo[d]imidazol-2-yl)methanol

Lithium aluminum hydride (596.57 mg, 15.72 mmol) was suspended in 10 mL anhydrous THF, ethyl 1-(but-3-en-1- yl)-4,5,6,7-tetrahydro-1H-benzo[d]imidazole-2-carboxylate 107c (1.30 g, 5.24 mmol) in 10 mL THF was slowly added dropwise under an ice-bath condition, and during the period of addition, the temperature of the reaction solution was no more than 5° C. After stirring for 1 h at r.t., ice-water was added to quench the reaction under an ice-bath condition, the reaction solution was filtered and the filtrate was concentrated under reduced pressure, the residue was purified by silica gel column chromatography with eluting system C to obtain (1-(but-3-en-1-yl)-4,5,6,7-tetrahydro-1H-benzo[d] imidazol-2-yl)methanol 107d (450 mg, white solid).

$^1$H NMR (400 MHz, CD$_3$OD) δ 5.90-5.65 (m, 1H), 4.99-5.30 (m, 2H), 4.63 (s, 2H), 3.89-4.06 (m, 2H), 2.55-2.45 (m, 6H), 1.83-1.82 (m, 4H).

Step 4

Isopropyl 1'-((1-(but-3-en-1-yl)-4,5,6,7-tetrahydro-1H-benzo[d]imidazol-2-yl)methyl)-6'-chloro-2'-oxospiro[azetidine-3,3'-indoline]-1-carboxylate (1-(But-3-en-1-yl)-4,5,6,7-tetrahydro-1H-benzo[d]imidazol-2-yl)methanol (100.00 mg, 0.48 mmol) was dissolved in 5 mL anhydrous THF, isopropyl 6'-chloro-2'-oxospiro[azetidine-3,3'-indoline]-1-carboxylate 107d (171.45 mg, 0.58 mmol) and triphenyl phosphine (152.58 mg, 0.58 mmol) were added in sequence, then diisopropyl azodicarboxylate (117.63 mg, 0.58 mmol) was added under an ice-bath condition. After stirring for 16 h at r.t., the reaction solution was concentrated under reduced pressure, 30 mL water was added, extracted with EA (30 mL×2), organic phases were combined and washed in sequence with water (30 mL×3), saturated sodium chloride solution (30 mL×2), dried over anhydrous sodium sulfate, filtered, the filtrate was concentrated under reduced pressure, preparative HPLC was used to purify and the target product isopropyl 1'-((1-(but-3-en-1-yl)-4,5,6,7-tetrahydro-1H-benzo[d]imidazol-2-yl) methyl)-6'-chloro-2'-oxospiro[azetidine-3,3'-indoline]-1-carboxylate 107 (30 mg, white solid) was given, yield: 12.81%.

MS m/z (ESI): 483.3 [M+1]

$^1$H NMR (400 MHz, MeOD) δ 7.62 (d, J=8.0 Hz, 1H), 7.17 (d, J=8.0 Hz, 1H), 7.09 (s, 1H), 5.85-5.73 (m, 2H), 5.12-5.02 (m, 3H), 4.37-4.26 (m, 3H), 4.22-4.12 (m, 3H), 4.09-3.96 (m, 3H), 2.61-2.47 (m, 2H), 2.43-2.30 (m, 2H), 1.90-1.77 (m, 4H), 1.30 (d, J=6.27 Hz, 6H).

Embodiment 108

Isopropyl 2'-oxo-1'-((7-oxo-1-(4,4,4-trifluorobutyl)-4,5,6,7-tetrahydro-1H-benzo[d]imidazol-2-yl) methyl)spiro[azetidine-3,3'-indoline]-1-carboxylate

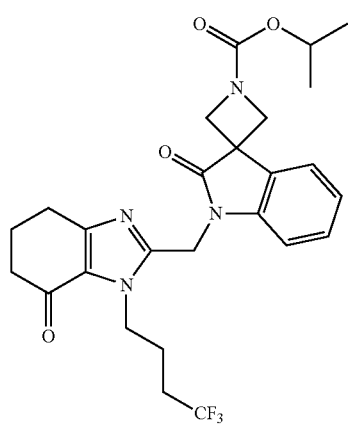

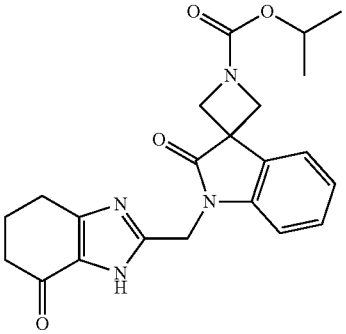

108a

108b

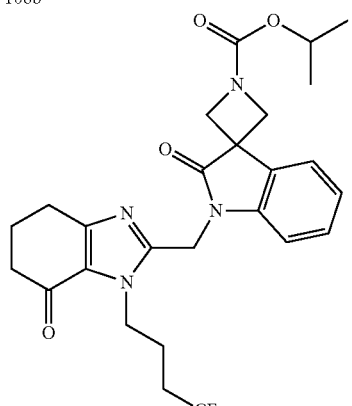

108

Step 1

Isopropyl 2'-oxo-1'-((7-oxo-4,5,6,7-tetrahydro-1H-benzo[d]azetidin-2-yl)methyl)spiro[imidazol-3,3'-indoline]-1-carboxylate Isopropyl 2'-oxo-1'-((4,5,6,7-tetrahydro-1H-benzo[d]azetidin-2-yl)methyl)spiro[imidazol-3,3'-indoline]-1-carboxylate 108a (1.00 g, 2.54 mmol) was dissolved in 20 mL acetic acid and 20 mL water, ammonium ceric nitrate (8.34 g, 15.21 mmol) was added, stirring for 2 h at r.t. 30 mL water was added into the reaction mixture, the mixture was extracted with EA (30 mL×3), organic phases were combined and washed in sequence with water (30 mL×3), saturated sodium chloride solution (30 mL×2), dried over anhydrous sodium sulfate, filtered, the filtrate was concentrated under reduced pressure, the residue was purified by silica gel column chromatography with eluting system C to obtain isopropyl 2'-oxo-1'-((7-oxo-4,5,6,7-tetrahydro-1H- benzo[d]azetidine-2-yl)methyl)spiro[imidazol-3,3'-indoline]-1-carboxylate 108b (300 mg, yellow solid), yield: 28.92%.

¹H NMR (400 MHz, CDCl₃) δ 7.58 (d, J=7.3 Hz, 1H), 7.37-7.30 (m, 1H), 7.21-7.14 (m, 2H), 7.03 (br. s., 1H), 5.14-4.85 (m, 3H), 4.43 (d, J=7.8 Hz, 2H), 4.18-4.12 (m, 2H), 2.85 (t, J=6.0 Hz, 2H), 2.52 (t, J=6.0 Hz, 2H), 2.22-2.12 (m, 2H), 1.28-1.26 (m, 6H).

Step 2

Isopropyl 2'-oxo-1'-((7-oxo-1-(4,4,4-trifluorobutyl)-4,5,6,7-tetrahydro-1H-benzo[d]imidazol-2-yl)methyl)spiro[azetidine-3,3'-indoline]-1-carboxylate Isopropyl 2'-oxo-1'-((7-oxo-4,5,6,7-tetrahydro-1H-benzo[d]imidazole-2-yl)methyl)spiro[imidazol-3,3'-indoline]-1-carboxylate 108b (298.17 mg, 0.73 mmol) and 4-bromo-1,1,1-trifluorobutane (139.42 mg, 0.73 mmol) were dissolved in 20 mL anhydrous DMF, cesium carbonate (475.70 mg, 1.46 mmol) was added, stirring for 4 h at 80° C. 30 mL water was added, the mixture was extracted with EA (30 mL×3), organic phases were combined and washed in sequence with water (30 mL×3), saturated sodium chloride solution (30 mL×2), dried over anhydrous sodium sulfate, filtered, the filtrate was concentrated under reduced pressure, preparative HPLC was used to purify and the target product isopropyl 2'-oxo-1'-((7-oxo-1-(4,4,4-trifluorobutyl)-4,5,6,7-tetrahydro-1H-benzo[d]imidazol-2-yl)methyl)spiro[azetidine-3,3'-indoline]-1-carboxylate 108 (60 mg, white solid) was given, yield: 28.92%.

MS m/z (ESI): 541.2 [M+23]

¹H NMR (400 MHz, MeOD) δ7.65 (d, J=7.3 Hz, 1H), 7.31 (t, J=7.6 Hz, 1H), 7.20 (t, J=7.6 Hz, 1H), 7.02 (d, J=7.8 Hz, 1H), 5.09 (s, 2H), 4.95-4.94 (m, 1H), 4.46 (t, J2=7.8 Hz, 2H), 4.35 (d, J=8.5 Hz, 2H), 4.16 (d, J=8.3 Hz, 2H), 2.76 (t, J=6.0 Hz, 2H), 2.52 (t, J=6.3 Hz, 2H), 2.30-2.29 (m, 2H), 2.17-2.05 (m, 2H), 1.96 (m, 2H), 1.29 (d, J=6.3 Hz, 6H).

Embodiment 109

Isopropyl 1'-((7-hydroxy-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate

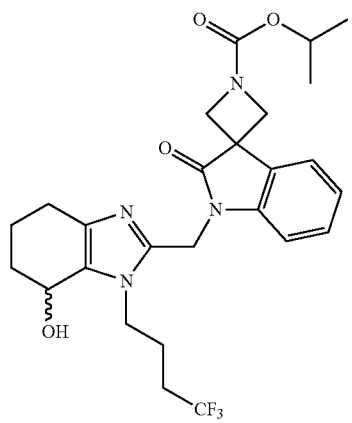

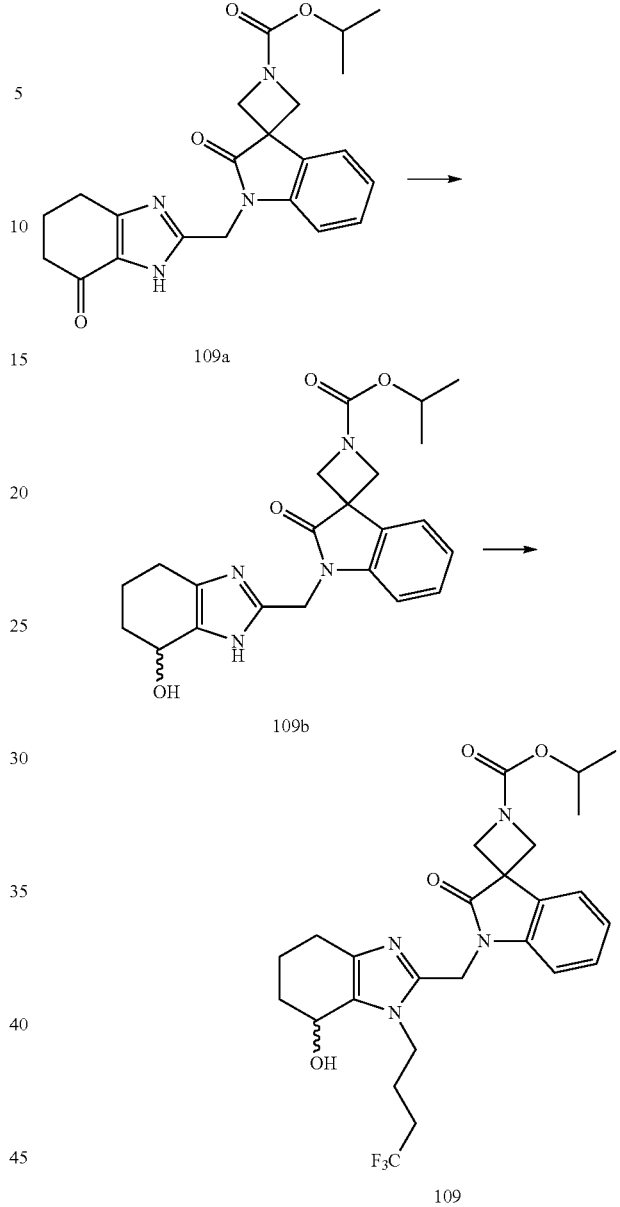

Step 1

Isopropyl 1'-((7-hydroxy-4,5,6,7-tetrahydro-1H-benzo[d]imidazol-2-yl)methyl)-2'-oxospiro[azetidine-3,3'-indoline]-1-carboxylate Isopropyl 2'-oxo-1'-((7-oxo-4,5,6,7-tetrahydro-1H-benzo[d]imidazole-2-yl)methyl)spiro[imidazol-3,3'-indoline]-1-carboxylate 109a (600 mg, 1.47 mmol) was dissolved in 10 mL methanol, sodium borohydride (166.83 mg, 4.41 mmol) was added, stirring for 12 h at r.t. 50 mL water was added, the mixture was extracted with DCM (50 mL×3), organic phases were combined and washed in sequence with water (50 mL×3), saturated sodium chloride solution (50 mL×2), dried over anhydrous sodium sulfate, filtered, the filtrate was concentrated under reduced pressure, the residue was purified by silica gel column chromatography with eluting system C to obtain the crude product isopropyl 1'-((7- hydroxy-4,5,6,7-tetrahydro-1H-benzo[d]imidazol-2-yl)methyl)-2'-oxospiro[azetidine-3,3'-indoline]-1-carboxylate 1109b (360 mg, yellow solid).

Step 2

Isopropyl 1'-((7-hydroxy-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate Isopropyl 1'-((7-hydroxy-4,5,6,7-tetrahydro-1H-benzo[d]imidazol-2-yl)methyl)-2'-oxospiro[azetidine-3,3'-indoline]-1-carboxylate 109b (360 mg, 0.877 mmol) and 4-bromo-1,1,1-trifluorobutane (335.01 mg, 1.75 mmol) were dissolved in 10 mL anhydrous DMF, cesium carbonate (571.51 mg, 1.75 mmol) was added, stirring for 2 h at 80° C. 50 mL water was added, the mixture was extracted with EA (50 mL×3), organic phases were combined and washed in sequence with water (50 mL×3), saturated sodium chloride solution (50 mL×2), dried over anhydrous sodium sulfate, filtered, the filtrate was concentrated under reduced pressure, preparative HPLC was used to purify and a pair of enantiomers 109 was separated by SFC, isopropyl 1'-((7-hydroxy-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate, (10 mg, white solid), yield: 28.92% and (12 mg, white solid), yield: 28.92%, respectively.

MS m/z (ESI): 521.3 [M+1]

$^1$H NMR (400 MHz, MeOD) δ7.65 (d, J=7.3 Hz, 1H), 7.31 (t, J=7.6 Hz, 1H), 7.20 (t, J=7.6 Hz, 1H), 7.02 (d, J=7.8 Hz, 1H), 5.09 (s, 2H), 4.95-4.94 (m, 1H), 4.46 (t, J2=7.8 Hz, 2H), 4.35 (d, J=8.5 Hz, 2H), 4.16 (d, J=8.3 Hz, 2H), 2.76 (t, J=6.0 Hz, 2H), 2.52 (t, J=6.3 Hz, 2H), 2.30-2.29 (m, 2H), 2.17-2.05 (m, 2H), 1.96 (m, 2H), 1.29 (d, J=6.3 Hz, 6H).

Embodiment 110

Ethyl 1'-((4-methyl-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate

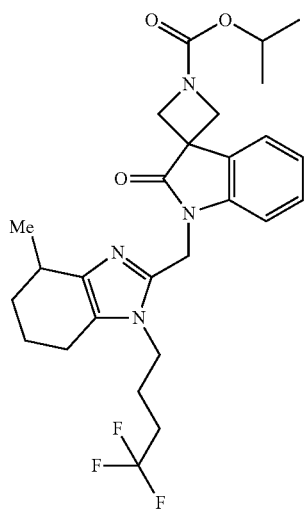

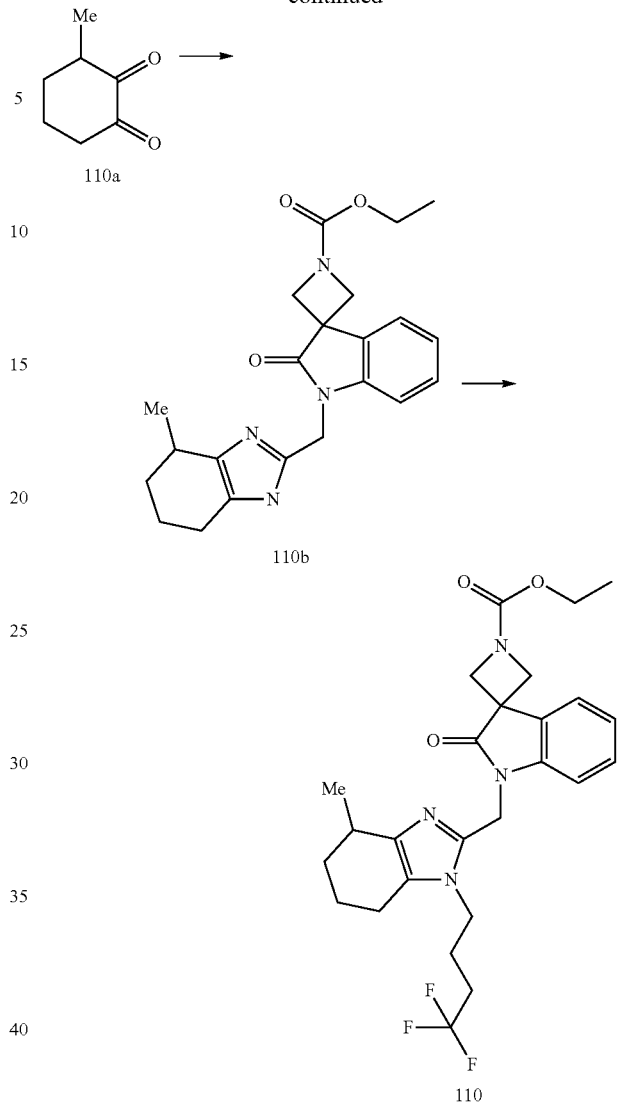

Step 1

Ethyl 1'-((7-methyl-4,5,6,7-tetrahydro-1H-benzo[d]imidazol-2-yl)methyl)-2'-oxospiro[azetidine-3,3'-indoline]-1-carboxylate 3-Methylcyclohexane-1,2-dione 110a (0.52 g, 4.16 mmol) was dissolved in 30 mL ethanol, ethyl 2'-oxo-1'-(2-ethoxy)spiro[azetidine-3,3'-indoline]-1-carboxylate (1.2 g, 4.16 mmol) and ammonium acetate (1.6 g, 20.8 mmol) were added, stirring for 8 h at 80° C. The reaction solution was concentrated under reduced pressure, 100 mL saturated sodium carbonate aqueous solution was added, extracted with EA (100 mL×3), organic phases were combined and washed in sequence with water (100 mL×2), saturated sodium chloride solution (100 mL×2), dried over anhydrous sodium sulfate, filtered, the filtrate was concentrated under reduced pressure, the residue was purified by silica gel column chromatography with eluting system C to obtain ethyl 1'-((7-methyl-4,5,6,7-tetrahydro-1H-benzo[d]imidazol-2-yl)methyl)-2'-oxospiro[azetidine-3,3'-indoline]-1-carboxylate 110b (1.1 g, yellow solid), yield: 67.70%.

$^1$H NMR (400 MHz, CDCl$_3$) δ 7.53 (d, J=7.53 Hz, 1H), 7.37-7.25 (m, 2H), 7.20-7.11 (m, 1H), 4.97-4.84 (m, 2H), 4.41 (dd, J=3.01, 8.28 Hz, 2H), 4.20 (q, J=7.19 Hz, 2H), 4.15-4.10 (m, 2H), 2.49 (t, J=5.40 Hz, 2H), 1.98-1.82 (m, 2H), 1.73-1.57 (m, 1H), 1.42-1.25 (m, 5H), 1.20 (d, J=7.03 Hz, 3H).

Step 2

Ethyl 1'-((4-methyl-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate Ethyl 1'-((7-methyl-4,5,6,7-tetrahydro-1H-benzo[d]imidazol-2-yl)methyl)-2'-oxospiro[azetidine-3,3'-indoline]-1-carboxylate 110b (0.2 g, 0.51 mmol) was dissolved in 10 mL DMF, 4-bromo-1,1,1-trifluorobutane (0.11 g, 0.56 mmol), cesium carbonate (0.33 g, 1.01 mmol) were added, stirring for 1 h at 80° C. The reaction solution was cooled to r.t., 30 mL water was added, extracted with EA (20 mL×3), organic phases were combined and washed in sequence with water (20 mL×2), saturated sodium chloride solution (20 mL×2), dried over anhydrous sodium sulfate, filtered, the filtrate was concentrated under reduced pressure, the preparative HPLC was used to purify and the target product ethyl 1'-((4-methyl-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate 110 (100 mg, white solid) was given, yield: 38.3%.

MS m/z (ESI): 505.5 [M+1]

$^1$H NMR (400 MHz, CD$_3$OD) δ 7.64 (d, J=7.28 Hz, 1H), 7.29 (d, J=7.78 Hz, 1H), 7.16-7.22 (m, 1H), 7.13 (d, J=8.03 Hz, 1H), 5.02 (d, J=14.56 Hz, 2H), 4.37 (d, J=7.78 Hz, 2H), 4.20 (q, J=7.03 Hz, 4H), 4.04 (t, J=7.91 Hz, 2H), 2.66-2.79 (m, 1H), 2.46-2.58 (m, 2H), 2.25 (dd, J=10.67, 16.44 Hz, 2H), 1.90-2.02 (m, 2H), 1.68-1.87 (m, 3H), 1.38-1.48 (m, 1H), 1.31 (t, J=7.03 Hz, 3H), 1.17-1.26 (m, 3H).

Experiment 1: In Vitro Assessment

RSV long CPE assay

Experimental Objective:

Detect EC$_{50}$ and CC$_{50}$ values of anti RSV respiratory tract virus compounds through the cytopathic effect assay.

Experimental Materials:

Cell lines: Hep2

Virus strain: RSV respiratory tract virus (A long strain)

Cell culture medium (DMEM/F12, Gibco#11330, add 10% serum Gibco#16140, and 1% penicillin-streptomycin (penicillin 5000 IU/mL, streptomycin 10 mg/mL), Gibco#15140)

Trypsin (Gibco#12605010)

PBS (Thermo#SH30264.01)

Trypan blue (Cat. Invitrogen#15250061)

CCK-8 (Dojindo#CK04-20)

CO2 incubator, Thermo 240 I

Multidrop, Thermo

POD 810 Plate Assembler, Labcyte

Scepter Handheld Automated Cell Counter, Millipore

Microplate Spectrophotometer, Molecular Device.

Experimental Procedure and Method:

A) Cell Vaccination (Cell Hep2)

1) absorb the culture medium of cell culture, clean with PBS 10 mL;

2) add preheated trypsin into a cleaned flask, revolve the flask to make it evenly covered by trypsin. And then suck it up, and placed into 37° C., 5% CO$_2$ incubator to digest;

3) 10~15 mL culture medium was used to suspend cells each T150, absorb 0.1 mL and then dilute it 2 times counted by trypan blue solution;

4) dilute cells to 5×10$^4$/mL with the culture medium, the diluted cells was added into Corning 384 plate (Cat. 3701) (30 μL/hole, 1500 cells/hole) with automatic liquid separator (Scientific Thermo). The cell plate was centrifugated (300 rpm) to make the cells adherent to the wall, placed into a 37° C., 5% CO$_2$ incubator overnight.

B) Compound Sampling 1) the compound in 100% DMSO underwent a semi logarithmic dilution, then was added to the cell plate with a Echo liquid handler. Ensure that the final concentration of DMSO was 1%;

| EC$_{50}$ (μM) | CC$_{50}$ (μM) |
|---|---|
| 50-0.07 μM (8 points semi logarithmic dilution) | 100-0.14 μM (8 points semi logarithmic dilution) |

2) Cell-control hole: no compound and viruse were added; virus-control hole: no compound was added.

c) Virus Inoculation:

dilute RSV viruses to 100 TCID50/30 μL with medium cultured with 4° C. cells, and then add the diluted viruses to a cell plate (30 μL/hole) with Multidrop® automatic liquid distributor, and then placed into a 37° C., 5% CO$_2$ culture incubator for 5 days.

d) Cytopathy Detection:

1) after 5 days, observe the pathological change in each hole. Under normal condition, there is no pathological change in the cell-control hole, and complete pathological change in the virus-control hole;

2) add CCK-8 (Dojindo-CK04-20, 6 μL/hole) to 384 well plate with Multidrop® automatic liquid distributor;

3) place the plate at a 37° C., 5% CO$_2$ culture incubator for 3~4 h, read the absorbance value with SPECTRA max 340PC_Molecular device at 450 nm and 630 nm;

4) analysis data.

The results of the experiment are shown in Table 1:

TABLE 1

Experimental results of CPE assay EC$_{50}$/CC$_{50}$

| Test sample (compound obtained from the Embodiment) | CPE assay EC$_{50}$/CC$_{50}$(μM) | |
|---|---|---|
|  | EC50 | CC50 |
| BMS433771 | A | >100 |
| Embodiment 62 | A | >100 |
| Embodiment 63 | A | >100 |
| Embodiment 64 | A | >100 |
| Embodiment 65 | A | >100 |
| Embodiment 66 | A | >100 |
| Embodiment 67 | B | >100 |
| Embodiment 68 | B | >100 |
| Embodiment 69 | A | >100 |
| Embodiment 70 | A | >100 |
| Embodiment 71 | B | >100 |
| Embodiment 72 | A | >100 |
| Embodiment 73 | A | >100 |
| Embodiment 74 | A | >100 |
| Embodiment 75 | A | >100 |
| Embodiment 76 | A | >100 |
| Embodiment 77 | A | >100 |
| Embodiment 78 | A | >100 |
| Embodiment 79 | A | >100 |
| Embodiment 80 | A | >100 |
| Embodiment 81 | A | >100 |

TABLE 1-continued

Experimental results of CPE assay $EC_{50}/CC_{50}$

| Test sample (compound obtained from the Embodiment) | CPE assay $EC_{50}/CC_{50}$ (μM) | |
|---|---|---|
| | EC50 | CC50 |
| Embodiment 82 | A | >100 |
| Embodiment 83 | A | >100 |
| Embodiment 84 | A | >100 |
| Embodiment 85 | A | >100 |
| Embodiment 86 | A | >100 |
| Embodiment 87 | A | >100 |
| Embodiment 88 | A | >100 |
| Embodiment 89 | A | >100 |
| Embodiment 90 | A | >100 |
| Embodiment 91 | A | >100 |
| Embodiment 92 | A | >100 |
| Embodiment 93 | A | >100 |
| Embodiment 94 | A | >100 |
| Embodiment 95 | A | >100 |
| Embodiment 96 | A | >100 |
| Embodiment 97 | A | >100 |
| Embodiment 98 | A | >100 |
| Embodiment 99 | A | >100 |
| Embodiment 100 | A | >100 |
| Embodiment 101 | — | >100 |
| Embodiment 102 | A | >100 |
| Embodiment 103 | A | >100 |
| Embodiment 104 | A | >100 |
| Embodiment 105 | A | >100 |
| Embodiment 106 | A | >100 |
| Embodiment 107 | A | >100 |
| Embodiment 108 | B | >100 |
| Embodiment 109 | B | >100 |
| Embodiment 110 | B | >100 |

Note:
$EC_{50}$ shows the in vitro activity of the molecule for anti-respiratory virus. According to the degree of the activity, two ranges are divided: A ($EC_{50}$ < 0.1 μM); B (0.1 μM < $EC_{50}$ < 1 μM). The numeric value of $CC_{50}$ indicates the degree of the toxicity of the molecule in vitro.
Conclusion: compared with BMS433771, the in vitro activity and toxicity of the compound of the present invention are similar or even better.

What is claimed is:

1. A process for treating respiratory syncytial virus infection in a subject thereof, comprising administering an effective amount of a compound having formula (XI) or a pharmaceutical acceptable salt thereof to the subject;

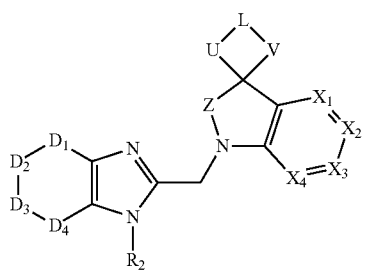
(XI)

wherein,
optionally, the compound or the pharmaceutical acceptable salt thereof containing one or more chiral centers
each of $X_1$, $X_2$ and $X_4$ independently represents CH, or substituted CH;
$X_3$ represents CH, N, or substituted CH;
$R_2$ is a $C_{1-6}$ alkyl group or a $C_{2-6}$ alkenyl group that are optionally substituted by 0-3 halogen atoms, CN or OH, and wherein optionally one of —C(═O)—, —S(═O)— or —S(═O)$_2$— is inserted into the chain of the alkyl or alkenyl group;

Z represents C═O;
each of U or V independently represents $CH_2$;
L represents NH, N-Boc, N—C(═O)OCH($CH_3$)$_2$, N—C(═O)CH($CH_3$)$_2$, N—C(O)—$R_{02}$, N—S(O)$_2R_{02}$, or N—C(O)—$OR_{02}$, wherein $R_{02}$ is a hydrogen, unsubstituted $C_{1-6}$ linear alkyl or $C_{3-5}$ cycloalkyl group, or $C_{1-6}$ linear alkyl or $C_{3-5}$ cycloalkyl group substituted by hydroxyl, halogen, or amino groups;
one of $D_{1-4}$ is —C($R_{d1}$)($R_{d2}$)— or —C(═O)—, and the remaining three are $CH_2$; and
each of $R_{d1}$ and $R_{d2}$ is independently selected from H, OH, or $CH_3$.

2. A process for treating respiratory syncytial virus infection in a subject thereof, comprising administering an effective amount of a compound of the following formula or a pharmaceutical acceptable salt thereof to the subject;

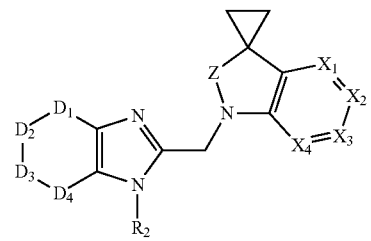

wherein
each of $X_1$, $X_2$, and $X_4$ independently represents CH, or substituted CH;
$X_3$ represents CH, N, or substituted CH;
$R_2$ is a $C_{1-6}$ alkyl group or a $C_{2-6}$ alkenyl group that are optionally substituted by 0-3 halogen atoms, CN or OH, and wherein optionally one of —C(═O)—, —S(═O)— or —S(═O)$_2$— is inserted into the chain of the alkyl or alkenyl group;
Z represents C═O;
one of $D_{1-4}$ is —C($R_{d1}$)($R_{d2}$)— or —C(═O)—, and the remaining three are $CH_2$;
each of $R_{d1}$ and $R_{d2}$ is independently selected from H, OH, or $CH_3$.

3. A process according to claim 1, wherein each of $R_{d1}$ and $R_{d2}$ is independently selected from H or $CH_3$.

4. A process according to claim 1, wherein both of $R_{d1}$ and $R_{d2}$ are $CH_3$.

5. A process according to claim 1, wherein $R_2$ is selected from the following groups:

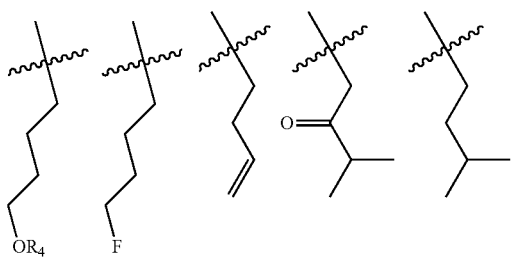

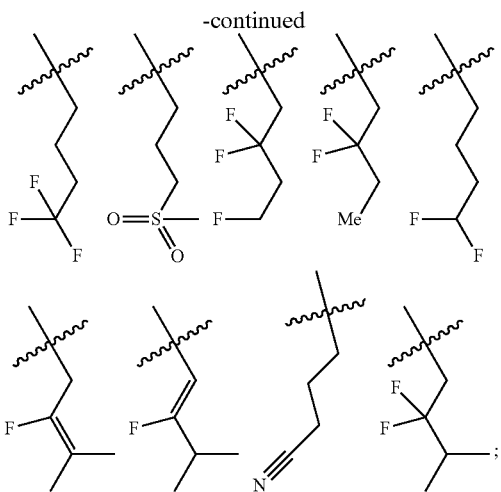

and
R₄ is H.

6. A process according to claim 1, wherein the compound is selected from the group consisting of the following compounds:

62) Isopropyl 1'-((1-(4-hydroxybutyl)-4,5,6,7-tetrahydro-1H-benzo[d]imidazol-2-yl)methyl)-2'-oxospiro[azetidine-3,3'-indoline]-1-carboxylate;
64) Isopropyl 1'-((1-(4,4-difluorobutyl)-4,5,6,7-tetrahydro-1H-benzo[d]imidazol-2-yl)methyl)-2'-oxospiro[azetidine-3,3'-indoline]-1-carboxylate;
65) Isopropyl 2'-oxo-1'-((1-(4,4,4-trifluorobutyl)-4,5,6,7-tetrahydro-1H-benzo[d]imidazol-2-yl)methyl)-spiro[azetidine-3,3'-indoline]-1-carboxylate;
66) Isopropyl 2'-oxo-1'-((1-(2,2,4-trifluorobutyl)-4,5,6,7-tetrahydro-1H-benzo[d]imidazol-2-yl)methyl)spiro[azetidine-3,3'-indoline]-1-carboxylate;
67) Isopropyl 1'-((1-(2,2-difluorobutyl)-4,5,6,7-tetrahydro-1H-benzo[d]imidazol-2-yl)methyl)-2'-oxospiro[azetidine-3,3'-indoline]-1-carboxylate;
68) Isopropyl 1'-((1-(3-methyl-2-oxobutyl)-4,5,6,7-tetrahydro-1H-benzo[d]imidazol-2-yl)methyl)-2'-oxospiro[azetidine-3,3'-indoline]-1-carboxylate;
69) Isopropyl 1'-((1-(2,2-difluoro-3-methylbutyl)-4,5,6,7-tetrahydro-1H-benzo[d]imidazol-2-yl)methyl)-2'-oxospiro[azetidine-3,3'-indoline]-1-carboxylate;
70) (Z)-isopropyl 1'-((1-(2-fluoro-3-methylbut-1-en-1-yl)-4,5,6,7-tetrahydro-1H-benzo[d]imidazol-2-yl)methyl)-2'-oxospiro[azetidine-3,3'-indoline]-1-carboxylate;
71) Isopropyl 1'-((1-(2-fluoro-3-methylbut-2-en-1-yl)-4,5,6,7-tetrahydro-1H-benzo[d]imidazol-2-yl)methyl)-2'-oxospiro[azetidine-3,3'-indoline]-1-carboxylate;
72) Ethyl 1'-((1-isopentyl-4,5,6,7-tetrahydro-1H-benzo[d]imidazol-2-yl)methyl)-2'-oxospiro[azetidine-3,3'-indoline]-1-carboxylate;
73) Ethyl 1'-((1-(3-fluorobutyl)-4,5,6,7-tetrahydro-1H-benzo[d]imidazol-2-yl)methyl)-2'-oxospiro[azetidine-3,3'-indoline]-1-carboxylate;
74) Ethyl 1'-((1-(3-cyanopropyl)-4,5,6,7-tetrahydro-1H-benzo[d]imidazol-2-yl)methyl)-2'-oxospiro[azetidine-3,3'-indoline]-1-carboxylate;
75) Ethyl 2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
76) Ethyl 1'-((1-(3-(methylsulfonyl)propyl)-4,5,6,7-tetrahydro-1H-benzo[d]imidazol-2-yl)methyl)-2'-oxospiro[azetidine-3,3'-indoline]-1-carboxylate;
77) Cyclopentyl 1'-((1-(3-hydroxybutyl)-4,5,6,7-tetrahydro-1H-benzo[d]imidazol-2-yl)methyl)-2'-oxospiro[azetidine-3,3'-indoline]-1-carboxylate;
78) Isopropyl 5'-bromo-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate;
79) Isopropyl 5'-bromo-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
80) Isopropyl 5'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
81) Isopropyl 6'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
82) Isopropyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
83) Ethyl 6'-fluoro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
84) 1-(Cyclopropanecarbonyl)-6'-fluoro-1'-((1-(4,4,4-trifluorobutyl)-4,5,6,7-tetrahydro-1H-benzo[d]imidazol-2-yl)methyl)spiro[azetidine-3,3'-indoline]-2'-one;
85) Isopropyl 4'-chloro-1'-((1-(4-hydroxybutyl)-4,5,6,7-tetrahydro-1H-benzo[d]imidazol-2-yl)methyl)-2'-oxospiro[azetidine-3,3'-indoline]-1-carboxylate;
86) Isopropyl 4'-chloro-2'-oxo-1'-((1-(4,4,4-trifluorobutyl)-4,5,6,7-tetrahydro-1H-benzo[d]imidazol-2-yl)methyl)spiro[azetidine-3,3'-indoline]-1-carboxylate;
87) Ethyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate;
88) Isopropyl 2'-oxo-1'-((1-(4,4,4-trifluorobutyl)-4,5,6,7-tetrahydro-1H-benzo[d]imidazol-2-yl)methyl)-1',2'-dihydrospiro[azetidine-3,3'-pyrrolo[2,3-c]pyridine]-1-carboxylate;
89) 1-(Cyclopropanecarbonyl)-1'-((1-(4,4,4-trifluorobutyl)-4,5,6,7-tetrahydro-1H-benzo[d]imidazol-2-yl)methyl)spiro[azetidine-3,3'-pyrrolo[2,3-c]pyridin]-2'(1'H)-one;
90) 2'-Oxo-1'-((1-(4,4,4-trifluorobutyl)-4,5,6,7-tetrahydro-1H-benzo[d]imidazol-2-yl)methyl)spiro[azetidine-3,3'-indoline]-1-carbaldehyde;
91) 1-(1-Methylcyclopropanecarbonyl)-1'-((1-(4,4,4-trifluorobutyl)-4,5,6,7-tetrahydro-1H-benzo[d]imidazol-2-yl)methyl)spiro[azetidine-3,3'-pyrrole[2,3-c]pyridine]-2'-one;
92) 1-Acetyl-1'-((1-(4,4,4-trifluorobutyl)-4,5,6,7-tetrahydro-1H-benzo[d]imidazol-2-yl)methyl)spiro[azetidine-3,3'-indoline]-2'-one;
93) 1-(Cyclopropanecarbonyl)-1'-((1-(4,4,4-trifluorobutyl)-4,5,6,7-tetrahydro-1H-benzo[d]imidazol-2-yl)methyl)spiro[azetidine-3,3'-indoline]-2'-one;
94) 1-Propionyl-1'-((1-(4,4,4-trifluorobutyl)-4,5,6,7-tetrahydro-1H-benzo[d]imidazol-2-yl)methyl)spiro[azetidine-3,3'-indoline]-2'-one;
95) 1-Isobutyryl-1'-((1-(4,4,4-trifluorobutyl)-4,5,6,7-tetrahydro-1H-benzo[d]imidazol-2-yl)methyl)spiro[azetidine-3,3'-indoline]-2'-one;
96) 1-(2,2-Difluoroacetyl)-1'-((1-(4,4,4-trifluorobutyl)-4,5,6,7-tetrahydro-1H-benzo[d]imidazol-2-yl)methyl)spiro[azetidine-3,3'-indoline]-2'-one;

97) 1-(Methylsulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one;
98) 1-(Cyclopropylsulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one;
99) 1-(Isopropylsulfonyl)-1'-((1-(4,4,4-trifluorobutyl)-4,5,6,7-tetrahydro-1H-benzo[d]imidazol-2-yl)methyl)spiro[azetidine-3,3'-indoline]-2'-one;
102) Isopropyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate;
103) Isopropyl 1'-((1-(4-hydroxybutyl)-1,4,5,6-tetrahydrocyclopenta[d]imidazol-2-yl)methyl)-2'-oxospiro[azetidine-3,3'-indoline]-1-carboxylate;
104) Ethyl 2'-oxo-1'-((1-(4,4,4-trifluorobutyl)-1,4,5,6-tetrahydrocyclopenta[d]imidazol-2-yl)methyl)spiro[azetidine-3,3'-indoline]-1-carboxylate;
105) 1-Isobutyryl-1'-((1-(4,4,4-trifluorobutyl)-1,4,5,6-tetrahydrocyclopenta[d]imidazol-2-yl)methyl)spiro[azetidine-3,3'-indoline]-2'-one;
106) 1-(Methylsulfonyl)-1'-((1-(4,4,4-trifluorobutyl)-1,4,5,6-tetrahydrocyclopenta[d]imidazol-2-yl)methyl)spiro[azetidine-3,3'-indoline]-2'-one;
107) Isopropyl 1'-((1-(but-3-en-1-yl)-4,5,6,7-tetrahydro-1H-benzo[d]imidazol-2-yl)methyl)-6'-chloro-2'-oxospiro[azetidine-3,3'-indoline]-1-carboxylate;
108) Isopropyl 2'-oxo-1'-((7-oxo-1-(4,4,4-trifluorobutyl)-4,5,6,7-tetrahydro-1H-benzo[d]imidazol-2-yl)methyl)spiro[azetidine-3,3'-indoline]-1-carboxylate;
109) Isopropyl 1'-((7-hydroxy-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate; and
110) Ethyl 1'-((4-methyl-1-(4,4,4-trifluorobutyl)-4,5,6,7-tetrahydro-1H-benzo[d]imidazol-2-yl)methyl)-2'-oxospiro[azetidine-3,3'-indoline]-1-carboxylate.

7. A process according to claim 2, wherein the compound is 1'-((1-(4-Hydroxybutyl)-4,5,6,7-tetrahydro-1H-benzo[d]imidazol-2-yl)methyl)spiro[cyclopropane-1,3'-indoline]-2'-one.

8. A process according to claim 2, wherein $R_2$ is substituted by 1-3 halogen atoms which are independently fluorine, chlorine, bromine or iodine.

9. A process according to claim 2, wherein substituted CH in $X_1$, $X_2$, $X_3$, or $X_4$ is CH wherein the H is replaced by halogen.

10. A process according to claim 9, wherein the halogen is independently selected from fluorine, chlorine, bromine or iodine.

11. A process according to claim 1, wherein $R_2$ is substituted by 1-3 halogen atoms which are independently fluorine, chlorine, bromine or iodine.

12. A process according to claim 1, wherein substituted CH in $X_1$, $X_2$, $X_3$, or $X_4$ is CH wherein the H is replaced by halogen.

13. A process according to claim 12, wherein the halogen is independently selected from fluorine, chlorine, bromine or iodine.

14. A process according to claim 2, wherein each of $R_{d1}$ and $R_{d2}$ is independently H or $CH_3$.

15. A process according to claim 1, wherein both of $R_{d1}$ and $R_{d2}$ are $CH_3$.

16. A process according to claim 1, wherein L is selected from;
—C(=O)OC(CH$_3$)$_3$, —C(=O)OCH(CH$_3$)$_2$, —C(=O)CH(CH$_3$)$_2$, —S(=O)$_2$CH$_3$,

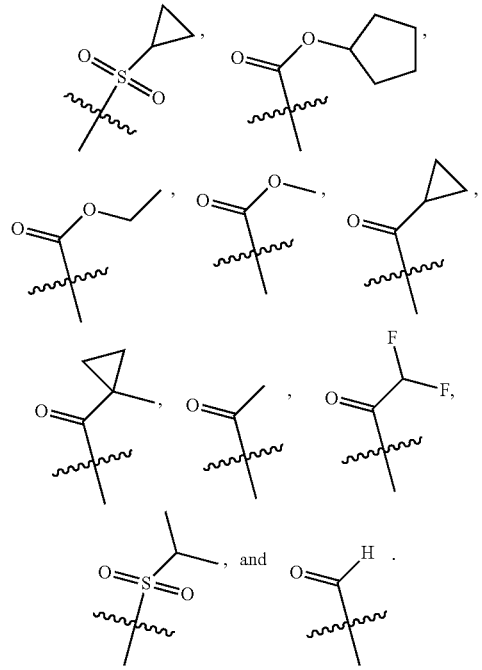

17. A process according to claim 1, wherein $R_{02}$ is substituted by halogen atoms which are independently fluorine, chlorine, bromine or iodine.

18. A process according to claim 2, wherein $R_2$ is selected from:

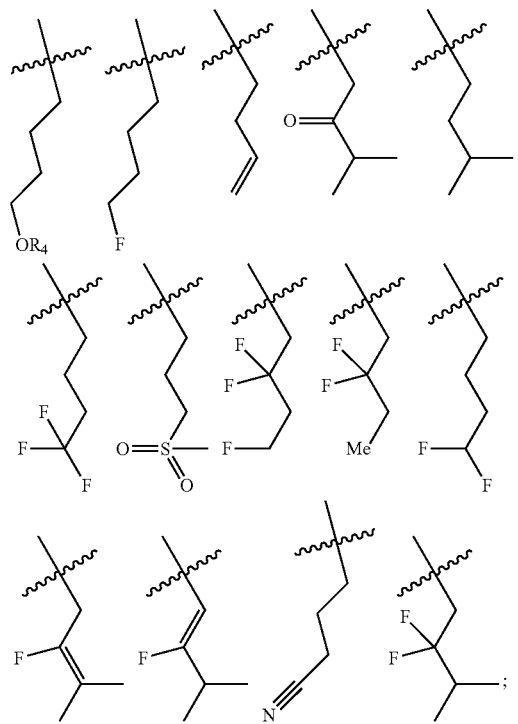

and $R_4$ is selected from H.

* * * * *